United States Patent
Bindschädler et al.

(10) Patent No.: US 10,533,002 B2
(45) Date of Patent: Jan. 14, 2020

(54) THIOPHENE- OR FURAN-SUBSTITUTED ISOTHIAZOLINE COMPOUNDS AS PESTICIDES

(71) Applicant: BOEHRINGER INGELHEIM ANIMAL HEATLH USA INC., Duluth, GA (US)

(72) Inventors: Pascal Bindschädler, Römerberg (DE); Wolfgang Von Deyn, Neustadt (DE); Karsten Körber, Eppelheim (DE); Deborah L. Culbertson, Fuquay Varina, NC (US); Koshi Gunjima, Toyohashi (JP); Franz Josef Braun, Durham, NC (US)

(73) Assignee: BOEHRINGER INGELHEIM ANIMAL HEALTH USA INC., Duluth, GA (US)

( * ) Notice: Subject to any disclaimer, the term of this patent is extended or adjusted under 35 U.S.C. 154(b) by 317 days.

(21) Appl. No.: 14/757,930

(22) PCT Filed: Jun. 23, 2014

(86) PCT No.: PCT/EP2014/063103
§ 371 (c)(1),
(2) Date: Jun. 30, 2016

(87) PCT Pub. No.: WO2014/206909
PCT Pub. Date: Dec. 31, 2014

(65) Prior Publication Data
US 2016/0297808 A1    Oct. 13, 2016

Related U.S. Application Data

(60) Provisional application No. 61/838,368, filed on Jun. 24, 2013.

(51) Int. Cl.
| | | |
|---|---|---|
| *C07D 417/14* | (2006.01) | |
| *A01N 43/80* | (2006.01) | |
| *C07D 417/04* | (2006.01) | |
| *C07D 471/04* | (2006.01) | |

(52) U.S. Cl.
CPC .......... *C07D 417/14* (2013.01); *A01N 43/80* (2013.01); *C07D 417/04* (2013.01); *C07D 471/04* (2013.01)

(58) Field of Classification Search
None
See application file for complete search history.

(56) References Cited

FOREIGN PATENT DOCUMENTS

| | | |
|---|---|---|
| EP | 1538138 | 6/2005 |
| JP | 20050272452 | 5/2010 |
| WO | 20090112275 | 9/2009 |
| WO | 20100070068 | 6/2010 |
| WO | 20100090344 | 8/2010 |
| WO | WO 2011/073444 | 6/2011 |
| WO | 20110092287 | 8/2011 |
| WO | 20110157748 | 12/2011 |
| WO | 20120107533 | 8/2012 |
| WO | 2012120135 | 12/2012 |
| WO | 20130037626 | 3/2013 |
| WO | WO 2013/079407 | 6/2013 |

OTHER PUBLICATIONS

English language Abstract for JP 2005-272452 printed from Espacenet.com on Aug. 7, 2018.

*Primary Examiner* — Po-Chih Chen
(74) *Attorney, Agent, or Firm* — Judy Jarecki-Black; John Ezcurra

(57) ABSTRACT

The present invention relates to thiophene- or furan-substituted isothiazoline compounds of formula I

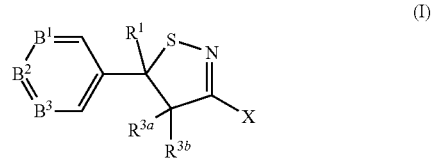

(I)

wherein the variables are as defined in the claims and description. The compounds are useful for combating or controlling invertebrate pests, in particular arthropod pests and nematodes. The invention also relates to a method for controlling invertebrate pests by using these compounds and to plant propagation material and to an agricultural and a veterinary composition comprising said compounds.

31 Claims, No Drawings

THIOPHENE- OR FURAN-SUBSTITUTED ISOTHIAZOLINE COMPOUNDS AS PESTICIDES

The present invention relates to thiophene- or furan-substituted isothiazoline compounds which are useful for combating or controlling invertebrate pests, in particular arthropod pests and nematodes. The invention also relates to a method for controlling invertebrate pests by using these compounds and to plant propagation material and to an agricultural and a veterinary composition comprising said compounds.

Invertebrate pests and in particular arthropods and nematodes destroy growing and harvested crops and attack wooden dwelling and commercial structures, causing large economic loss to the food supply and to property. While a large number of pesticidal agents are known, due to the ability of target pests to develop resistance to said agents, there is an on-going need for new agents for combating invertebrate pests, in particular insects, arachnids and nematodes.

Related insecticidal aryl isothiazoline compounds are described in WO 2013/037626. However, this document does not describe compounds having the characteristic substituents and substituents' arrangement as claimed in the present invention. Related insecticidal aryl azoline compounds are further described in WO 2011/092287, WO 2011/073444, WO 2010/090344, WO 2009/112275 and WO 97/23212. These documents do not describe compounds having the characteristic substituents and substituents' arrangement as claimed in the present invention, either.

It is an object of the present invention to provide compounds that have a good pesticidal activity, in particular insecticidal activity, and show a broad activity spectrum against a large number of different invertebrate pests, especially against difficult to control arthropod pests and/or nematodes.

It has been found that these objectives can be achieved by isothiazoline compounds of the formula I below, by their stereoisomers and by their salts, in particular their agriculturally or veterinarily acceptable salts.

Therefore, in a first aspect, the invention relates to isothiazoline compounds of formula I

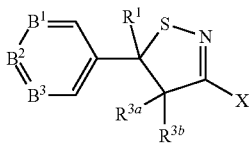

wherein
X is a heterocyclic radical of formula II

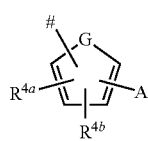

wherein
# is the attachment point to the remainder of the molecule;
A is a group $A^1$, $A^2$, $A^3$ or $A^4$;

wherein
$A^1$ is selected from the group consisting of —C(=NR$^6$)R$^8$, —S(O)$_n$R$^9$, —N(R$^5$)R$^6$ and —CN;
$A^2$ is a group of following formula:

wherein
# denotes the bond to the aromatic ring of formula (I);
W is selected from O and S;
Y is selected from hydrogen, —N(R$^5$)R$^6$ and —OR$^9$;
$A^3$ is a group of following formula:

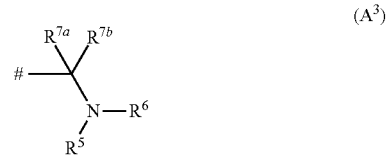

wherein
# denotes the bond to the aromatic ring of formula (I);
$A^4$ is a 3-, 4-, 5-, 6- or 7-membered saturated, partially unsaturated or maximally unsaturated heteromonocyclic ring containing 1, 2, 3 or 4 heteroatoms or heteroatom groups selected from N, O, S, NO, SO and SO$_2$, as ring members, or is a 8-, 9- or 10-membered saturated, partially unsaturated or maximally unsaturated heterobicyclic ring containing 1, 2, 3 or 4 heteroatoms or heteroatom groups selected from N, O, S, NO, SO and SO$_2$, as ring members, where the heteromonocyclic or heterobicyclic ring is optionally substituted with one or more substituents R$^{11}$;
G is O or S;
$B^1$, $B^2$ and $B^3$ are each independently selected from the group consisting of N and CR$^2$, with the proviso that at most two of $B^1$, $B^2$ and $B^3$ are N;
$R^1$ is selected from the group consisting of C$_1$-C$_4$-alkyl, C$_1$-C$_4$-haloalkyl, C$_1$-C$_4$-alkoxy-C$_1$-C$_4$-alkyl, C$_1$-C$_4$-haloalkoxy-C$_1$-C$_4$-alkyl-, C$_2$-C$_4$-alkenyl, C$_2$-C$_4$-haloalkenyl, C$_2$-C$_4$-alkynyl, C$_2$-C$_4$-haloalkynyl, C$_3$-C$_6$-cycloalkyl, C$_3$-C$_6$-halocycloalkyl and —C(=O)OR$^{15}$;
each $R^2$ is independently selected from the group consisting of hydrogen, halogen, cyano, azido, nitro, —SCN, —SF$_5$, C$_1$-C$_6$-alkyl, C$_3$-C$_8$-cycloalkyl, C$_2$-C$_6$-alkenyl, C$_2$-C$_6$-alkynyl, wherein the four last mentioned aliphatic and cycloaliphatic radicals may be partially or fully halogenated and/or may be substituted by one or more radicals R$^8$,
—Si(R$^{12}$)$_3$, —OR$^9$, —S(O)$_n$R$^9$, —NR$^{10a}$R$^{10b}$,
phenyl which may be substituted by 1, 2, 3, 4 or 5 radicals R$^{11}$, and a 3-, 4-, 5-, 6-7-, 8-, 9- or 10-membered saturated, partially unsaturated or maximally unsaturated heteromonocyclic or heterobicyclic ring containing 1, 2, 3 or 4 heteroatoms or heteroatom groups selected from N, O, S, NO, SO and SO$_2$, as ring members, where the heteromono- or heterobicyclic ring may be substituted by one or more radicals R$^{11}$;
$R^{3a}$, $R^{3b}$ are each independently selected from the group consisting of hydrogen, halogen, hydroxyl, —CO$_2$R$^{3d}$, $C_1$-$C_3$-alkyl, $C_1$-$C_3$-haloalkyl, $C_2$-$C_3$-alkenyl, $C_2$-$C_3$-alkynyl, $C_1$-$C_3$-alkoxy, $C_1$-$C_3$-haloalkoxy, $C_1$-$C_3$-alkylthio, $C_1$-$C_3$-haloalkylthio, $C_1$-$C_3$-alkylsulfonyl and $C_1$-$C_3$-haloalkylsulfonyl; or $R^{3a}$ and $R^{3b}$ together form a group =O, =C($R^{3c}$)$_2$, =NOH or =NOCH$_3$;

each $R^{3c}$ is independently selected from the group consisting of hydrogen, halogen, CH$_3$ and CF$_3$;

$R^{3d}$ is selected from the group consisting of hydrogen, $C_1$-$C_6$-alkyl and $C_1$-$C_3$-alkyloxy-$C_1$-$C_3$-alkyl-;

$R^{4a}$ and $R^{4b}$ are independently selected from the group consisting of hydrogen, halogen, cyano, azido, nitro, —SCN, —SF$_5$, $C_1$-$C_6$-alkyl which may be partially or fully halogenated and/or may be substituted by one or more radicals $R^8$, $C_3$-$C_8$-cycloalkyl which may be partially or fully halogenated and/or may be substituted by one or more radicals $R^8$, $C_2$-$C_6$-alkenyl which may be partially or fully halogenated and/or may be substituted by one or more radicals $R^8$, $C_2$-$C_6$-alkynyl which may be partially or fully halogenated and/or may be substituted by one or more radicals $R^8$, —Si($R^{12}$)$_3$, —OR$^9$, —S(O)$_n$R$^9$, —NR$^{10a}$R$^{10b}$, phenyl which may be substituted by 1, 2, 3, 4 or 5 radicals $R^{11}$, and a 3-, 4-, 5-, 6-7-, 8-, 9- or 10-membered saturated, partially unsaturated or maximally unsaturated heteromonocyclic or heterobicyclic ring containing 1, 2, 3 or 4 heteroatoms or heteroatom groups selected from N, O, S, NO, SO and SO$_2$, as ring members, where the heteromonocyclic or heterobicyclic ring may be substituted by one or more radicals $R^{11}$;

each $R^5$ is independently selected from the group consisting of hydrogen, cyano, $C_1$-$C_{10}$-alkyl, $C_3$-$C_8$-cycloalkyl, $C_2$-$C_{10}$-alkenyl, $C_2$-$C_{10}$-alkynyl, wherein the four last-mentioned aliphatic and cycloaliphatic radicals may be partially or fully halogenated and/or may be substituted with one or more substituents $R^8$; and —S(O)$_n$R$^9$, each $R^6$ is independently selected from the group consisting of hydrogen, cyano, $C_1$-$C_{10}$-alkyl, $C_3$-$C_8$-cycloalkyl, $C_2$-$C_{10}$-alkenyl, $C_2$-$C_{10}$-alkynyl, wherein the four last-mentioned aliphatic and cycloaliphatic radicals may be partially or fully halogenated and/or may be substituted by one or more substituents $R^8$, —OR$^9$, —NR$^{10a}$R$^{10b}$, —S(O)$_n$R$^9$, —C(=O)NR$^{10a}$N(R$^{10a}$)R$^{10b}$, —Si($R^{12}$)$_3$, —C(=O)R$^8$, —CH=NOR$^9$, phenyl which may be substituted with 1, 2, 3, 4, or 5 substituents $R^{11}$, and a 3-, 4-, 5-, 6-, 7-, 8-, 9- or 10-membered saturated, partially unsaturated or maximally unsaturated heteromonocyclic or heterobicyclic ring containing 1, 2, 3 or 4 heteroatoms or heteroatom groups independently selected from N, O, S, NO, SO and SO$_2$, as ring members, where the heteromonocyclic or heterobicyclic ring may be substituted with one or more substituents $R^{11}$;

or $R^5$ and $R^6$, together with the nitrogen atom to which they are bound, form a 3-, 4-, 5-, 6-, 7- or 8-membered saturated, partially unsaturated or maximally unsaturated heterocyclic ring, where the ring may further contain 1, 2, 3 or 4 heteroatoms or heteroatom-containing groups selected from O, S, N, SO, SO$_2$, C=O and C=S as ring members, wherein the heterocyclic ring may be substituted with 1, 2, 3, 4 or 5 substituents independently selected from the group consisting of halogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, wherein the aliphatic or cycloaliphatic moieties in the twelve last-mentioned radicals may be substituted by one or more radicals $R^8$, and phenyl which may be substituted with 1, 2, 3, 4 or 5 substituents $R^{11}$;

or $R^5$ and $R^6$ together form a group =C($R^8$)$_2$, =S(O)$_m$(R$^9$)$_2$, =NR$^{10a}$ or =NOR$^9$;

$R^{7a}$, $R^{7b}$ are each independently selected from the group consisting of hydrogen, halogen, cyano, $C_1$-$C_6$-alkyl, $C_3$-$C_8$-cycloalkyl, $C_2$-$C_6$-alkenyl and $C_2$-$C_6$-alkynyl, wherein the four last-mentioned aliphatic and cycloaliphatic radicals may be partially or fully halogenated and/or may be substituted by one or more radicals $R^8$;

each $R^8$ is independently selected from the group consisting of cyano, azido, nitro, —SCN, —SF$_5$, $C_3$-$C_8$-cycloalkyl, $C_3$-$C_8$-halocycloalkyl, $C_3$-$C_8$-cycloalkenyl, $C_3$-$C_8$-halocycloalkenyl, where the cycloaliphatic moieties in the four last-mentioned radicals may be substituted by one or more radicals $R^{13}$;

—Si($R^{12}$)$_3$, —OR$^9$, —OSO$_2$R$^9$, —S(O)$_n$R$^9$, —N(R$^{10a}$)R$^{10b}$, —C(=O)N(R$^{10a}$)R$^{10b}$, —C(=S)N(R$^{10a}$)R$^{10b}$, —C(=O)OR$^9$, —CH=NOR$^9$, phenyl, optionally substituted with 1, 2, 3, 4 or 5 substituents $R^{16}$, and a 3-, 4-, 5-, 6- or 7-membered saturated, partially unsaturated or maximally unsaturated heterocyclic ring comprising 1, 2 or 3 heteroatoms or heteroatom groups selected from N, O, S, NO, SO and SO$_2$, as ring members, where the heterocyclic ring is optionally substituted with one or more substituents $R^{16}$, or two $R^8$ present on the same carbon atom of an alkyl, alkenyl, alkynyl or cycloalkyl group together form a group =O, =C($R^{13}$)$_2$, =S; =S(O)$_m$(R$^{15}$)$_2$, =S(O)$_m$R$^{15}$N(R$^{14a}$)R$^{14b}$, =NR$^{10a}$, =NOR$^9$; or =NN(R$^{10a}$)R$^{10b}$;

or two radicals $R^8$, together with the carbon atoms of an alkyl, alkenyl, alkynyl or cycloalkyl group which they are bonded to, form a 3-, 4-, 5-, 6-, 7- or 8-membered saturated or partially unsaturated carbocyclic or heterocyclic ring, where the heterocyclic ring comprises 1, 2, 3 or 4 heteroatoms or heteroatom groups independently selected from N, O, S, NO, SO and SO$_2$, as ring members, and where the carbocyclic or heterocyclic ring is optionally substituted with one or more substituents $R^{18}$; and $R^8$ as a substituent on a cycloalkyl ring is additionally selected from the group consisting of $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl and $C_2$-$C_6$-haloalkynyl, where the aliphatic moieties in these six radicals may be substituted by one or more radicals $R^{13}$; and $R^8$ in the groups —C(=NR$^6$)R$^8$, —C(=O)R$^8$ and =C($R^8$)$_2$ is additionally selected from the group consisting of hydrogen, halogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl and $C_2$-$C_6$-haloalkynyl, where the aliphatic moieties in the six last-mentioned radicals may be substituted by one or more radicals $R^{13}$;

each $R^9$ is independently selected from the group consisting of hydrogen, cyano, $C_1$-$C_6$-alkyl, $C_1$-$C_6$-haloalkyl, $C_3$-$C_8$-cycloalkyl, $C_3$-$C_8$-cycloalkyl-$C_1$-$C_4$-alkyl-, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, where the aliphatic and cycloaliphatic moieties in the nine last-mentioned radicals may be substituted by one or more radicals $R^{13}$, —$C_1$-$C_6$-alkyl-C(=O)O$R^{15}$, —$C_1$-$C_6$-alkyl-C(=O)N($R^{14a}$)$R^{14b}$, —$C_1$-$C_6$-alkyl-C(=S)N($R^{14a}$)$R^{14b}$, —$C_1$-$C_6$-alkyl-C(=N$R^{14}$)N($R^{14a}$)$R^{14b}$, —Si($R^{12}$)$_3$, —S(O)$_n$$R^{15}$, —S(O)$_n$N($R^{14a}$)$R^{14b}$, —N($R^{10a}$)$R^{10b}$, —N=C($R^{13}$)$_2$, —C(=O)$R^{13}$, —C(=O)N($R^{14a}$)$R^{14b}$, —C(=S)N($R^{14a}$)$R^{14b}$, —C(=O)O$R^{15}$, phenyl, optionally substituted with one or more substituents $R^{16}$; and a 3-, 4-, 5-, 6- or 7-membered saturated, partially unsaturated or maximally unsaturated heterocyclic ring comprising 1, 2 or 3 heteroatoms or heteroatom groups selected from N, O, S, NO, SO and SO$_2$, as ring members, where the heterocyclic ring is optionally substituted with one or more substituents $R^{16}$; and $R^9$ in the groups —S(O)$_n$$R^9$ and —OSO$_2$$R^9$ is additionally selected from the group consisting of $C_1$-$C_6$-alkoxy and $C_1$-$C_6$-haloalkoxy;

$R^{10a}$, $R^{10b}$ are selected independently from one another from the group consisting of hydrogen, $C_1$-$C_6$-alkyl, $C_1$-$C_6$-haloalkyl, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, where the aliphatic and cycloaliphatic moieties in the eight last-mentioned radicals may be substituted by one or more radicals $R^{13}$:
—$C_1$-$C_6$-alkyl-C(=O)O$R^{15}$, —$C_1$-$C_6$-alkyl-C(=O)N($R^{14a}$)$R^{14b}$, —$C_1$-$C_6$-alkyl-C(=S)N($R^{14a}$)$R^{14b}$, —$C_1$-$C_6$-alkyl-C(=N$R^{14}$)N($R^{14a}$)$R^{14b}$, $C_1$-$C_6$-alkoxy, $C_1$-$C_6$-haloalkoxy, $C_1$-$C_6$-alkylthio, $C_1$-$C_6$-haloalkylthio,
—S(O)$_n$$R^{16}$, —S(O)$_n$N($R^{14a}$)$R^{14b}$, —C(=O)$R^{13}$, —C(=O)O$R^{15}$, —C(=O)N($R^{14a}$)$R^{14b}$, —C(=S)$R^{13}$, —C(=S)S$R^{15}$, —C(=S)N($R^{14a}$)$R^{14b}$, —C(=N$R^{14}$)$R^{13}$;

phenyl, optionally substituted with 1, 2, 3, 4 or 5 substituents $R^{16}$; and a 3-, 4-, 5-, 6- or 7-membered saturated, partially unsaturated or maximally unsaturated heterocyclic ring comprising 1, 2, 3 or 4 heteroatoms or heteroatom groups selected from N, O, S, NO, SO and SO$_2$, as ring members, where the heterocyclic ring is optionally substituted with one or more substituents $R^{16}$; or $R^{10a}$ and $R^{10b}$ form together with the nitrogen atom they are bonded to a 3-, 4-, 5-, 6-, 7- or 8-membered saturated, partially unsaturated or maximally unsaturated heterocyclic ring, wherein the heterocyclic ring may additionally contain one or two heteroatoms or heteroatom groups selected from N, O, S, NO, SO and SO$_2$, as ring members, where the heterocyclic ring optionally carries one or more substituents selected from halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, phenyl, optionally substituted with 1, 2, 3, 4 or 5 substituents $R^{16}$, and a 3-, 4-, 5-, 6, or 7-membered saturated, partially unsaturated or maximally unsaturated heterocyclic ring comprising 1, 2 or 3 heteroatoms or heteroatom groups selected from N, O, S, NO, SO and SO$_2$, as ring members, where the heterocyclic ring optionally carries one or more substituents $R^{16}$;

or $R^{10a}$, and $R^{10b}$ together form a group =C($R^{13}$)$_2$, =S(O)$_m$($R^{15}$)$_2$, =S(O)$_m$$R^{16}$N($R^{14a}$)$R^{14b}$, =N$R^{14}$ or =NO$R^{15}$;

$R^{11}$ is independently selected from the group consisting of halogen, cyano, azido, nitro, —SCN, —SF$_5$, $C_1$-$C_{10}$-alkyl, $C_3$-$C_8$-cycloalkyl, $C_2$-$C_{10}$-alkenyl, $C_2$-$C_{10}$-alkynyl, wherein the four last-mentioned aliphatic and cycloaliphatic radicals may be partially or fully halogenated and/or may be substituted with one or more radicals $R^8$, —O$R^9$, —N$R^{10a}$$R^{10b}$, —S(O)$_n$$R^9$, —Si($R^{12}$)$_3$;

phenyl, optionally substituted with 1, 2, 3, 4, or 5 substituents selected independently from $R^{16}$; and a 3-, 4-, 5-, 6- or 7-membered saturated, partially unsaturated or maximally unsaturated aromatic heterocyclic ring comprising 1, 2, 3 or 4 heteroatoms or heteroatom groups selected from N, O, S, NO, SO and SO$_2$, as ring members, where the heterocyclic ring is optionally substituted with one or more substituents selected independently from $R^{16}$;

or two $R^{11}$ present on the same ring carbon atom of an unsaturated or partially unsaturated heterocyclic ring may together form a group =O, =C($R^{13}$)$_2$; =S; =S(O)$_m$($R^{15}$)$_2$; =S(O)$_m$$R^{15}$N($R^{14a}$)$R^{14b}$, =N$R^{14}$, =NO$R^{15}$, or =NN($R^{14a}$)$R^{14b}$;

or two $R^{11}$ bound on adjacent ring atoms form together with the ring atoms to which they are bound a saturated 3-, 4-, 5-, 6-, 7-, 8- or 9-membered ring, wherein the ring may contain 1 or 2 heteroatoms or heteroatom groups selected from O, S, N, N$R^{14}$, NO, SO and SO$_2$ and/or 1 or 2 groups selected from C=O, C=S and C=N$R^{14}$ as ring members, and wherein the ring may be substituted by one or more radicals selected from the group consisting of halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, phenyl which may be substituted by 1, 2, 3, 4 or 5 radicals $R^{16}$, and a 3-, 4-, 5-, 6- or 7-membered saturated, partially unsaturated or maximally unsaturated heterocyclic ring containing 1, 2 or 3 heteroatoms or heteroatom groups selected from N, O, S, NO, SO and SO$_2$, as ring members, where the heterocyclic ring may be substituted by one or more radicals $R^{16}$;

each $R^{12}$ is independently selected from the group consisting of hydrogen, halogen, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy-$C_1$-$C_6$-alkyl, $C_1$-$C_6$-haloalkoxy-$C_1$-$C_6$-alkyl, and phenyl, optionally substituted with 1, 2, 3, 4, or 5 substituents $R^{16}$;

each $R^{13}$ is independently selected from the group consisting of cyano, nitro, —OH, —SH, —SCN, —SF$_5$, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —N$R^{14a}$$R^{14b}$, trimethylsilyl, triethylsilyl, tert-butyldimethylsilyl, —C(=O)N($R^{14a}$)$R^{14b}$, $C_3$-$C_8$-cycloalkyl which may be unsubstituted, partially or fully halogenated and/or may carry 1 or 2 radicals selected from cyano, $C_1$-$C_4$-alkyl, $C_3$-$C_4$-cycloalkyl, $C_1$-$C_4$-alkoxy, $C_1$-$C_4$-haloalkoxy and oxo; phenyl, benzyl, phenoxy, where the phenyl moiety in the three last-mentioned radicals may be unsubstituted or carry 1, 2, 3, 4 or 5 substituents $R^{16}$; and a 3-, 4-, 5-, 6- or 7-membered saturated, partially unsaturated or maximally unsaturated heterocyclic ring containing 1, 2 or 3 heteroatoms or heteroatom groups selected from N, O, S, NO, SO and SO$_2$, as ring members, where the heterocyclic ring may be substituted by 1, 2 or 3 substituents $R^{16}$;

or
two $R^{13}$ present on the same carbon atom of an alkyl, alkenyl, alkynyl or cycloalkyl group may together be =O, =CH($C_1$-$C_4$-alkyl), =C($C_1$-$C_4$-alkyl)$C_1$-$C_4$-alkyl, =N$R^{17}$ or =NO$R^{17}$;
and
$R^{13}$ as a substituent on a cycloalkyl ring is additionally selected from the group consisting of $C_1$-$C_6$-alkyl, $C_2$-$C_6$-alkenyl and $C_2$-$C_6$-alkynyl, wherein the three last-mentioned aliphatic radicals may be unsubstituted, partially or fully halogenated and/or may carry 1 or 2 substituents selected from CN, $C_3$-$C_4$-cycloalkyl, $C_1$-$C_4$-alkoxy, $C_1$-$C_4$-haloalkoxy and oxo;
and
$R^{13}$ in the groups =C($R^{13}$)$_2$, —N=C($R^{13}$)$_2$, —C(=O)$R^{13}$, —C(=S)$R^{13}$ and —C(=N$R^{14}$)$R^{13}$ is additionally selected from the group consisting of hydrogen, halogen, $C_1$-$C_6$-alkyl, $C_2$-$C_6$-alkenyl and $C_2$-$C_6$-alkynyl, wherein the three last-mentioned aliphatic radicals may be unsubstituted, partially or fully halogenated and/or may carry 1 or 2 radicals selected from CN, $C_3$-$C_4$-cycloalkyl, $C_1$-$C_4$-alkoxy, $C_1$-$C_4$-haloalkoxy and oxo;
each $R^{14}$ is independently selected from the group consisting of hydrogen, cyano, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —C(=O)N$R^{18a}R^{18b}$, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last-mentioned aliphatic radicals may be unsubstituted, partially or fully halogenated and/or may carry 1 or 2 radicals selected from CN, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_3$-$C_6$-cycloalkyl which may be substituted by 1 or 2 substituents selected from halogen and cyano; and oxo;
$C_3$-$C_8$-cycloalkyl which may be unsubstituted, partially or fully halogenated and/or may carry 1 or 2 radicals selected from cyano, $C_1$-$C_4$-alkyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_3$-$C_4$-cycloalkyl, $C_3$-$C_4$-cycloalkyl-$C_1$-$C_4$-alkyl-, where the cycloalkyl moiety in the two last-mentioned radicals may be substituted by 1 or 2 substituents selected from halogen and cyano; and oxo;
phenyl, benzyl, pyridyl, phenoxy, wherein the cyclic moieties in the four last-mentioned radicals may be unsubstituted and/or carry 1, 2, 3 or 4 substituents selected from halogen, cyano, nitro, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, and ($C_1$-$C_6$-alkoxy)carbonyl; and a 3-, 4-, 5- or 6-membered saturated, partially unsaturated or maximally unsaturated heterocyclic ring comprising 1, 2 or 3 heteroatoms or heteroatom groups selected from N, O, S, NO, SO and $SO_2$, as ring members, where the heterocyclic ring is optionally substituted with one or more substituents $R^{16}$;
$R^{14a}$ and $R^{14b}$, independently of each other, have one of the meanings given for $R^{14}$; or
$R^{14a}$ and $R^{14b}$, together with the nitrogen atom to which they are bound, form a 3-, 4-, 5-, 6- or 7-membered saturated, partially unsaturated or maximally unsaturated heterocyclic ring, wherein the heterocyclic ring may additionally contain 1 or 2 heteroatoms or heteroatom groups selected from N, O, S, NO, SO and $SO_2$, as ring members, where the heterocyclic ring optionally carries one or more substituents selected from halogen, $C_1$-$C_4$-alkyl, $C_1$-$C_4$-haloalkyl, $C_1$-$C_4$-alkoxy and $C_1$-$C_4$-haloalkoxy;
or
$R^{14a}$ and $R^{14}$ or $R^{14b}$ and $R^{14}$, together with the nitrogen atoms to which they are bound in the group —C(=N$R^{14}$)N($R^{14a}$)$R^{14b}$, form a 3-, 4-, 5-, 6- or 7-membered partially unsaturated or maximally unsaturated heterocyclic ring, wherein the heterocyclic ring may additionally contain 1 or 2 heteroatoms or heteroatom groups selected from N, O, S, NO, SO and $SO_2$, as ring members, where the heterocyclic ring optionally carries one or more substituents selected from halogen, $C_1$-$C_4$-haloalkyl, $C_1$-$C_4$-alkoxy and $C_1$-$C_4$-haloalkoxy;
each $R^{15}$ is independently selected from the group consisting of hydrogen, cyano, trimethylsilyl, triethylsilyl, tert-butyldimethylsilyl,
$C_1$-$C_6$-alkyl, $C_2$-$C_6$-alkenyl, $C_2$-$C_6$-alkynyl, wherein the three last-mentioned aliphatic radicals may be unsubstituted, partially or fully halogenated and/or may carry 1 or 2 radicals selected from $C_3$-$C_4$-cycloalkyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl and oxo; $C_3$-$C_8$-cycloalkyl which may be unsubstituted, partially or fully halogenated and/or may carry 1 or 2 radicals selected from $C_1$-$C_4$-alkyl, $C_3$-$C_4$-cycloalkyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl and oxo;
phenyl, benzyl, pyridyl and phenoxy, wherein the four last-mentioned radicals may be unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$-haloalkoxy and ($C_1$-$C_6$-alkoxy)carbonyl;
each $R^{16}$ is independently selected from the group consisting of halogen, nitro, cyano, —OH, —SH, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, aminocarbonyl, $C_1$-$C_4$-alkylaminocarbonyl, di-($C_1$-$C_4$-alkyl)-aminocarbonyl, trimethylsilyl, triethylsilyl, tert-butyldimethylsilyl;
$C_1$-$C_6$-alkyl, $C_2$-$C_6$-alkenyl, $C_2$-$C_6$-alkynyl, wherein the three last-mentioned aliphatic radicals may be unsubstituted, partially or fully halogenated and/or may carry 1 or 2 radicals selected from cyano, $C_3$-$C_4$-cycloalkyl, $C_1$-$C_4$-alkoxy, $C_1$-$C_4$-haloalkoxy and oxo;
$C_3$-$C_8$-cycloalkyl which may be unsubstituted, partially or fully halogenated and/or may carry 1 or 2 radicals selected from cyano, $C_1$-$C_4$-alkyl, $C_1$-$C_4$-cycloalkyl, $C_1$-$C_4$-alkoxy, $C_1$-$C_4$-haloalkoxy and oxo;
phenyl, benzyl, pyridyl and phenoxy, wherein the four last mentioned radicals may be unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$-haloalkoxy and ($C_1$-$C_6$-alkoxy)carbonyl;
or
two $R^{16}$ present together on the same atom of an unsaturated or partially unsaturated ring may be =O, =S, =N($C_1$-$C_6$-alkyl), =NO($C_1$-$C_6$-alkyl), =CH($C_1$-$C_4$-alkyl) or =C($C_1$-$C_4$-alkyl)$C_1$-$C_4$-alkyl;

or two $R^{16}$ on two adjacent carbon atoms form together with the carbon atoms they are bonded to a 4-, 5-, 6-, 7- or 8-membered saturated, partially unsaturated or maximally unsaturated ring, wherein the ring may contain 1 or 2 heteroatoms or heteroatom groups selected from N, O, S, NO, SO and $SO_2$, as ring members, and wherein the ring optionally carries one or more substituents selected from halogen, $C_1$-$C_4$-alkyl, $C_1$-$C_4$-haloalkyl, $C_1$-$C_4$-alkoxy and $C_1$-$C_4$-haloalkoxy;

$R^{17}$, $R^{18a}$ and $R^{18b}$, independently of each other and independently of each occurrence, are selected from the group consisting of hydrogen, $C_1$-$C_6$-alkyl, $C_2$-$C_6$-alkenyl, $C_2$-$C_6$-alkynyl, wherein the three last-mentioned aliphatic radicals may be unsubstituted, partially or fully halogenated and/or may carry 1 or 2 radicals selected from CN, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-cycloalkyl which may be substituted by 1 or 2 substituents selected from halogen and cyano; and oxo;

$C_3$-$C_8$-cycloalkyl which may be unsubstituted, partially or fully halogenated and/or may carry 1 or 2 radicals selected from cyano, $C_1$-$C_4$-alkyl and $C_1$-$C_4$-haloalkyl; phenyl and benzyl;

each n is independently 0, 1 or 2; and each m is independently 0 or 1;

and the N-oxides, stereoisomers and agriculturally or veterinarily acceptable salts thereof.

The present invention also provides an agricultural composition comprising at least one compound of the formula I as defined herein and/or an agriculturally acceptable salt thereof and at least one liquid or solid carrier.

The present invention also provides a veterinary composition comprising at least one compound of the formula I as defined herein and/or a veterinarily acceptable salt thereof and at least one liquid or solid carrier.

The present invention also provides a method for controlling invertebrate pests which method comprises treating the pests, their food supply, their habitat or their breeding ground or a cultivated plant, plant propagation materials (such as seed), soil, area, material or environment in which the pests are growing or may grow, or the materials, cultivated plants, plant propagation materials (such as seed), soils, surfaces or spaces to be protected from pest attack or infestation with a pesticidally effective amount of a compound of formula I or a salt thereof as defined herein.

The present invention also relates to plant propagation material, in particular seed, comprising at least one compound of formula I and/or an agriculturally acceptable salt thereof as defined herein.

The present invention further relates to a method for treating or protecting an animal from infestation or infection by parasites which comprises bringing the animal in contact with a parasiticidally effective amount of a compound of the formula I or a veterinarily acceptable salt thereof as defined herein. Bringing the animal in contact with the compound I, its salt or the veterinary composition of the invention means applying or administering it to the animal.

The term "steroisomers" encompasses both optical isomers, such as enantiomers or diastereomers, the latter existing due to more than one center of chirality in the molecule, as well as geometrical isomers (cis/trans isomers).

Depending on the substitution pattern, the compounds of the formula I may have one or more centers of chirality, in which case they are present as mixtures of enantiomers or diastereomers. One center of chirality is the carbon ring atom of the isothiazoline ring carrying radical $R^1$. The invention provides both the pure enantiomers or diastereomers and their mixtures and the use according to the invention of the pure enantiomers or diastereomers of the compound I or its mixtures. Suitable compounds of the formula I also include all possible geometrical stereoisomers (cis/trans isomers) and mixtures thereof.

The term N-oxides relates to a form of compounds I in which at least one nitrogen atom is present in oxidized form (as NO). To be more precise, it relates to any compound of the present invention which has at least one tertiary nitrogen atom that is oxidized to an N-oxide moiety. N-oxides of compounds I can in particular be prepared by e.g. oxidizing the ring nitrogen atom of the isothiazoline moiety and/or of any nitrogen-containing heterocyclic group present in group A with a suitable oxidizing agent, such as peroxo carboxylic acids or other peroxides. The person skilled in the art knows if and in which positions compounds of the present invention may form N-oxides.

The compounds of the present invention may be amorphous or may exist in one ore more different crystalline states (polymorphs) which may have a different macroscopic properties such as stability or show different biological properties such as activities. The present invention includes both amorphous and crystalline compounds of the formula I, mixtures of different crystalline states of the respective compound I, as well as amorphous or crystalline salts thereof.

Salts of the compounds of the formula I are preferably agriculturally and veterinarily acceptable salts. They can be formed in a customary method, e.g. by reacting the compound with an acid of the anion in question if the compound of formula I has a basic functionality or by reacting an acidic compound of formula I with a suitable base.

Suitable agriculturally acceptable salts are especially the salts of those cations or the acid addition salts of those acids whose cations and anions, respectively, do not have any adverse effect on the action of the compounds according to the present invention. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium ($NH^{4+}$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)ethylammonium, bis(2-hydroxyethyl)ammonium, benzyltrimethylammonium and benzl-triethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$-$C_4$-alkanoic acids, preferably formate, acetate, propionate and butyrate. They can be formed by reacting a compound of formulae I with an acid of the corresponding anion, preferably of hydrochloric acid, hydrobromic acid, sulfuric acid, phosphoric acid or nitric acid.

By the term "veterinarily acceptable salts" is meant salts of those cations or anions which are known and accepted in the art for the formation of salts for veterinary use. Suitable acid addition salts, e.g. formed by compounds of formula I containing a basic nitrogen atom, e.g. an amino group, include salts with inorganic acids, for example hydrochlorids, sulphates, phosphates, and nitrates and salts of organic acids for example acetic acid, maleic acid, dimaleic acid, fumaric acid, difumaric acid, methane sulfenic acid, methane sulfonic acid, and succinic acid.

The term "invertebrate pest" as used herein encompasses animal populations, such as insects, arachnids and nematodes, which may attack plants, thereby causing substantial damage to the plants attacked, as well as ectoparasites which may infest animals, in particular warm blooded animals such as e.g. mammals or birds, or other higher animals such as reptiles, amphibians or fish, thereby causing substantial damage to the animals infested.

The term "plant propagation material" is to be understood to denote all the generative parts of the plant such as seeds and vegetative plant material such as cuttings and tubers (e. g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. The plant propagation materials may be treated prophylactically with a plant protection compound either at or before planting or transplanting. Said young plants may also be protected before transplantation by a total or partial treatment by immersion or pouring.

The term "plants" comprises any types of plants including "non-cultivated plants" and in particular "cultivated plants".

The term "non-cultivated plants" refers to any wild type species or related species or related genera of a cultivated plant.

The term "cultivated plants" is to be understood as including plants which have been modified by breeding, mutagenesis or genetic engineering including but not limiting to agricultural biotech products on the market or in development (cf. http://www.bio.org/speeches/pubs/er/agri_products.asp). Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-translational modification of protein(s), oligo- or polypeptides e. g. by glycosylation or polymer additions such as prenylated, acetylated or farnesylated moieties or PEG moieties.

Plants that have been modified by breeding, mutagenesis or genetic engineering, e. g. have been rendered tolerant to applications of specific classes of herbicides, such as auxin herbicides such as dicamba or 2,4-D; bleacher herbicides such as hydroxyl-phenylpyruvate dioxygenase (HPPD) inhibitors or phytoene desaturase (PDS) inhibitors; acetolactate synthase (ALS) inhibitors such as sulfonyl ureas or imidazolinones; enolpyruvylshikimate-3-phosphate synthase (EPSPS) inhibitors, such as glyphosate; glutamine synthetase (GS) inhibitors such as glufosinate; protoporphyrinogen-IX oxidase inhibitors; lipid biosynthesis inhibitors such as acetyl CoA carboxylase (AC-Case) inhibitors; or oxynil (i. e. bromoxynil or ioxynil) herbicides as a result of conventional methods of breeding or genetic engineering.

Furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or AC-Case inhibitors. These herbicide resistance technologies are e. g. described in Pest Managem. Sci. 61, 2005, 246; 61, 2005, 258; 61, 2005, 277; 61, 2005, 269; 61, 2005, 286; 64, 2008, 326; 64, 2008, 332; Weed Sci. 57, 2009, 108; Austral. J. Agricult. Res. 58, 2007, 708; Science 316, 2007, 1185; and references quoted therein. Several cultivated plants have been rendered tolerant to herbicides by conventional methods of breeding (mutagenesis), e. g. Clearfield® summer rape (Canola, BASF SE, Germany) being tolerant to imidazolinones, e. g. imazamox, or ExpressSun® sunflowers (DuPont, USA) being tolerant to sulfonyl ureas, e. g. tribenuron. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.), Cultivance® (imidazolinone tolerant, BASF SE, Germany) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as δ-endotoxins, e. g. CryIA(b), CryIA(c), CryIF, CryIF(a2), CryIIA(b), CryIIIA, CryIIIB(b1) or Cry9c; vegetative insecticidal proteins (VIP), e. g. VIP1, VIP2, VIP3 or VIP3A; insecticidal proteins of bacteria colonizing nematodes, e. g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e. g. WO 02/015701). Further examples of such toxins or genetically modified plants capable of synthesizing such toxins are disclosed, e. g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e. g. in the publications mentioned above. These insecticidal proteins contained in the genetically modified plants impart to the plants producing these proteins tolerance to harmful pests from all taxonomic groups of athropods, especially to beetles (Coeloptera), two-winged insects (Diptera), and moths (Lepidoptera) and to nematodes (Nematoda). Genetically modified plants capable to synthesize one or more insecticidal proteins are, e. g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e. g. Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e. g. EP-A 392 225), plant disease resistance genes (e. g. potato cultivars, which express resistance genes acting against *Phytophthora infestans* derived from the mexican wild potato *Solanum bulbocastanum*) or T4-lysozym (e. g. potato cultivars capable of synthesizing these proteins with increased resistance against bacteria such as *Erwinia amylvora*). The methods for producing such genetically modified plants are generally known to the person skilled in the art and are described, e. g. in the publications mentioned above.

Furthermore, plants are also covered that are by the use of recombinant DNA techniques capable to synthesize one or more proteins to increase the productivity (e. g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e. g. oil crops that produce health-promoting long-chain omega-3 fatty acids or unsaturated omega-9 fatty acids (e. g. Nexera® rape, DOW Agro Sciences, Canada).

Furthermore, plants are also covered that contain by the use of recombinant DNA techniques a modified amount of substances of content or new substances of content, specifically to improve raw material production, e. g. potatoes that produce increased amounts of amylopectin (e. g. Amflora® potato, BASF SE, Germany).

The organic moieties mentioned in the above definitions of the variables are—like the term halogen—collective terms for individual listings of the individual group members. The prefix $C_n$-$C_m$ indicates in each case the possible number of carbon atoms in the group.

The term halogen denotes in each case fluorine, bromine, chlorine or iodine, in particular fluorine, chlorine or bromine.

The term "alkyl" as used herein and in the alkyl moieties of alkoxy, alkylthio, alkylsulfinyl, alkylsulfonyl, alkylcarbonyl, alkoxycarbonyl and the like refers to saturated straight-chain or branched hydrocarbon radicals having 1 to 2 ("$C_1$-$C_2$-alkyl"), 1 to 3 ("$C_1$-$C_3$-alkyl"), 1 to 4 ("$C_1$-$C_4$-alkyl"), 1 to 6 ("$C_1$-$C_6$-alkyl"), 1 to 8 ("$C_1$-$C_8$-alkyl") or 1 to 10 ("$C_1$-$C_{10}$-alkyl") carbon atoms. $C_1$-$C_2$-Alkyl is methyl or ethyl. $C_1$-$C_3$-Alkyl is additionally propyl and isopropyl. $C_1$-$C_4$-Alkyl is additionally butyl, 1-methylpropyl (sec-butyl), 2-methylpropyl (isobutyl) or 1,1-dimethylethyl (tert-butyl). $C_1$-$C_6$-Alkyl is additionally also, for example, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl. $C_1$-$C_8$-Alkyl is additionally also, for example, heptyl, octyl, 2-ethylhexyl and positional isomers thereof. $C_1$-$C_{10}$-Alkyl is additionally also, for example, nonyl, decyl and positional isomers thereof.

The term "haloalkyl" as used herein, which is also expressed as "alkyl which is partially or fully halogenated", refers to straight-chain or branched alkyl groups having 1 to 2 ("$C_1$-$C_2$-haloalkyl"), 1 to 3 ("$C_1$-$C_3$-haloalkyl"), 1 to 4 ("$C_1$-$C_4$-haloalkyl"), 1 to 6 ("$C_1$-$C_6$-haloalkyl"), 1 to 8 ("$C_1$-$C_8$-haloalkyl") or 1 to 10 ("$C_1$-$C_{10}$-haloalkyl") carbon atoms (as mentioned above), where some or all of the hydrogen atoms in these groups are replaced by halogen atoms as mentioned above: in particular $C_1$-$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl. $C_1$-$C_3$-haloalkyl is additionally, for example, 1-fluoropropyl, 2-fluoropropyl, 3-fluoropropyl, 1,1-difluoropropyl, 2,2-difluoropropyl, 1,2-difluoropropyl, 3,3-difluoropropyl, 3,3,3-trifluoropropyl, heptafluoropropyl, 1,1,1-trifluoroprop-2-yl, 3-chloropropyl and the like. Examples for $C_1$-$C_4$-haloalkyl are, apart those mentioned for $C_1$-$C_3$-haloalkyl, 4-chlorobutyl and the like.

"Halomethyl" is methyl in which 1, 2 or 3 of the hydrogen atoms are replaced by halogen atoms. Examples are bromomethyl, chloromethyl, fluoromethyl, dichloromethyl, trichloromethyl, difluoromethyl, trifluoromethyl, chlorofluoromethyl, dichlorofluoromethyl, chlorodifluoromethyl and the like.

The term "alkenyl" as used herein refers to monounsaturated straight-chain or branched hydrocarbon radicals having 2 to 3 ("$C_2$-$C_3$-alkenyl"), 2 to 4 ("$C_2$-$C_4$-alkenyl"), 2 to 6 ("$C_2$-$C_6$-alkenyl"), 2 to 8 ("$C_2$-$C_8$-alkenyl") or 2 to 10 ("$C_2$-$C_{10}$-alkenyl") carbon atoms and a double bond in any position, for example $C_2$-$C_3$-alkenyl, such as ethenyl, 1-propenyl, 2-propenyl or 1-methylethenyl; $C_2$-$C_4$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl or 2-methyl-2-propenyl; $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl and the like, or $C_2$-$C_{10}$-alkenyl, such as the radicals mentioned for $C_2$-$C_6$-alkenyl and additionally 1-heptenyl, 2-heptenyl, 3-heptenyl, 1-octenyl, 2-octenyl, 3-octenyl, 4-octenyl, 1-nonenyl, 2-nonenyl, 3-nonenyl, 4-nonenyl, 1-decenyl, 2-decenyl, 3-decenyl, 4-decenyl, 5-decenyl and the positional isomers thereof.

The term "haloalkenyl" as used herein, which is also expressed as "alkenyl which is partially or fully halogenated", refers to unsaturated straight-chain or branched hydrocarbon radicals having 2 to 3 ("$C_2$-$C_3$-haloalkenyl"), 2 to 4 ("$C_2$-$C_4$-haloalkenyl"), 2 to 6 ("$C_2$-$C_6$-haloalkenyl"), 2 to 8 ("$C_2$-$C_6$-haloalkenyl") or 2 to 10 ("$C_2$-$C_{10}$-haloalkenyl") carbon atoms and a double bond in any position (as mentioned above), where some or all of the hydrogen atoms in these groups are replaced by halogen atoms as mentioned above, in particular fluorine, chlorine and bromine, for example chlorovinyl, chloroallyl and the like.

The term "alkynyl" as used herein refers to straight-chain or branched hydrocarbon groups having 2 to 3 ("$C_2$-$C_3$-alkynyl"), 2 to 4 ("$C_2$-$C_4$-alkynyl"), 2 to 6 ("$C_2$-$C_6$-alkynyl"), 2 to 8 ("$C_2$-$C_8$-alkynyl"), or 2 to 10 ("$C_2$-$C_{10}$-alkynyl") carbon atoms and one or two triple bonds in any position, for example $C_2$-$C_3$-alkynyl, such as ethynyl, 1-propynyl or 2-propynyl; $C_2$-$C_4$-alkynyl, such as ethynyl, 1-propynyl, 2-propynyl, 1-butynyl, 2-butynyl, 3-butynyl, 1-methyl-2-propynyl and the like, $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl and the like;

The term "haloalkynyl" as used herein, which is also expressed as "alkynyl which is partially or fully halogenated", refers to unsaturated straight-chain or branched hydrocarbon radicals having 2 to 3 ("$C_2$-$C_3$-haloalkynyl"), 2 to 4 ("$C_2$-$C_4$-haloalkynyl"), 3 to 4 ("$C_3$-$C_4$-haloalkynyl"), 2 to 6 ("$C_2$-$C_6$-haloalkynyl"), 2 to 8 ("$C_2$-$C_8$-haloalkynyl") or 2 to 10 ("$C_2$-$C_{10}$-haloalkynyl") carbon atoms and one or two triple bonds in any position (as mentioned above), where some or all of the hydrogen atoms in these groups are replaced by halogen atoms as mentioned above, in particular fluorine, chlorine and bromine;

The term "cycloalkyl" as used herein refers to mono- or bi- or polycyclic saturated hydrocarbon radicals having 3 to 8 ("$C_3$-$C_8$-cycloalkyl"), in particular 3 to 6 ("$C_3$-$C_6$-cycloalkyl") or 3 to 5 ("$C_3$-$C_5$-cycloalkyl") or 3 to 4 ("$C_3$-$C_4$-cycloalkyl") carbon atoms. Examples of monocyclic radicals having 3 to 4 carbon atoms comprise cyclopropyl and cyclobutyl. Examples of monocyclic radicals having 3 to 5 carbon atoms comprise cyclopropyl, cyclobutyl and cyclopentyl. Examples of monocyclic radicals having 3 to 6 carbon atoms comprise cyclopropyl, cyclobutyl, cyclopentyl and cyclohexyl. Examples of monocyclic radicals having 3 to 8 carbon atoms comprise cyclopropyl, cyclobutyl, cyclopentyl, cyclohexyl, cycloheptyl and cyclooctyl. Examples of bicyclic radicals having 7 or 8 carbon atoms comprise bicyclo[2.2.1]heptyl, bicyclo[3.1.1]heptyl, bicyclo[2.2.2]octyl and bicyclo[3.2.1]octyl. Preferably, the term cycloalkyl denotes a monocyclic saturated hydrocarbon radical.

The term "halocycloalkyl" as used herein, which is also expressed as "cycloalkyl which is partially or fully halogenated", refers to mono- or bi- or polycyclic saturated hydrocarbon groups having 3 to 8 ("$C_2$-$C_8$-halocycloalkyl") or preferably 3 to 6 ("$C_3$-$C_6$-halocycloalkyl") or 3 to 5 ("$C_3$-$C_5$-halocycloalkyl") or 3 to 4 ("$C_3$-$C_4$-halocycloalkyl") carbon ring members (as mentioned above) in which some or all of the hydrogen atoms are replaced by halogen atoms as mentioned above, in particular fluorine, chlorine and bromine.

The term "cycloalkyl-$C_1$-$C_4$-alkyl" refers to a $C_3$-$C_8$-cycloalkyl group ("$C_3$-$C_8$-cycloalkyl-$C_1$-$C_4$-alkyl"), preferably a $C_3$-$C_6$-cycloalkyl group ("$C_3$-$C_6$-cycloalkyl-$C_1$-$C_4$-alkyl"), more preferably a $C_3$-$C_4$-cycloalkyl group ("$C_3$-$C_4$-cycloalkyl-$C_1$-$C_4$-alkyl") as defined above (preferably a monocyclic cycloalkyl group) which is bound to the remainder of the molecule via a $C_1$-$C_4$-alkyl group, as defined above. Examples for $C_3$-$C_4$-cycloalkyl-$C_1$-$C_4$-alkyl are cyclopropylmethyl, cyclopropylethyl, cyclopropylpropyl, cyclobutylmethyl, cyclobutylethyl and cyclobutylpropyl, Examples for $C_3$-$C_6$-cycloalkyl-$C_1$-$C_4$-alkyl, apart those mentioned for $C_3$-$C_4$-cycloalkyl-$C_1$-$C_4$-alkyl, are cyclopentylmethyl, cyclopentylethyl, cyclopentylpropyl, cyclohexylmethyl, cyclohexylethyl and cyclohexylpropyl. Examples for $C_3$-$C_8$-cycloalkyl-$C_1$-$C_4$-alkyl, apart those mentioned for $C_3$-$C_6$-cycloalkyl-$C_1$-$C_4$-alkyl, are cycloheptylmethyl, cycloheptylethyl, cyclooctylmethyl and the like.

The term "$C_3$-$C_6$-cycloalkyl-methyl" refers to a $C_3$-$C_6$-cycloalkyl group which is bound to the remainder of the molecule via a methyl group Examples are cyclopropylmethyl, cyclobutylmethyl, cyclopentylmethyl and cyclohexylmethyl.

The term "$C_3$-$C_8$-halocycloalkyl-$C_1$-$C_4$-alkyl" refers to a $C_3$-$C_8$-halocycloalkyl group as defined above which is bound to the remainder of the molecule via a $C_1$-$C_4$-alkyl group, as defined above.

The term "cycloalkenyl" as used herein refers to monocyclic hydrocarbon radicals with at least one C=C double bond in the ring, which ring is however not aromatic, the hydrocarbon radicals having 3 to 8 ("$C_3$-$C_8$-cycloalkyl) carbon atoms. Examples are cyclopropenyl, such as cycloprop-1-enyl and cycloprop-2-yl, cyclobutenyl, such as cyclobut-1-enyl and cyclobut-2-enyl, cyclopentenyl, such as cyclopent-1-enyl, cyclopent-2-enyl and cyclopent-3-enyl, cyclopentadienyl, such as cyclopenta-1,3-dienyl, cyclopenta-1,4-dienyl and cyclopenta-2,4-dienyl, cyclohexenyl, such as cyclohex-1-enyl, cyclohex-2-enyl and cyclohex-3- enyl, cyclohexadienyl, such as cyclohexa-1,3-dienyl, cyclohexa-1,4-dienyl, cyclohexa-1,5-dienyl and cyclohexa-2,5-dienyl, cycloheptenyl, cycloheptadienyl, cycloheptatrienyl cyclooctenyl, cyclooctadieny, cyclooctatrienyl and cyclooctatetraenyl.

The term "halocycloalkenyl" as used herein refers to monocyclic hydrocarbon radicals with at least one C=C double bond in the ring, which ring is however not aromatic, the hydrocarbon radicals having 3 to 8 ("$C_3$-$C_8$-halocycloalkyl") carbon atoms, and wherein some or all of the hydrogen atoms are replaced by halogen atoms as mentioned above, in particular fluorine, chlorine and bromine.

The term "$C_1$-$C_2$-alkoxy" is a $C_1$-$C_2$-alkyl group, as defined above, attached via an oxygen atom. The term "$C_1$-$C_3$-alkoxy" is a $C_1$-$C_3$-alkyl group, as defined above, attached via an oxygen atom. The term "$C_1$-$C_4$-alkoxy" is a $C_1$-$C_4$-alkyl group, as defined above, attached via an oxygen atom. The term "$C_1$-$C_6$-alkoxy" is a $C_1$-$C_6$-alkyl group, as defined above, attached via an oxygen atom. The term "$C_1$-$C_{10}$-alkoxy" is a $C_1$-$C_{10}$-alkyl group, as defined above, attached via an oxygen atom. $C_1$-$C_2$-Alkoxy is methoxy or ethoxy. $C_1$-$C_3$-Alkoxy is additionally, for example, n-propoxy and 1-methylethoxy (isopropoxy). $C_1$-$C_4$-Alkoxy is additionally, for example, butoxy, 1-methylpropoxy (sec-butoxy), 2-methylpropoxy (isobutoxy) or 1,1-dimethylethoxy (tert-butoxy). $C_1$-$C_6$-Alkoxy is additionally, for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy. $C_1$-$C_8$-Alkoxy is additionally, for example, heptyloxy, octyloxy, 2-ethylhexyloxy and positional isomers thereof. $C_1$-$C_{10}$-Alkoxy is additionally, for example, nonyloxy, decyloxy and positional isomers thereof.

The term "$C_1$-$C_2$-haloalkoxy" is a $C_1$-$C_2$-haloalkyl group, as defined above, attached via an oxygen atom. The term "$C_1$-$C_3$-haloalkoxy" is a $C_1$-$C_3$-haloalkyl group, as defined above, attached via an oxygen atom. The term "$C_1$-$C_4$-haloalkoxy" is a $C_1$-$C_4$-haloalkyl group, as defined above, attached via an oxygen atom. The term "$C_1$-$C_6$-haloalkoxy" is a $C_1$-$C_6$-haloalkyl group, as defined above, attached via an oxygen atom. The term "$C_1$-$C_{10}$-haloalkoxy" is a $C_1$-$C_{10}$-haloalkyl group, as defined above, attached via an oxygen atom. $C_1$-$C_2$-Haloalkoxy is, for example, $OCH_2F$, $OCHF_2$, $OCF_3$, $OCH_2Cl$, $OCHCl_2$, $OCCl3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or $OC_2F_5$. $C_1$-$C_3$-Haloalkoxy is additionally, for example, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy or 1-($CH_2Br$)-2-bromoethoxy.

$C_1$-$C_4$-Haloalkoxy is additionally, for example, 4-fluorobutoxy, 4-chlorobutoxy, 4-bromobutoxy or nonafluorobutoxy. $C_1$-$C_6$-Haloalkoxy is additionally, for example, 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy or dodecafluorohexoxy.

The term "$C_1$-$C_3$-alkoxy-$C_1$-$C_3$-alkyl" as used herein, refers to a straight-chain or branched alkyl group having 1 to 3 carbon atoms, as defined above, where one hydrogen atom is replaced by a $C_1$-$C_3$-alkoxy group, as defined above. The term "$C_1$-$C_4$-alkoxy-$C_1$-$C_4$-alkyl" as used herein, refers to a straight-chain or branched alkyl group having 1 to 4 carbon atoms, as defined above, where one hydrogen atom is replaced by a $C_1$-$C_4$-alkoxy group, as defined above. The term "$C_1$-$C_6$-alkoxy-$C_1$-$C_6$-alkyl" as used herein, refers to a straight-chain or branched alkyl group having 1 to 6 carbon atoms, as defined above, where one hydrogen atom is replaced by a $C_1$-$C_6$-alkoxy group, as defined above. Examples are methoxymethyl, ethoxymethyl, propoxymethyl, isopropoxymethyl, n-butoxymethyl, sec-butoxymethyl, isobutoxymethyl, tert-butoxymethyl, 1-methoxyethyl, 1-ethoxyethyl, 1-propoxyethyl, 1-isopropoxyethyl, 1-n-butoxyethyl, 1-sec-butoxyethyl, 1-isobutoxyethyl, 1-tert-butoxyethyl, 2-methoxyethyl, 2-ethoxyethyl, 2-propoxyethyl, 2-isopropoxyethyl, 2-n-butoxyethyl, 2-sec-butoxyethyl, 2-isobutoxyethyl, 2-tert-butoxyethyl, 1-methoxypropyl, 1-ethoxypropyl, 1-propoxypropyl, 1-isopropoxypropyl, 1-n-butoxypropyl, 1-sec-butoxypropyl, 1-isobutoxypropyl, 1-tert-butoxypropyl, 2-methoxypropyl, 2-ethoxypropyl, 2-propoxypropyl, 2-isopropoxypropyl, 2-n-butoxypropyl, 2-sec-butoxypropyl, 2-isobutoxypropyl, 2-tert-butoxypropyl, 3-methoxypropyl, 3-ethoxypropyl, 3-propoxypropyl, 3-isopropoxypropyl, 3-n-butoxypropyl, 3-sec-butoxypropyl, 3-isobutoxypropyl, 3-tert-butoxypropyl and the like.

The term "$C_1$-$C_4$-alkoxy-methyl" as used herein, refers to methyl in which one hydrogen atom is replaced by a $C_1$-$C_4$-alkoxy group, as defined above. The term "$C_1$-$C_6$-alkoxy-methyl" as used herein, refers to methyl in which one hydrogen atom is replaced by a $C_1$-$C_6$-alkoxy group, as defined above. Examples are methoxymethyl, ethoxymethyl, propoxymethyl, isopropoxymethyl, n-butoxymethyl, sec-butoxymethyl, isobutoxymethyl, tert-butoxymethyl, pentyloxymethyl, hexyloxymethyl and the like.

$C_1$-$C_6$-Haloalkoxy-$C_1$-$C_6$-alkyl is a straight-chain or branched alkyl group having from 1 to 6, especially 1 to 4 carbon atoms (=$C_1$-$C_6$-haloalkoxy-$C_1$-$C_4$-alkyl), wherein one of the hydrogen atoms is replaced by a $C_1$-$C_6$-alkoxy group and wherein at least one, e.g. 1, 2, 3, 4 or all of the remaining hydrogen atoms (either in the alkoxy moiety or in the alkyl moiety or in both) are replaced by halogen atoms. $C_1$-$C_4$-Haloalkoxy-$C_1$-$C_4$-alkyl is a straight-chain or branched alkyl group having from 1 to 4 carbon atoms, wherein one of the hydrogen atoms is replaced by a $C_1$-$C_4$-alkoxy group and wherein at least one, e.g. 1, 2, 3, 4 or all of the remaining hydrogen atoms (either in the alkoxy moiety or in the alkyl moiety or in both) are replaced by halogen atoms. Examples are difluoromethoxymethyl ($CHF_2OCH_2$), trifluoromethoxymethyl, 1-difluoromethoxyethyl, 1-trifluoromethoxyethyl, 2-difluoromethoxyethyl, 2-trifluoromethoxyethyl, difluoro-methoxy-methyl ($CH_3OCF_2$), 1,1-difluoro-2-methoxyethyl, 2,2-difluoro-2-methoxyethyl and the like.

The term "$C_1$-$C_2$-alkylthio" is a $C_1$-$C_2$-alkyl group, as defined above, attached via a sulfur atom. The term "$C_1$-$C_3$-alkylthio" is a $C_1$-$C_3$-alkyl group, as defined above, attached via a sulfur atom. The term "$C_1$-$C_4$-alkylthio" is a $C_1$-$C_4$-alkyl group, as defined above, attached via a sulfur atom. The term "$C_1$-$C_6$-alkylthio" is a $C_1$-$C_6$-alkyl group, as defined above, attached via a sulfur atom. The term "$C_1$-$C_{10}$-alkylthio" is a $C_1$-$C_{10}$-alkyl group, as defined above, attached via a sulfur atom. $C_1$-$C_2$-Alkylthio is methylthio or ethylthio. $C_1$-$C_3$-Alkylthio is additionally, for example, n-propylthio or 1-methylethylthio (isopropylthio). $C_1$-$C_4$-Alkylthio is additionally, for example, butylthio, 1-methylpropylthio (sec-butylthio), 2-methylpropylthio (isobutylthio) or 1,1-dimethylethylthio (tert-butylthio). $C_1$-$C_6$-Alkylthio is additionally, for example, pentylthio, 1-methylbutylthio, 2-methylbutylthio, 3-methylbutylthio, 1,1-dimethylpropylthio, 1,2-dimethylpropylthio, 2,2-dimethylpropylthio, 1-ethylpropylthio, hexylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio. $C_1$-$C_8$-Alkylthio is additionally, for example, heptylthio, octylthio, 2-ethylhexylthio and positional isomers thereof. $C_1$-$C_{10}$-Alkylthio is additionally, for example, nonylthio, decylthio and positional isomers thereof.

The term "$C_1$-$C_2$-haloalkylthio" is a $C_1$-$C_2$-haloalkyl group, as defined above, attached via a sulfur atom. The term "$C_1$-$C_3$-haloalkylthio" is a $C_1$-$C_3$-haloalkyl group, as defined above, attached via a sulfur atom. The term "$C_1$-$C_4$-haloalkylthio" is a $C_1$-$C_4$-haloalkyl group, as defined above, attached via a sulfur atom. The term "$C_1$-$C_6$-haloalkylthio" is a $C_1$-$C_6$-haloalkyl group, as defined above, attached via a sulfur atom. The term "$C_1$-$C_{10}$-haloalkylthio" is a $C_1$-$C_{10}$-haloalkyl group, as defined above, attached via a sulfur atom. $C_1$-$C_2$-Haloalkylthio is, for example, $SCH_2F$, $SCHF_2$, $SCF_3$, $SCH_2Cl$, $SCHCl_2$, $SCCl_3$, chlorofluoromethylthio, dichlorofluoromethylthio, chlorodifluoromethylthio, 2-fluoroethylthio, 2-chloroethylthio, 2-bromoethylthio, 2-iodoethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or $SC_2F_5$. $C_1$-$C_3$-Haloalkylthio is additionally, for example, 2-fluoropropylthio, 3-fluoropropylthio, 2,2-difluoropropylthio, 2,3-difluoropropylthio, 2-chloropropylthio, 3-chloropropylthio, 2,3-dichloropropylthio, 2-bromopropylthio, 3-bromopropylthio, 3,3,3-trifluoropropylthio, 3,3,3-trichloropropylthio, $SCH_2$—$C_2F_5$, $SCF_2$—$C_2F_5$, 1-($CH_2F$)-2-fluoroethylthio, 1-($CH_2Cl$)-2-chloroethylthio or 1-($CH_2Br$)-2-bromoethylthio. $C_1$-$C_4$-Haloalkylthio is additionally, for example, 4-fluorobutylthio, 4-chlorobutylthio, 4-bromobutylthio or nonafluorobutylthio. $C_1$-$C_6$-Haloalkylthio is additionally, for example, 5-fluoropentylthio, 5-chloropentylthio, 5-brompentylthio, 5-iodopentylthio, undecafluoropentylthio, 6-fluorohexylthio, 6-chlorohexylthio, 6-bromohexylthio, 6-iodohexylthio or dodecafluorohexylthio.

The term "$C_1$-$C_2$-alkylsulfinyl" is a $C_1$-$C_2$-alkyl group, as defined above, attached via a sulfinyl [S(O)] group. The term "$C_1$-$C_3$-alkylsulfinyl" is a $C_1$-$C_3$-alkyl group, as defined above, attached via a sulfinyl [S(O)] group. The term "$C_1$-$C_4$-alkylsulfinyl" is a $C_1$-$C_4$-alkyl group, as defined above, attached via a sulfinyl [S(O)] group. The term "$C_1$-$C_6$-alkylsulfinyl" is a $C_1$-$C_6$-alkyl group, as defined above, attached via a sulfinyl [S(O)] group. The term "$C_1$-$C_{10}$-alkylsulfinyl" is a $C_1$-$C_{10}$-alkyl group, as defined above, attached via a sulfinyl [S(O)] group. $C_1$-$C_2$-Alkylsulfinyl is methylsulfinyl or ethylsulfinyl. $C_1$-$C_3$-Alkylsulfinyl is additionally, for example, n-propylsulfinyl and 1-methylethylsulfinyl (isopropylsulfinyl). $C_1$-$C_4$-Alkylsulfinyl is additionally, for example, butylsulfinyl, 1-methylpropylsulfinyl (sec-butylsulfinyl), 2-methylpropylsulfinyl (isobutylsulfinyl) or 1,1-dimethylethylsulfinyl (tert-butylsulfinyl). $C_1$-$C_6$-Alkylsulfinyl is additionally, for example, pentylsulfinyl, 1-methylbutylsulfinyl, 2-methylbutylsulfinyl, 3-methylbutylsulfinyl, 1,1-dimethylpropylsulfinyl, 1,2-dimethylpropylsulfinyl, 2,2-dimethylpropylsulfinyl, 1-ethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl. $C_1$-$C_8$-Alkylsulfinyl is additionally, for example, heptylsulfinyl, octylsulfinyl, 2-ethylhexylsulfinyl and positional isomers thereof. $C_1$-$C_{10}$-Alkylsulfinyl is additionally, for example, nonylsulfinyl, decylsulfinyl and positional isomers thereof.

The term "$C_1$-$C_2$-haloalkylsulfinyl" is a $C_1$-$C_2$-haloalkyl group, as defined above, attached via a sulfinyl [S(O)] group. The term "$C_1$-$C_3$-haloalkylsulfinyl" is a $C_1$-$C_3$-haloalkyl group, as defined above, attached via a sulfinyl [S(O)] group. The term "$C_1$-$C_4$-haloalkylsulfinyl" is a $C_1$-$C_4$-haloalkyl group, as defined above, attached via a sulfinyl [S(O)] group. The term "$C_1$-$C_6$-haloalkylsulfinyl" is a $C_1$-$C_6$-haloalkyl group, as defined above, attached via a sulfinyl [S(O)] group. The term "$C_1$-$C_{10}$-haloalkylsulfinyl" is a $C_1$-$C_{10}$-haloalkyl group, as defined above, attached via a sulfinyl [S(O)] group. $C_1$-$C_2$-Haloalkylsulfinyl is, for example, $S(O)CH_2F$, $S(O)CHF_2$, $S(O)CF_3$, $S(O)CH_2Cl$, $S(O)CHCl_2$, $S(O)CCl_3$, chlorofluoromethylsulfinyl, dichlorofluoromethylsulfinyl, chlorodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2-chloro-2-fluoroethylsulfinyl, 2-chloro-2,2-difluoroethylsulfinyl, 2,2-dichloro-2-fluoroethylsulfinyl, 2,2,2-trichloroethylsulfinyl or $S(O)C_2F_5$. $C_1$-$C_3$-Haloalkylsulfinyl is additionally, for example, 2-fluoropropylsulfinyl, 3-fluoropropylsulfinyl, 2,2-difluoropropylsulfinyl, 2,3-difluoropropylsulfinyl, 2-chloropropylsulfinyl, 3-chloropropylsulfinyl, 2,3-dichloropropylsulfinyl, 2-bromopropylsulfinyl, 3-bromopropylsulfinyl, 3,3,3-trifluoropropylsulfinyl, 3,3,3-trichloropropylsulfinyl, $S(O)CH_2$—$C_2F_5$, $S(O)CF_2$—$C_2F_5$, 1-($CH_2F$)-2-fluoroethylsulfinyl, 1-($CH_2Cl$)-2-chloroethylsulfinyl and 1-($CH_2Br$)-2-bromoethylsulfinyl. $C_1$-$C_4$-Haloalkylsulfinyl is additionally, for example, 4-fluorobutylsulfinyl, 4-chlorobutylsulfinyl, 4-bromobutylsulfinyl or nonafluorobutylsulfinyl. $C_1$-$C_6$-Haloalkylsulfinyl is additionally, for example, 5-fluoropentylsulfinyl, 5-chloropentylsulfinyl, 5-brompentylsulfinyl, 5-iodopentylsulfinyl, undecafluoropentylsulfinyl, 6-fluorohexylsulfinyl, 6-chlorohexylsulfinyl, 6-bromohexylsulfinyl, 6-iodohexylsulfinyl or dodecafluorohexylsulfinyl.

The term "$C_1$-$C_2$-alkylsulfonyl" is a $C_1$-$C_2$-alkyl group, as defined above, attached via a sulfonyl [S(O)$_2$] group. The term "$C_1$-$C_3$-alkylsulfonyl" is a $C_1$-$C_3$-alkyl group, as defined above, attached via a sulfonyl [S(O)$_2$] group. The term "$C_1$-$C_4$-alkylsulfonyl" is a $C_1$-$C_4$-alkyl group, as defined above, attached via a sulfonyl [S(O)$_2$] group. The term "$C_1$-$C_6$-alkylsulfonyl" is a $C_1$-$C_6$-alkyl group, as defined above, attached via a sulfonyl [S(O)$_2$] group. The term "$C_1$-$C_{10}$-alkylsulfonyl" is a $C_1$-$C_{10}$-alkyl group, as defined above, attached via a sulfonyl [S(O)$_2$] group. $C_1$-$C_2$-Alkylsulfonyl is methylsulfonyl or ethylsulfonyl. $C_1$-$C_3$-Alkylsulfonyl is additionally, for example, n-propylsulfonyl or 1-methylethylsulfonyl (isopropylsulfonyl). $C_1$-$C_4$-Alkylsulfonyl is additionally, for example, butylsulfonyl, 1-methylpropylsulfonyl (sec-butylsulfonyl), 2-methylpropylsulfonyl (isobutylsulfonyl) or 1,1-dimethylethylsulfonyl (tert-butylsulfonyl). $C_1$-$C_6$-Alkylsulfonyl is additionally, for example, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl. $C_1$-$C_8$-Alkylsulfonyl is additionally, for example, heptylsulfonyl, octylsulfonyl, 2-ethylhexylsulfonyl and positional isomers thereof. $C_1$-$C_{10}$-Alkylsulfonyl is additionally, for example, nonylsulfonyl, decylsulfonyl and positional isomers thereof.

The term "$C_1$-$C_2$-haloalkylsulfonyl" is a $C_1$-$C_2$-haloalkyl group, as defined above, attached via a sulfonyl $[S(O)_2]$ group. The term "$C_1$-$C_3$-haloalkylsulfonyl" is a $C_1$-$C_3$-haloalkyl group, as defined above, attached via a sulfonyl $[S(O)_2]$ group. The term "$C_1$-$C_4$-haloalkylsulfonyl" is a $C_1$-$C_4$-haloalkyl group, as defined above, attached via a sulfonyl $[S(O)_2]$ group. The term "$C_1$-$C_6$-haloalkylsulfonyl" is a $C_1$-$C_6$-haloalkyl group, as defined above, attached via a sulfonyl $[S(O)_2]$ group. The term "$C_1$-$C_1$-haloalkylsulfonyl" is a $C_1$-$C_{10}$-haloalkyl group, as defined above, attached via a sulfonyl $[S(O)_2]$ group. $C_1$-$C_2$-Haloalkylsulfonyl is, for example, $S(O)_2CH_2F$, $S(O)_2CHF_2$, $S(O)_2CF_3$, $S(O)_2CH_2Cl$, $S(O)_2CHCl_2$, $S(O)_2CCl_3$, chlorofluoromethylsulfonyl, dichlorofluoromethylsulfonyl, chlorodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl or $S(O)_2C_2F_5$. $C_1$-$C_3$-Haloalkylsulfonyl is additionally, for example, 2-fluoropropylsulfonyl, 3-fluoropropylsulfonyl, 2,2-difluoropropylsulfonyl, 2,3-difluoropropylsulfonyl, 2-chloropropylsulfonyl, 3-chloropropylsulfonyl, 2,3-dichloropropylsulfonyl, 2-bromopropylsulfonyl, 3-bromopropylsulfonyl, 3,3,3-trifluoropropylsulfonyl, 3,3,3-trichloropropylsulfonyl, $S(O)_2CH_2$—$C_2F_5$, $S(O)_2CF_2$—$C_2F_5$, 1-($CH_2F$)-2-fluoroethylsulfonyl, 1-($CH_2Cl$)-2-chloroethylsulfonylor 1-($CH_2Br$)-2-bromoethylsulfonyl. $C_1$-$C_4$-Haloalkylsulfonyl is additionally, for example, 4-fluorobutylsulfonyl, 4-chlorobutylsulfonyl, 4-bromobutylsulfonyl or nonafluorobutylsulfonyl. $C_1$-$C_6$-Haloalkylsulfonyl is additionally, for example, 5-fluoropentylsulfonyl, 5-chloropentylsulfonyl, 5-brompentylsulfonyl, 5-iodopentylsulfonyl, undecafluoropentylsulfonyl, 6-fluorohexylsulfonyl, 6-chlorohexylsulfonyl, 6-bromohexylsulfonyl, 6-iodohexylsulfonyl or dodecafluorohexylsulfonyl.

The substituent "oxo" replaces a $CH_2$ group by a $C(=O)$ group.

The term "alkylcarbonyl" is a $C_1$-$C_6$-alkyl ("$C_1$-$C_6$-alkylcarbonyl"), preferably a $C_1$-$C_4$-alkyl ("$C_1$-$C_4$-alkylcarbonyl") group, as defined above, attached via a carbonyl $[C(=O)]$ group. Examples are acetyl (methylcarbonyl), propionyl (ethylcarbonyl), propylcarbonyl, isopropylcarbonyl, n-butylcarbonyl and the like.

The term "haloalkylcarbonyl" is a $C_1$-$C_6$-haloalkyl ("$C_1$-$C_6$-haloalkylcarbonyl"), preferably a $C_1$-$C_4$-haloalkyl ("$C_1$-$C_4$-haloalkylcarbonyl") group, as defined above, attached via a carbonyl $[C(=O)]$ group. Examples are trifluoromethylcarbonyl, 2,2,2-trifluoroethylcarbonyl and the like.

The term "alkoxycarbonyl" is a $C_1$-$C_6$-alkoxy ("$C_1$-$C_6$-alkoxycarbonyl"), preferably a $C_1$-$C_4$-alkoxy ("$C_1$-$C_4$-alkoxycarbonyl") group, as defined above, attached via a carbonyl $[C(=O)]$ group. Examples are methoxycarbonyl), ethoxycarbonyl, propoxycarbonyl, isopropoxycarbonyl, n-butoxycarbonyl and the like.

The term "haloalkoxycarbonyl" is a $C_1$-$C_6$-haloalkoxy ("$C_1$-$C_6$-haloalkoxycarbonyl"), preferably a $C_1$-$C_4$-haloalkoxy ("$C_1$-$C_4$-haloalkoxycarbonyl") group, as defined above, attached via a carbonyl $[C(=O)]$ group. Examples are trifluoromethoxycarbonyl, 2,2,2-trifluoroethoxycarbonyl and the like.

The term "$C_1$-$C_6$-alkylamino" is a group —$N(H)C_1$-$C_6$-alkyl. Examples are methylamino, ethylamino, propylamino, isopropylamino, butylamino and the like.

The term "di-($C_1$-$C_6$-alkyl)amino" is a group —$N(C_1$-$C_6$-alkyl$)_2$. Examples are dimethylamino, diethylamino, ethylmethylamino, dipropylamino, diisopropylamino, methylpropylamino, methylisopropylamino, ethylpropylamino, ethylisopropylamino, dibutylamino and the like.

The term "aminocarbonyl" is a group —$C(O)$—$NH_2$.

The term "$C_1$-$C_6$-alkylaminocarbonyl" is a group —$C(O)$—$N(H)C_1$-$C_6$-alkyl. Examples are methylaminocarbonyl, ethylaminocarbonyl, propylaminocarbonyl, isopropylaminocarbonyl, butylaminocarbonyl and the like.

The term "di-($C_1$-$C_6$-alkyl)aminocarbonyl" is a group —$C(O)$—$N(C_1$-$C_6$-alkyl$)_2$. Examples are dimethylaminocarbonyl, diethylaminocarbonyl, ethylmethylaminocarbonyl, dipropylaminocarbonyl, diisopropylaminocarbonyl, methylpropylaminocarbonyl, methylisopropylaminocarbonyl, ethylpropylaminocarbonyl, ethylisopropylaminocarbonyl, dibutylaminocarbonyl and the like.

The term "3-, 4-, 5-, 6-, 7-, 8-, 9- or 10-membered saturated, partially unsaturated or maximally unsaturated heterocyclic ring containing 1, 2 or 3 (or 4) heteroatoms or heteroatom groups selected from N, O, S, NO, SO and $SO_2$, as ring members" denotes a 3-, 4-, 5-, 6- or 7-membered saturated, partially unsaturated or maximum unsaturated heteromonocyclic ring or a 8-, 9- or 10-membered saturated, partially unsaturated or maximally unsaturated heterobicyclic ring containing 1, 2 or 3 (or 4) heteroatoms or heteroatom groups selected from N, O, S, NO, SO and $SO_2$, as ring members.

Unsaturated rings contain at least one C—C and/or C—N and/or N—N double bond(s). Maximally unsaturated rings contain as many conjugated C—C and/or C—N and/or N—N double bonds as allowed by the ring size. Maximally unsaturated 5- or 6-membered heterocyclic rings are aromatic. The heterocyclic ring may be attached to the remainder of the molecule via a carbon ring member or via a nitrogen ring member. As a matter of course, the heterocyclic ring contains at least one carbon ring atom. If the ring contains more than one O ring atom, these are not adjacent.

The term "3-, 4-, 5-, 6- or 7-membered saturated, partially unsaturated or maximum unsaturated heterocyclic ring containing 1, 2 or 3 (or 4) heteroatoms or heteroatom groups selected from N, O, S, NO, SO and $SO_2$, as ring members" [wherein "maximum unsaturated" includes also "aromatic"] as used herein denotes monocyclic radicals, the monocyclic radicals being saturated, partially unsaturated or maximum unsaturated (including aromatic). The term "3-, 4-, 5-, 6-, 7- or 8-membered saturated, partially unsaturated or maximum unsaturated heterocyclic ring containing 1, 2 or 3 (or 4) heteroatoms or heteroatom groups selected from N, O, S, NO, SO and $SO_2$, as ring members" [wherein "maximum unsaturated" includes also "aromatic"] as used herein further also encompasses 8-membered heteromonocyclic radicals containing 1, 2 or 3 (or 4) heteroatoms or heteroatom groups selected from N, O, S, NO, SO and SO$_2$, as ring members, the monocyclic radicals being saturated, partially unsaturated or maximum unsaturated (including aromatic). Unsaturated rings contain at least one C—C and/or C—N and/or N—N double bond(s). Maximum unsaturated rings contain as many conjugated C—C and/or C—N and/or N—N double bonds as allowed by the ring size. Maximum unsaturated 5- or 6-membered heterocyclic rings are aromatic. 7- and 8-membered rings cannot be aromatic. They are homoaromatic (7-membered ring, 3 double bonds) or have 4 double bonds (8-membered ring). The heterocyclic ring may be attached to the remainder of the molecule via a carbon ring member or via a nitrogen ring member. As a matter of course, the heterocyclic ring contains at least one carbon ring atom. If the ring contains more than one O ring atom, these are not adjacent.

Examples of a 3-, 4-, 5-, 6- or 7-membered saturated heterocyclic ring include: Oxiranyl, thiiranyl, aziridinyl, oxetanyl, thietanyl, azetidinyl, tetrahydrofuran-2-yl, tetrahydrofuran-3-yl, tetrahydrothien-2-yl, tetrahydrothien-3-yl, pyrrolidin-1-yl, pyrrolidin-2-yl, pyrrolidin-3-yl, pyrazolidin-1-yl, pyrazolidin-3-yl, pyrazolidin-4-yl, pyrazolidin-5-yl, imidazolidin-1-yl, imidazolidin-2-yl, imidazolidin-4-yl, oxazolidin-2-yl, oxazolidin-3-yl, oxazolidin-4-yl, oxazolidin-5-yl, isoxazolidin-2-yl, isoxazolidin-3-yl, isoxazolidin-4-yl, isoxazolidin-5-yl, thiazolidin-2-yl, thiazolidin-3-yl, thiazolidin-4-yl, thiazolidin-5-yl, isothiazolidin-2-yl, isothiazolidin-3-yl, isothiazolidin-4-yl, isothiazolidin-5-yl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-1-yl, 1,3,4-triazolidin-2-yl, 2-tetrahydropyranyl, 4-tetrahydropyranyl, 1,3-dioxan-5-yl, 1,4-dioxan-2-yl, piperidin-1-yl, piperidin-2-yl, piperidin-3-yl, piperidin-4-yl, hexahydropyridazin-3-yl, hexahydropyridazin-4-yl, hexahydropyrimidin-2-yl, hexahydropyrimidin-4-yl, hexahydropyrimidin-5-yl, piperazin-1-yl, piperazin-2-yl, 1,3,5-hexahydrotriazin-1-yl, 1,3,5-hexahydrotriazin-2-yl and 1,2,4-hexahydrotriazin-3-yl, morpholin-2-yl, morpholin-3-yl, morpholin-4-yl, thiomorpholin-2-yl, thiomorpholin-3-yl, thiomorpholin-4-yl, 1-oxothiomorpholin-2-yl, 1-oxothiomorpholin-3-yl, 1-oxothiomorpholin-4-yl, 1,1-dioxothiomorpholin-2-yl, 1,1-dioxothiomorpholin-3-yl, 1,1-dioxothiomorpholin-4-yl, azepan-1-, -2-, -3- or -4-yl, oxepan-2-, -3-, -4- or -5-yl, hexahydro-1,3-diazepinyl, hexahydro-1,4-diazepinyl, hexahydro-1,3-oxazepinyl, hexahydro-1,4-oxazepinyl, hexahydro-1,3-dioxepinyl, hexahydro-1,4-dioxepinyl and the like.

Examples of a 3-, 4-, 5-, 6- or 7-membered partially unsaturated heterocyclic ring include: 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-, 3-, 4-, 5- or 6-di- or tetrahydropyridinyl, 3-di- or tetrahydropyridazinyl, 4-di- or tetrahydropyridazinyl, 2-di- or tetrahydropyrimidinyl, 4-di- or tetrahydropyrimidinyl, 5-di- or tetrahydropyrimidinyl, di- or tetrahydropyrazinyl, 1,3,5-di- or tetrahydrotriazin-2-yl, 1,2,4-di- or tetrahydrotriazin-3-yl, 2,3,4,5-tetrahydro[1H]azepin-1-, -2-, -3-, -4-, -5-, -6- or -7-yl, 3,4,5,6-tetrahydro[2H]azepin-2-, -3-, -4-, -5-, -6- or -7-yl, 2,3,4,7-tetrahydro[1H]azepin-1-, -2-, -3-, -4-, -5-, -6- or -7-yl, 2,3,6,7-tetrahydro[1H]azepin-1-, -2-, -3-, -4-, -5-, -6- or -7-yl, tetrahydrooxepinyl, such as 2,3,4,5-tetrahydro[1H]oxepin-2-, -3-, -4-, -5-, -6- or -7-yl, 2,3,4,7-tetrahydro[1H]oxepin-2-, -3-, -4-, -5-, -6- or -7-yl, 2,3,6,7-tetrahydro[1H]oxepin-2-, -3-, -4-, -5-, -6- or -7-yl, tetrahydro-1,3-diazepinyl, tetrahydro-1,4-diazepinyl, tetrahydro-1,3-oxazepinyl, tetrahydro-1,4-oxazepinyl, tetrahydro-1,3-dioxepinyl and tetrahydro-1,4-dioxepinyl.

Examples for a 3-, 4-, 5-, 6- or 7-membered maximally unsaturated (including aromatic) heterocyclic ring are 5- or 6-membered heteroaromatic rings, such as 2-furyl, 3-furyl, 2-thienyl, 3-thienyl, 1-pyrrolyl, 2-pyrrolyl, 3-pyrrolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 1,3,4-triazol-1-yl, 1,3,4-triazol-2-yl, 2-pyridinyl, 3-pyridinyl, 4-pyridinyl, 1-oxopyridin-2-yl, 1-oxopyridin-3-yl, 1-oxopyridin-4-yl, 3-pyridazinyl, 4-pyridazinyl, 2-pyrimidinyl, 4-pyrimidinyl, 5-pyrimidinyl and 2-pyrazinyl, and also homoaromatic radicals, such as 1H-azepine, 1H-[1,3]-diazepine and 1H-[1,4]-diazepine.

Examples for a 8-, 9- or 10-membered saturated heterobicyclic ring containing 1, 2 or 3 (or 4) heteroatoms or heteroatom groups selected from N, O, S, NO, SO and SO$_2$, as ring members are:

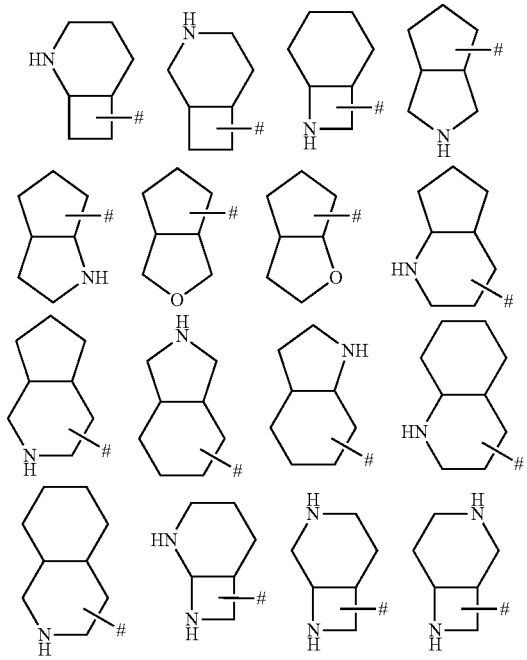

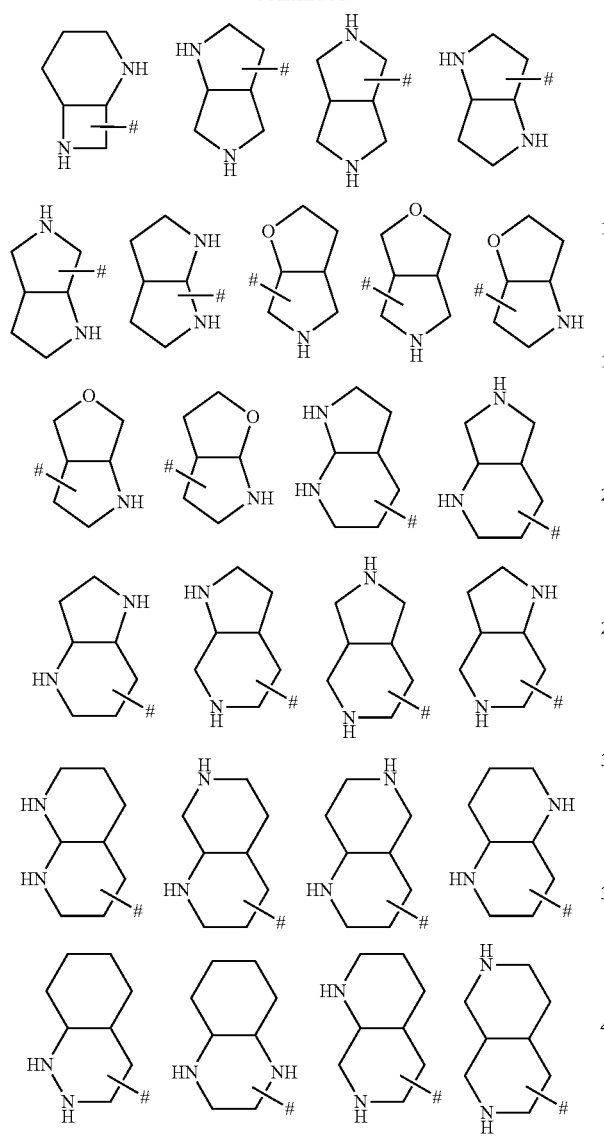
Examples for a 8-, 9- or 10-membered partially unsaturated heterobicyclic ring containing 1, 2 or 3 (or 4) heteroatoms or heteroatom groups selected from N, O, S, NO, SO and SO$_2$, as ring members are:
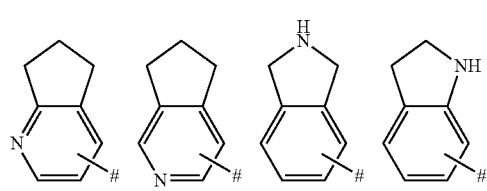
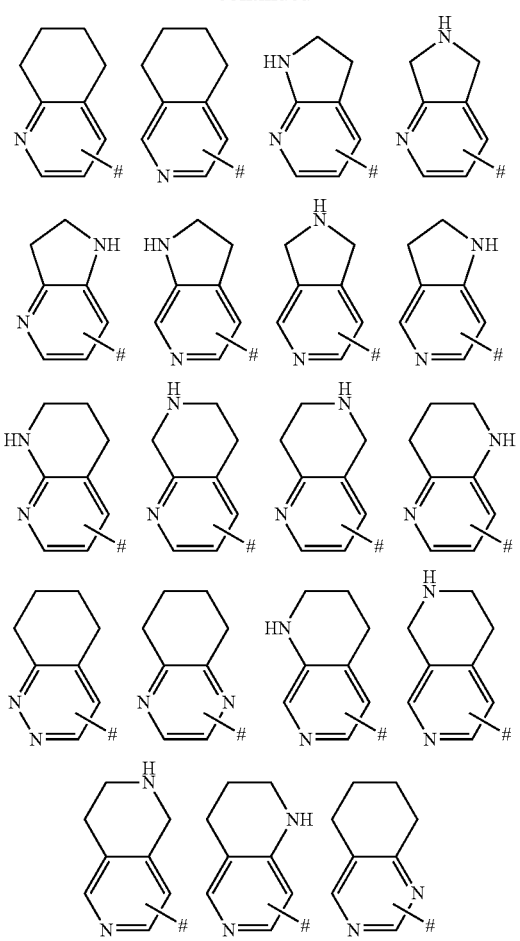
Examples for a 8-, 9- or 10-membered maximally unsaturated heterobicyclic ring containing 1, 2 or 3 (or 4) heteroatoms or heteroatom groups selected from N, O, S, NO, SO and SO$_2$, as ring members are:
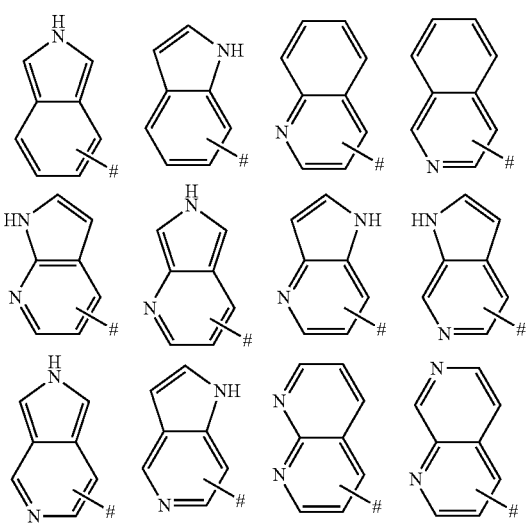

-continued

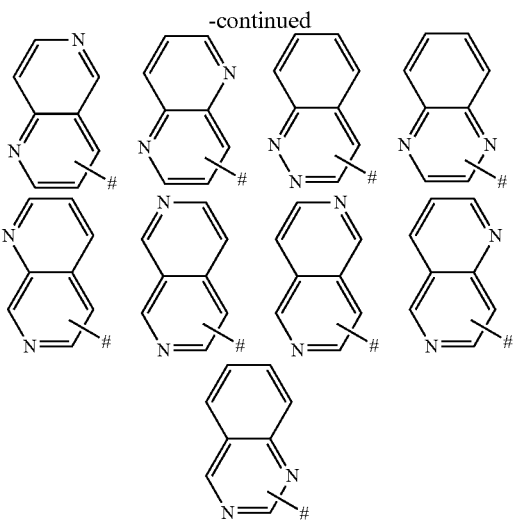

In the above structures # denotes the attachment point to the remainder of the molecule. The attachment point is not restricted to the ring on which is shown, but can be on either of the fused rings, and may be on a carbon or on a nitrogen ring atom. If the rings carry one or more substituents, these may be bound to carbon and/or to nitrogen ring atoms (if the latter are not part of a double bond).

A saturated 3-, 4-, 5-, 6-, 7-, 8- or 9-membered ring, wherein the ring may contain 1 or 2 heteroatoms or heteroatom groups selected from O, S, N, $NR^{14}$, NO, SO and $SO_2$ and/or 1 or 2 groups selected from C=O, C=S and C=$NR^{14}$ as ring members is either carbocyclic or heterocyclic. Examples are, in addition to the saturated heteromonocyclic rings mentioned above, carbocyclic rings, such as cyclopropyl, cyclopropanonyl, cyclobutyl, cyclobutanonyl, cyclopentyl, cyclopentanonyl, cyclohexyl, cyclohexanonyl, cyclohexadienonyl, cycloheptyl, cycloheptanonyl, cyclooctyl, cyclooctanonyl, furan-2-onyl, pyrrolidine-2-onyl, pyrrolidine-2,5-dionyl, piperidine-2-only, piperidine-2,6-dionyl and the like.

The remarks made below concerning preferred embodiments of the variables of the compounds of formula I, especially with respect to their substituents A, $A^1$, $A^2$, $A^3$, $A^4$, $B^1$, $B^2$, $B^3$, G, W, X, Y, $R^1$, $R^2$, $R^{3a}$, $R^{3b}$, $R^{3c}$, $R^{3d}$, $R^{4a}$, $R^{4b}$, $R^5$, $R^6$, $R^{7a}$, $R^{7b}$, $R^8$, $R^9$, $R^{10a}$, $R^{10b}$, $R^{11}$, $R^{12}$, $R^{13}$, $R^{14}$, $R^{14a}$, $R^{14b}$, $R^{15}$, $R^{16}$, $R^{17}$, $R^{18a}$, $R^{18b}$, m and n, the features of the use and method according to the invention and of the composition of the invention are valid both on their own and, in particular, in every possible combination with each other.

In a preferred embodiment, X is selected from heterocyclic radicals of formulae II.1, II.2 and II.3

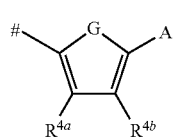 (II.1)

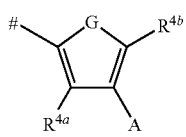 (II.2)

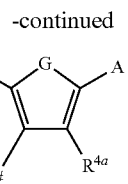 (II.3)

wherein
# is the attachment point to the remainder of the molecule; and
G, A, $R^{4a}$ and $R^{4b}$ have one of the above general meanings, or, in particular, one of the below preferred meanings.

More preferably, X is the heterocyclic radical of formula II.1.

In a preferred embodiment, G is S.

In particular, X is the heterocyclic radical of formula II.1, in which G is S.

In one embodiment of the invention, A is $A^1$.

In one preferred embodiment, $A^1$ is CN.

In another preferred embodiment, $A^1$ is selected from —C(=$NR^6$)$R^8$ and —N($R^5$)$R^6$ and is more preferably —C(=$NR^6$)$R^8$; wherein $R^5$, $R^6$ and $R^8$ have one of the above general meanings, or, in particular, one of the below preferred meanings.

$R^6$ as a radical in the group —C(=$NR^6$)$R^8$ is preferably selected from hydrogen, cyano, $C_1$-$C_{10}$-alkyl, $C_3$-$C_8$-cycloalkyl, $C_2$-$C_{10}$-alkenyl, $C_2$-$C_{10}$-alkynyl, wherein the four last-mentioned aliphatic and cycloaliphatic radicals each independently may be partially or fully halogenated and/or may be substituted with 1, 2, 3, 4, 5 or 6, preferably 1, 2 or 3, in particular 1, substituents $R^8$; —$OR^9$ and —$NR^{10a}R^{10b}$; wherein $R^8$, $R^9$, $R^{10a}$ and $R^{10b}$ have one of the above general meanings, or, in particular, one of the below preferred meanings.

More preferably, $R^6$ in —C(=$NR^6$)$R^8$ is selected from hydrogen, $C_1$-$C_{10}$-alkyl, $C_3$-$C_8$-cycloalkyl, wherein the two last-mentioned aliphatic and cycloaliphatic radicals each independently may be partially or fully halogenated and/or may be substituted with 1, 2 or 3, preferably 1 or 2, in particular 1, substituents $R^8$; $OR^9$ and $NR^{10a}R^{10b}$; wherein $R^8$, $R^9$, $R^{10a}$ and $R^{10b}$ have one of the above general meanings, or, in particular, one of the below preferred meanings.

Even more preferably, $R^6$ in —C(=$NR^6$)$R^8$ is selected from —$OR^9$ and —$NR^{10a}R^{10b}$; wherein $R^8$, $R^9$, $R^{10a}$ and $R^{10b}$ have one of the above general meanings, or, in particular, one of the below preferred meanings.

In $OR^9$ as a preferred meaning of $R^6$ in —C(=$NR^6$)$R^8$, $R^9$ is preferably selected from hydrogen, $C_1$-$C_6$-alkyl, $C_1$-$C_6$-haloalkyl, $C_3$-$C_8$-cycloalkyl, $C_3$-$C_8$-halocycloalkyl, $C_3$-$C_8$-cycloalkyl-$C_1$-$C_4$-alkyl-, $C_2$-$C_6$-alkenyl, $C_2$-$C_6$-haloalkenyl, $C_2$-$C_6$-alkynyl and $C_2$-$C_6$-haloalkynyl, and more preferably from hydrogen, $C_1$-$C_6$-alkyl, $C_1$-$C_6$-haloalkyl, $C_3$-$C_8$-cycloalkyl, $C_3$-$C_8$-halocycloalkyl and $C_3$-$C_8$-cycloalkyl-$C_1$-$C_4$-alkyl-.

In $NR^{10a}R^{10b}$ as a preferred meaning of $R^6$ in —C(=$NR^6$)$R^8$, $R^{10a}$ and $R^{10b}$, independently of each other, are selected from the group consisting of hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkylcarbonyl, $C_1$-$C_6$-haloalkylcarbonyl, —C(=O)$OR^{15}$, —C(=O)N($R^{14a}$)$R^{14b}$, —C(=S)N($R^{14a}$)$R^{14b}$, phenyl which is optionally substituted with 1, 2, 3 or 4 substituents $R^{16}$, and a 3-, 4-, 5-, 6- or 7-membered saturated, partially unsaturated or maximally unsaturated heterocyclic ring comprising 1, 2, 3 or 4 heteroatoms or heteroatom groups selected from N, O, S, NO, SO and $SO_2$, as ring members, where the heterocyclic ring is optionally substituted with one or more substituents $R^{16}$; or $R^{10a}$ and $R^{10b}$ form together with the nitrogen atom they are bonded to a 3-, 4-, 5-, 6-, 7- or 8-membered saturated, partially unsaturated or maximally unsaturated heterocyclic ring, wherein the heterocyclic ring may additionally contain one or two heteroatoms or heteroatom groups selected from N, O, S, NO, SO and $SO_2$, as ring members, where the heterocyclic ring optionally carries one or more substituents selected from halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl and $C_2$-$C_6$-haloalkynyl;

wherein $R^{14a}$, $R^{14b}$, $R^{15}$ and $R^{16}$ have one of the above general meanings, or, in particular, one of the below preferred meanings.

More preferably, $R^{10a}$ is selected from hydrogen, $C_1$-$C_6$-alkyl and $C_1$-$C_6$-haloalkyl; and $R^{10b}$ is selected from $C_1$-$C_6$-alkyl, $C_1$-$C_6$-haloalkyl, $C_1$-$C_6$-alkylcarbonyl, $C_1$-$C_6$-haloalkylcarbonyl, —C(=O)OR$^{15}$, —C(=O)N(R$^{14a}$)R$^{14b}$, —C(=S)N(R$^{14a}$)R$^{14b}$, phenyl which is optionally substituted with 1, 2, 3 or 4 substituents $R^{16}$, and a 5- or 6-membered heteroaromatic ring comprising 1, 2 or 3 heteroatoms selected from N, O and S, as ring members, where the heteroaromatic ring is optionally substituted with one or more substituents $R^{16}$; wherein $R^{14a}$, $R^{14b}$, $R^{15}$ and $R^{16}$ have one of the above general meanings, or, in particular, one of the below preferred meanings.

Even more preferably, $R^{10a}$ is selected from hydrogen, $C_1$-$C_6$-alkyl and $C_1$-$C_6$-haloalkyl; and $R^{10b}$ is selected from —C(=O)N(R$^{14a}$)R$^{14b}$ and —C(=S)N(R$^{14a}$)R$^{14b}$;

wherein $R^{14a}$ and $R^{14b}$ have one of the above general meanings, or, in particular, one of the below preferred meanings.

In the above radicals $R^{10a}$ and $R^{10b}$, $R^{14a}$ is selected from hydrogen, $C_1$-$C_6$-alkyl and $C_1$-$C_6$-haloalkyl; and $R^{14b}$ is selected from hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_6$-halocycloalkyl, $C_3$-$C_6$-cycloalkyl-$C_1$-$C_4$-alkyl-, $C_1$-$C_6$-alkyl substituted with a CN group, $C_1$-$C_6$-alkoxy, $C_1$-$C_6$-haloalkoxy, phenyl which is optionally substituted with 1, 2, 3 or 4 substituents each independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_2$-$C_4$-haloalkynyl; and a heterocyclic ring selected from rings of formulae E-1 to E-54

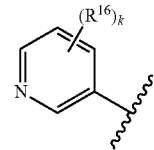 E-1

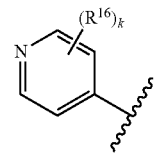 E-2

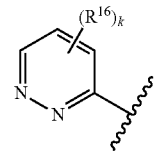 E-3

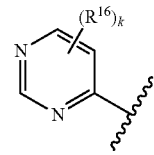 E-4

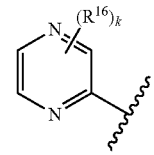 E-5

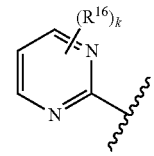 E-6

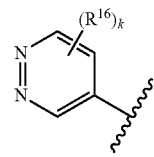 E-7

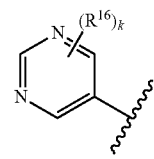 E-8

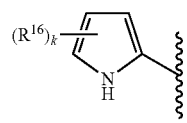 E-9

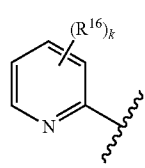 E-10

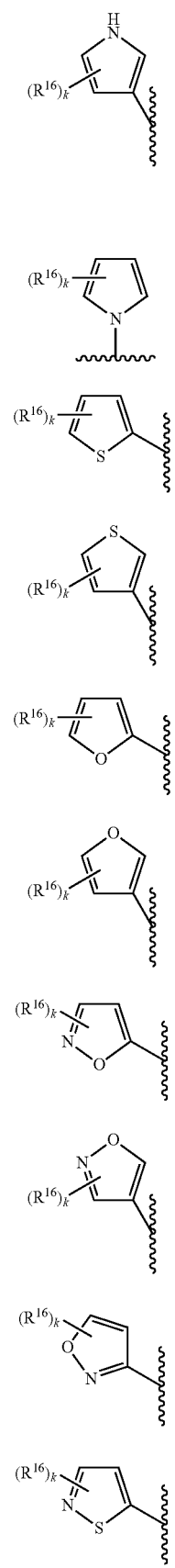
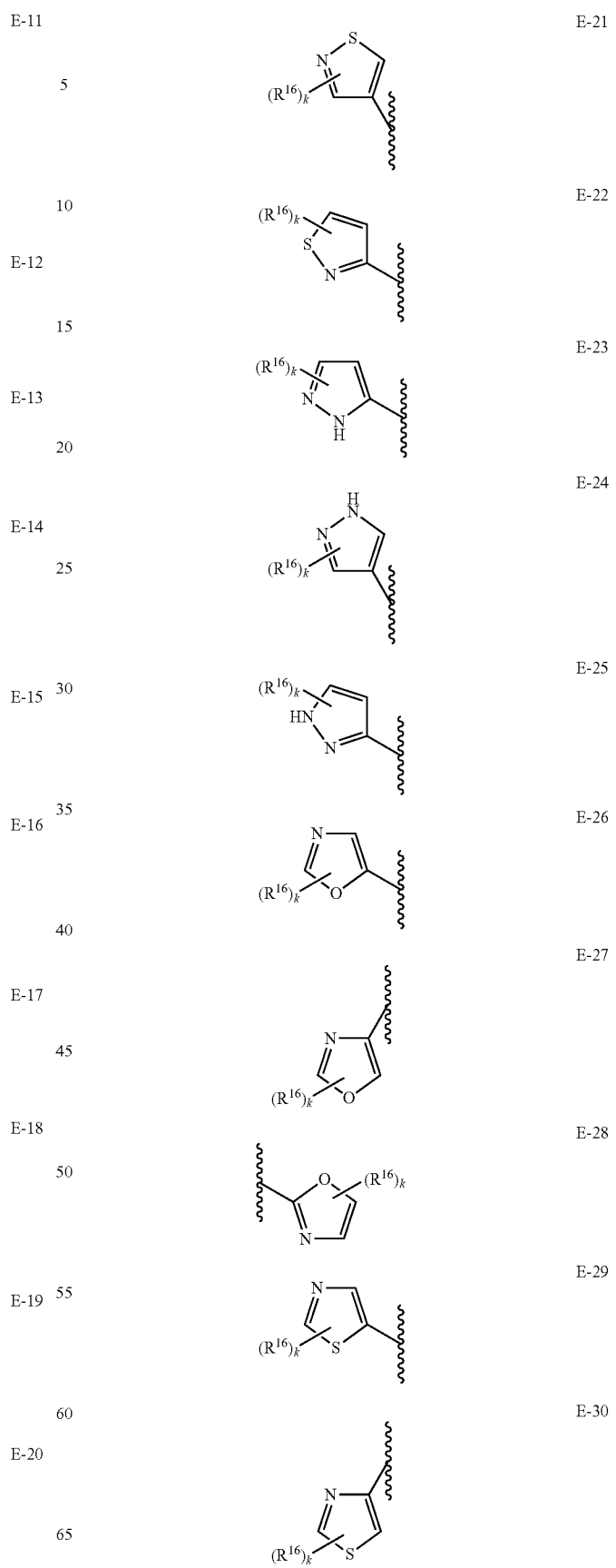

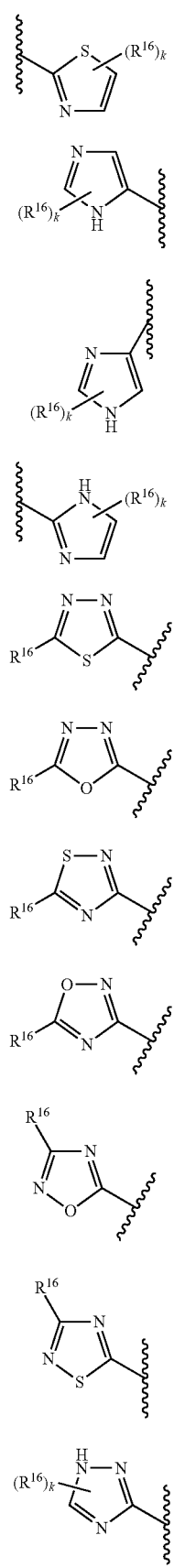
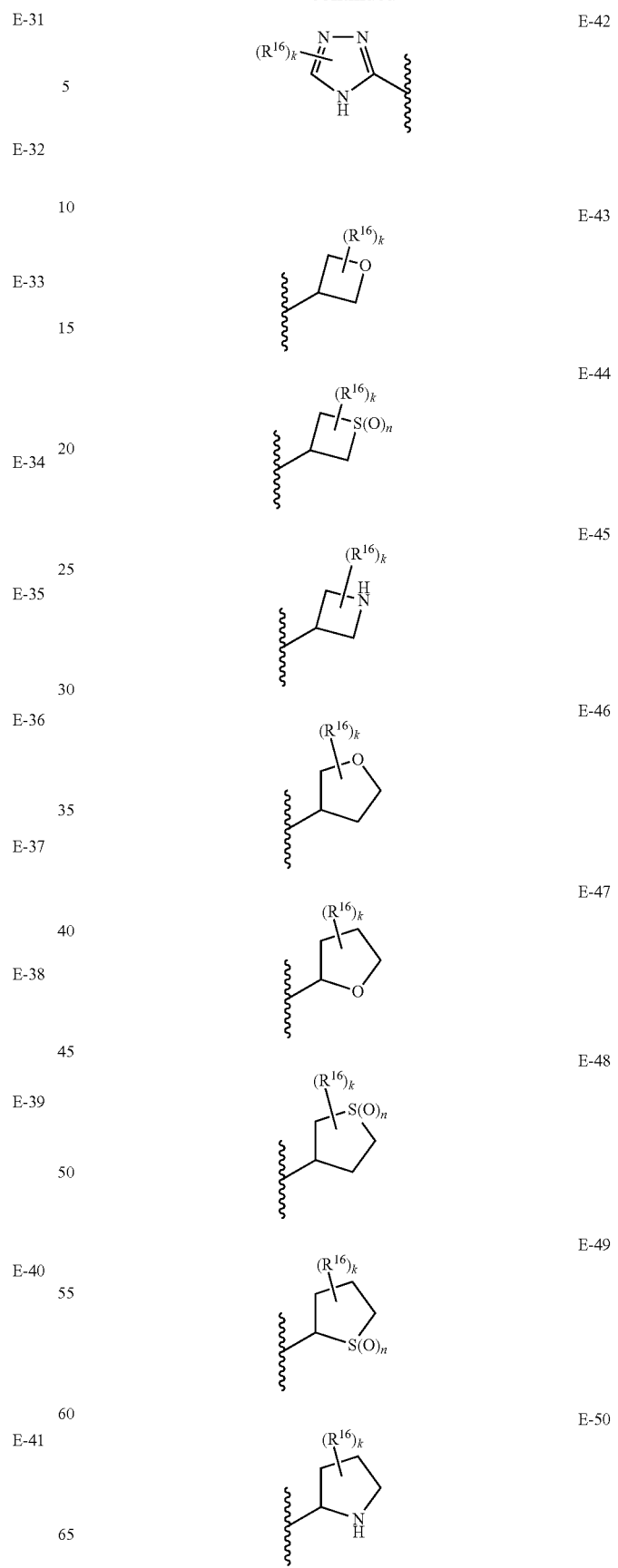

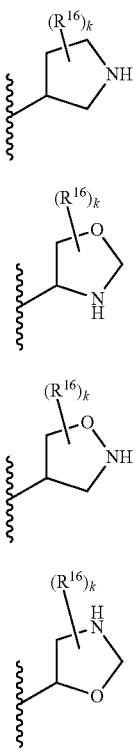

wherein k is 0, 1, 2 or 3, n is 0, 1 or 2; and each $R^{16}$ is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylcarbonyl, $C_1$-$C_4$-haloalkylcarbonyl, aminocarbonyl, $C_1$-$C_4$-alkylaminocarbonyl and di-($C_1$-$C_4$-alkyl)aminocarbonyl; or two $R^{16}$ present on the same carbon atom of a saturated ring may form together =O or =S.

More preferably, in the above radicals $R^{10a}$ and $R^{10b}$, $R^{14a}$ is selected from hydrogen and methyl; and $R^{14b}$ is selected from hydrogen, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $C_3$-$C_6$-cycloalkyl-methyl-, $C_3$-$C_6$-cycloalkyl substituted with a CN group, $C_1$-$C_6$-alkoxy, $C_1$-$C_6$-haloalkoxy, phenyl which is optionally substituted with 1, 2, 3 or 4, preferably 1, 2 or 3, in particular 1, substituents $R^{16}$ selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_2$-$C_4$-haloalkynyl; and a 4-membered saturated heterocyclic ring comprising one heteroatom or heteroatom group selected from S, SO and $SO_2$ as ring member (ring E-44), where the heterocyclic ring is optionally substituted with one or more, preferably 1 or 2, in particular 1, substituents $R^{16}$;

wherein each $R^{16}$ is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_2$-$C_4$-haloalkynyl; or two $R^{16}$ present on the same carbon atom may form together a group =O or =S.

Even more preferably, in the above radicals $R^{10a}$ and $R^{10b}$, $R^{14}$ is selected from hydrogen and methyl; and $R^{14b}$ is selected from hydrogen, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $C_3$-$C_6$-cycloalkyl-methyl-, $C_3$-$C_6$-cycloalkyl substituted with a CN group, $C_1$-$C_6$-alkyl substituted with a CN group, $C_1$-$C_6$-alkoxy and $C_1$-$C_6$-haloalkoxy.

Preferably, in the above radicals, each $R^{16}$ is independently selected from halogen, CN, $C_1$-$C_4$-alkyl, $C_1$-$C_4$-haloalkyl, $C_1$-$C_4$-alkoxy and $C_1$-$C_4$-haloalkoxy.

$R^8$ as a radical in the group —C(=NR$^6$)R$^8$ is preferably selected from hydrogen, $C_1$-$C_4$-alkyl, $C_1$-$C_4$-haloalkyl and $NR^{10a}R^{10b}$, and more preferably from hydrogen and $NR^{10a}R^{10b}$, and is specifically hydrogen, wherein $R^{10a}$ and $R^{10b}$ have one of the above general meanings, or, in particular, one of the below preferred meanings.

In this case (i.e. in $NR^{10a}R^{10b}$ as a meaning of $R^8$), $R^{10a}$ and $R^{10b}$ are preferably selected, independently of each other, from hydrogen, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $C_1$-$C_4$-alkylcarbonyl, $C_1$-$C_4$-haloalkylcarbonyl, $C_1$-$C_4$-alkylaminocarbonyl, $C_1$-$C_4$-haloalkylaminocarbonyl, $C_3$-$C_6$-cycloalkylaminocarbonyl and $C_3$-$C_6$-halocycloalkylaminocarbonyl, or, together with the nitrogen atom to which they are bound, form a 5- or 6-membered saturated, partially unsaturated or aromatic heterocyclic ring, which additionally may contain 1 or 2 further heteroatoms or heteroatom groups selected from N, O, S, NO, SO and $SO_2$, as ring members, where the heterocyclic ring may carry 1 or 2, in particular 1, substituents selected from halogen, CN, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $C_1$-$C_4$-alkoxy, $C_1$-$C_4$-haloalkoxy, $C_1$-$C_4$-alkylthio and $C_1$-$C_4$-haloalkylthio.

More preferably, $R^{10a}$ and $R^{10b}$ are in this case selected, independently of each other, from hydrogen, $C_1$-$C_4$-alkyl, $C_1$-$C_4$-haloalkyl, $C_3$-$C_6$-cycloalkyl, $C_3$-$C_6$-halocycloalkyl, $C_1$-$C_4$-alkylaminocarbonyl and $C_1$-$C_4$-haloalkylaminocarbonyl.

In an alternative embodiment of the invention, A is $A^2$.

In $A^2$, W is preferably O.

In $A^2$, Y is preferably $N(R^5)R^6$; wherein $R^5$ and $R^6$ have one of the above general meanings, or, in particular, one of the below preferred meanings.

In an alternatively preferred embodiment, in $A^2$ Y is hydrogen.

In an alternatively preferred embodiment, in $A^2$ Y is —OR$^9$. $R^9$ has one of the above general meanings, or, in particular, is selected from hydrogen, $C_1$-$C_6$-alkyl, $C_1$-$C_6$-haloalkyl and $C_1$-$C_6$-alkyl substituted by one radical $R^{13}$, where $R^{13}$ has one of the above general meanings, or, in particular, one of the below preferred meanings and is preferably selected from CN, $C_1$-$C_6$-alkoxy, $C_1$-$C_6$-haloalkoxy, $C_1$-$C_6$-alkylthio, $C_1$-$C_6$-haloalkylthio, $C_1$-$C_6$- alkylsulfinyl, $C_1$-$C_6$-haloalkylsulfinyl, $C_1$-$C_6$-alkylsulfonyl, $C_1$-$C_6$-haloalkylsulfonyl and a heterocyclic ring selected from rings of formulae E-1 to E-54 as defined above.

More preferably, in $A^2$, W is O and Y is —$N(R^5)R^6$; wherein $R^5$ and $R^6$ have one of the above general meanings, or, in particular, one of the below preferred meanings.

In alternatively more preferred embodiment, in $A^2$, W is O and Y H.

In alternatively more preferred embodiment, in $A^2$, W is O and Y is —$OR^9$, where $R^9$ has one of the above general meanings, or, in particular, is selected from hydrogen, $C_1$-$C_6$-alkyl, $C_1$-$C_6$-haloalkyl and $C_1$-$C_6$-alkyl substituted by one radical $R^{13}$, where $R^{13}$ has one of the above general meanings, or, in particular, one of the below preferred meaning—sand is preferably selected from CN, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl and a heterocyclic ring selected from rings of formulae E-1 to E-54 as defined above.

In —$N(R^5)R^6$ as a radical Y,
$R^5$ is preferably selected from hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl and $C_3$-$C_8$-halocycloalkyl, where the aforementioned aliphatic and cycloaliphatic radicals may be substituted by 1, 2 or 3, preferably 1, radicals $R^8$; and
$R^6$ is preferably selected from hydrogen, $C_1$-$C_{10}$-alkyl, $C_3$-$C_8$-cycloalkyl, $C_2$-$C_{10}$-alkenyl, $C_2$-$C_{10}$-alkynyl, wherein the four last-mentioned aliphatic and cycloaliphatic radicals may be partially or fully halogenated and/or may be substituted by one or more, preferably 1, 2 or 3, in particular 1, substituents $R^8$,
—$OR^9$, —$NR^{10a}R^{10b}$, —$S(O)_nR^9$, —$C(=O)NR^{10a}N(R^{10a}R^{10b})$, —$C(=O)R^8$, —$CH=NOR^9$, phenyl which may be substituted with 1, 2, 3, 4, or 5, preferably 1, 2 or 3, in particular 1, substituents $R^{11}$, and
a 3-, 4-, 5-, 6-, 7-, 8-, 9- or 10-membered saturated, partially unsaturated or maximally unsaturated heteromonocyclic or heterobicyclic ring containing 1, 2, 3 or 4 heteroatoms or heteroatom groups independently selected from N, O, S, NO, SO and $SO_2$, as ring members, where the heteromonocyclic or heterobicyclic ring may be substituted with one or more, preferably 1, 2 or 3, in particular 1, substituents $R^{11}$;
or
$R^5$ and $R^6$, together with the nitrogen atom to which they are bound, form a 3-, 4-, 5-, 6-, 7- or 8-membered saturated, partially unsaturated or maximally unsaturated heterocyclic ring, where the ring may further contain 1, 2, 3 or 4 heteroatoms or heteroatom-containing groups selected from O, S, SO, $SO_2$, N, NH, C=O and C=S as ring members, wherein the heterocyclic ring may be substituted with 1, 2, 3, 4 or 5, preferably 1, 2 or 3, in particular 1, substituents independently selected from the group consisting of halogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, wherein the aliphatic or cycloaliphatic moieties in the twelve last-mentioned radicals may be substituted by one or more, preferably 1, 2 or 3, in particular 1, radicals $R^8$, and phenyl which may be substituted with 1, 2, 3, 4, or 5, preferably 1, 2 or 3, in particular 1, substituents $R^{11}$
or
$R^5$ and $R^6$ together form a group =$C(R^8)_2$, =$S(O)_m(R^9)_2$, =$NR^{10a}$ or =$NOR^9$;
wherein $R^8$, $R^9$, $R^{10a}$, $R^{10b}$ and $R^{11}$ have one of the above general meanings, or, in particular, one of the below preferred meanings.

More preferably, in —$N(R^5)R^6$ as a radical Y,
$R^5$ is selected from hydrogen, $C_1$-$C_6$-alkyl, $C_2$-$C_3$-alkynyl and —$CH_2$—CN; and
$R^6$ is selected from hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_6$-halocycloalkyl, where the eight last-mentioned aliphatic and cycloaliphatic radicals may carry 1, 2 or 3 radicals $R^8$; $C_1$-$C_6$-alkoxy, $C_1$-$C_6$-haloalkoxy, —$N(R^{10a})R^{10b}$, —$CH=NOR^9$, phenyl which may be substituted with 1, 2, 3, 4, or 5 substituents $R^{11}$, and a 3-, 4-, 5- or 6-membered saturated, partially unsaturated or maximally unsaturated heteromonocyclic ring containing 1, 2 or 3 heteroatoms or heteroatom groups independently selected from N, O, S, NO, SO and $SO_2$, as ring members, where the heteromonocyclic ring may be substituted with one or more substituents $R^{11}$;
wherein $R^8$, $R^9$, $R^{10a}$, $R^{10b}$ and $R^{11}$ have one of the above general meanings, or, in particular, one of the below preferred meanings;
or
$R^5$ and $R^6$, together with the nitrogen atom to which they are bound, form a 3-, 4-, 5- or 6-membered saturated heterocyclic ring, where the ring may further contain 1 or 2 heteroatoms or heteroatom-containing groups selected from O, S, SO, $SO_2$, NH and C=O as ring members, wherein the heterocyclic ring may be substituted with 1, 2, 3, 4 or 5, preferably 1, 2 or 3, in particular 1, substituents independently selected from the group consisting of halogen, cyano, $C_1$-$C_6$-alkyl, $C_1$-$C_6$-haloalkyl, $C_1$-$C_6$-alkoxy and $C_1$-$C_6$-haloalkoxy;
or
$R^5$ and $R^6$, together with the nitrogen atom to which they are bound, form a group =$S(R^9)_2$, where $R^9$ is selected from $C_1$-$C_6$-alkyl and $C_1$-$C_6$-haloalkyl.

Even more preferably, in —$N(R^5)R^6$ as a radical Y,
$R^5$ is selected from hydrogen, $C_1$-$C_6$-alkyl, $C_2$-$C_3$-alkynyl and $CH_2$—CN; and
$R^6$ is selected from hydrogen, $C_1$-$C_6$-alkyl, $C_1$-$C_6$-haloalkyl, $C_1$-$C_4$-alkyl which carries one radical $R^8$, $C_2$-$C_6$-alkenyl, $C_2$-$C_{10}$-haloalkenyl, $C_2$-$C_6$-alkynyl, $C_3$-$C_6$-cycloalkyl which may be substituted by 1 or 2 substituents selected from F, CN and pyridyl; —$N(R^{10a})R^{10b}$, —$CH=NOR^9$, phenyl which may be substituted with 1, 2, 3, 4, or 5, preferably 1, 2 or 3, in particular 1, substituents $R^{11}$, and a 3-, 4-, 5- or 6-membered saturated, partially unsaturated or maximally unsaturated heteromonocyclic ring containing 1, 2 or 3 heteroatoms or heteroatom groups independently selected from N, O, S, NO, SO and $SO_2$, as ring members, where the heteromonocyclic ring may be substituted with one or more, preferably 1, 2 or 3, in particular 1, substituents $R^{11}$;
wherein $R^8$, $R^9$, $R^{10a}$, $R^{10b}$ and $R^{11}$ have one of the above general meanings, or, in particular, one of the below preferred meanings;
or
$R^5$ and $R^6$, together with the nitrogen atom to which they are bound, form a 3-, 4-, 5- or 6-membered saturated heterocyclic ring, where the ring may further contain 1 or 2 heteroatoms or heteroatom-containing groups selected from O, S, SO, $SO_2$, NH and C=O as ring members, wherein the heterocyclic ring may be substituted with 1, 2 or 3, in particular 1, substituents independently selected from the group consisting of halogen, cyano, $C_1$-$C_6$-alkyl, $C_1$-$C_6$-haloalkyl, $C_1$-$C_6$-alkoxy and $C_1$-$C_6$-haloalkoxy;
or
$R^5$ and $R^6$, together with the nitrogen atom to which they are bound, form a group =$S(R^9)_2$, where $R^9$ is selected from $C_1$-$C_6$-alkyl and $C_1$-$C_6$-haloalkyl.

Particularly preferably, in —$N(R^5)R^6$ as a radical Y,
$R^5$ selected from hydrogen, $C_1$-$C_6$-alkyl, $C_2$-$C_3$-alkynyl and $CH_2$—CN; and
$R^6$ is selected from hydrogen, $C_1$-$C_6$-alkyl, $C_1$-$C_6$-haloalkyl, $C_1$-$C_4$-alkyl which carries one radical $R^8$, $C_2$-$C_6$-alkenyl, $C_2$-$C_{10}$-haloalkenyl, $C_2$-$C_6$-alkynyl, $C_3$-$C_6$-cycloalkyl which may be substituted by 1 or 2 substituents selected from F, CN and pyridyl; —$N(R^{10a})R^{10b}$,
wherein
$R^{10a}$ is selected from hydrogen and $C_1$-$C_6$-alkyl; and
$R^{10b}$ is selected from hydrogen, —$C(=O)N(R^{14a})R^{14b}$, phenyl, optionally substituted with 1, 2, 3, 4 or 5 substituents $R^{16}$, and a heterocyclic ring selected from rings of formulae E-1 to E-54 as defined above;
—CH=$NOR^9$, wherein $R^9$ is selected from hydrogen, $C_1$-$C_6$-alkyl and $C_1$-$C_6$-haloalkyl;
phenyl which may be substituted with 1, 2, 3, 4, or 5, preferably 1, 2 or 3, in particular 1, substituents $R^{11}$, and
a 3-, 4-, 5- or 6-membered saturated, partially unsaturated or maximally unsaturated heteromonocyclic ring containing 1, 2 or 3 heteroatoms or heteroatom groups independently selected from N, O, S, NO, SO and $SO_2$, as ring members, where the heteromonocyclic ring may be substituted with one or more, preferably 1, 2 or 3, in particular 1, substituents $R^{11}$;
wherein
each $R^{11}$ is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_3$-$C_6$-cycloalkyl, $C_3$-$C_8$-halocycloalkyl, $C_2$-$C_4$-alkenyl, $C_2$-$C_4$-haloalkenyl, $C_2$-$C_4$-alkynyl and $C_2$-$C_4$-haloalkynyl; or two $R^{11}$ present on the same carbon atom of a saturated heterocyclic ring may form together =O or =S;
each $R^8$ is independently selected from OH, CN, $C_3$-$C_8$-cycloalkyl which optionally carries a CN substituent, $C_3$-$C_8$-halocycloalkyl, $C_1$-$C_8$-alkoxy, $C_1$-$C_6$-haloalkoxy, $C_1$-$C_6$-alkylthio, $C_1$-$C_6$-haloalkylthio, $C_1$-$C_6$-alkylsulfonyl, $C_1$-$C_6$-haloalkylsulfonyl, —$C(=O)N(R^{10a})R^{10b}$, phenyl, optionally substituted with 1, 2, 3, 4 or 5, preferably 1, 2 or 3, in particular 1, substituents $R^{16}$, and a 3-, 4-, 5- or 6-membered saturated, partially unsaturated or maximally unsaturated heteromonocyclic ring containing 1, 2 or 3 heteroatoms or heteroatom groups independently selected from N, O, S, NO, SO and $SO_2$, as ring members, where the heteromonocyclic ring may be substituted with one or more, preferably 1, 2 or 3, in particular 1, substituents $R^{16}$;
wherein
$R^{10a}$ is selected from the group consisting of hydrogen, $C_1$-$C_6$-alkyl, $C_2$-$C_3$-alkynyl and $CH_2$—CN;
$R^{10b}$ is selected from the group consisting of hydrogen, $C_1$-$C_6$-alkyl, $C_2$-$C_4$-alkenyl, $C_2$-$C_4$-alkynyl, $CH_2$—CN, $C_1$-$C_6$-haloalkyl, $C_3$-$C_6$-cycloalkyl, $C_3$-$C_6$-halocycloalkyl, $C_3$-$C_6$-cycloalkylmethyl, $C_1$-$C_6$-alkoxy, $C_1$-$C_6$-haloalkoxy, phenyl which is optionally substituted with 1, 2, 3, 4 or 5, preferably 1, 2 or 3, in particular 1, substituents selected from the group consisting of halogen, cyano, nitro, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $C_1$-$C_4$-alkoxy, $C_1$-$C_4$-haloalkoxy, $C_1$-$C_4$-alkylthio and $C_1$-$C_4$-haloalkylthio; and a heterocyclic ring selected from rings of formulae E-1 to E-54 as defined above; and
each $R^{16}$ as a substituent on phenyl or the heterocyclic rings is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_2$-$C_4$-haloalkynyl; or two $R^{16}$ present on the same carbon atom of a saturated heterocyclic ring may form together =O or =S;
or
$R^5$ and $R^6$, together with the nitrogen atom to which they are bound, form a 5- or 6-membered saturated heterocyclic ring, where the ring may further contain 1 or 2 heteroatoms or heteroatom-containing groups selected from O, S, SO, $SO_2$, NH and C=O as ring members, wherein the heterocyclic ring may be substituted with 1, 2 or 3, in particular 1, substituents independently selected from the group consisting of halogen, cyano, $C_1$-$C_6$-alkyl, $C_1$-$C_6$-haloalkyl, $C_1$-$C_6$-alkoxy and $C_1$-$C_6$-haloalkoxy;
or
$R^5$ and $R^6$ together form a group =$S(R^9)_2$, where $R^9$ is selected from $C_1$-$C_6$-alkyl and $C_1$-$C_6$-haloalkyl.

In particular, in $N(R^5)R^6$ as a radical Y,
$R^5$ is hydrogen or $C_1$-$C_3$-alkyl;
$R^6$ is selected from hydrogen, $C_1$-$C_6$-alkyl, $C_1$-$C_6$-haloalkyl, $C_1$-$C_4$-alkyl which carries one radical $R^8$, wherein $R^8$ is as defined below; $C_2$-$C_6$-alkenyl, $C_2$-$C_6$-haloalkenyl, $C_2$-$C_6$-alkynyl, $C_3$-$C_6$-cycloalkyl which may be substituted by 1 or 2 substituents selected from F, CN and pyridyl;
—$N(R^{10a})R^{10b}$, wherein $R^{10a}$ is selected from hydrogen and $C_1$-$C_6$-alkyl and $R^{10b}$ is selected from hydrogen, —$C(=O)N(R^{14a})R^{14b}$, wherein $R^{14a}$ is selected from the group consisting of hydrogen and $C_1$-$C_6$-alkyl and $R^{14b}$ is selected from the group consisting of hydrogen, $C_1$-$C_6$-alkyl, $C_2$-$C_4$-alkynyl, $CH_2$—CN, $C_1$-$C_6$-haloalkyl, $C_3$-$C_6$-cycloalkyl, $C_3$-$C_6$-halocycloalkyl, $C_1$-$C_4$-alkoxy and $C_1$-$C_4$-haloalkoxy; phenyl, optionally substituted with 1, 2, 3, 4 or 5, preferably 1, 2 or 3, in particular 1, substituents $R^{11}$, wherein $R^{11}$ is as defined below; and a heteroaromatic ring selected from rings of formulae F-1 to F-54;
—CH=$NOR^9$, wherein $R^9$ is selected from hydrogen, $C_1$-$C_6$-alkyl and $C_1$-$C_6$-haloalkyl;
phenyl which may be substituted with 1, 2, 3, 4, or 5, preferably 1, 2 or 3, in particular 1, substituents $R^{11}$, wherein $R^{11}$ is as defined below; and a heteromonocyclic ring selected from rings of formulae F-1 to F-54

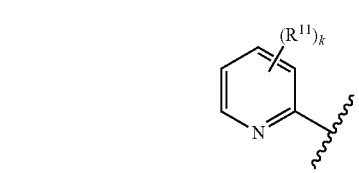

F-1

-continued

F-2, F-3, F-4, F-5, F-6, F-7, F-8, F-9, F-10

F-11, F-12, F-13, F-14, F-15, F-16, F-17, F-18, F-19, F-20

-continued
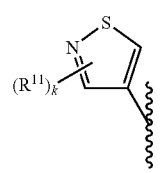 F-21
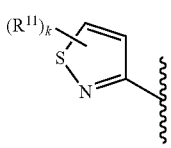 F-22
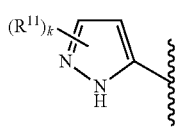 F-23
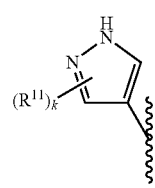 F-24
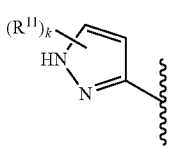 F-25
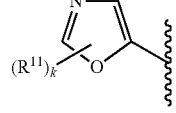 F-26
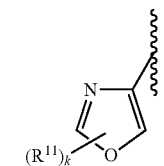 F-27
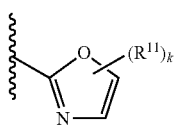 F-28
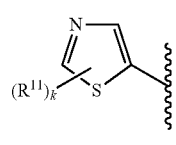 F-29
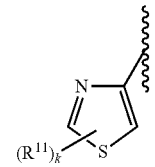 F-30
-continued
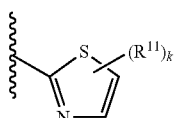 F-31
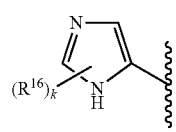 F-32
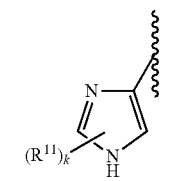 F-33
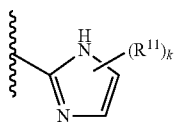 F-34
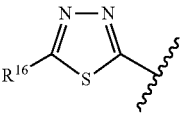 F-35
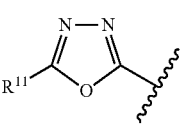 F-36
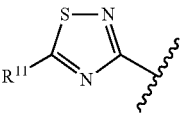 F-37
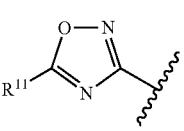 F-38
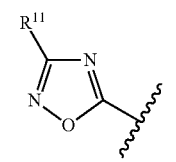 F-39
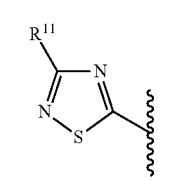 F-40
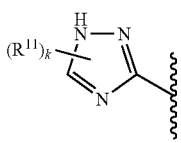 F-41

-continued

F-42
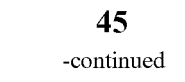

F-43
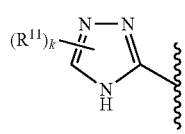

F-44
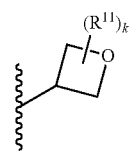

F-45
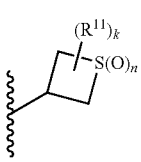

F-46
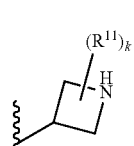

F-47
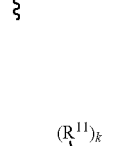

F-48
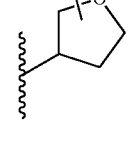

F-49
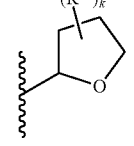

F-50
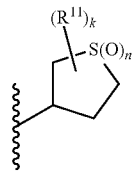

-continued

F-51
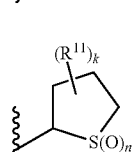

F-52

F-53

F-54
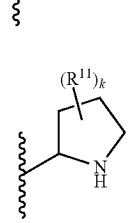

wherein
k is 0, 1, 2 or 3,
n is 0, 1 or 2, and
each $R^{11}$ is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylcarbonyl, $C_1$-$C_4$-haloalkylcarbonyl, aminocarbonyl, $C_1$-$C_4$-alkylaminocarbonyl and di-($C_1$-$C_4$-alkyl)-aminocarbonyl; or
two $R^{11}$ present on the same carbon atom of a saturated heterocyclic ring may form together =O or =S;
$R^8$ is selected from OH, CN, $C_3$-$C_8$-cycloalkyl which optionally carries a CN substituent, $C_3$-$C_8$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —C(=O)N($R^{10a}$)$R^{10b}$, phenyl, optionally substituted with 1, 2, 3, 4 or 5, preferably 1, 2 or 3, in particular 1, substituents $R^{16}$, and a heterocyclic ring selected from rings of formulae E-1 to E-54 as defined above;
wherein
$R^{10a}$ is selected from the group consisting of hydrogen and $C_1$-$C_6$-alkyl;
$R^{10b}$ is selected from the group consisting of hydrogen, $C_1$-$C_6$-alkyl, $C_1$-$C_6$-haloalkyl, $C_2$-$C_4$-alkynyl, $C_3$-$C_6$-cycloalkyl, $C_3$-$C_6$-halocycloalkyl, CH$_2$—CN, $C_1$-$C_6$-alkoxy and $C_1$-$C_6$-haloalkoxy; and
each $R^{16}$ as a substituent on phenyl or heterocyclic rings of formulae E-1 to E-54 is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylcarbonyl, $C_1$-$C_4$-haloalkylcarbonyl, aminocarbonyl, $C_1$-$C_4$-alkylaminocarbonyl and di-($C_1$-$C_4$-alkyl)aminocarbonyl; or two $R^{16}$ present on the same carbon atom of a saturated heterocyclic ring may form together =O or =S.

Even more particularly, in —N($R^5$)$R^6$ as a radical Y, $R^5$ is hydrogen;

$R^6$ is selected from hydrogen, $C_1$-$C_6$-alkyl, $C_1$-$C_6$-haloalkyl, $C_1$-$C_4$-alkyl which carries one radical $R^8$, $C_2$-$C_6$-alkenyl, $C_2$-$C_6$-haloalkenyl, $C_2$-$C_6$-alkynyl, $C_3$-$C_6$-cycloalkyl which may be substituted by 1 or 2 substituents selected from F and CN;

—N($R^{10a}$)$R^{10b}$, wherein $R^{10a}$ is hydrogen and $R^{10b}$ is —C(=O)N($R^{14a}$)$R^{14b}$, wherein $R^{14a}$ is selected from the group consisting of hydrogen and $C_1$-$C_6$-alkyl; and $R^{14b}$ is selected from the group consisting of hydrogen, $C_1$-$C_6$-alkyl, $C_1$-$C_6$-haloalkyl, $C_2$-$C_4$-alkynyl, $C_3$-$C_6$-cycloalkyl, $C_3$-$C_6$-halocycloalkyl, $CH_2$—CN, $C_1$-$C_4$-alkoxy and $C_1$-$C_4$-haloalkoxy;

—CH=NO$R^9$, wherein $R^9$ is selected from hydrogen, $C_1$-$C_6$-alkyl and $C_1$-$C_6$-haloalkyl;

phenyl which may be substituted with 1, 2, 3, 4, or 5 substituents $R^{11}$, and a heteromonocyclic ring selected from rings of formulae F-1 to F-54 as defined above; wherein $R^8$ is selected from CN, $C_3$-$C_8$-cycloalkyl which optionally carries a CN substituent, $C_3$-$C_8$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —C(=O)N($R^{10a}$)$R^{10b}$, phenyl, optionally substituted with 1, 2, 3, 4 or 5 substituents $R^{16}$, and a heterocyclic ring selected from rings of formulae E-1 to E-54 as defined above; wherein $R^{10a}$ is selected from the group consisting of hydrogen and $C_1$-$C_6$-alkyl;

$R^{10b}$ is selected from the group consisting of hydrogen, $C_1$-$C_6$-alkyl, $C_2$-$C_4$-alkynyl, $CH_2$—CN, $C_1$-$C_6$-haloalkyl, $C_3$-$C_6$-cycloalkyl, $C_3$-$C_6$-halocycloalkyl, $C_1$-$C_4$-alkoxy and $C_1$-$C_4$-haloalkoxy, and $R^{11}$ and $R^{16}$; independently of each occurrence and independently of each other, are selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylcarbonyl, $C_1$-$C_4$-haloalkylcarbonyl, aminocarbonyl, $C_1$-$C_4$-alkylaminocarbonyl and di-($C_1$-$C_4$-alkyl)-aminocarbonyl; or two $R^{16}$ present on the same carbon atom of a saturated heterocyclic ring may form together =O or =S.

Specifically, in —N($R^5$)$R^6$ as a radical Y, $R^5$ is hydrogen;

$R^6$ is selected from $C_1$-$C_6$-alkyl, $C_1$-$C_6$-haloalkyl, $C_1$-$C_4$-alkyl which carries one radical $R^8$, and a heteromonocyclic ring selected from rings of formulae F-1 to F-54, preferably F-43 to F-49, especially F-44, as defined above;

wherein $R^8$ is selected from CN, $C_3$-$C_8$-cycloalkyl which optionally carries a CN substituent, $C_3$-$C_8$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —C(=O)N($R^{10a}$)$R^{10b}$, phenyl, optionally substituted with 1, 2, 3, 4 or 5 substituents $R^{16}$, and a heterocyclic ring selected from rings of formulae E-1 to E-54, preferably E-1 to E-34, especially E-1 to E-3, E-7 and E-26 to E-31, as defined above; wherein $R^{10a}$ is selected from the group consisting of hydrogen and $C_1$-$C_6$-alkyl;

$R^{10b}$ is selected from the group consisting of hydrogen, $C_1$-$C_6$-alkyl, and $C_1$-$C_6$-haloalkyl, and $R^{11}$ and $R^{16}$; independently of each occurrence and independently of each other, are selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_3$-$C_6$-cycloalkyl, $C_3$-$C_8$-halocycloalkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylcarbonyl, $C_1$-$C_4$-haloalkylcarbonyl, aminocarbonyl, $C_1$-$C_4$-alkylaminocarbonyl and di-($C_1$-$C_4$-alkyl)-aminocarbonyl; or two $R^{16}$ present on the same carbon atom of a saturated heterocyclic ring may form together =O or =S.

In an alternative embodiment of the invention, A is $A^3$.

Preferably, $R^{7a}$ and $R^{7b}$ in the group $A^3$ are independently of each other selected from hydrogen, cyano, $C_1$-$C_4$-alkyl and $C_1$-$C_4$-haloalkyl, more preferably from hydrogen, $C_1$-$C_4$-alkyl and $C_1$-$C_4$-haloalkyl. Even more preferably, one of $R^{7a}$ and $R^{7b}$ is hydrogen and the other is hydrogen or methyl. Specifically, both are hydrogen.

In the group $A^3$, $R^5$ is preferably selected from hydrogen, cyano, $C_1$-$C_6$-alkyl, $C_3$-$C_8$-cycloalkyl, $C_2$-$C_6$-alkenyl, $C_2$-$C_6$-alkynyl, wherein the four last-mentioned aliphatic and cycloaliphatic radicals may be partially or fully halogenated and/or may be substituted with one or more, preferably 1, 2 or 3, in particular 1, substituents $R^8$; and $R^6$ is preferably selected from hydrogen, $C_1$-$C_6$-alkyl, $C_3$-$C_8$-cycloalkyl, $C_2$-$C_6$-alkenyl, $C_2$-$C_6$-alkynyl, wherein the four last-mentioned aliphatic and cycloaliphatic radicals may be partially or fully halogenated and/or may be substituted by one or more, preferably 1, 2 or 3, in particular 1, substituents $R^8$, —O$R^9$, —N$R^{10a}R^{10b}$, —S(O)$_n R^9$, —C(=O)N$R^{10a}$N($R^{10a}$)$R^{10b}$, —C(=O)$R^8$, and a 3-, 4-, 5-, 6- or 7-membered saturated, partially unsaturated or maximally unsaturated heteromonocyclic or heterobicyclic ring containing 1, 2, 3 or 4 heteroatoms or heteroatom groups independently selected from N, O, S, NO, SO and $SO_2$, as ring members, where the heteromonocyclic or heterobicyclic ring may be substituted with one or more, preferably 1, 2 or 3, in particular 1, substituents $R^{11}$;

or $R^5$ and $R^6$, together with the nitrogen atom to which they are bound, form a 3-, 4-, 5- or 6-membered saturated, partially unsaturated or maximally unsaturated heterocyclic ring, where the ring may further contain 1, 2, 3 or 4 heteroatoms or heteroatom-containing groups selected from O, S, N, SO, $SO_2$, C=O and C=S as ring members, wherein the heterocyclic ring may be substituted with 1, 2, 3, 4 or 5, preferably 1, 2 or 3, in particular 1, substituents independently selected from the group consisting of halogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, wherein the aliphatic or cycloaliphatic moieties in the twelve last-mentioned radicals may be substituted by one or more, preferably 1, 2 or 3, in particular 1, radicals $R^8$, and phenyl which may be substituted with 1, 2, 3, 4 or 5, preferably 1, 2 or 3, in particular 1, substituents $R^{11}$;
or
$R^5$ and $R^6$ together form a group =$C(R^8)_2$, =$S(O)_m(R^9)_2$, =$NR^{10a}$ or =$NOR^9$;
wherein m, n, $R^8$, $R^9$, $R^{10a}$, $R^{10b}$ and $R^{11}$ have one of the above general meanings, or, in particular, one of the below preferred meanings.

More preferably, in the group $A^3$,
$R^5$ is selected from hydrogen, $C_1$-$C_4$-alkyl, $C_2$-$C_3$-alkynyl, —$CH_2$—CN and $C_1$-$C_6$-alkoxy-methyl- and preferably from hydrogen and $C_1$-$C_4$-alkyl; and
$R^6$ is —C(=O)$R^8$;
wherein $R^8$ has one of the above general meanings, or, in particular, one of the below preferred meanings.

$R^8$ in —C(=O)$R^8$ as a meaning of the radicals $R^5$ and $R^6$ of the group $A^3$ is preferably selected from the group consisting of hydrogen, $C_1$-$C_6$-alkyl, $C_1$-$C_6$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_8$-cycloalkyl, $C_3$-$C_8$-halocycloalkyl, where the aliphatic and cycloaliphatic moieties in the eight last-mentioned radicals may be substituted by one or more, preferably 1, 2 or 3, in particular 1, radicals $R^{13}$;
—$OR^9$, —$S(O)_nR^9$, —$N(R^{10a})R^{10b}$, —$C(=O)N(R^{10a})R^{10b}$, —CH=$NOR^9$,
phenyl, optionally substituted with 1, 2, 3, 4 or 5, preferably 1, 2 or 3, in particular 1, substituents $R^{16}$, and a 3-, 4-, 5- or 6-membered saturated, partially unsaturated or maximally unsaturated heterocyclic ring comprising 1, 2 or 3 heteroatoms or heteroatom groups selected from N, O, S, NO, SO and $SO_2$, as ring members, where the heterocyclic ring is optionally substituted with one or more, preferably 1, 2 or 3, in particular 1, substituents $R^{16}$,
wherein n, $R^9$, $R^{10a}$, $R^{10b}$, $R^{13}$ and $R^{16}$ have one of the above general meanings, or, in particular, one of the below preferred meanings.

More preferably, $R^8$ in —C(=O)$R^8$ as a meaning of the radicals $R^5$ and $R^6$ of the group $A^3$ is selected from the group consisting of hydrogen, $C_1$-$C_6$-alkyl, $C_1$-$C_6$-haloalkyl, $C_1$-$C_6$-alkyl substituted with one radical $R^{13}$, $C_2$-$C_4$-alkenyl, $C_2$-$C_4$-haloalkenyl, $C_2$-$C_4$-alkynyl, $C_2$-$C_4$-haloalkynyl, $C_3$-$C_8$-cycloalkyl which optionally carries a CN substituent, $C_3$-$C_8$-halocycloalkyl,
—$N(R^{10a})R^{10b}$, —$C(=O)N(R^{10a})R^{10b}$, —CH=$NOR^9$,
phenyl, optionally substituted with 1, 2, 3, 4 or 5, preferably 1, 2 or 3, in particular 1, substituents $R^{16}$, and a 3-, 4-, 5- or 6-membered saturated, partially unsaturated or maximally unsaturated heterocyclic ring comprising 1, 2 or 3 heteroatoms or heteroatom groups selected from N, O, S, NO, SO and $SO_2$, as ring members, where the heterocyclic ring is optionally substituted with one or more, preferably 1, 2 or 3, in particular 1, substituents $R^{16}$,
wherein $R^9$, $R^{10a}$, $R^{10b}$, $R^{13}$ and $R^{16}$ have one of the above general meanings, or, in particular, one of the below preferred meanings.

$R^9$ in —CH=$NOR^9$ as a meaning of $R^8$ in the group —C(=O)$R^8$ as a meaning of the radicals $R^5$ and $R^6$ of the group $A^3$ is preferably selected from hydrogen, $C_1$-$C_6$-alkyl and $C_1$-$C_6$-haloalkyl.

$R^{10a}$ and $R^{10b}$, in —$C(=O)N(R^{10a})R^{10b}$ and —$N(R^{10a})R^{10b}$ as a meaning of $R^8$ in the group —C(=O)$R^8$ as a meaning of the radicals $R^5$ and $R^6$ of the group $A^3$ are, independently of each other, preferably selected from hydrogen, $C_1$-$C_6$-alkyl, $C_1$-$C_6$-haloalkyl, $C_2$-$C_3$-alkenyl, $C_2$-$C_3$-haloalkenyl, $C_2$-$C_3$-alkynyl, $C_2$-$C_3$-haloalkynyl, $C_3$-$C_6$-cycloalkyl which optionally carries a CN substituent, $C_3$-$C_8$-halocycloalkyl, where the aliphatic and cycloaliphatic moieties in the 9 last-mentioned radicals may be substituted by one or more radicals $R^{13}$; —$C(=O)NR^{(14a)}R^{14b}$, phenyl, optionally substituted with 1, 2, 3, 4 or 5 substituents $R^{16}$; and a heteromonocyclic ring selected from rings of formulae E-1 to E-54 as defined above.

$R^{13}$ in $R^8$ in the radicals $R^5$ and $R^6$ of the group $A^3$ is preferably selected from CN, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —$C(=O)N(R^{14a})R^{14b}$, phenyl, optionally substituted with 1, 2, 3, 4 or 5 substituents $R^{16}$; and a heterocyclic ring selected from rings of formulae E-1 to E-54 as defined above.

$R^{14a}$ and $R^{14b}$ in —$C(=O)NR^{(14a)}R^{14b}$ as a meaning for $R^{10a}$ and $R^{10b}$ as well as a meaning for $R^{13}$, independently of each other and independently of each occurrence, are preferably selected from hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, wherein the six last-mentioned aliphatic radicals may carry 1 substituent selected from cyano, $C_1$-$C_4$-alkoxy, $C_1$-$C_4$-haloalkoxy, $C_3$-$C_4$-cycloalkyl which may be substituted by 1 cyano group; and $C_3$-$C_4$-halocycloalkyl; $C_3$-$C_8$-cycloalkyl which may carry 1 cyano group; and $C_3$-$C_8$-halocycloalkyl; and more preferably from hydrogen, $C_1$-$C_6$-alkyl, $C_1$-$C_6$-haloalkyl, $CH_2$—CN, $C_2$-$C_4$-alkenyl, $C_2$-$C_4$-alkynyl, $C_3$-$C_6$-cycloalkyl, $C_3$-$C_6$-halocycloalkyl, $C_3$-$C_6$-cycloalkylmethyl-, $C_1$-$C_4$-alkoxy and $C_1$-$C_4$-haloalkoxy.

Preferably, each $R^{16}$ as a substituent on phenyl or heterocyclic rings of formulae E-1 to E-54 is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylcarbonyl, $C_1$-$C_4$-haloalkylcarbonyl, aminocarbonyl, $C_1$-$C_4$-alkylaminocarbonyl and di-($C_1$-$C_4$-alkyl)aminocarbonyl; or
two $R^{16}$ present on the same carbon atom of a saturated heterocyclic ring may form together =O or =S.

In particular, $R^8$ in —C(=O)$R^8$ as a meaning of the radicals $R^5$ and $R^6$ of the group $A^3$ is selected from the group consisting of hydrogen, $C_1$-$C_6$-alkyl, $C_1$-$C_6$-haloalkyl, $C_1$-$C_4$-alkyl substituted by one radical $R^{13}$, $C_2$-$C_4$-alkenyl, $C_2$-$C_4$-haloalkenyl, $C_2$-$C_4$-alkynyl, $C_2$-$C_4$-haloalkynyl, $C_3$-$C_8$-cycloalkyl which optionally carries a CN substituent, $C_3$-$C_8$-halocycloalkyl, —$N(R^{10a})R^{10b}$, —$C(=O)N(R^{10a})R^{10b}$, —CH=$NOR^9$, phenyl which is optionally substituted with 1, 2, 3, 4 or 5 substituents $R^{16}$; and a heterocyclic ring selected from rings of formulae E-1 to E-54 as defined above,
wherein
$R^9$ is selected from hydrogen, $C_1$-$C_6$-alkyl and $C_1$-$C_6$-haloalkyl;
$R^{10a}$ is selected from hydrogen, $C_1$-$C_4$-alkyl, $C_1$-$C_4$-haloalkyl and $C_3$-$C_6$-cycloalkyl, and preferably from hydrogen and $C_1$-$C_4$-alkyl;
$R^{10b}$ is selected from hydrogen, $C_1$-$C_6$-alkyl, $C_1$-$C_6$-haloalkyl, $C_3$-$C_6$-cycloalkyl which optionally carries a CN substituent; —C(=O)N($R^{14a}$)$R^{14b}$; phenyl, optionally substituted with 1, 2, 3, 4 or 5 substituents $R^{16}$; and a heteromonocyclic ring selected from rings of formulae E-1 to E-54 as defined above;
$R^{13}$ is selected from CN, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —C(=O)N($R^{14a}$)$R^{14b}$, phenyl, optionally substituted with 1, 2, 3, 4 or 5 substituents $R^{16}$; and a heterocyclic ring selected from rings of formulae E-1 to E-54 as defined above;
$R^{14a}$ is selected from hydrogen and $C_1$-$C_6$-alkyl;
$R^{14b}$ is selected from hydrogen, $C_1$-$C_6$-alkyl, $C_1$-$C_6$-haloalkyl, $CH_2$—CN, $C_2$-$C_4$-alkenyl, $C_2$-$C_4$-alkynyl, $C_3$-$C_6$-cycloalkyl, $C_3$-$C_6$-halocycloalkyl, $C_3$-$C_6$-cycloalkylmethyl-, $C_1$-$C_4$-alkoxy and $C_1$-$C_4$-haloalkoxy; and
each $R^{16}$ as a substituent on phenyl or heterocyclic rings of formulae E-1 to E-54 is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylcarbonyl, $C_1$-$C_4$-haloalkylcarbonyl, aminocarbonyl, $C_1$-$C_4$-alkylaminocarbonyl and di-($C_1$-$C_4$-alkyl)aminocarbonyl; or two $R^{16}$ present on the same carbon atom of a saturated heterocyclic ring may form together =O or =S.

In an alternative embodiment of the invention, A is $A^4$.

$A^4$ is preferably selected from a 3-, 4-, 5-, 6- or 7-membered saturated, partially unsaturated or maximally unsaturated heteromonocyclic ring containing 1, 2, 3 or 4 heteroatoms or heteroatom groups selected from N, O, S, NO, SO and $SO_2$, as ring members, where the heteromonocyclic ring is optionally substituted with one or more, preferably 1, 2 or 3, in particular 1, substituents $R^{11}$, where $R^{11}$ has one of the above general meanings, or, in particular, one of the below preferred meanings.

More preferably, $A^4$ is selected from a 3-, 4-, 5-, 6- or 7-membered saturated heteromonocyclic ring containing 1 or 2 heteroatoms or heteroatom groups selected from N, O, S, NO, SO and $SO_2$, as ring members, a 5-, 6- or 7-membered partially unsaturated heteromonocyclic ring containing 1, 2 or 3 heteroatoms or heteroatom groups selected from N, O, S, NO, SO and $SO_2$, as ring members, and a 5- or 6-membered aromatic heteromonocyclic ring containing 1, 2, 3 or 4 heteroatoms selected from N, O and S as ring members, where the heteromonocyclic ring is optionally substituted with one or more, preferably 1, 2 or 3, in particular 1, substituents $R^{11}$, where $R^{11}$ has one of the above general meanings, or, in particular, one of the below preferred meanings.

$A^4$ is even more preferably selected from rings of formulae D-1 to D-173

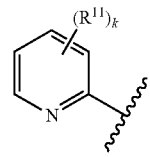 D-1

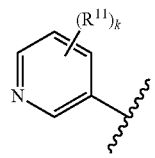 D-2

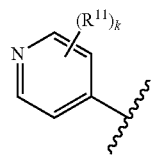 D-3

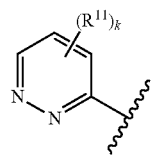 D-4

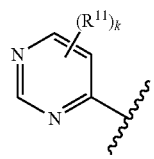 D-5

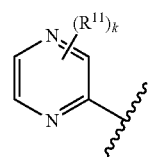 D-6

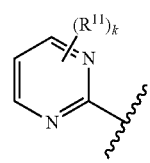 D-7

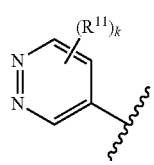 D-8

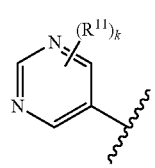 D-9

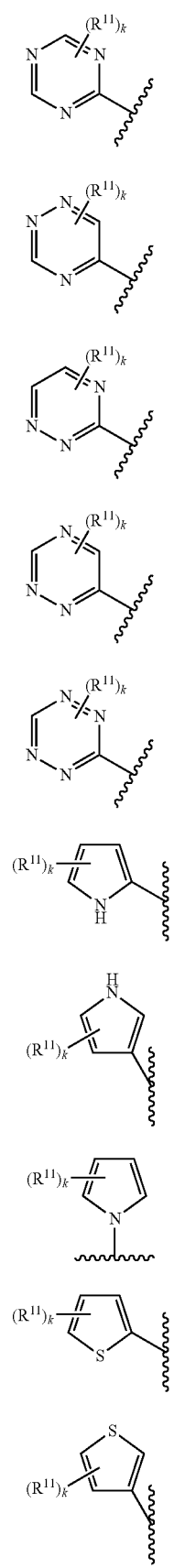
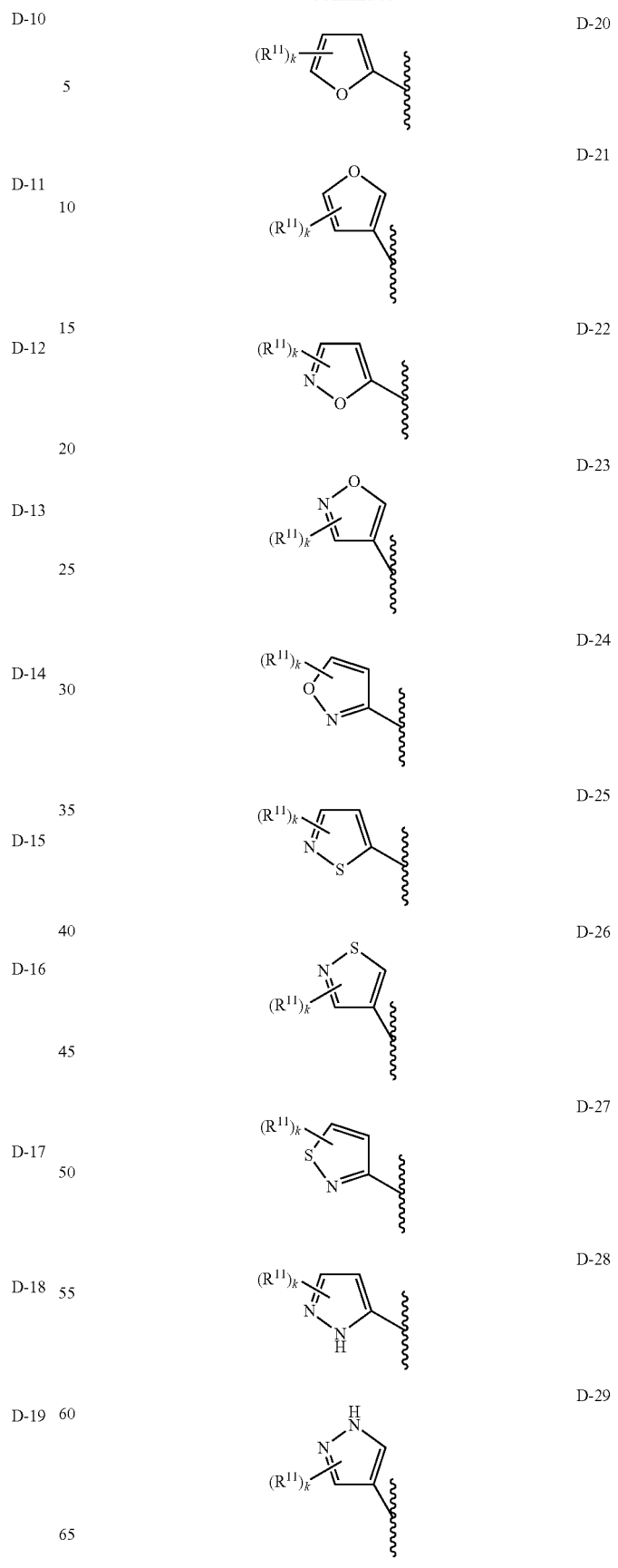

| | |
|---|---|
| 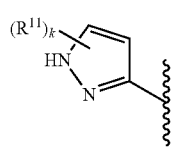 D-30 | 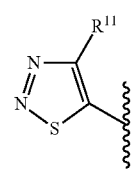 D-40 |
| 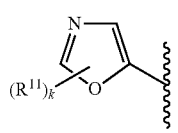 D-31 | 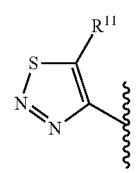 D-41 |
| 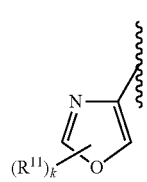 D-32 | 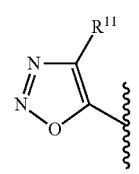 D-42 |
| 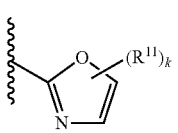 D-33 | 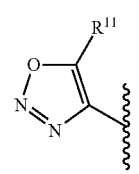 D-43 |
| 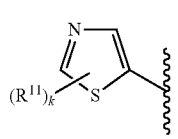 D-34 | 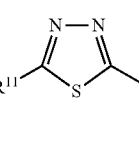 D-44 |
| 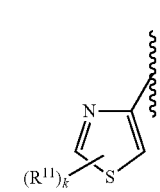 D-35 | 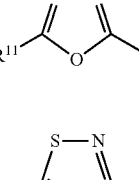 D-45 |
| 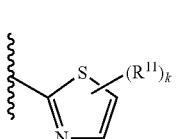 D-36 | 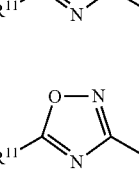 D-46 |
| 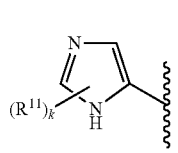 D-37 | 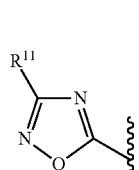 D-47 |
| 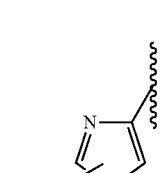 D-38 | 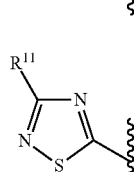 D-48 |
| 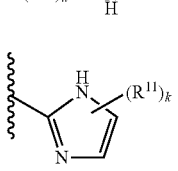 D-39 | D-49 |

-continued
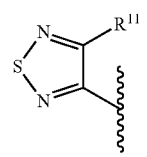 D-50
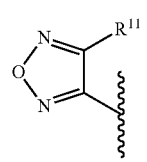 D-51
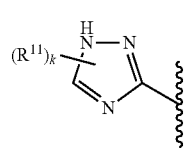 D-52
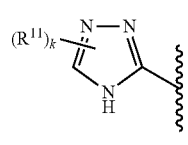 D-53
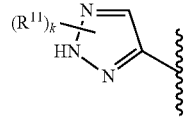 D-54
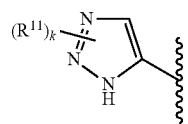 D-55
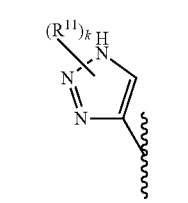 D-56
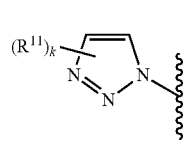 D-57
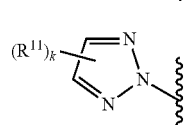 D-58
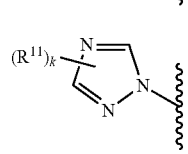 D-59
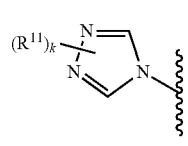 D-60
-continued
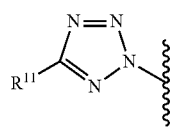 D-61
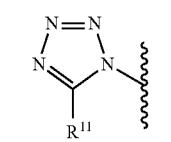 D-62
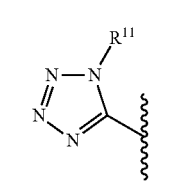 D-63
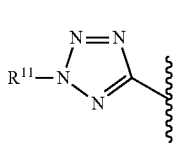 D-64
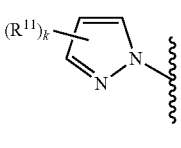 D-65
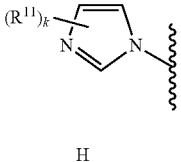 D-66
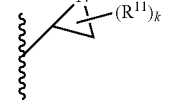 D-67
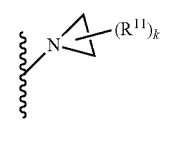 D-68
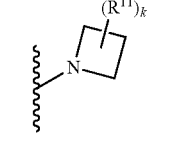 D-69
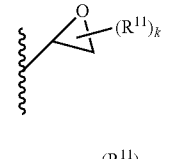 D-70
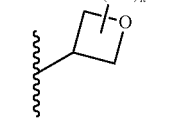 D-71

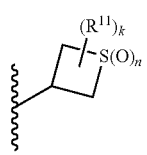 D-72
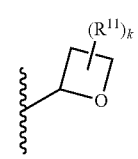 D-73
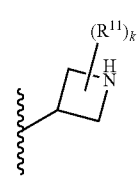 D-74
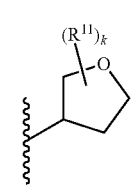 D-75
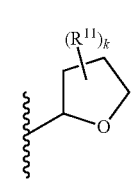 D-76
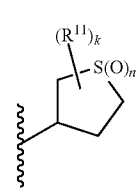 D-77
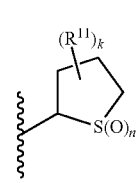 D-78
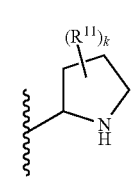 D-79
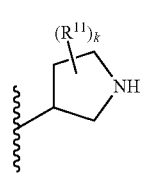 D-80
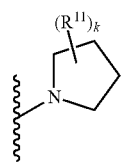 D-81
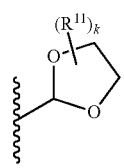 D-82
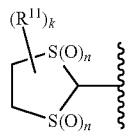 D-83
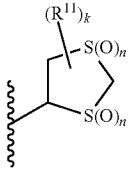 D-84
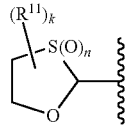 D-85
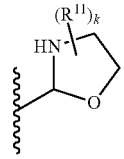 D-86
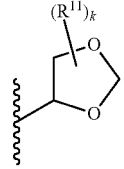 D-87
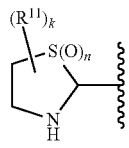 D-88
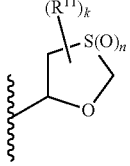 D-89

-continued
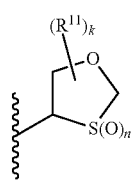 D-90
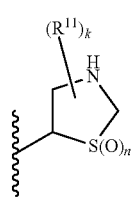 D-91
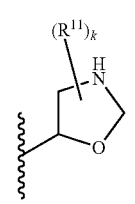 D-92
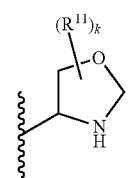 D-93
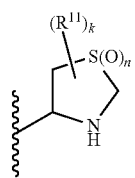 D-94
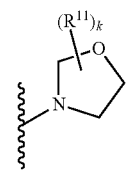 D-95
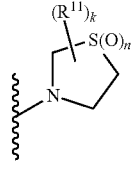 D-96
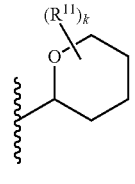 D-97
-continued
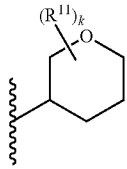 D-98
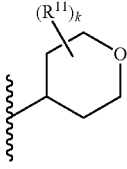 D-99
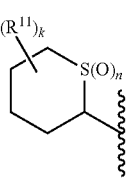 D-100
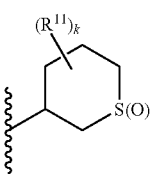 D-101
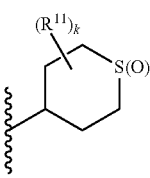 D-102
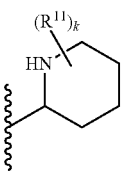 D-103
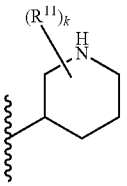 D-104
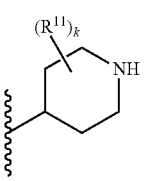 D-105
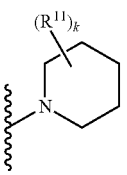 D-106

-continued
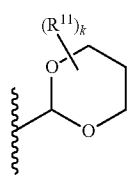
D-107
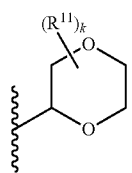
D-108
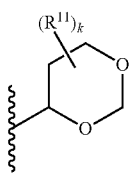
D-109
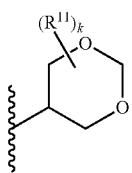
D-110
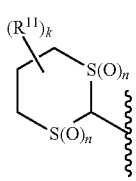
D-111
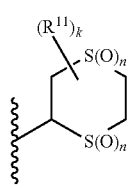
D-112
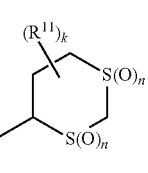
D-113
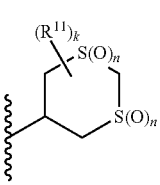
D-114
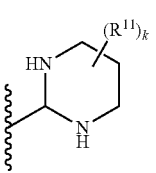
D-115
-continued
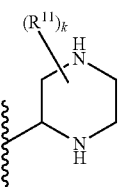
D-116
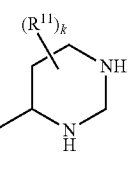
D-117
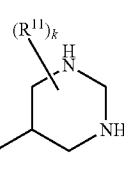
D-118
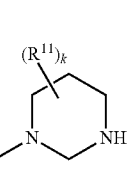
D-119
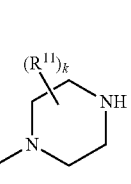
D-120
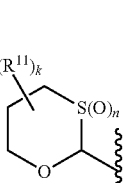
D-121
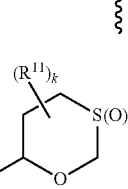
D-122
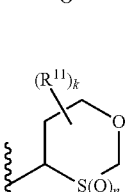
D-123
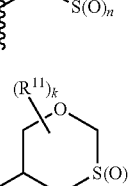
D-124

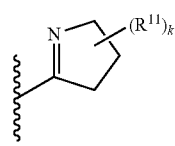 D-125
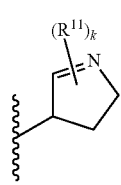 D-126
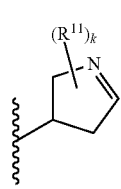 D-127
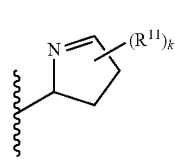 D-128
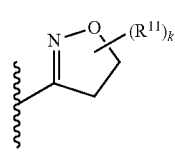 D-129
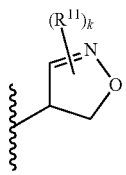 D-130
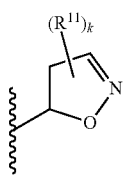 D-131
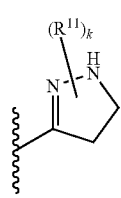 D-132
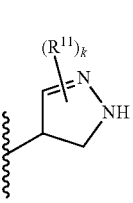 D-133
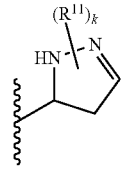 D-134
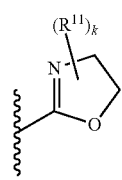 D-135
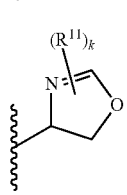 D-136
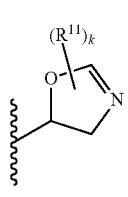 D-137
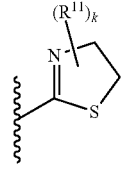 D-138
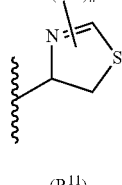 D-139
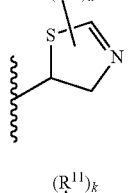 D-140
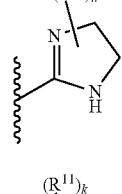 D-141
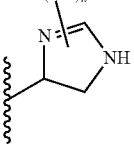 D-142

-continued
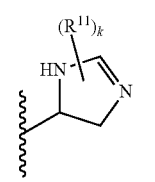 D-143
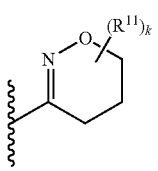 D-144
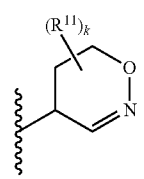 D-145
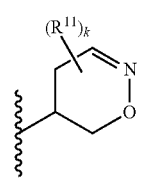 D-146
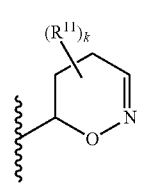 D-147
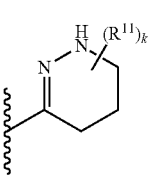 D-148
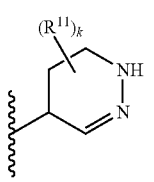 D-149
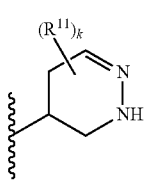 D-150
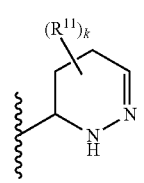 D-151
-continued
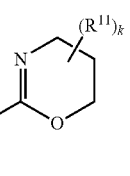 D-152
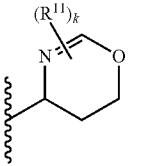 D-153
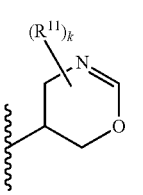 D-154
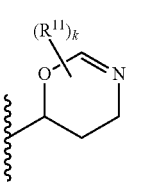 D-155
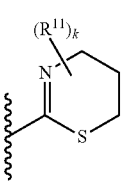 D-156
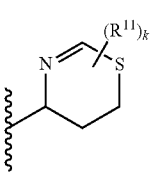 D-157
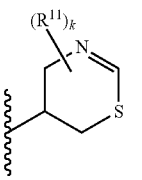 D-158
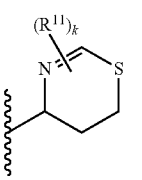 D-159
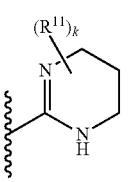 D-160

-continued

D-161 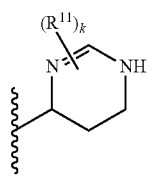

D-162 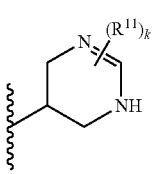

D-163 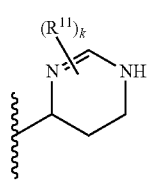

D-164 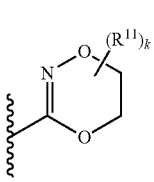

D-165 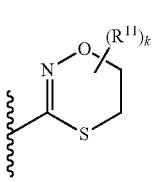

D-166 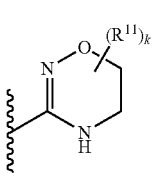

D-167 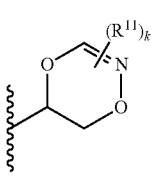

D-168 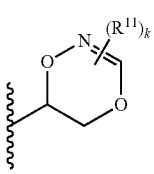

D-169 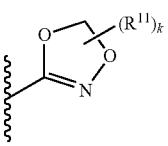

-continued

D-170 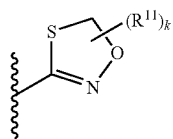

D-171 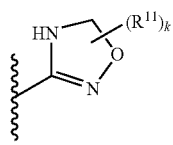

D-172 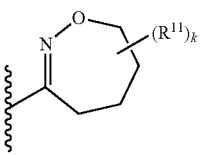

D-173 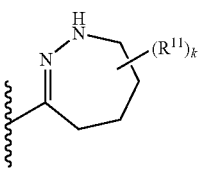

wherein k is 0, 1, 2 or 3, n is 0, 1 or 2 and $R^{11}$ has one of the above general meanings, or, in particular, one of the below preferred meanings;
and is in particular selected from D-59, D-65 and D-66 and is specifically D-59.

Preferably, in the above rings D-1 to D-173,
each $R^{11}$ is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylcarbonyl, $C_1$-$C_4$-haloalkylcarbonyl, aminocarbonyl, $C_1$-$C_4$-alkylaminocarbonyl and di-($C_1$-$C_4$-alkyl)-aminocarbonyl; or
two $R^{11}$ present on the same carbon atom of a saturated or partially unsaturated ring may form together =O or =S.

Among the radicals $A^1$, $A^2$, $A^3$ and $A^4$, preference is given to $A^2$.

Preferably, $B^1$, $B^2$ and $B^3$ are $CR^2$.

More preferably, $B^1$ is $CR^2$, where $R^2$ is not hydrogen, and $B^2$ and $B^3$ are $CR^2$, where $R^2$ has one of the above general meanings or, in particular, one of the below preferred meanings.

Preferably, $R^2$ is selected from hydrogen, halogen, cyano, azido, nitro, —SCN, —SF$_5$, $C_1$-$C_6$-alkyl, $C_3$-$C_8$-cycloalkyl, $C_2$-$C_6$-alkenyl, $C_2$-$C_6$-alkynyl, wherein the four last mentioned aliphatic and cycloaliphatic radicals may be partially or fully halogenated and/or may be substituted by one or more radicals $R^8$; —$OR^9$, —$S(O)_nR^9$ and —$NR^{10a}R^{10b}$, wherein $R^8$, $R^9$, $R^{10a}$ and $R^{10b}$ have one of the above general meanings, or, in particular, one of the below preferred meanings.

More preferably, $R^2$ is selected from hydrogen, halogen and $C_1$-$C_2$-haloalkyl, preferably from hydrogen, F, Cl, Br and CF$_3$.

Preferably, $R^1$ is selected from $C_1$-$C_4$-alkyl, $C_1$-$C_4$-haloalkyl, $C_1$-$C_4$-alkoxy-$C_1$-$C_4$-alkyl, $C_1$-$C_4$-haloalkoxy-$C_1$-$C_4$-alkyl, $C_3$-$C_6$-cycloalkyl $C_3$-$C_6$-halocycloalkyl or C(=O)$OR^{13}$; more preferably, from $C_1$-$C_4$-alkyl, $C_1$-$C_4$-haloalkyl, $C_3$-$C_6$-cycloalkyl, $C_3$-$C_6$-halocycloalkyl and C(=O)$OR^{15}$, even more preferably from $C_1$-$C_4$-alkyl, $C_1$-$C_4$-haloalkyl and —C(=O)$OR^{15}$, and particularly preferably from $C_1$-$C_4$-haloalkyl and —C(=O)$OR^{15}$, wherein $R^{15}$ is preferably $C_1$-$C_4$-alkyl. In particular, $R^1$ is $C_1$-$C_4$-haloalkyl, specifically $C_1$-$C_2$-haloalkyl and more specifically halomethyl, in particular fluoromethyl, such as fluoromethyl, difluoromethyl and trifluoromethyl, and is very specifically trifluoromethyl.

Preferably, $R^{3a}$ and $R^{3b}$ are selected, independently of each other, from hydrogen, halogen, hydroxyl, $C_1$-$C_3$-alkyl, $C_1$-$C_3$-alkenyl, $C_1$-$C_3$-alkynyl, $C_1$-$C_3$-haloalkyl, $C_1$-$C_3$-alkoxy, $C_1$-$C_3$-alkylthio and $C_1$-$C_3$-alkylsulfonyl, more preferably from hydrogen and halogen, in particular from hydrogen and fluorine and are specifically hydrogen.

Preferably, $R^{3a}$ and $R^{3b}$ are selected, independently of each other, from hydrogen, halogen, cyano, $C_1$-$C_4$-alkyl, $C_1$-$C_4$-haloalkyl, $C_3$-$C_5$-cycloalkyl, $C_3$-$C_5$-halocycloalkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkoxy, $C_1$-$C_4$-haloalkoxy, $C_1$-$C_4$-alkylthio and $C_1$-$C_4$-haloalkylthio. More preferably, $R^{4a}$ is hydrogen and $R^{4b}$ is selected from methyl, trifluoromethyl, F, Cl and Br.

If not specified otherwise above, $R^8$, $R^9$, $R^{10a}$, $R^{10b}$, $R^{11}$, $R^{12}$, $R^{13}$, $R^{15}$ and $R^{16}$ have following preferred meanings:

In case $R^8$ is a substituent on an alkyl, alkenyl or alkynyl group, it is preferably selected from the group consisting of cyano, $C_3$-$C_8$-cycloalkyl, $C_3$-$C_8$-halocycloalkyl, —$OR^9$, —$SR^9$, —C(=O)N($R^{10a}$)$R^{10b}$, —C(=S)N($R^{10a}$)$R^{10b}$, —C(=O)$OR^9$, phenyl which may be substituted by 1, 2, 3, 4 or 5 radicals $R^{16}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{16}$; where $R^9$, $R^{10a}$, $R^{10b}$ and $R^{16}$ have one of the meanings given above or in particular one of the preferred meanings given below.

In case $R^8$ is a substituent on an alkyl, alkenyl or alkynyl group, it is even more preferably selected from the group consisting of cyano, $C_3$-$C_6$-cycloalkyl, $C_3$-$C_6$-halocycloalkyl, $C_1$-$C_4$-alkoxy, $C_1$-$C_4$-haloalkoxy, $C_1$-$C_4$-alkylthio, $C_1$-$C_4$-haloalkylthio, —C(=O)N($R^{10a}$)$R^{10b}$, —C(=S)N($R^{10a}$)$R^{10b}$, —C(=O)$OR^9$, phenyl which may be substituted by 1, 2, 3, 4 or 5 radicals $R^{16}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{16}$; where $R^9$, $R^{10a}$, $R^{10b}$ and $R^{16}$ have one of the meanings given above or in particular one of the preferred meanings given below. In particular it is selected from the group consisting of cyano, $C_3$-$C_6$-cycloalkyl, $C_3$-$C_6$-halocycloalkyl, —C(=O)N($R^{10a}$)$R^{10b}$, —C(=S)N($R^{10a}$)$R^{10b}$, —C(=O)$OR^9$, phenyl which may be substituted by 1, 2, 3, 4 or 5 radicals $R^{16}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{16}$; where $R^9$, $R^{10a}$, $R^{10b}$ and $R^{16}$ have one of the meanings given above or in particular one of the preferred meanings given below.

In case $R^8$ is a substituent on a cycloalkyl group, it is preferably selected from the group consisting of cyano, $C_1$-$C_6$-alkyl, $C_1$-$C_6$-haloalkyl, $C_1$-$C_6$-alkoxy-$C_1$-$C_6$-alkyl, —$OR^9$, —$OSO_2R^9$, —$SR^9$, —N($R^{10a}$)$R^{10b}$, —C(=S)N($R^{10a}$)$R^{10b}$, —C(=O)$OR^9$, phenyl which may be substituted by 1, 2, 3, 4 or 5 radicals $R^{16}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{16}$; where $R^9$, $R^{10a}$, $R^{10b}$ and $R^{16}$ have one of the meanings given above or in particular one of the preferred meanings given below.

In case $R^8$ is a substituent on a cycloalkyl group, it is even more preferably selected from the group consisting of cyano, $C_1$-$C_4$-alkyl, $C_1$-$C_3$-haloalkyl, $C_1$-$C_4$-alkoxy and $C_1$-$C_3$-haloalkoxy. In particular, $R^6$ as a substituent on a cycloalkyl group is selected from cyano, $C_1$-$C_4$-alkyl and $C_1$-$C_3$-haloalkyl.

In case of $R^8$ in a group —C(=O)$R^8$, =C($R^8$)$_2$ or —C(=N$R^6$)$R^8$, $R^8$ is preferably selected from the group consisting of hydrogen, $C_1$-$C_6$-alkyl, $C_1$-$C_6$-haloalkyl, $C_1$-$C_6$-alkoxy-$C_1$-$C_6$-alkyl, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, —$OR^9$, —$SR^9$, —N($R^{10a}$)$R^{10b}$, phenyl which may be substituted by 1, 2, 3, 4 or 5 radicals $R^{16}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{16}$; where $R^9$, $R^{10a}$, $R^{10b}$ and $R^{16}$ have one of the meanings given above or in particular one of the preferred meanings given below.

In case of $R^8$ in a group —C(=O)$R^8$, =C($R^8$)$_2$ or —C(=N$R^6$)$R^8$, $R^8$ is more preferably selected from the group consisting of $C_1$-$C_6$-alkyl, $C_1$-$C_6$-haloalkyl, $C_3$-$C_8$-cycloalkyl, $C_3$-$C_8$-halocycloalkyl, $C_1$-$C_6$-alkoxy, $C_1$-$C_6$-haloalkoxy, —N($R^{10a}$)$R^{10b}$, phenyl which may be substituted by 1, 2, 3, 4 or 5 radicals $R^{16}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{16}$; where $R^{10a}$, $R^{10b}$ and $R^{16}$ have has one of the meanings given above or in particular one of the preferred meanings given below.

Preferably, each $R^9$ is independently selected from the group consisting of hydrogen, $C_1$-$C_6$-alkyl, $C_1$-$C_6$-haloalkyl, $C_3$-$C_8$-cycloalkyl, $C_3$-$C_8$-halocycloalkyl, $C_3$-$C_8$-cycloalkyl-$C_1$-$C_4$-alkyl, phenyl which may be substituted by 1, 2, 3, 4 or 5 radicals $R^{16}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{16}$, where $R^{16}$ has one of the meanings given above or in particular one of the preferred meanings given below.

More preferably, each $R^9$ is independently selected from the group consisting of hydrogen, $C_1$-$C_6$-alkyl, $C_1$-$C_6$-haloalkyl, phenyl which may be substituted by 1, 2, 3, 4 or 5 radicals $R^{16}$; and a 5- or 6-membered heteroaromatic ring containing 1, 2 or 3 heteroatoms selected from N, O and S, as ring members, where the heteroaromatic ring may be substituted by one or more radicals $R^{16}$; where $R^{16}$ has one of the meanings given above or in particular one of the preferred meanings given below.

$R^{10a}$ and $R^{10b}$, are, independently of each other, preferably selected from hydrogen, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $C_1$-$C_4$-alkylcarbonyl, $C_1$-$C_4$-haloalkylcarbonyl, $C_1$-$C_4$-alkylaminocarbonyl, $C_1$-$C_4$-haloalkylaminocarbonyl, $C_3$-$C_6$-cycloalkylaminocarbonyl, $C_3$-$C_6$-halocycloalkylaminocarbonyl, and a 3-, 4-, 5-, 6- or 7-membered saturated, partially unsaturated or maximally unsaturated heterocyclic ring comprising 1, 2 or 3 heteroatoms or heteroatom groups selected from N, O, S, NO, SO and $SO_2$, as ring members, where the heterocyclic ring is optionally substituted with one or more, preferably 1, 2 or 3, in particular 1, substituents selected from halogen, CN, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $C_1$-$C_4$-alkoxy, $C_1$-$C_4$-haloalkoxy, $C_1$-$C_4$-alkylthio and $C_1$-$C_4$-haloalkylthio;

or, $R^{10a}$ and $R^{10b}$, together with the nitrogen atom to which they are bound, form a 5- or 6-membered saturated, partially unsaturated or aromatic heterocyclic ring, which additionally may contain 1 or 2 further heteroatoms or heteroatom groups selected from N, O, S, NO, SO and $SO_2$, as ring members, where the heterocyclic ring may carry 1 or 2, in particular 1, substituents selected from halogen, CN, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $C_1$-$C_4$-alkoxy, $C_1$-$C_4$-haloalkoxy, $C_1$-$C_4$-alkylthio and $C_1$-$C_4$-haloalkylthio.

More preferably, $R^{10a}$ and $R^{10b}$ are, independently of each other, selected from hydrogen, $C_1$-$C_4$-alkyl, $C_1$-$C_4$-haloalkyl, $C_3$-$C_6$-cycloalkyl, $C_3$-$C_6$-halocycloalkyl, and a 3- or 4-membered saturated heterocyclic ring comprising 1 heteroatom or heteroatom group selected from N, O, S, NO, SO and $SO_2$, as ring member, where the heterocyclic ring is optionally substituted with one or more, preferably 1, 2 or 3, in particular 1, substituents selected from halogen, CN, $C_1$-$C_4$-alkyl, $C_1$-$C_4$-haloalkyl, $C_1$-$C_4$-alkoxy and $C_1$-$C_4$-haloalkoxy; and are specifically, independently of each other, selected from hydrogen, $C_1$-$C_4$-alkyl and $C_1$-$C_4$-haloalkyl.

Each $R^{11}$ and each $R^{16}$ are independently of each occurrence and independently of each other preferably selected from halogen, CN, $C_1$-$C_4$-alkyl, $C_1$-$C_4$-haloalkyl, $C_1$-$C_4$-alkoxy, $C_1$-$C_4$-haloalkoxy, $C_1$-$C_4$-aralkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl and $C_1$-$C_4$-haloalkylsulfonyl, and more preferably from halogen, CN, $C_1$-$C_4$-alkyl, $C_1$-$C_4$-haloalkyl, $C_1$-$C_4$-alkoxy and $C_1$-$C_4$-haloalkoxy.

Each $R^{12}$ is preferably selected from $C_1$-$C_4$-alkyl and is in particular methyl.

In case $R^{13}$ is a substituent on an alkyl, alkenyl or alkynyl group, it is preferably selected from the group consisting of cyano, $C_3$-$C_8$-cycloalkyl, $C_3$-$C_8$-halocycloalkyl, —OH, —SH, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl and phenyl which may be substituted by 1, 2 or 3 radicals selected from halogen, $C_1$-$C_4$-alkyl, $C_1$-$C_4$-haloalkyl, $C_1$-$C_4$-alkoxy and $C_1$-$C_4$-haloalkoxy.

In case $R^{13}$ is a substituent on a cycloalkyl group, it is preferably selected from the group consisting of cyano, $C_1$-$C_6$-alkyl, $C_1$-$C_6$-haloalkyl, $C_3$-$C_8$-cycloalkyl, $C_3$-$C_8$-halocycloalkyl, —OH, —SH, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl and phenyl which may be substituted by 1, 2 or 3 radicals selected from halogen, $C_1$-$C_4$-alkyl, $C_1$-$C_4$-haloalkyl, $C_1$-$C_4$-alkoxy and $C_1$-$C_4$-haloalkoxy.

In case $R^{13}$ is a substituent on a cycloalkyl group, it is even more preferably selected from the group consisting of halogen, $C_1$-$C_4$-alkyl, $C_1$-$C_3$-haloalkyl, $C_1$-$C_4$-alkoxy and $C_1$-$C_3$-haloalkoxy. In particular, $R^{13}$ as a substituent on a cycloalkyl group is selected from halogen, $C_1$-$C_4$-alkyl and $C_1$-$C_3$-haloalkyl.

In case of $R^{13}$ in a group —C(=O)$R^{13}$, —C(=S)$R^{13}$, =C($R^{13}$)$_2$ or —C(=N$R^{14}$)$R^{13}$, $R^8$ is preferably selected from the group consisting of hydrogen, $C_1$-$C_6$-alkyl, $C_1$-$C_6$-haloalkyl, $C_3$-$C_8$-cycloalkyl, $C_3$-$C_8$-halocycloalkyl, —OH, —SH, $C_1$-$C_6$-alkoxy, $C_1$-$C_6$-haloalkoxy and phenyl which may be substituted by 1, 2 or 3 radicals selected from halogen, $C_1$-$C_4$-alkyl, $C_1$-$C_4$-haloalkyl, $C_1$-$C_4$-alkoxy and $C_1$-$C_4$-haloalkoxy.

$R^{14}$, $R^{14a}$ and $R^{14b}$ are, independently of each other, preferably selected from hydrogen, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl and benzyl, where the phenyl ring in benzyl is optionally substituted 1, 2 or 3, in particular 1, substituents selected from halogen, $C_1$-$C_4$-alkyl, $C_1$-$C_4$-haloalkyl, $C_1$-$C_4$-alkoxy and $C_1$-$C_4$-haloalkoxy; or, $R^{14a}$ and $R^{14b}$, together with the nitrogen atom to which they are bound, form a 5- or 6-membered saturated, partially unsaturated or aromatic heterocyclic ring, which additionally may contain 1 or 2 further heteroatoms or heteroatom groups selected from N, O, S, NO, SO and $SO_2$, as ring members, where the heterocyclic ring may carry 1 or 2, in particular 1, substituents selected from halogen, $C_1$-$C_4$-alkyl, $C_1$-$C_4$-haloalkyl, $C_1$-$C_4$-alkoxy and $C_1$-$C_4$-haloalkoxy.

More preferably, $R^{14}$, $R^{14a}$ and $R^{14b}$ are, independently of each other, selected from hydrogen, $C_1$-$C_4$-alkyl, $C_1$-$C_4$-haloalkyl, $C_3$-$C_6$-cycloalkyl, $C_3$-$C_6$-halocycloalkyl and benzyl, where the phenyl ring in benzyl is optionally substituted 1, 2 or 3, in particular 1, substituents selected from halogen, $C_1$-$C_4$-alkyl, $C_1$-$C_4$-haloalkyl, $C_1$-$C_4$-alkoxy and $C_1$-$C_4$-haloalkoxy;

or, $R^{14a}$ and $R^{14b}$, together with the nitrogen atom to which they are bound, form a 5- or 6-membered saturated, partially unsaturated or aromatic heterocyclic ring, which additionally may contain 1 or 2 further heteroatoms or heteroatom groups selected from N, O, S, NO, SO and $SO_2$, as ring members, where the heterocyclic ring may carry 1 or 2, in particular 1, substituents selected from halogen, $C_1$-$C_4$-alkyl, $C_1$-$C_4$-haloalkyl, $C_1$-$C_4$-alkoxy and $C_1$-$C_4$-haloalkoxy.

Each $R^{15}$ is preferably selected from hydrogen, $C_1$-$C_6$-alkyl, $C_1$-$C_6$-haloalkyl, phenyl, benzyl, pyridyl and phenoxy, wherein the four last-mentioned radicals may be unsubstituted and/or carry 1, 2 or 3 substituents selected from $C_1$-$C_6$-alkyl, $C_1$-$C_6$-haloalkyl, $C_1$-$C_6$-alkoxy and $C_1$-$C_6$-haloalkoxy.

In a particular embodiment of the invention, compound I is a compound of formula IA

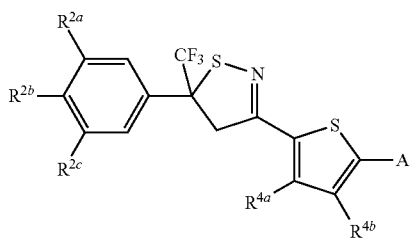
(IA)

where A, $R^{4a}$ and $R^{4b}$ have one of the above-given general or, in particular, one of the above-given preferred meanings, and $R^{2a}$, $R^{2b}$ and $R^{2c}$, independently of each other, have one of the general or, in particular, one of the preferred meanings given above for $R^2$, and where $R^{4a}$ is preferably hydrogen.

Examples of preferred compounds are compounds of the following formulae Ia.1 to Ia.37, where $R^{2a}$, $R^{2b}$ and $R^{2c}$ have one of the general or preferred meanings given above for $R^2$ and the other variables have one of the general or preferred meanings given above. Examples of preferred compounds are the individual compounds compiled in the tables 1 to 4376 below, Moreover, the meanings mentioned below for the individual variables in the tables are per se, independently of the combination in which they are mentioned, a particularly preferred embodiment of the substituents in question.

(Ia.1)

(Ia.2)

(Ia.3)

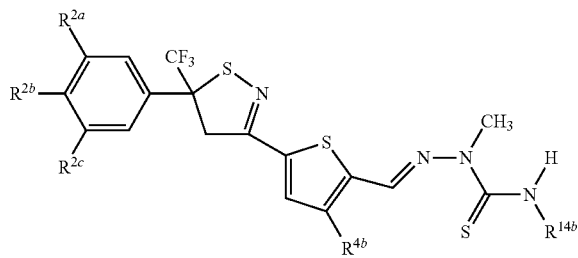
(Ia.4)

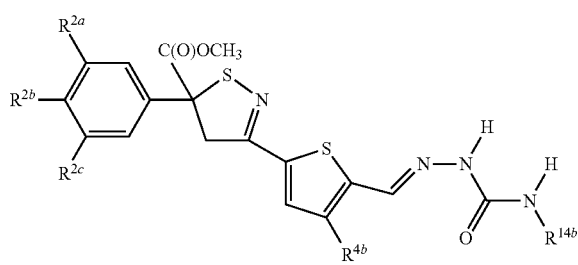
(Ia.5)

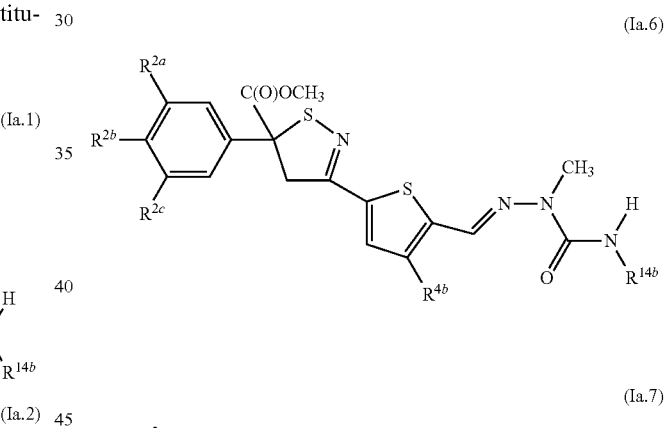
(Ia.6)

(Ia.7)

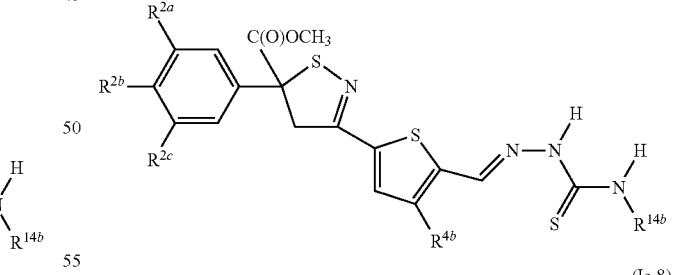
(Ia.8)

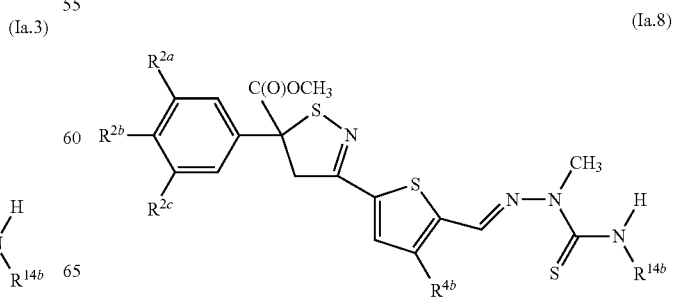

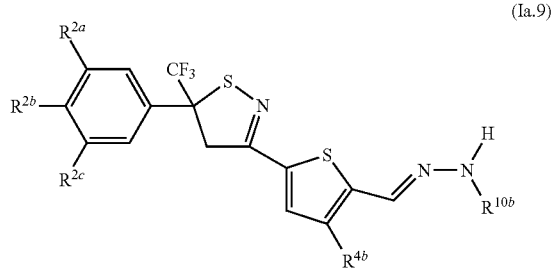
(Ia.9)
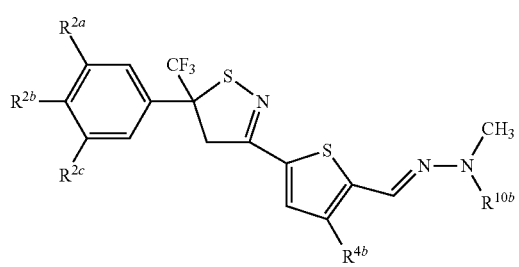
(Ia.10)
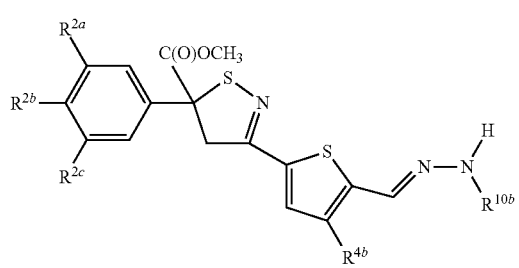
(Ia.11)
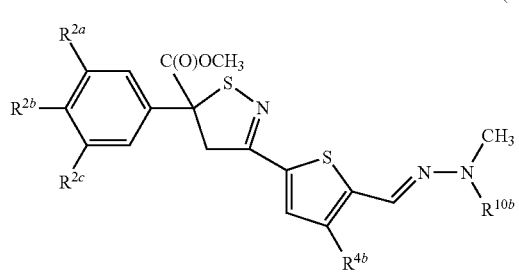
(Ia.12)
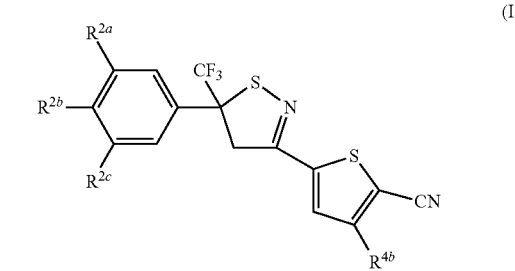
(Ia.13)
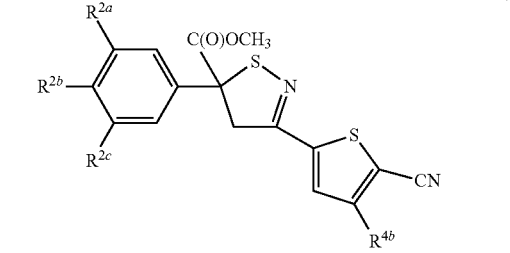
(Ia.14)
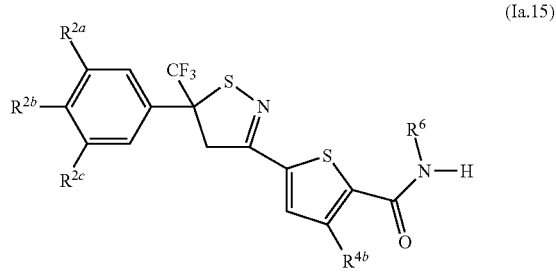
(Ia.15)
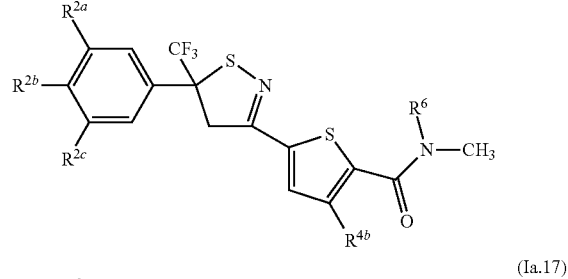
(Ia.16)
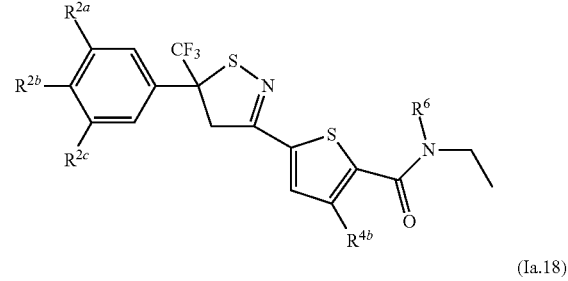
(Ia.17)
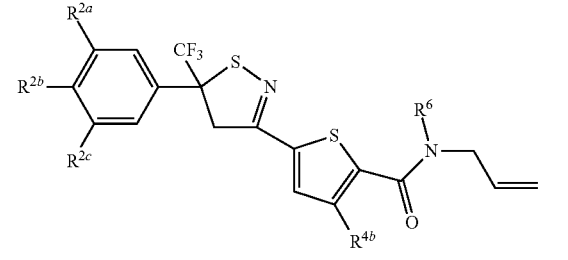
(Ia.18)
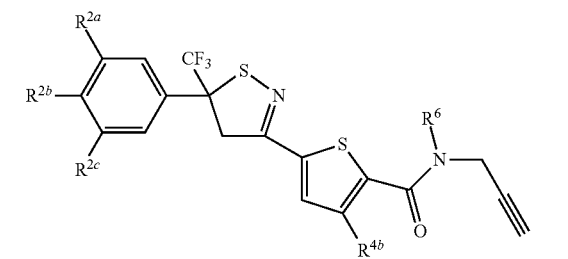
(Ia.19)
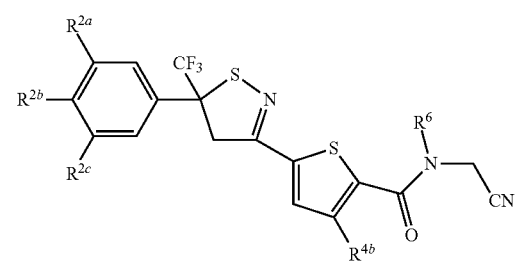
(Ia.20)

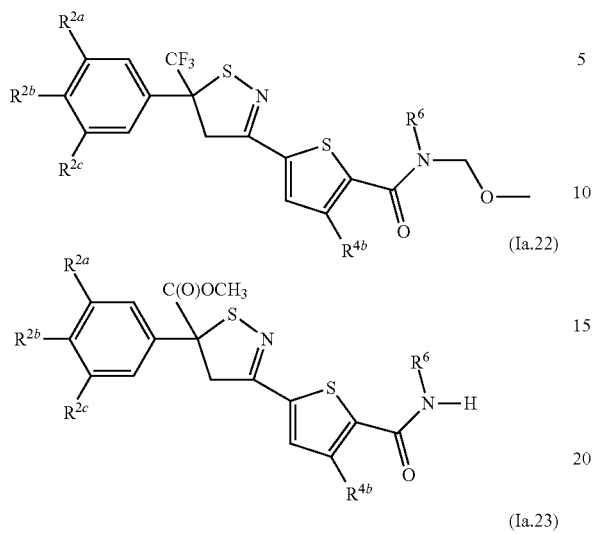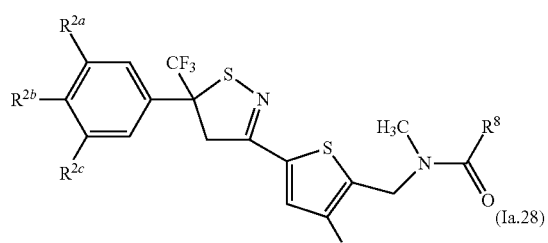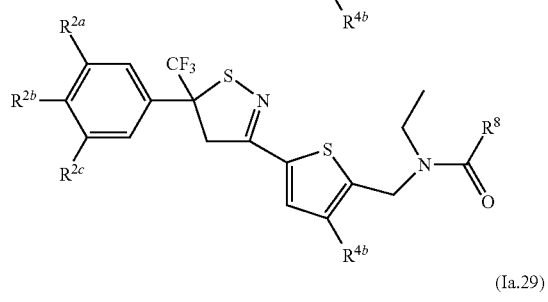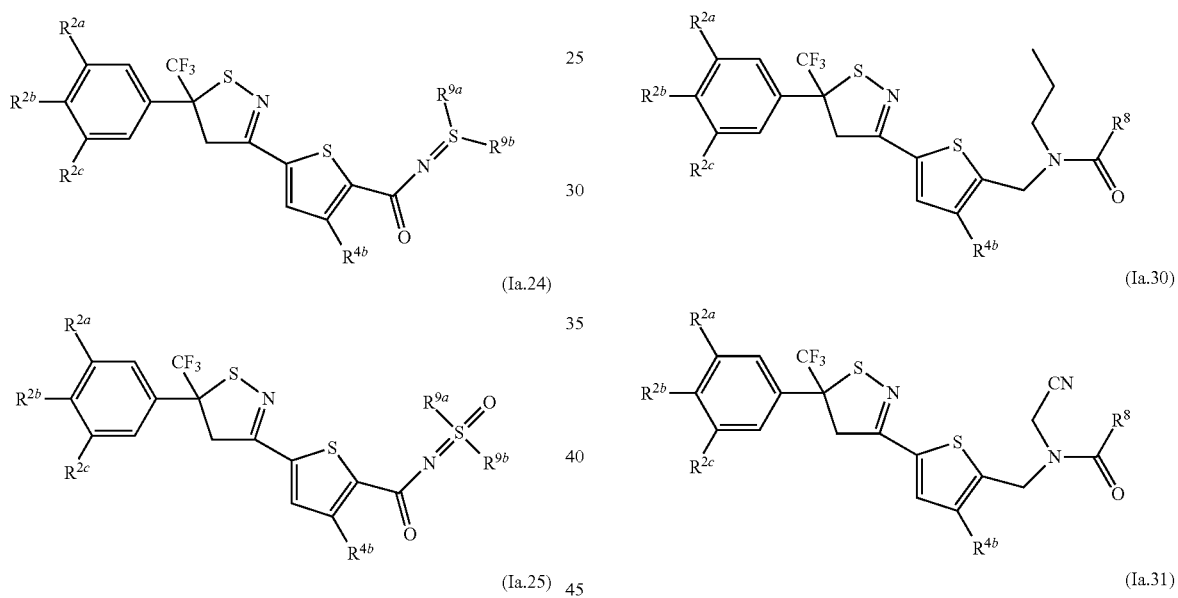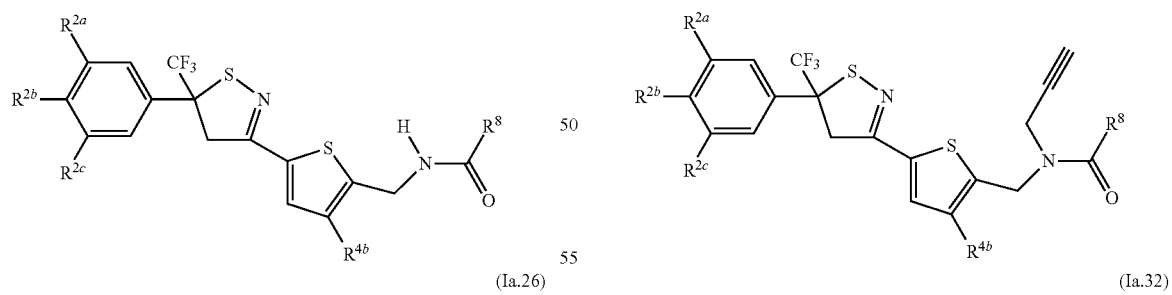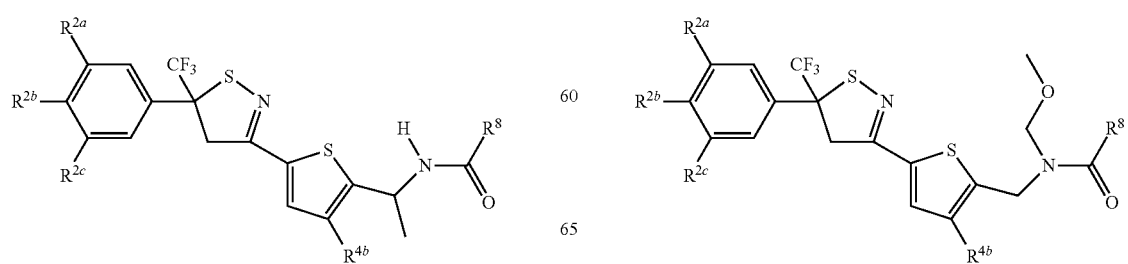

(Ia.33)
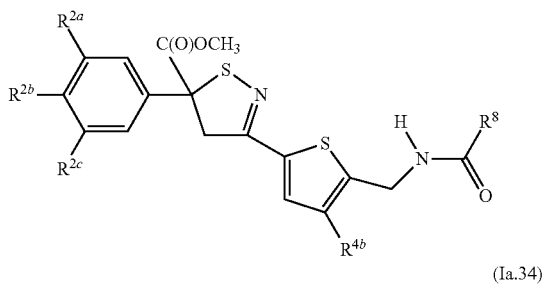

(Ia.34)
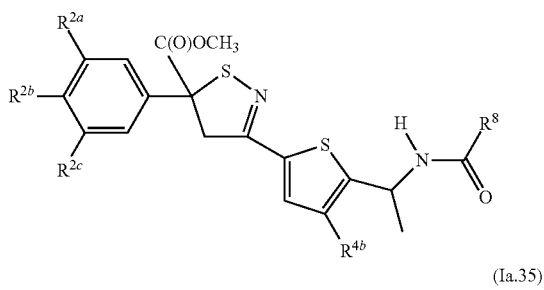

(Ia.35)
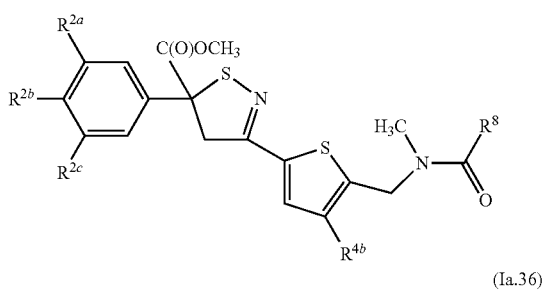

(Ia.36)
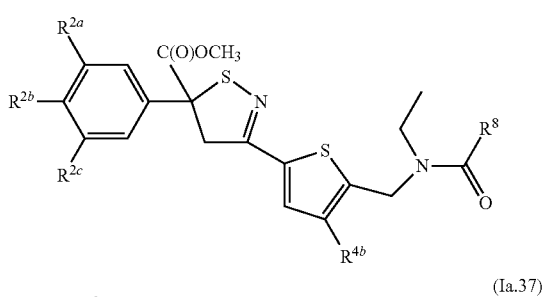

(Ia.37)
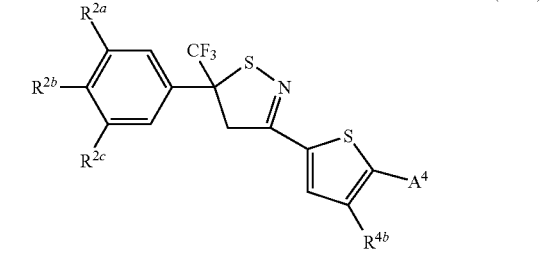

Table 1

Compounds of the formula Ia.1 in which $R^{14b}$ is hydrogen, and the combination of $R^{2a}$, $R^{2b}$, $R^{2c}$ and $R^{4b}$ for a compound corresponds in each case to one row of Table A Table 2

Compounds of the formula Ia.1 in which $R^{14b}$ is methyl, and the combination of $R^{2a}$, $R^{2b}$, $R^{2c}$ and $R^{4b}$ for a compound corresponds in each case to one row of Table A Table 3

Compounds of the formula Ia.1 in which $R^{14b}$ is ethyl, and the combination of $R^{2a}$, $R^{2b}$, $R^{2c}$ and $R^{4b}$ for a compound corresponds in each case to one row of Table A Table 4

Compounds of the formula Ia.1 in which $R^{14b}$ is propyl, and the combination of $R^{2a}$, $R^{2b}$, $R^{2c}$ and $R^{4b}$ for a compound corresponds in each case to one row of Table A Table 5

Compounds of the formula Ia.1 in which $R^{14b}$ is isopropyl, and the combination of $R^{2a}$, $R^{2b}$, $R^{2c}$ and $R^{4b}$ for a compound corresponds in each case to one row of Table A Table 6

Compounds of the formula Ia.1 in which $R^{14b}$ is n-butyl, and the combination of $R^{2a}$, $R^{2b}$, $R^{2c}$ and $R^{4b}$ for a compound corresponds in each case to one row of Table A Table 7

Compounds of the formula Ia.1 in which $R^{14b}$ is sec-butyl, and the combination of $R^{2a}$, $R^{2b}$, $R^{2c}$ and $R^{4b}$ for a compound corresponds in each case to one row of Table A Table 8

Compounds of the formula Ia.1 in which $R^{14b}$ is isobutyl, and the combination of $R^{2a}$, $R^{2b}$, $R^{2c}$ and $R^{4b}$ for a compound corresponds in each case to one row of Table A Table 9

Compounds of the formula Ia.1 in which $R^{14b}$ is tert-butyl, and the combination of $R^{2a}$, $R^{2b}$, $R^{2c}$ and $R^{4b}$ for a compound corresponds in each case to one row of Table A Table 10

Compounds of the formula Ia.1 in which $R^{14b}$ is 2,2-difluoroethyl, and the combination of $R^{2a}$, $R^{2b}$, $R^{2c}$ and $R^{4b}$ for a compound corresponds in each case to one row of Table A Table 11

Compounds of the formula Ia.1 in which $R^{14b}$ is 2,2,2-trifluoroethyl, and the combination of $R^{2a}$, $R^{2b}$, $R^{2c}$ and $R^{4b}$ for a compound corresponds in each case to one row of Table A Table 12

Compounds of the formula Ia.1 in which $R^{14b}$ is 3,3,3-trifluoropropyl, and the combination of $R^{2a}$, $R^{2b}$, $R^{2c}$ and $R^{4b}$ for a compound corresponds in each case to one row of Table A Table 13

Compounds of the formula Ia.1 in which $R^{14b}$ is allyl, and the combination of $R^{2a}$, $R^{2b}$, $R^{2c}$ and $R^{4b}$ for a compound corresponds in each case to one row of Table A Table 14

Compounds of the formula Ia.1 in which $R^{14b}$ is propargyl, and the combination of $R^{2a}$, $R^{2b}$, $R^{2c}$ and $R^{4b}$ for a compound corresponds in each case to one row of Table A Table 15

Compounds of the formula Ia.1 in which $R^{14b}$ is cyclopropyl, and the combination of $R^{2a}$, $R^{2b}$, $R^{2c}$ and $R^{4b}$ for a compound corresponds in each case to one row of Table A Table 16

Compounds of the formula Ia.1 in which $R^{14b}$ is 1-cyanocyclopropyl, and the combination of $R^{2a}$, $R^{2b}$, $R^{2c}$ and $R^{4b}$ for a compound corresponds in each case to one row of Table A Table 17

Compounds of the formula Ia.1 in which $R^{14b}$ is cyclobutyl, and the combination of $R^{2a}$, $R^{2b}$, $R^{2c}$ and $R^{4b}$ for a compound corresponds in each case to one row of Table A Table 18

Compounds of the formula Ia.1 in which $R^{14b}$ is 1-cyanocyclobutyl, and the combination of $R^{2a}$, $R^{2b}$, $R^{2c}$ and $R^{4b}$ for a compound corresponds in each case to one row of Table A Table 19

Compounds of the formula Ia.1 in which $R^{14b}$ is cyclopentyl, and the combination of $R^{2a}$, $R^{2b}$, $R^{2c}$ and $R^{4b}$ for a compound corresponds in each case to one row of Table A Table 20

Compounds of the formula Ia.1 in which $R^{14b}$ is 1-cyanocyclopentyl, and the combination of $R^{2a}$, $R^{2b}$, $R^{2c}$ and $R^{4b}$ for a compound corresponds in each case to one row of Table A Table 21

Compounds of the formula Ia.1 in which $R^{14b}$ is $CH_2$—CN, and the combination of $R^{2a}$, $R^{2b}$, $R^{2c}$ and $R^{4b}$ for a compound corresponds in each case to one row of Table A Table 22

Compounds of the formula Ia.1 in which $R^{14b}$ is $CH_2$-cyclopropyl, and the combination of $R^{2a}$, $R^{2b}$, $R^{2c}$ and $R^{4b}$ for a compound corresponds in each case to one row of Table A Table 23

Compounds of the formula Ia.1 in which $R^{14b}$ is $CH_2$-(1-cyanocyclopropyl), and the combination of $R^{2a}$, $R^{2b}$, $R^{2c}$ and $R^{4b}$ for a compound corresponds in each case to one row of Table A Table 24

Compounds of the formula Ia.1 in which $R^{14b}$ is $CH_2$-cyclobutyl, and the combination of $R^{2a}$, $R^{2b}$, $R^{2c}$ and $R^{4b}$ for a compound corresponds in each case to one row of Table A Table 25

Compounds of the formula Ia.1 in which $R^{14b}$ is $CH_2$-(1-cyanocyclobutyl), and the combination of $R^{2a}$, $R^{2b}$, $R^{2c}$ and $R^{4b}$ for a compound corresponds in each case to one row of Table A Table 26

Compounds of the formula Ia.1 in which $R^{14b}$ is $CH_2$-cyclopentyl, and the combination of $R^{2a}$, $R^{2b}$, $R^{2c}$ and $R^{4b}$ for a compound corresponds in each case to one row of Table A Table 27

Compounds of the formula Ia.1 in which $R^{14b}$ is $CH_2$-(1-cyanocyclopentyl), and the combination of $R^{2a}$, $R^{2b}$, $R^{2c}$ and $R^{4b}$ for a compound corresponds in each case to one row of Table A Table 28

Compounds of the formula Ia.1 in which $R^{14b}$ is methoxy, and the combination of $R^{2a}$, $R^{2b}$, $R^{2c}$ and $R^{4b}$ for a compound corresponds in each case to one row of Table A Table 29

Compounds of the formula Ia.1 in which $R^{14b}$ is ethoxy, and the combination of $R^{2a}$, $R^{2b}$, $R^{2c}$ and $R^{4b}$ for a compound corresponds in each case to one row of Table A Table 30

Compounds of the formula Ia.1 in which $R^{14b}$ is isopropoxy, and the combination of $R^{2a}$, $R^{2b}$, $R^{2c}$ and $R^{4b}$ for a compound corresponds in each case to one row of Table A Tables 31 to 60

Compounds of the formula Ia.2 in which $R^{14b}$ is as defined in any of tables 1 to 30 and the combination of $R^{2a}$, $R^{2b}$, $R^{2c}$ and $R^{4b}$ for a compound corresponds in each case to one row of Table A Tables 61 to 90

Compounds of the formula Ia.3 in which $R^{14b}$ is as defined in any of tables 1 to 30 and the combination of $R^{2a}$, $R^{2b}$, $R^{2c}$ and $R^{4b}$ for a compound corresponds in each case to one row of Table A Tables 91 to 120

Compounds of the formula Ia.4 in which $R^{14b}$ is as defined in any of tables 1 to 30 and the combination of $R^{2a}$, $R^{2b}$, $R^{2c}$ and $R^{4b}$ for a compound corresponds in each case to one row of Table A Tables 121 to 150

Compounds of the formula Ia.5 in which $R^{14b}$ is as defined in any of tables 1 to 30 and the combination of $R^{2a}$, $R^{2b}$, $R^{2c}$ and $R^{4b}$ for a compound corresponds in each case to one row of Table A Tables 151 to 180

Compounds of the formula Ia.6 in which $R^{14b}$ is as defined in any of tables 1 to 30 and the combination of $R^{2a}$, $R^{2b}$, $R^{2c}$ and $R^{4b}$ for a compound corresponds in each case to one row of Table A Tables 181 to 210

Compounds of the formula Ia.7 in which $R^{14b}$ is as defined in any of tables 1 to 30 and the combination of $R^{2a}$, $R^{2b}$, $R^{2c}$ and $R^{4b}$ for a compound corresponds in each case to one row of Table A Tables 211 to 240

Compounds of the formula Ia.8 in which $R^{14b}$ is as defined in any of tables 1 to 30 and the combination of $R^{2a}$, $R^{2b}$, $R^{2c}$ and $R^{4b}$ for a compound corresponds in each case to one row of Table A Table 241

Compounds of the formula Ia.9 in which $R^{10b}$ is phenyl, and the combination of $R^{2a}$, $R^{2b}$, $R^{2c}$ and $R^{4b}$ for a compound corresponds in each case to one row of Table A Table 242

Compounds of the formula Ia.9 in which $R^{10b}$ is 2-fluorophenyl, and the combination of $R^{2a}$, $R^{2b}$, $R^{2c}$ and $R^{4b}$ for a compound corresponds in each case to one row of Table A Table 243

Compounds of the formula Ia.9 in which $R^{10b}$ is 3-fluorophenyl, and the combination of $R^{2a}$, $R^{2b}$, $R^{2c}$ and $R^{4b}$ for a compound corresponds in each case to one row of Table A Table 244

Compounds of the formula Ia.9 in which $R^{10b}$ is 4-fluorophenyl, and the combination of $R^{2a}$, $R^{2b}$, $R^{2c}$ and $R^{4b}$ for a compound corresponds in each case to one row of Table A Table 245

Compounds of the formula Ia.9 in which $R^{10b}$ is 2-chlorophenyl, and the combination of $R^{2a}$, $R^{2b}$, $R^{2c}$ and $R^{4b}$ for a compound corresponds in each case to one row of Table A Table 246

Compounds of the formula Ia.9 in which $R^{10b}$ is 3-chlorophenyl, and the combination of $R^{2a}$, $R^{2b}$, $R^{2c}$ and $R^{4b}$ for a compound corresponds in each case to one row of Table A Table 247

Compounds of the formula Ia.9 in which $R^{4b}$ is 4-chlorophenyl, and the combination of $R^{2a}$, $R^{2b}$, $R^{2c}$ and $R^{4b}$ for a compound corresponds in each case to one row of Table A Table 248

Compounds of the formula Ia.9 in which $R^{10b}$ is 2,3-difluorophenyl, and the combination of $R^{2a}$, $R^{2b}$, $R^{2c}$ and $R^{4b}$ for a compound corresponds in each case to one row of Table A Table 249

Compounds of the formula Ia.9 in which $R^{10b}$ is 2,4-difluorophenyl, and the combination of $R^{2a}$, $R^{2b}$, $R^{2c}$ and $R^{4b}$ for a compound corresponds in each case to one row of Table A
Table 250
Compounds of the formula Ia.9 in which $R^{10b}$ is 2,5-difluorophenyl, and the combination of $R^{2a}$, $R^{2b}$, $R^{2c}$ and $R^{4b}$ for a compound corresponds in each case to one row of Table A
Table 251
Compounds of the formula Ia.9 in which $R^{10b}$ is 2,6-difluorophenyl, and the combination of $R^{2a}$, $R^{2b}$, $R^{2c}$ and $R^{4b}$ for a compound corresponds in each case to one row of Table A
Table 252
Compounds of the formula Ia.9 in which $R^{10b}$ is 3,4-difluorophenyl, and the combination of $R^{2a}$, $R^{2b}$, $R^{2c}$ and $R^{4b}$ for a compound corresponds in each case to one row of Table A
Table 253
Compounds of the formula Ia.9 in which $R^{10b}$ is 3,5-difluorophenyl, and the combination of $R^{2a}$, $R^{2b}$, $R^{2c}$ and $R^{4b}$ for a compound corresponds in each case to one row of Table A
Table 254
Compounds of the formula Ia.9 in which $R^{10b}$ is 2-methylphenyl, and the combination of $R^{2a}$, $R^{2b}$, $R^{2c}$ and $R^{4b}$ for a compound corresponds in each case to one row of Table A
Table 255
Compounds of the formula Ia.9 in which $R^{10b}$ is 3-methylphenyl, and the combination of $R^{2a}$, $R^{2b}$, $R^{2c}$ and $R^{4b}$ for a compound corresponds in each case to one row of Table A
Table 256
Compounds of the formula Ia.9 in which $R^{10b}$ is 4-methylphenyl, and the combination of $R^{2a}$, $R^{2b}$, $R^{2c}$ and $R^{4b}$ for a compound corresponds in each case to one row of Table A
Table 257
Compounds of the formula Ia.9 in which $R^{10b}$ is 2-methoxyphenyl, and the combination of $R^{2a}$, $R^{2b}$, $R^{2c}$ and $R^{4b}$ for a compound corresponds in each case to one row of Table A
Table 258
Compounds of the formula Ia.9 in which $R^{10b}$ is 3-methoxyphenyl, and the combination of $R^{2a}$, $R^{2b}$, $R^{2c}$ and $R^{4b}$ for a compound corresponds in each case to one row of Table A
Table 259
Compounds of the formula Ia.9 in which $R^{10b}$ is 4-methoxyphenyl, and the combination of $R^{2a}$, $R^{2b}$, $R^{2c}$ and $R^{4b}$ for a compound corresponds in each case to one row of Table A
Table 260
Compounds of the formula Ia.9 in which $R^{10b}$ is pyridin-2-yl, and the combination of $R^{2a}$, $R^{2b}$, $R^{2c}$ and $R^{4b}$ for a compound corresponds in each case to one row of Table A
Table 261
Compounds of the formula Ia.9 in which $R^{10b}$ is pyridin-3-yl, and the combination of $R^{2a}$, $R^{2b}$, $R^{2c}$ and $R^{4b}$ for a compound corresponds in each case to one row of Table A
Table 262
Compounds of the formula Ia.9 in which $R^{10b}$ is pyridin-4-yl, and the combination of $R^{2a}$, $R^{2b}$, $R^{2c}$ and $R^{4b}$ for a compound corresponds in each case to one row of Table A
Table 263
Compounds of the formula Ia.9 in which $R^{10b}$ is pyrrol-2-yl, and the combination of $R^{2a}$, $R^{2b}$, $R^{2c}$ and $R^{4b}$ for a compound corresponds in each case to one row of Table A
Table 264
Compounds of the formula Ia.9 in which $R^{10b}$ is pyrrol-3-yl, and the combination of $R^{2a}$, $R^{2b}$, $R^{2c}$ and $R^{4b}$ for a compound corresponds in each case to one row of Table A
Table 265
Compounds of the formula Ia.9 in which $R^{10b}$ is hydrogen, and the combination of $R^{2a}$, $R^{2b}$, $R^{2c}$ and $R^{4b}$ for a compound corresponds in each case to one row of Table A
Table 266
Compounds of the formula Ia.9 in which $R^{10b}$ is methyl, and the combination of $R^{2a}$, $R^{2b}$, $R^{2c}$ and $R^{4b}$ for a compound corresponds in each case to one row of Table A
Table 267
Compounds of the formula Ia.9 in which $R^{10b}$ is ethyl, and the combination of $R^{2a}$, $R^{2b}$, $R^{2c}$ and $R^{4b}$ for a compound corresponds in each case to one row of Table A
Table 268
Compounds of the formula Ia.9 in which $R^{10b}$ is propyl, and the combination of $R^{2a}$, $R^{2b}$, $R^{2c}$ and $R^{4b}$ for a compound corresponds in each case to one row of Table A
Table 269
Compounds of the formula Ia.9 in which $R^{10b}$ is isopropyl, and the combination of $R^{2a}$, $R^{2b}$, $R^{2c}$ and $R^{4b}$ for a compound corresponds in each case to one row of Table A
Table 270
Compounds of the formula Ia.9 in which $R^{10b}$ is methylcarbonyl, and the combination of $R^{2a}$, $R^{2b}$, $R^{2c}$ and $R^{4b}$ for a compound corresponds in each case to one row of Table A
Table 271
Compounds of the formula Ia.9 in which $R^{10b}$ is ethylcarbonyl, and the combination of $R^{2a}$, $R^{2b}$, $R^{2c}$ and $R^{4b}$ for a compound corresponds in each case to one row of Table A
Table 272
Compounds of the formula Ia.9 in which $R^{10b}$ is isopropylcarbonyl, and the combination of $R^{2a}$, $R^{2b}$, $R^{2c}$ and $R^{4b}$ for a compound corresponds in each case to one row of Table A
Table 273
Compounds of the formula Ia.9 in which $R^{10b}$ is methoxycarbonyl, and the combination of $R^{2a}$, $R^{2b}$, $R^{2c}$ and $R^{4b}$ for a compound corresponds in each case to one row of Table A
Table 274
Compounds of the formula Ia.9 in which $R^{10b}$ is ethoxycarbonyl, and the combination of $R^{2a}$, $R^{2b}$, $R^{2c}$ and $R^{4b}$ for a compound corresponds in each case to one row of Table A
Table 275
Compounds of the formula Ia.9 in which $R^{10b}$ is isopropoxycarbonyl, and the combination of $R^{2a}$, $R^{2b}$, $R^{2c}$ and $R^{4b}$ for a compound corresponds in each case to one row of Table A
Tables 276 to 310
Compounds of the formula Ia.10 in which $R^{10b}$ is as defined in tables 241 to 275, and the combination of $R^{2a}$, $R^{2b}$, $R^{2c}$ and $R^{4b}$ for a compound corresponds in each case to one row of Table A
Tables 311 to 345
Compounds of the formula Ia.11 in which $R^{10b}$ is as defined in tables 241 to 275, and the combination of $R^{2a}$, $R^{2b}$, $R^{2c}$ and $R^{4b}$ for a compound corresponds in each case to one row of Table A
Tables 346 to 380
Compounds of the formula Ia.12 in which $R^{10b}$ is as defined in tables 241 to 275, and the combination of $R^{2a}$, $R^{2b}$, $R^{2c}$ and $R^{4b}$ for a compound corresponds in each case to one row of Table A Table 381
Compounds of the formula Ia.13 in which the combination of $R^{2a}$, $R^{2b}$, $R^{2c}$ and $R^{4b}$ for a compound corresponds in each case to one row of Table A Table 382
Compounds of the formula Ia.14 in which the combination of $R^{2a}$, $R^{2b}$, $R^{2c}$ and $R^{4b}$ for a compound corresponds in each case to one row of Table A Table 383
Compounds of the formula Ia.15 in which $R^6$ is hydrogen, and the combination of $R^{2a}$, $R^{2b}$, $R^{2c}$ and $R^{4b}$ for a compound corresponds in each case to one row of Table A Table 384
Compounds of the formula Ia.15 in which $R^6$ is methyl, and the combination of $R^{2a}$, $R^{2b}$, $R^{2c}$ and $R^{4b}$ for a compound corresponds in each case to one row of Table A Table 385
Compounds of the formula Ia.15 in which $R^6$ is ethyl, and the combination of $R^{2a}$, $R^{2b}$, $R^{2c}$ and $R^{4b}$ for a compound corresponds in each case to one row of Table A Table 386
Compounds of the formula Ia.15 in which $R^6$ is propyl, and the combination of $R^{2a}$, $R^{2b}$, $R^{2c}$ and $R^{4b}$ for a compound corresponds in each case to one row of Table A Table 387
Compounds of the formula Ia.15 in which $R^6$ is isopropyl, and the combination of $R^{2a}$, $R^{2b}$, $R^{2c}$ and $R^{4b}$ for a compound corresponds in each case to one row of Table A Table 388
Compounds of the formula Ia.15 in which $R^6$ is n-butyl, and the combination of $R^{2a}$, $R^{2b}$, $R^{2c}$ and $R^{4b}$ for a compound corresponds in each case to one row of Table A Table 389
Compounds of the formula Ia.15 in which $R^6$ is sec-butyl, and the combination of $R^{2a}$, $R^{2b}$, $R^{2c}$ and $R^{4b}$ for a compound corresponds in each case to one row of Table A Table 390
Compounds of the formula Ia.15 in which $R^6$ is isobutyl, and the combination of $R^{2a}$, $R^{2b}$, $R^{2c}$ and $R^{4b}$ for a compound corresponds in each case to one row of Table A Table 391
Compounds of the formula Ia.15 in which $R^6$ is tert-butyl, and the combination of $R^{2a}$, $R^{2b}$, $R^{2c}$ and $R^{4b}$ for a compound corresponds in each case to one row of Table A Table 392
Compounds of the formula Ia.15 in which $R^6$ is $CH_2$—$C(CH_3)_3$, and the combination of $R^{2a}$, $R^{2b}$, $R^{2c}$ and $R^{4b}$ for a compound corresponds in each case to one row of Table A Table 393
Compounds of the formula Ia.15 in which $R^6$ is —$CH_2CN$, and the combination of $R^{2a}$, $R^{2b}$, $R^{2c}$ and $R^{4b}$ for a compound corresponds in each case to one row of Table A Table 394
Compounds of the formula Ia.15 in which $R^6$ is —$CH_2$—$CH$=$CH_2$, and the combination of $R^{2a}$, $R^{2b}$, $R^{2c}$ and $R^{4b}$ for a compound corresponds in each case to one row of Table A Table 395
Compounds of the formula Ia.15 in which $R^6$ is —$CH_2$—$CH_2$—$CH$=$CH_2$, and the combination of $R^{2a}$, $R^{2b}$, $R^{2c}$ and $R^{4b}$ for a compound corresponds in each case to one row of Table A Table 396
Compounds of the formula Ia.15 in which $R^6$ is —$CH_2C$≡$CH$, and the combination of $R^{2a}$, $R^{2b}$, $R^{2c}$ and $R^{4b}$ for a compound corresponds in each case to one row of Table A Table 397
Compounds of the formula Ia.15 in which $R^6$ is —$CH_2CH_2C$≡$CH$, and the combination of $R^{2a}$, $R^{2b}$, $R^{2c}$ and $R^{4b}$ for a compound corresponds in each case to one row of Table A Table 398
Compounds of the formula Ia.15 in which $R^6$ is —$CH_2CH_2OH$, and the combination of $R^{2a}$, $R^{2b}$, $R^{2c}$ and $R^{4b}$ for a compound corresponds in each case to one row of Table A Table 399
Compounds of the formula Ia.15 in which $R^6$ is —$CH_2CH_2OCH_3$, and the combination of $R^{2a}$, $R^{2b}$, $R^{2c}$ and $R^{4b}$ for a compound corresponds in each case to one row of Table A Table 400
Compounds of the formula Ia.15 in which $R^6$ is —$CH_2CH_2OCH_2CH_3$, and the combination of $R^{2a}$, $R^{2b}$, $R^{2c}$ and $R^{4b}$ for a compound corresponds in each case to one row of Table A Table 401
Compounds of the formula Ia.15 in which $R^6$ is —$CH_2CH_2OCH_2CH$=$CH_2$, and the combination of $R^{2a}$, $R^{2b}$, $R^{2c}$ and $R^{4b}$ for a compound corresponds in each case to one row of Table A Table 402
Compounds of the formula Ia.15 in which $R^6$ is —$CH_2CH_2OCH_2C$≡$CH$, and the combination of $R^{2a}$, $R^{2b}$, $R^{2c}$ and $R^{4b}$ for a compound corresponds in each case to one row of Table A Table 403
Compounds of the formula Ia.15 in which $R^6$ is —$CH_2CH_2OCH_2$-cyclopropyl, and the combination of $R^{2a}$, $R^{2b}$, $R^{2c}$ and $R^{4b}$ for a compound corresponds in each case to one row of Table A Table 404
Compounds of the formula Ia.15 in which $R^6$ is —$CH_2CH_2OCF_3$, and the combination of $R^{2a}$, $R^{2b}$, $R^{2c}$ and $R^{4b}$ for a compound corresponds in each case to one row of Table A Table 405
Compounds of the formula Ia.15 in which $R^6$ is —$CH_2CH_2OCH_2CF_3$, and the combination of $R^{2a}$, $R^{2b}$, $R^{2c}$ and $R^{4b}$ for a compound corresponds in each case to one row of Table A Table 406
Compounds of the formula Ia.15 in which $R^6$ is —$CH(CH_3)CH_2OCH_3$, and the combination of $R^{2a}$, $R^{2b}$, $R^{2c}$ and $R^{4b}$ for a compound corresponds in each case to one row of Table A Table 407
Compounds of the formula Ia.15 in which $R^6$ is —$CH(CH_3)CH_2OCH_2CH_3$, and the combination of $R^{2a}$, $R^{2b}$, $R^{2c}$ and $R^{4b}$ for a compound corresponds in each case to one row of Table A Table 408
Compounds of the formula Ia.15 in which $R^6$ is —$CH_2CH_2SCH_3$, and the combination of $R^{2a}$, $R^{2b}$, $R^{2c}$ and $R^{4b}$ for a compound corresponds in each case to one row of Table A Table 409
Compounds of the formula Ia.15 in which $R^6$ is —$CH_2CH_2S(O)CH_3$, and the combination of $R^{2a}$, $R^{2b}$, $R^{2c}$ and $R^{4b}$ for a compound corresponds in each case to one row of Table A Table 410
Compounds of the formula Ia.15 in which $R^6$ is —$CH_2CH_2S(O)_2CH_3$, and the combination of $R^{2a}$, $R^{2b}$, $R^{2c}$ and $R^{4b}$ for a compound corresponds in each case to one row of Table A Table 411
Compounds of the formula Ia.15 in which $R^6$ is —$CH_2CH_2SCH_2CH_3$, and the combination of $R^{2a}$, $R^{2b}$, $R^{2c}$ and $R^{4b}$ for a compound corresponds in each case to one row of Table A Table 412
Compounds of the formula Ia.15 in which $R^6$ is —$CH_2CH_2S(O)CH_2CH_3$, and the combination of $R^{2a}$, $R^{2b}$, $R^{2c}$ and $R^{4b}$ for a compound corresponds in each case to one row of Table A Table 413
Compounds of the formula Ia.15 in which $R^6$ is —$CH_2CH_2S(O)_2CH_2CH_3$, and the combination of $R^{2a}$, $R^{2b}$, $R^{2c}$ and $R^{4b}$ for a compound corresponds in each case to one row of Table A Table 414
Compounds of the formula Ia.15 in which $R^6$ is —$CH_2CH_2S(O)_2CH_2CH=CH_2$, and the combination of $R^{2a}$, $R^{2b}$, $R^{2c}$ and $R^{4b}$ for a compound corresponds in each case to one row of Table A Table 415
Compounds of the formula Ia.15 in which $R^6$ is —$CH_2CH_2S(O)_2CH_2C\equiv CH$, and the combination of $R^{2a}$, $R^{2b}$, $R^{2c}$ and $R^{4b}$ for a compound corresponds in each case to one row of Table A Table 416
Compounds of the formula Ia.15 in which $R^6$ is —$CH_2CH_2S(O)_2CH_2$-cyclopropyl, and the combination of $R^{2a}$, $R^{2b}$, $R^{2c}$ and $R^{4b}$ for a compound corresponds in each case to one row of Table A Table 417
Compounds of the formula Ia.15 in which $R^6$ is —$CH(CH_3)CH_2SCH_3$, and the combination of $R^{2a}$, $R^{2b}$, $R^{2c}$ and $R^{4b}$ for a compound corresponds in each case to one row of Table A Table 418
Compounds of the formula Ia.15 in which $R^6$ is —$CH(CH_3)CH_2S(O)CH_3$, and the combination of $R^{2a}$, $R^{2b}$, $R^{2c}$ and $R^{4b}$ for a compound corresponds in each case to one row of Table A Table 419
Compounds of the formula Ia.15 in which $R^6$ is —$CH(CH_3)CH_2S(O)_2CH_3$, and the combination of $R^{2a}$, $R^{2b}$, $R^{2c}$ and $R^{4b}$ for a compound corresponds in each case to one row of Table A Table 420
Compounds of the formula Ia.15 in which $R^6$ is —$C(CH_3)_2 CH_2SCH_3$, and the combination of $R^{2a}$, $R^{2b}$, $R^{2c}$ and $R^{4b}$ for a compound corresponds in each case to one row of Table A Table 421
Compounds of the formula Ia.15 in which $R^6$ is —$C(CH_3)_2 CH_2S(O)CH_3$, and the combination of $R^{2a}$, $R^{2b}$, $R^{2c}$ and $R^{4b}$ for a compound corresponds in each case to one row of Table A Table 422
Compounds of the formula Ia.15 in which $R^6$ is —$C(CH_3)_2 CH_2S(O)_2CH_3$, and the combination of $R^{2a}$, $R^{2b}$, $R^{2c}$ and $R^{4b}$ for a compound corresponds in each case to one row of Table A Table 423
Compounds of the formula Ia.15 in which $R^6$ is —$CH_2CH_2SCF_3$, and the combination of $R^{2a}$, $R^{2b}$, $R^{2c}$ and $R^{4b}$ for a compound corresponds in each case to one row of Table A Table 424
Compounds of the formula Ia.15 in which $R^6$ is $NH_2$, and the combination of $R^{2a}$, $R^{2b}$, $R^{2c}$ and $R^{4b}$ for a compound corresponds in each case to one row of Table A Table 425
Compounds of the formula Ia.15 in which $R^6$ is $CH_2CHF_2$, and the combination of $R^{2a}$, $R^{2b}$, $R^{2c}$ and $R^{4b}$ for a compound corresponds in each case to one row of Table A Table 426
Compounds of the formula Ia.15 in which $R^6$ is $CH_2CF_3$, and the combination of $R^{2a}$, $R^{2b}$, $R^{2c}$ and $R^{4b}$ for a compound corresponds in each case to one row of Table A Table 427
Compounds of the formula Ia.15 in which $R^6$ is $CH_2CH_2CF_3$, and the combination of $R^{2a}$, $R^{2b}$, $R^{2c}$ and $R^{4b}$ for a compound corresponds in each case to one row of Table A Table 428
Compounds of the formula Ia.15 in which $R^6$ is $CH(CH_3)CF_3$, and the combination of $R^{2a}$, $R^{2b}$, $R^{2c}$ and $R^{4b}$ for a compound corresponds in each case to one row of Table A Table 429
Compounds of the formula Ia.15 in which $R^6$ is $CH(CF_3)_2$, and the combination of $R^{2a}$, $R^{2b}$, $R^{2c}$ and $R^{4b}$ for a compound corresponds in each case to one row of Table A Table 430
Compounds of the formula Ia.15 in which $R^6$ is $CH_2CH_2CH_2CF_3$, and the combination of $R^{2a}$, $R^{2b}$, $R^{2c}$ and $R^{4b}$ for a compound corresponds in each case to one row of Table A Table 431
Compounds of the formula Ia.15 in which $R^6$ is $CH_2CH=CF_2$, and the combination of $R^{2a}$, $R^{2b}$, $R^{2c}$ and $R^{4b}$ for a compound corresponds in each case to one row of Table A Table 432
Compounds of the formula Ia.15 in which $R^6$ is $CH_2CF=CF_2$, and the combination of $R^{2a}$, $R^{2b}$, $R^{2c}$ and $R^{4b}$ for a compound corresponds in each case to one row of Table A Table 433
Compounds of the formula Ia.15 in which $R^6$ is $CH_2CH_2CH=CF_2$, and the combination of $R^{2a}$, $R^{2b}$, $R^{2c}$ and $R^{4b}$ for a compound corresponds in each case to one row of Table A Table 434
Compounds of the formula Ia.15 in which $R^6$ is $CH_2CH_2CF=CF_2$, and the combination of $R^{2a}$, $R^{2b}$, $R^{2c}$ and $R^{4b}$ for a compound corresponds in each case to one row of Table A Table 435
Compounds of the formula Ia.15 in which $R^6$ is cyclopropyl, and the combination of $R^{2a}$, $R^{2b}$, $R^{2c}$ and $R^{4b}$ for a compound corresponds in each case to one row of Table A Table 436
Compounds of the formula Ia.15 in which $R^6$ is 1-cyanocyclopropyl, and the combination of $R^{2a}$, $R^{2b}$, $R^{2c}$ and $R^{4b}$ for a compound corresponds in each case to one row of Table A Table 437
Compounds of the formula Ia.15 in which $R^6$ is 1-(pyridin-2-yl)-cyclopropyl, and the combination of $R^{2a}$, $R^{2b}$, $R^{2c}$ and $R^{4b}$ for a compound corresponds in each case to one row of Table A Table 438
Compounds of the formula Ia.15 in which $R^6$ is cyclobutyl, and the combination of $R^{2a}$, $R^{2b}$, $R^{2c}$ and $R^{4b}$ for a compound corresponds in each case to one row of Table A Table 439
Compounds of the formula Ia.15 in which $R^6$ is 1-cyano-cyclobutyl, and the combination of $R^{2a}$, $R^{2b}$, $R^{2c}$ and $R^{4b}$ for a compound corresponds in each case to one row of Table A Table 440
Compounds of the formula Ia.15 in which $R^6$ is 3,3-difluorocyclobutyl, and the combination of $R^{2a}$, $R^{2b}$, $R^{2c}$ and $R^{4b}$ for a compound corresponds in each case to one row of Table A Table 441
Compounds of the formula Ia.15 in which $R^6$ is cyclopentyl, and the combination of $R^{2a}$, $R^{2b}$, $R^{2c}$ and $R^{4b}$ for a compound corresponds in each case to one row of Table A Table 442
Compounds of the formula Ia.15 in which $R^6$ is 1-cyano-cyclopentyl, and the combination of $R^{2a}$, $R^{2b}$, $R^{2c}$ and $R^{4b}$ for a compound corresponds in each case to one row of Table A Table 443
Compounds of the formula Ia.15 in which $R^6$ is cyclohexyl, and the combination of $R^{2a}$, $R^{2b}$, $R^{2c}$ and $R^{4b}$ for a compound corresponds in each case to one row of Table A Table 444
Compounds of the formula Ia.15 in which $R^6$ is 1-cyano-cyclohexyl, and the combination of $R^{2a}$, $R^{2b}$, $R^{2c}$ and $R^{4b}$ for a compound corresponds in each case to one row of Table A Table 445
Compounds of the formula Ia.15 in which $R^6$ is —$CH_2$-cyclopropyl, and the combination of $R^{2a}$, $R^{2b}$, $R^{2c}$ and $R^{4b}$ for a compound corresponds in each case to one row of Table A Table 446
Compounds of the formula Ia.15 in which $R^6$ is —$CH_2$-(1-cyano-cyclopropyl), and the combination of $R^{2a}$, $R^{2b}$, $R^{2c}$ and $R^{4b}$ for a compound corresponds in each case to one row of Table A Table 447
Compounds of the formula Ia.15 in which $R^6$ is —$CH_2$-(1-fluoro-cyclopropyl), and the combination of $R^{2a}$, $R^{2b}$, $R^{2c}$ and $R^{4b}$ for a compound corresponds in each case to one row of Table A Table 448
Compounds of the formula Ia.15 in which $R^6$ is —$CH_2$-(1-chloro-cyclopropyl), and the combination of $R^{2a}$, $R^{2b}$, $R^{2c}$ and $R^{4b}$ for a compound corresponds in each case to one row of Table A Table 449
Compounds of the formula Ia.15 in which $R^6$ is —$CH_2$-(1-bromo-cyclopropyl), and the combination of $R^{2a}$, $R^{2b}$, $R^{2c}$ and $R^{4b}$ for a compound corresponds in each case to one row of Table A Table 450
Compounds of the formula Ia.15 in which $R^6$ is —$CH_2$-(2,2-difluorocyclopropyl), and the combination of $R^{2a}$, $R^{2b}$, $R^{2c}$ and $R^{4b}$ for a compound corresponds in each case to one row of Table A Table 451
Compounds of the formula Ia.15 in which $R^6$ is —$CH_2$-(2,2-dichlorocyclopropyl), and the combination of $R^{2a}$, $R^{2b}$, $R^{2c}$ and $R^{4b}$ for a compound corresponds in each case to one row of Table A Table 452
Compounds of the formula Ia.15 in which $R^6$ is —$CH_2$-(2,2-dibromocyclopropyl), and the combination of $R^{2a}$, $R^{2b}$, $R^{2c}$ and $R^{4b}$ for a compound corresponds in each case to one row of Table A Table 453
Compounds of the formula Ia.15 in which $R^6$ is —$CH_2$-cyclobutyl, and the combination of $R^{2a}$, $R^{2b}$, $R^{2c}$ and $R^{4b}$ for a compound corresponds in each case to one row of Table A Table 454
Compounds of the formula Ia.15 in which $R^6$ is —$CH_2$-(1-cyano-cyclobutyl), and the combination of $R^{2a}$, $R^{2b}$, $R^{2c}$ and $R^{4b}$ for a compound corresponds in each case to one row of Table A Table 455
Compounds of the formula Ia.15 in which $R^6$ is —$CH_2$-(1-fluoro-cyclobutyl), and the combination of $R^{2a}$, $R^{2b}$, $R^{2c}$ and $R^{4b}$ for a compound corresponds in each case to one row of Table A Table 456
Compounds of the formula Ia.15 in which $R^6$ is —$CH_2$-(1-chloro-cyclobutyl), and the combination of $R^{2a}$, $R^{2b}$, $R^{2c}$ and $R^{4b}$ for a compound corresponds in each case to one row of Table A Table 457
Compounds of the formula Ia.15 in which $R^6$ is —$CH_2$-(2,2-difluorocyclobutyl), and the combination of $R^{2a}$, $R^{2b}$, $R^{2c}$ and $R^{4b}$ for a compound corresponds in each case to one row of Table A Table 458
Compounds of the formula Ia.15 in which $R^6$ is —$CH_2$-(3,3-difluorocyclobutyl), and the combination of $R^{2a}$, $R^{2b}$, $R^{2c}$ and $R^{4b}$ for a compound corresponds in each case to one row of Table A Table 459
Compounds of the formula Ia.15 in which $R^6$ is —$CH_2$-(2,2,3,3-tetrafluorocyclobutyl), and the combination of $R^{2a}$, $R^{2b}$, $R^{2c}$ and $R^{4b}$ for a compound corresponds in each case to one row of Table A Table 460
Compounds of the formula Ia.15 in which $R^6$ is —$CH_2$-(2,2,3,3,4,4-hexafluorocyclobutyl), and the combination of $R^{2a}$, $R^{2b}$, $R^{2c}$ and $R^{4b}$ for a compound corresponds in each case to one row of Table A Table 461
Compounds of the formula Ia.15 in which $R^6$ is —$CH_2$-cyclopentyl, and the combination of $R^{2a}$, $R^{2b}$, $R^{2c}$ and $R^{4b}$ for a compound corresponds in each case to one row of Table A Table 462
Compounds of the formula Ia.15 in which $R^6$ is —$CH_2$-(1-fluoro-cyclopentyl), and the combination of $R^{2a}$, $R^{2b}$, $R^{2c}$ and $R^{4b}$ for a compound corresponds in each case to one row of Table A Table 463
Compounds of the formula Ia.15 in which $R^6$ is —$CH_2$-(1-chloro-cyclopentyl), and the combination of $R^{2a}$, $R^{2b}$, $R^{2c}$ and $R^{4b}$ for a compound corresponds in each case to one row of Table A Table 464
Compounds of the formula Ia.15 in which $R^6$ is —CH$_2$-(1-cyano-cyclopentyl), and the combination of $R^{2a}$, $R^{2b}$, $R^{2c}$ and $R^{4b}$ for a compound corresponds in each case to one row of Table A Table 465
Compounds of the formula Ia.15 in which $R^6$ is —CH$_2$-(2,2-difluorocyclopentyl), and the combination of $R^{2a}$, $R^{2b}$, $R^{2c}$ and $R^{4b}$ for a compound corresponds in each case to one row of Table A Table 466
Compounds of the formula Ia.15 in which $R^6$ is $R^6$ is —CH$_2$-(3,3-difluorocyclopentyl), and the combination of $R^{2a}$, $R^{2b}$, $R^{2c}$ and $R^{4b}$ for a compound corresponds in each case to one row of Table A Table 467
Compounds of the formula Ia.15 in which $R^6$ is —CH$_2$-(1-fluorocyclohexyl), and the combination of $R^{2a}$, $R^{2b}$, $R^{2c}$ and $R^{4b}$ for a compound corresponds in each case to one row of Table A Table 468
Compounds of the formula Ia.15 in which $R^6$ is —CH$_2$-(1-chlorocyclohexyl), and the combination of $R^{2a}$, $R^{2b}$, $R^{2c}$ and $R^{4b}$ for a compound corresponds in each case to one row of Table A Table 469
Compounds of the formula Ia.15 in which $R^6$ is —CH$_2$-(1-cyanocyclohexyl), and the combination of $R^{2a}$, $R^{2b}$, $R^{2c}$ and $R^{4b}$ for a compound corresponds in each case to one row of Table A Table 470
Compounds of the formula Ia.15 in which $R^6$ is thietan-3-yl, and the combination of $R^{2a}$, $R^{2b}$, $R^{2c}$ and $R^{4b}$ for a compound corresponds in each case to one row of Table A Table 471
Compounds of the formula Ia.15 in which $R^6$ is 1-oxo-thietan-3-yl, and the combination of $R^{2a}$, $R^{2b}$, $R^{2c}$ and $R^{4b}$ for a compound corresponds in each case to one row of Table A Table 472
Compounds of the formula Ia.15 in which $R^6$ is 1,1-dioxo-thietan-3-yl, and the combination of $R^{2a}$, $R^{2b}$, $R^{2c}$ and $R^{4b}$ for a compound corresponds in each case to one row of Table A Table 473
Compounds of the formula Ia.15 in which $R^6$ is 3-methyl-thietan-3-yl, and the combination of $R^{2a}$, $R^{2b}$, $R^{2c}$ and $R^{4b}$ for a compound corresponds in each case to one row of Table A Table 474
Compounds of the formula Ia.15 in which $R^6$ is 3-methyl-1-oxo-thietan-3-yl, and the combination of $R^{2a}$, $R^{2b}$, $R^{2c}$ and $R^{4b}$ for a compound corresponds in each case to one row of Table A Table 475
Compounds of the formula Ia.15 in which $R^6$ is 3-methyl-1,1-dioxo-thietan-3-yl, and the combination of $R^{2a}$, $R^{2b}$, $R^{2c}$ and $R^{4b}$ for a compound corresponds in each case to one row of Table A Table 476
Compounds of the formula Ia.15 in which $R^6$ is —CH$_2$-(thietan-3-yl), and the combination of $R^{2a}$, $R^{2b}$, $R^{2c}$ and $R^{4b}$ for a compound corresponds in each case to one row of Table A Table 477
Compounds of the formula Ia.15 in which $R^6$ is —CH$_2$-(1-oxo-thietan-3-yl), and the combination of $R^{2a}$, $R^{2b}$, $R^{2c}$ and $R^{4b}$ for a compound corresponds in each case to one row of Table A Table 478
Compounds of the formula Ia.15 in which $R^6$ is —CH$_2$-(1,1-dioxo-thietan-3-yl), and the combination of $R^{2a}$, $R^{2b}$, $R^{2c}$ and $R^{4b}$ for a compound corresponds in each case to one row of Table A Table 479
Compounds of the formula Ia.15 in which $R^6$ is tetrahydrothiophen-3-yl, and the combination of $R^{2a}$, $R^{2b}$, $R^{2c}$ and $R^{4b}$ for a compound corresponds in each case to one row of Table A Table 480
Compounds of the formula Ia.15 in which $R^6$ is 1-oxo-tetrahydrothiophen-3-yl, and the combination of $R^{2a}$, $R^{2b}$, $R^{2c}$ and $R^{4b}$ for a compound corresponds in each case to one row of Table A Table 481
Compounds of the formula Ia.15 in which $R^6$ is 1,1-dioxo-tetrahydrothiophen-3-yl, and the combination of $R^{2a}$, $R^{2b}$, $R^{2c}$ and $R^{4b}$ for a compound corresponds in each case to one row of Table A Table 482
Compounds of the formula Ia.15 in which $R^6$ is phenyl, and the combination of $R^{2a}$, $R^{2b}$, $R^{2c}$ and $R^{4b}$ for a compound corresponds in each case to one row of Table A Table 483
Compounds of the formula Ia.15 in which $R^6$ is CH$_2$—CONH$_2$, and the combination of $R^{2a}$, $R^{2b}$, $R^{2c}$ and $R^{4b}$ for a compound corresponds in each case to one row of Table A Table 484
Compounds of the formula Ia.15 in which $R^6$ is pyridin-2-yl, and the combination of $R^{2a}$, $R^{2b}$, $R^{2c}$ and $R^{4b}$ for a compound corresponds in each case to one row of Table A Table 485
Compounds of the formula Ia.15 in which $R^6$ is pyridin-3-yl, and the combination of $R^{2a}$, $R^{2b}$, $R^{2c}$ and $R^{4b}$ for a compound corresponds in each case to one row of Table A Table 486
Compounds of the formula Ia.15 in which $R^6$ is pyridin-4-yl, and the combination of $R^{2a}$, $R^{2b}$, $R^{2c}$ and $R^{4b}$ for a compound corresponds in each case to one row of Table A Table 487
Compounds of the formula Ia.15 in which $R^6$ is pyrimidin-2-yl, and the combination of $R^{2a}$, $R^{2b}$, $R^{2c}$ and $R^{4b}$ for a compound corresponds in each case to one row of Table A Table 488
Compounds of the formula Ia.15 in which $R^6$ is pyrimidin-4-yl, and the combination of $R^{2a}$, $R^{2b}$, $R^{2c}$ and $R^{4b}$ for a compound corresponds in each case to one row of Table A Table 489
Compounds of the formula Ia.15 in which $R^6$ is pyrimidin-5-yl, and the combination of $R^{2a}$, $R^{2b}$, $R^{2c}$ and $R^{4b}$ for a compound corresponds in each case to one row of Table A Table 490
Compounds of the formula Ia.15 in which $R^6$ is thiazol-2-yl, and the combination of $R^{2a}$, $R^{2b}$, $R^{2c}$ and $R^{4b}$ for a compound corresponds in each case to one row of Table A Table 491
Compounds of the formula Ia.15 in which $R^6$ is 4-trifluoromethylthiazol-2-yl, and the combination of $R^{2a}$, $R^{2b}$, $R^{2c}$ and $R^{4b}$ for a compound corresponds in each case to one row of Table A Table 492
Compounds of the formula Ia.15 in which $R^6$ is oxetan-3-yl, and the combination of $R^{2a}$, $R^{2b}$, $R^{2c}$ and $R^{4b}$ for a compound corresponds in each case to one row of Table A Table 493
Compounds of the formula Ia.15 in which $R^6$ is tetrahydrofuran-2-yl, and the combination of $R^{2a}$, $R^{2b}$, $R^{2c}$ and $R^{4b}$ for a compound corresponds in each case to one row of Table A Table 494
Compounds of the formula Ia.15 in which $R^6$ is tetrahydrofuran-3-yl, and the combination of $R^{2a}$, $R^{2b}$, $R^{2c}$ and $R^{4b}$ for a compound corresponds in each case to one row of Table A Table 495
Compounds of the formula Ia.15 in which $R^6$ is 2-oxo-tetrahydrofuran-3-yl, and the combination of $R^{2a}$, $R^{2b}$, $R^{2c}$ and $R^{4b}$ for a compound corresponds in each case to one row of Table A Table 496
Compounds of the formula Ia.15 in which $R^6$ is 2-oxopyrrolidin-3-yl, and the combination of $R^{2a}$, $R^{2b}$, $R^{2c}$ and $R^{4b}$ for a compound corresponds in each case to one row of Table A Table 497
Compounds of the formula Ia.15 in which $R^6$ is 1-methyl-2-oxopyrrolidin-3-yl, and the combination of $R^{2a}$, $R^{2b}$, $R^{2c}$ and $R^{4b}$ for a compound corresponds in each case to one row of Table A Table 498
Compounds of the formula Ia.15 in which $R^6$ is 2-oxo-1-(2,2,2-trifluoroethyl)-pyrrolidin-3-yl, and the combination of $R^{2a}$, $R^{2b}$, $R^{2c}$ and $R^{4b}$ for a compound corresponds in each case to one row of Table A Table 499
Compounds of the formula Ia.15 in which $R^6$ is azetidin-3-yl, and the combination of $R^{2a}$, $R^{2b}$, $R^{2c}$ and $R^{4b}$ for a compound corresponds in each case to one row of Table A Table 500
Compounds of the formula Ia.15 in which $R^6$ is 1-acetyl-azetidin-3-yl, and the combination of $R^{2a}$, $R^{2b}$, $R^{2c}$ and $R^{4b}$ for a compound corresponds in each case to one row of Table A Table 501
Compounds of the formula Ia.15 in which $R^6$ is —NH-phenyl, and the combination of $R^{2a}$, $R^{2b}$, $R^{2c}$ and $R^{4b}$ for a compound corresponds in each case to one row of Table A Table 502
Compounds of the formula Ia.15 in which $R^6$ is —NH-pyridin-2-yl, and the combination of $R^{2a}$, $R^{2b}$, $R^{2c}$ and $R^{4b}$ for a compound corresponds in each case to one row of Table A Table 503
Compounds of the formula Ia.15 in which $R^6$ is —NH-pyridin-3-yl, and the combination of $R^{2a}$, $R^{2b}$, $R^{2c}$ and $R^{4b}$ for a compound corresponds in each case to one row of Table A Table 504
Compounds of the formula Ia.15 in which $R^6$ is —NH-pyridin-4-yl, and the combination of $R^{2a}$, $R^{2b}$, $R^{2c}$ and $R^{4b}$ for a compound corresponds in each case to one row of Table A Table 505
Compounds of the formula Ia.15 in which $R^6$ is —N(CH$_3$)-pyridin-2-yl, and the combination of $R^{2a}$, $R^{2b}$, $R^{2c}$ and $R^{4b}$ for a compound corresponds in each case to one row of Table A Table 506
Compounds of the formula Ia.15 in which $R^6$ is —N(CH$_3$)-pyrimidin-2-yl, and the combination of $R^{2a}$, $R^{2b}$, $R^{2c}$ and $R^{4b}$ for a compound corresponds in each case to one row of Table A Table 507
Compounds of the formula Ia.15 in which $R^6$ is —NH-pyrimidin-4-yl, and the combination of $R^{2a}$, $R^{2b}$, $R^{2c}$ and $R^{4b}$ for a compound corresponds in each case to one row of Table A Table 508
Compounds of the formula Ia.15 in which $R^6$ is —NH-pyrimidin-5-yl, and the combination of $R^{2a}$, $R^{2b}$, $R^{2c}$ and $R^{4b}$ for a compound corresponds in each case to one row of Table A Table 509
Compounds of the formula Ia.15 in which $R^6$ is —CH$_2$—C(=O)OCH$_3$, and the combination of $R^{2a}$, $R^{2b}$, $R^{2c}$ and $R^{4b}$ for a compound corresponds in each case to one row of Table A Table 510
Compounds of the formula Ia.15 in which $R^6$ is —CH$_2$—C(=O)O—CH$_2$CH$_3$, and the combination of $R^{2a}$, $R^{2b}$, $R^{2c}$ and $R^{4b}$ for a compound corresponds in each case to one row of Table A Table 511
Compounds of the formula Ia.15 in which $R^6$ is —CH$_2$—CONH—CH$_3$, and the combination of $R^{2a}$, $R^{2b}$, $R^{2c}$ and $R^{4b}$ for a compound corresponds in each case to one row of Table A Table 512
Compounds of the formula Ia.15 in which $R^6$ is —CH$_2$—CONH—CH$_2$CH$_3$, and the combination of $R^{2a}$, $R^{2b}$, $R^{2c}$ and $R^{4b}$ for a compound corresponds in each case to one row of Table A Table 513
Compounds of the formula Ia.15 in which $R^6$ is —CH$_2$—CONH—CH$_2$CHF$_2$, and the combination of $R^{2a}$, $R^{2b}$, $R^{2c}$ and $R^{4b}$ for a compound corresponds in each case to one row of Table A Table 514
Compounds of the formula Ia.15 in which $R^6$ is —CH$_2$—CONH—CH$_2$CF$_3$, and the combination of $R^{2a}$, $R^{2b}$, $R^{2c}$ and $R^{4b}$ for a compound corresponds in each case to one row of Table A Table 515
Compounds of the formula Ia.15 in which $R^6$ is —CH$_2$—CONH-cyclopropyl, and the combination of $R^{2a}$, $R^{2b}$, $R^{2c}$ and $R^{4b}$ for a compound corresponds in each case to one row of Table A Table 516
Compounds of the formula Ia.15 in which $R^6$ is —CH$_2$—CONH-isopropyl, and the combination of $R^{2a}$, $R^{2b}$, $R^{2c}$ and $R^{4b}$ for a compound corresponds in each case to one row of Table A Table 517
Compounds of the formula Ia.15 in which $R^6$ is —CH$_2$—CONH—CH(CF$_3$)CH$_3$, and the combination of $R^{2a}$, $R^{2b}$, $R^{2c}$ and $R^{4b}$ for a compound corresponds in each case to one row of Table A Table 518
Compounds of the formula Ia.15 in which $R^6$ is —CH$_2$—CONH—CH(CF$_3$)$_2$, and the combination of $R^{2a}$, $R^{2b}$, $R^{2c}$ and $R^{4b}$ for a compound corresponds in each case to one row of Table A Table 519
Compounds of the formula Ia.15 in which $R^6$ is —$CH_2$—CONH—$CH_2CH_2CF_3$, and the combination of $R^{2a}$, $R^{2b}$, $R^{2c}$ and $R^{4b}$ for a compound corresponds in each case to one row of Table A Table 520
Compounds of the formula Ia.15 in which $R^6$ is —$CH_2$—CONH—$CH_2CN$, and the combination of $R^{2a}$, $R^{2b}$, $R^{2c}$ and $R^{4b}$ for a compound corresponds in each case to one row of Table A Table 521
Compounds of the formula Ia.15 in which $R^6$ is —$CH_2$—CONH—$CH_2CH=CH_2$, and the combination of $R^{2a}$, $R^{2b}$, $R^{2c}$ and $R^{4b}$ for a compound corresponds in each case to one row of Table A Table 522
Compounds of the formula Ia.15 in which $R^6$ is —$CH_2$—CONH—$CH_2C\equiv CH$, and the combination of $R^{2a}$, $R^{2b}$, $R^{2c}$ and $R^{4b}$ for a compound corresponds in each case to one row of Table A Table 523
Compounds of the formula Ia.15 in which $R^6$ is —$CH_2$—CON($CH_3$)—$CH_2CF_3$, and the combination of $R^{2a}$, $R^{2b}$, $R^{2c}$ and $R^{4b}$ for a compound corresponds in each case to one row of Table A Table 524
Compounds of the formula Ia.15 in which $R^6$ is —CH($CH_3$)—CONH—$CH_2CF_3$, and the combination of $R^{2a}$, $R^{2b}$, $R^{2c}$ and $R^{4b}$ for a compound corresponds in each case to one row of Table A Table 525
Compounds of the formula Ia.15 in which $R^6$ is —$CH_2$—CONH—$CH_2$-cyclopropyl, and the combination of $R^{2a}$, $R^{2b}$, $R^{2c}$ and $R^{4b}$ for a compound corresponds in each case to one row of Table A Table 526
Compounds of the formula Ia.15 in which $R^6$ is —$CH_2$—CONH—$CH_2$-(1-cyano-cyclopropyl), and the combination of $R^{2a}$, $R^{2b}$, $R^{2c}$ and $R^{4b}$ for a compound corresponds in each case to one row of Table A Table 527
Compounds of the formula Ia.15 in which $R^6$ is —$CH_2$—CONH-(thietan-3-yl), and the combination of $R^{2a}$, $R^{2b}$, $R^{2c}$ and $R^{4b}$ for a compound corresponds in each case to one row of Table A Table 528
Compounds of the formula Ia.15 in which $R^6$ is —$CH_2$—CONH-(1-oxo-thietan-3-yl), and the combination of $R^{2a}$, $R^{2b}$, $R^{2c}$ and $R^{4b}$ for a compound corresponds in each case to one row of Table A Table 529
Compounds of the formula Ia.15 in which $R^6$ is —$CH_2$—CONH-(1,1-dioxo-thietan-3-yl), and the combination of $R^{2a}$, $R^{2b}$, $R^{2c}$ and $R^{4b}$ for a compound corresponds in each case to one row of Table A Table 530
Compounds of the formula Ia.15 in which $R^6$ is benzyl, and the combination of $R^{2a}$, $R^{2b}$, $R^{2c}$ and $R^{4b}$ for a compound corresponds in each case to one row of Table A Table 531
Compounds of the formula Ia.15 in which $R^6$ is 2-fluorobenzyl, and the combination of $R^{2a}$, $R^{2b}$, $R^{2c}$ and $R^{4b}$ for a compound corresponds in each case to one row of Table A Table 532
Compounds of the formula Ia.15 in which $R^6$ is 3-fluorobenzyl, and the combination of $R^{2a}$, $R^{2b}$, $R^{2c}$ and $R^{4b}$ for a compound corresponds in each case to one row of Table A Table 533
Compounds of the formula Ia.15 in which $R^6$ is 4-fluorobenzyl, and the combination of $R^{2a}$, $R^{2b}$, $R^{2c}$ and $R^{4b}$ for a compound corresponds in each case to one row of Table A Table 534
Compounds of the formula Ia.15 in which $R^6$ is 2-chlorobenzyl, and the combination of $R^{2a}$, $R^{2b}$, $R^{2c}$ and $R^{4b}$ for a compound corresponds in each case to one row of Table A Table 535
Compounds of the formula Ia.15 in which $R^6$ is 3-chlorobenzyl, and the combination of $R^{2a}$, $R^{2b}$, $R^{2c}$ and $R^{4b}$ for a compound corresponds in each case to one row of Table A Table 536
Compounds of the formula Ia.15 in which $R^6$ is 4-chlorobenzyl, and the combination of $R^{2a}$, $R^{2b}$, $R^{2c}$ and $R^{4b}$ for a compound corresponds in each case to one row of Table A Table 537
Compounds of the formula Ia.15 in which $R^6$ is pyridazin-4-yl-methyl, and the combination of $R^{2a}$, $R^{2b}$, $R^{2c}$ and $R^{4b}$ for a compound corresponds in each case to one row of Table A Table 538
Compounds of the formula Ia.15 in which $R^6$ is tetrahydrofuran-2-yl-methyl, and the combination of $R^{2a}$, $R^{2b}$, $R^{2c}$ and $R^{4b}$ for a compound corresponds in each case to one row of Table A Table 539
Compounds of the formula Ia.15 in which $R^6$ is ([1,2,3]-thiadiazol-5-yl)-methyl, and the combination of $R^{2a}$, $R^{2b}$, $R^{2c}$ and $R^{4b}$ for a compound corresponds in each case to one row of Table A Table 540
Compounds of the formula Ia.15 in which $R^6$ is 2-methylsulfanylbenzyl, and the combination of $R^{2a}$, $R^{2b}$, $R^{2c}$ and $R^{4b}$ for a compound corresponds in each case to one row of Table A Table 541
Compounds of the formula Ia.15 in which $R^6$ is 3-methylsulfanylbenzyl, and the combination of $R^{2a}$, $R^{2b}$, $R^{2c}$ and $R^{4b}$ for a compound corresponds in each case to one row of Table A Table 542
Compounds of the formula Ia.15 in which $R^6$ is 4-methylsulfanylbenzyl, and the combination of $R^{2a}$, $R^{2b}$, $R^{2c}$ and $R^{4b}$ for a compound corresponds in each case to one row of Table A Table 543
Compounds of the formula Ia.15 in which $R^6$ is 2-methylsulfonylbenzyl, and the combination of $R^{2a}$, $R^{2b}$, $R^{2c}$ and $R^{4b}$ for a compound corresponds in each case to one row of Table A Table 544
Compounds of the formula Ia.15 in which $R^6$ is 3-methylsulfonylbenzyl, and the combination of $R^{2a}$, $R^{2b}$, $R^{2c}$ and $R^{4b}$ for a compound corresponds in each case to one row of Table A Table 545
Compounds of the formula Ia.15 in which $R^6$ is 4-methylsulfonylbenzyl, and the combination of $R^{2a}$, $R^{2b}$, $R^{2c}$ and $R^{4b}$ for a compound corresponds in each case to one row of Table A Table 546
Compounds of the formula Ia.15 in which $R^6$ is pyridin-2-yl-methyl, and the combination of $R^{2a}$, $R^{2b}$, $R^{2c}$ and $R^{4b}$ for a compound corresponds in each case to one row of Table A Table 547
Compounds of the formula Ia.15 in which $R^6$ is pyridin-3-yl-methyl, and the combination of $R^{2a}$, $R^{2b}$, $R^{2c}$ and $R^{4b}$ for a compound corresponds in each case to one row of Table A Table 548
Compounds of the formula Ia.15 in which $R^6$ is (6-chloropyridin-3-yl)-methyl, and the combination of $R^{2a}$, $R^{2b}$, $R^{2c}$ and $R^{4b}$ for a compound corresponds in each case to one row of Table A Table 549
Compounds of the formula Ia.15 in which $R^6$ is pyridin-4-yl-methyl, and the combination of $R^{2a}$, $R^{2b}$, $R^{2c}$ and $R^{4b}$ for a compound corresponds in each case to one row of Table A Table 550
Compounds of the formula Ia.15 in which $R^6$ is (5-chloropyridin-2-yl)-methyl, and the combination of $R^{2a}$, $R^{2b}$, $R^{2c}$ and $R^{4b}$ for a compound corresponds in each case to one row of Table A Table 551
Compounds of the formula Ia.15 in which $R^6$ is [6-(trifluoromethyl)-pyridin-2-yl]-methyl, and the combination of $R^{2a}$, $R^{2b}$, $R^{2c}$ and $R^{4b}$ for a compound corresponds in each case to one row of Table A Table 552
Compounds of the formula Ia.15 in which $R^6$ is [6-(trifluoromethyl)-pyridin-3-yl]-methyl, and the combination of $R^{2a}$, $R^{2b}$, $R^{2c}$ and $R^{4b}$ for a compound corresponds in each case to one row of Table A Table 553
Compounds of the formula Ia.15 in which $R^6$ is pyrimidin-2-yl-methyl, and the combination of $R^{2a}$, $R^{2b}$, $R^{2c}$ and $R^{4b}$ for a compound corresponds in each case to one row of Table A Table 554
Compounds of the formula Ia.15 in which $R^6$ is pyrimidin-4-yl-methyl, and the combination of $R^{2a}$, $R^{2b}$, $R^{2c}$ and $R^{4b}$ for a compound corresponds in each case to one row of Table A Table 555
Compounds of the formula Ia.15 in which $R^6$ is pyrimidin-5-yl-methyl, and the combination of $R^{2a}$, $R^{2b}$, $R^{2c}$ and $R^{4b}$ for a compound corresponds in each case to one row of Table A Table 556
Compounds of the formula Ia.15 in which $R^6$ is pyridazin-3-yl-methyl, and the combination of $R^{2a}$, $R^{2b}$, $R^{2c}$ and $R^{4b}$ for a compound corresponds in each case to one row of Table A Table 557
Compounds of the formula Ia.15 in which $R^6$ is pyrazin-2-yl-methyl, and the combination of $R^{2a}$, $R^{2b}$, $R^{2c}$ and $R^{4b}$ for a compound corresponds in each case to one row of Table A Table 558
Compounds of the formula Ia.15 in which $R^6$ is thien-2-yl-methyl, and the combination of $R^{2a}$, $R^{2b}$, $R^{2c}$ and $R^{4b}$ for a compound corresponds in each case to one row of Table A Table 559
Compounds of the formula Ia.15 in which $R^6$ is thien-3-yl-methyl, and the combination of $R^{2a}$, $R^{2b}$, $R^{2c}$ and $R^{4b}$ for a compound corresponds in each case to one row of Table A Table 560
Compounds of the formula Ia.15 in which $R^6$ is thiazol-2-yl-methyl, and the combination of $R^{2a}$, $R^{2b}$, $R^{2c}$ and $R^{4b}$ for a compound corresponds in each case to one row of Table A Table 561
Compounds of the formula Ia.15 in which $R^6$ is thiazol-4-yl-methyl, and the combination of $R^{2a}$, $R^{2b}$, $R^{2c}$ and $R^{4b}$ for a compound corresponds in each case to one row of Table A Table 562
Compounds of the formula Ia.15 in which $R^6$ is thiazol-5-yl-methyl, and the combination of $R^{2a}$, $R^{2b}$, $R^{2c}$ and $R^{4b}$ for a compound corresponds in each case to one row of Table A Table 563
Compounds of the formula Ia.15 in which $R^6$ is (2-chlorothiazol-5-yl)-methyl, and the combination of $R^{2a}$, $R^{2b}$, $R^{2c}$ and $R^{4b}$ for a compound corresponds in each case to one row of Table A Table 564
Compounds of the formula Ia.15 in which $R^6$ is isothiazol-3-yl-methyl, and the combination of $R^{2a}$, $R^{2b}$, $R^{2c}$ and $R^{4b}$ for a compound corresponds in each case to one row of Table A Table 565
Compounds of the formula Ia.15 in which $R^6$ is isothiazol-4-yl-methyl, and the combination of $R^{2a}$, $R^{2b}$, $R^{2c}$ and $R^{4b}$ for a compound corresponds in each case to one row of Table A Table 566
Compounds of the formula Ia.15 in which $R^6$ is isothiazol-5-yl-methyl, and the combination of $R^{2a}$, $R^{2b}$, $R^{2c}$ and $R^{4b}$ for a compound corresponds in each case to one row of Table A Table 567
Compounds of the formula Ia.15 in which $R^6$ is oxazol-2-yl-methyl, and the combination of $R^{2a}$, $R^{2b}$, $R^{2c}$ and $R^{4b}$ for a compound corresponds in each case to one row of Table A Table 568
Compounds of the formula Ia.15 in which $R^6$ is oxazol-4-yl-methyl, and the combination of $R^{2a}$, $R^{2b}$, $R^{2c}$ and $R^{4b}$ for a compound corresponds in each case to one row of Table A Table 569
Compounds of the formula Ia.15 in which $R^6$ is oxazol-5-yl-methyl, and the combination of $R^{2a}$, $R^{2b}$, $R^{2c}$ and $R^{4b}$ for a compound corresponds in each case to one row of Table A Table 570
Compounds of the formula Ia.15 in which $R^6$ is isoxazol-3-yl-methyl, and the combination of $R^{2a}$, $R^{2b}$, $R^{2c}$ and $R^{4b}$ for a compound corresponds in each case to one row of Table A Table 571
Compounds of the formula Ia.15 in which $R^6$ is isoxazol-4-yl-methyl, and the combination of $R^{2a}$, $R^{2b}$, $R^{2c}$ and $R^{4b}$ for a compound corresponds in each case to one row of Table A Table 572
Compounds of the formula Ia.15 in which $R^6$ is isoxazol-5-yl-methyl, and the combination of $R^{2a}$, $R^{2b}$, $R^{2c}$ and $R^{4b}$ for a compound corresponds in each case to one row of Table A Table 573
Compounds of the formula Ia.15 in which $R^6$ is ([1,2,3]-thiadiazol-4-yl)-methyl, and the combination of $R^{2a}$, $R^{2b}$, $R^{2c}$ and $R^{4b}$ for a compound corresponds in each case to one row of Table A Table 574
Compounds of the formula Ia.15 in which $R^6$ is ([1,3,4]-thiadiazol-2-yl)-methyl, and the combination of $R^{2a}$, $R^{2b}$, $R^{2c}$ and $R^{4b}$ for a compound corresponds in each case to one row of Table A Table 575
Compounds of the formula Ia.15 in which $R^6$ is (1-methyl-imidazol-2-yl)-methyl, and the combination of $R^{2a}$, $R^{2b}$, $R^{2c}$ and $R^{4b}$ for a compound corresponds in each case to one row of Table A Table 576
Compounds of the formula Ia.15 in which $R^6$ is (1-methyl-imidazol-4-yl)-methyl, and the combination of $R^{2a}$, $R^{2b}$, $R^{2c}$ and $R^{4b}$ for a compound corresponds in each case to one row of Table A Table 577
Compounds of the formula Ia.15 in which $R^6$ is (1-methyl-imidazol-5-yl)-methyl, and the combination of $R^{2a}$, $R^{2b}$, $R^{2c}$ and $R^{4b}$ for a compound corresponds in each case to one row of Table A Table 578
Compounds of the formula Ia.15 in which $R^6$ is (1-methyl-pyrazol-3-yl)-methyl, and the combination of $R^{2a}$, $R^{2b}$, $R^{2c}$ and $R^{4b}$ for a compound corresponds in each case to one row of Table A Table 579
Compounds of the formula Ia.15 in which $R^6$ is (2-methyl-pyrazol-3-yl)-methyl, and the combination of $R^{2a}$, $R^{2b}$, $R^{2c}$ and $R^{4b}$ for a compound corresponds in each case to one row of Table A Table 580
Compounds of the formula Ia.15 in which $R^6$ is tetrahydrofuran-3-yl-methyl, and the combination of $R^{2a}$, $R^{2b}$, $R^{2c}$ and $R^{4b}$ for a compound corresponds in each case to one row of Table A Table 581
Compounds of the formula Ia.15 in which $R^6$ is (1,3-dioxolan-2-yl)-methyl, and the combination of $R^{2a}$, $R^{2b}$, $R^{2c}$ and $R^{4b}$ for a compound corresponds in each case to one row of Table A Table 582
Compounds of the formula Ia.15 in which $R^6$ is 2-pyridyl-eth-1-yl, and the combination of $R^{2a}$, $R^{2b}$, $R^{2c}$ and $R^{4b}$ for a compound corresponds in each case to one row of Table A Table 583
Compounds of the formula Ia.15 in which $R^6$ is (1R)-2-pyridyl-eth-1-yl, and the combination of $R^{2a}$, $R^{2b}$, $R^{2c}$ and $R^{4b}$ for a compound corresponds in each case to one row of Table A Table 584
Compounds of the formula Ia.15 in which $R^6$ is (1S)-2-pyridyl-eth-1-yl, and the combination of $R^{2a}$, $R^{2b}$, $R^{2c}$ and $R^{4b}$ for a compound corresponds in each case to one row of Table A Table 585
Compounds of the formula Ia.15 in which $R^6$ is —$CONH_2$, and the combination of $R^{2a}$, $R^{2b}$, $R^{2c}$ and $R^{4b}$ for a compound corresponds in each case to one row of Table A Table 586
Compounds of the formula Ia.15 in which $R^6$ is —$CONN$—$CH_3$, and the combination of $R^{2a}$, $R^{2b}$, $R^{2c}$ and $R^{4b}$ for a compound corresponds in each case to one row of Table A Table 587
Compounds of the formula Ia.15 in which $R^6$ is —$CONH$—$CH_2CH_3$, and the combination of $R^{2a}$, $R^{2b}$, $R^{2c}$ and $R^{4b}$ for a compound corresponds in each case to one row of Table A Table 588
Compounds of the formula Ia.15 in which $R^6$ is —$CONH$—$CH_2CH_2CH_3$, and the combination of $R^{2a}$, $R^{2b}$, $R^{2c}$ and $R^{4b}$ for a compound corresponds in each case to one row of Table A Table 589
Compounds of the formula Ia.15 in which $R^6$ is —$CONH$-cyclopropyl, and the combination of $R^{2a}$, $R^{2b}$, $R^{2c}$ and $R^{4b}$ for a compound corresponds in each case to one row of Table A Table 590
Compounds of the formula Ia.15 in which $R^6$ is —$CONH$—$CH_2$-cyclopropyl, and the combination of $R^{2a}$, $R^{2b}$, $R^{2c}$ and $R^{4b}$ for a compound corresponds in each case to one row of Table A Table 591
Compounds of the formula Ia.15 in which $R^6$ is —$CONH$-phenyl, and the combination of $R^{2a}$, $R^{2b}$, $R^{2c}$ and $R^{4b}$ for a compound corresponds in each case to one row of Table A Table 592
Compounds of the formula Ia.15 in which $R^6$ is —$CONH$-benzyl, and the combination of $R^{2a}$, $R^{2b}$, $R^{2c}$ and $R^{4b}$ for a compound corresponds in each case to one row of Table A Table 593
Compounds of the formula Ia.15 in which $R^6$ is —$NHCO$—$NH$—$CH_3$, and the combination of $R^{2a}$, $R^{2b}$, $R^{2c}$ and $R^{4b}$ for a compound corresponds in each case to one row of Table A Table 594
Compounds of the formula Ia.15 in which $R^6$ is —$NHCO$—$NH$—$CH_2CH_3$, and the combination of $R^{2a}$, $R^{2b}$, $R^{2c}$ and $R^{4b}$ for a compound corresponds in each case to one row of Table A Table 595
Compounds of the formula Ia.15 in which $R^6$ is —$NHCO$—$NH$—$CH_2CH_2CH_3$, and the combination of $R^{2a}$, $R^{2b}$, $R^{2c}$ and $R^{4b}$ for a compound corresponds in each case to one row of Table A Table 596
Compounds of the formula Ia.15 in which $R^6$ is —$NHCO$—$NH$—$CH(CH_3)_2$, and the combination of $R^{2a}$, $R^{2b}$, $R^{2c}$ and $R^{4b}$ for a compound corresponds in each case to one row of Table A Table 597
Compounds of the formula Ia.15 in which $R^6$ is —$NHCO$—$NH$—$CH_2CF_3$, and the combination of $R^{2a}$, $R^{2b}$, $R^{2c}$ and $R^{4b}$ for a compound corresponds in each case to one row of Table A Table 598
Compounds of the formula Ia.15 in which $R^6$ is —$NHCO$—$NH$—$CH_2CHF_2$, and the combination of $R^{2a}$, $R^{2b}$, $R^{2c}$ and $R^{4b}$ for a compound corresponds in each case to one row of Table A Table 599
Compounds of the formula Ia.15 in which $R^6$ is —$NHCO$—$NH$—$CH(CH_3)CF_3$, and the combination of $R^{2a}$, $R^{2b}$, $R^{2c}$ and $R^{4b}$ for a compound corresponds in each case to one row of Table A Table 600
Compounds of the formula Ia.15 in which $R^6$ is —NHCO—NH—CH(CF$_3$)$_2$, and the combination of $R^{2a}$, $R^{2b}$, $R^{2c}$ and $R^{4b}$ for a compound corresponds in each case to one row of Table A Table 601
Compounds of the formula Ia.15 in which $R^6$ is —NHCO—NH—CH$_2$CN, and the combination of $R^{2a}$, $R^{2b}$, $R^{2c}$ and $R^{4b}$ for a compound corresponds in each case to one row of Table A Table 602
Compounds of the formula Ia.15 in which $R^6$ is —NHCO—NH—CH$_2$—CH=CH$_2$, and the combination of $R^{2a}$, $R^{2b}$, $R^{2c}$ and $R^{4b}$ for a compound corresponds in each case to one row of Table A Table 603
Compounds of the formula Ia.15 in which $R^6$ is —NHCO—NH—CH$_2$—C≡CH, and the combination of $R^{2a}$, $R^{2b}$, $R^{2c}$ and $R^{4b}$ for a compound corresponds in each case to one row of Table A Table 604
Compounds of the formula Ia.15 in which $R^6$ is —NHCO—NH-cyclopropyl, and the combination of $R^{2a}$, $R^{2b}$, $R^{2c}$ and $R^{4b}$ for a compound corresponds in each case to one row of Table A Table 605
Compounds of the formula Ia.15 in which $R^6$ is —NHCO—NH-(1-cyanocyclopropyl), and the combination of $R^{2a}$, $R^{2b}$, $R^{2c}$ and $R^{4b}$ for a compound corresponds in each case to one row of Table A Table 606
Compounds of the formula Ia.15 in which $R^6$ is —NHCO—NH-cyclobutyl, and the combination of $R^{2a}$, $R^{2b}$, $R^{2c}$ and $R^{4b}$ for a compound corresponds in each case to one row of Table A Table 607
Compounds of the formula Ia.15 in which $R^6$ is —NHCO—NH-(1-cyanocyclobutyl), and the combination of $R^{2a}$, $R^{2b}$, $R^{2c}$ and $R^{4b}$ for a compound corresponds in each case to one row of Table A Table 608
Compounds of the formula Ia.15 in which $R^6$ is —NHCO—NH—CH$_2$-cyclopropyl, and the combination of $R^{2a}$, $R^{2b}$, $R^{2c}$ and $R^{4b}$ for a compound corresponds in each case to one row of Table A Table 609
Compounds of the formula Ia.15 in which $R^6$ is —NHCO—NH—CH$_2$-(1-cyanocyclopropyl), and the combination of $R^{2a}$, $R^{2b}$, $R^{2c}$ and $R^{4b}$ for a compound corresponds in each case to one row of Table A Table 610
Compounds of the formula Ia.15 in which $R^6$ is —CH=NOCH$_3$, and the combination of $R^{2a}$, $R^{2b}$, $R^{2c}$ and $R^{4b}$ for a compound corresponds in each case to one row of Table A Table 611
Compounds of the formula Ia.15 in which $R^6$ is —CH=NOCH$_2$CF$_3$, and the combination of $R^{2a}$, $R^{2b}$, $R^{2c}$ and $R^{4b}$ for a compound corresponds in each case to one row of Table A Table 612
Compounds of the formula Ia.15 in which $R^6$ is 3-oxo-isoxazolidin-4-yl, and the combination of $R^{2a}$, $R^{2b}$, $R^{2c}$ and $R^{4b}$ for a compound corresponds in each case to one row of Table A Table 613
Compounds of the formula Ia.15 in which $R^6$ is 2-methyl-3-oxo-isoxazolidin-4-yl, and the combination of $R^{2a}$, $R^{2b}$, $R^{2c}$ and $R^{4b}$ for a compound corresponds in each case to one row of Table A Table 614
Compounds of the formula Ia.15 in which $R^6$ is 2-ethyl-3-oxo-isoxazolidin-4-yl, and the combination of $R^{2a}$, $R^{2b}$, $R^{2c}$ and $R^{4b}$ for a compound corresponds in each case to one row of Table A Table 615
Compounds of the formula Ia.15 in which $R^6$ is 2-propyl-3-oxo-isoxazolidin-4-yl, and the combination of $R^{2a}$, $R^{2b}$, $R^{2c}$ and $R^{4b}$ for a compound corresponds in each case to one row of Table A Table 616
Compounds of the formula Ia.15 in which $R^6$ is 2-butyl-3-oxo-isoxazolidin-4-yl, and the combination of $R^{2a}$, $R^{2b}$, $R^{2c}$ and $R^{4b}$ for a compound corresponds in each case to one row of Table A Table 617
Compounds of the formula Ia.15 in which $R^6$ is 2-(but-2-yl)-3-oxo-isoxazolidin-4-yl, and the combination of $R^{2a}$, $R^{2b}$, $R^{2c}$ and $R^{4b}$ for a compound corresponds in each case to one row of Table A Table 618
Compounds of the formula Ia.15 in which $R^6$ is 2-(3-bromopropyl)-3-oxo-isoxazolidin-4-yl, and the combination of $R^{2a}$, $R^{2b}$, $R^{2c}$ and $R^{4b}$ for a compound corresponds in each case to one row of Table A Table 619
Compounds of the formula Ia.15 in which $R^6$ is 2-(2-fluoroethyl)-3-oxo-isoxazolidin-4-yl, and the combination of $R^{2a}$, $R^{2b}$, $R^{2c}$ and $R^{4b}$ for a compound corresponds in each case to one row of Table A Table 620
Compounds of the formula Ia.15 in which $R^6$ is 2-(2,2-difluoroethyl)-3-oxo-isoxazolidin-4-yl, and the combination of $R^{2a}$, $R^{2b}$, $R^{2c}$ and $R^{4b}$ for a compound corresponds in each case to one row of Table A Table 621
Compounds of the formula Ia.15 in which $R^6$ is 2-(2,2,2-trifluoroethyl)-3-oxo-isoxazolidin-4-yl, and the combination of $R^{2a}$, $R^{2b}$, $R^{2c}$ and $R^{4b}$ for a compound corresponds in each case to one row of Table A Table 622
Compounds of the formula Ia.15 in which $R^6$ is 2-(3,3,3-trifluoropropyl)-3-oxo-isoxazolidin-4-yl, and the combination of $R^{2a}$, $R^{2b}$, $R^{2c}$ and $R^{4b}$ for a compound corresponds in each case to one row of Table A Table 623
Compounds of the formula Ia.15 in which $R^6$ is 2-(2-methoxyethyl)-3-oxo-isoxazolidin-4-yl, and the combination of $R^{2a}$, $R^{2b}$, $R^{2c}$ and $R^{4b}$ for a compound corresponds in each case to one row of Table A Table 624
Compounds of the formula Ia.15 in which $R^6$ is 2-(1-methoxy-prop-2-yl)-3-oxo-isoxazolidin-4-yl, and the combination of $R^{2a}$, $R^{2b}$, $R^{2c}$ and $R^{4b}$ for a compound corresponds in each case to one row of Table A Table 625
Compounds of the formula Ia.15 in which $R^6$ is 2-cyclobutyl-3-oxo-isoxazolidin-4-yl, and the combination of $R^{2a}$, $R^{2b}$, $R^{2c}$ and $R^{4b}$ for a compound corresponds in each case to one row of Table A Table 626
Compounds of the formula Ia.15 in which $R^6$ is 2-(2-methylcyclohex-1-yl)-3-oxo-isoxazolidin-4-yl, and the combination of $R^{2a}$, $R^{2b}$, $R^{2c}$ and $R^{4b}$ for a compound corresponds in each case to one row of Table A Table 627
Compounds of the formula Ia.15 in which $R^6$ is 2-(phenylmethyl)-3-oxo-isoxazolidin-4-yl, and the combination of $R^{2a}$, $R^{2b}$, $R^{2c}$ and $R^{4b}$ for a compound corresponds in each case to one row of Table A Table 628
Compounds of the formula Ia.15 in which $R^6$ is 2-(1-phenyl-eth-1-yl)-3-oxo-isoxazolidin-4-yl, and the combination of $R^{2a}$, $R^{2b}$, $R^{2c}$ and $R^{4b}$ for a compound corresponds in each case to one row of Table A Table 629
Compounds of the formula Ia.15 in which $R^6$ is 2-(2-phenyl-eth-1-yl)-3-oxo-isoxazolidin-4-yl, and the combination of $R^{2a}$, $R^{2b}$, $R^{2c}$ and $R^{4b}$ for a compound corresponds in each case to one row of Table A Table 630
Compounds of the formula Ia.15 in which $R^6$ is 2-[(3-chlorophenyl)-methyl]-3-oxo-isoxazolidin-4-yl, and the combination of $R^{2a}$, $R^{2b}$, $R^{2c}$ and $R^{4b}$ for a compound corresponds in each case to one row of Table A Table 631
Compounds of the formula Ia.15 in which $R^6$ is 2-[(2-fluorophenyl)-methyl]-3-oxo-isoxazolidin-4-yl, and the combination of $R^{2a}$, $R^{2b}$, $R^{2c}$ and $R^{4b}$ for a compound corresponds in each case to one row of Table A Table 632
Compounds of the formula Ia.15 in which $R^6$ is 2-[(4-methoxyphenyl)-methyl]-3-oxo-isoxazolidin-4-yl, and the combination of $R^{2a}$, $R^{2b}$, $R^{2c}$ and $R^{4b}$ for a compound corresponds in each case to one row of Table A Table 633
Compounds of the formula Ia.15 in which $R^6$ is 2-[(2-trifluoromethylphenyl)-methyl]-3-oxo-isoxazolidin-4-yl, and the combination of $R^{2a}$, $R^{2b}$, $R^{2c}$ and $R^{4b}$ for a compound corresponds in each case to one row of Table A Table 634
Compounds of the formula Ia.15 in which $R^6$ is $R^6$ is 2-[(2-trifluoromethoxyphenyl)methyl]-3-oxo-isoxazolidin-4-yl, and the combination of $R^{2a}$, $R^{2b}$, $R^{2c}$ and $R^{4b}$ for a compound corresponds in each case to one row of Table A Table 635
Compounds of the formula Ia.15 in which $R^6$ is 2-(pyridin-2-yl-methyl)-3-oxo-isoxazolidin-4-yl, and the combination of $R^{2a}$, $R^{2b}$, $R^{2c}$ and $R^{4b}$ for a compound corresponds in each case to one row of Table A Table 636
Compounds of the formula Ia.15 in which $R^6$ is 2-(pyridin-3-yl-methyl)-3-oxo-isoxazolidin-4-yl, and the combination of $R^{2a}$, $R^{2b}$, $R^{2c}$ and $R^{4b}$ for a compound corresponds in each case to one row of Table A Table 637
Compounds of the formula Ia.15 in which $R^6$ is 2-[(2-chloropyridin-5-yl)-methyl]-3-oxo-isoxazolidin-4-yl, and the combination of $R^{2a}$, $R^{2b}$, $R^{2c}$ and $R^{4b}$ for a compound corresponds in each case to one row of Table A Table 638
Compounds of the formula Ia.15 in which $R^6$ is 2-[(1-methyl-1H-imidazol-4-yl)-methyl]-3-oxo-isoxazolidin-4-yl, and the combination of $R^{2a}$, $R^{2b}$, $R^{2c}$ and $R^{4b}$ for a compound corresponds in each case to one row of Table A Table 639
Compounds of the formula Ia.15 in which $R^6$ is 2-[(furan-2-yl)-methyl]-3-oxo-isoxazolidin-4-yl, and the combination of $R^{2a}$, $R^{2b}$, $R^{2c}$ and $R^{4b}$ for a compound corresponds in each case to one row of Table A Table 640
Compounds of the formula Ia.15 in which $R^6$ is 2-[(2-thiophen-2'-yl)-eth-1-yl]-3-oxo-isoxazolidin-4-yl, and the combination of $R^{2a}$, $R^{2b}$, $R^{2c}$ and $R^{4b}$ for a compound corresponds in each case to one row of Table A Table 641
Compounds of the formula Ia.15 in which $R^6$ is 2-[2-(indol-3'-yl)-eth-1-yl]-3-oxo-isoxazolidin-4-yl, and the combination of $R^{2a}$, $R^{2b}$, $R^{2c}$ and $R^{4b}$ for a compound corresponds in each case to one row of Table A Table 642
Compounds of the formula Ia.15 in which $R^6$ is 2-[(1H-benzimidazol-2-yl)-methyl]-3-oxo-isoxazolidin-4-yl, and the combination of $R^{2a}$, $R^{2b}$, $R^{2c}$ and $R^{4b}$ for a compound corresponds in each case to one row of Table A Table 643
Compounds of the formula Ia.15 in which $R^6$ is 2-[(oxetan-2-yl)-methyl]-3-oxo-isoxazolidin-4-yl, and the combination of $R^{2a}$, $R^{2b}$, $R^{2c}$ and $R^{4b}$ for a compound corresponds in each case to one row of Table A Table 644
Compounds of the formula Ia.15 in which $R^6$ is 2-[(tetrahydrofuran-2-yl)-methyl]-3-oxo-isoxazolidin-4-yl, and the combination of $R^{2a}$, $R^{2b}$, $R^{2c}$ and $R^{4b}$ for a compound corresponds in each case to one row of Table A Table 645
Compounds of the formula Ia.15 in which $R^6$ is 2-[(2-[1',3']dioxolan-2'-yl)-eth-1-yl]-3-oxo-isoxazolidin-4-yl, and the combination of $R^{2a}$, $R^{2b}$, $R^{2c}$ and $R^{4b}$ for a compound corresponds in each case to one row of Table A Table 646
Compounds of the formula Ia.15 in which $R^6$ is 2-[(2-morpholin-4'-yl)-eth-1-yl]-3-oxo-isoxazolidin-4-yl, and the combination of $R^{2a}$, $R^{2b}$, $R^{2c}$ and $R^{4b}$ for a compound corresponds in each case to one row of Table A Table 647
Compounds of the formula Ia.15 in which $R^6$ is 2-[(2-benzo[1',3']dioxol-5'-yl)-eth-1-yl]-3-oxo-isoxazolidin-4-yl, and the combination of $R^{2a}$, $R^{2b}$, $R^{2c}$ and $R^{4b}$ for a compound corresponds in each case to one row of Table A Table 648
Compounds of the formula Ia.15 in which $R^6$ is 2-[(2,3-dihydro-benzo[1,4]dioxin-6-yl)methyl]-3-oxo-isoxazolidin-4-yl, and the combination of $R^{2a}$, $R^{2b}$, $R^{2c}$ and $R^{4b}$ for a compound corresponds in each case to one row of Table A Table 649
Compounds of the formula Ia.15 in which $R^6$ is 2-(2-chlorophenyl)-3-oxo-isoxazolidin-4-yl, and the combination of $R^{2a}$, $R^{2b}$, $R^{2c}$ and $R^{4b}$ for a compound corresponds in each case to one row of Table A Table 650
Compounds of the formula Ia.15 in which $R^6$ is 2-(3-fluorophenyl)-3-oxo-isoxazolidin-4-yl, and the combination of $R^{2a}$, $R^{2b}$, $R^{2c}$ and $R^{4b}$ for a compound corresponds in each case to one row of Table A Table 651
Compounds of the formula Ia.15 in which $R^6$ is 2-(2-methylphenyl)-3-oxo-isoxazolidin-4-yl, and the combination of $R^{2a}$, $R^{2b}$, $R^{2c}$ and $R^{4b}$ for a compound corresponds in each case to one row of Table A Table 652
Compounds of the formula Ia.15 in which $R^6$ is 2-(2-chloro-6-methylphenyl)-3-oxo-isoxazolidin-4-yl, and the combination of $R^{2a}$, $R^{2b}$, $R^{2c}$ and $R^{4b}$ for a compound corresponds in each case to one row of Table A Table 653
Compounds of the formula Ia.15 in which $R^6$ is 2-(2-trifluoromethylphenyl)-3-oxo-isoxazolidin-4-yl, and the combination of $R^{2a}$, $R^{2b}$, $R^{2c}$ and $R^{4b}$ for a compound corresponds in each case to one row of Table A Table 654
Compounds of the formula Ia.15 in which $R^6$ is 2-(2,4-dimethoxyphenyl)-3-oxo-isoxazolidin-4-yl, and the combination of $R^{2a}$, $R^{2b}$, $R^{2c}$ and $R^{4b}$ for a compound corresponds in each case to one row of Table A Table 655
Compounds of the formula Ia.15 in which $R^6$ is 2-(3-methylpyrid-2-yl)-3-oxo-isoxazolidin-4-yl, and the combination of $R^{2a}$, $R^{2b}$, $R^{2c}$ and $R^{4b}$ for a compound corresponds in each case to one row of Table A Table 656
Compounds of the formula Ia.15 in which $R^6$ is 2-(1,3-dimethyl-1H-pyrazol-5-yl)-3-oxo-isoxazolidin-4-yl, and the combination of $R^{2a}$, $R^{2b}$, $R^{2c}$ and $R^{4b}$ for a compound corresponds in each case to one row of Table A Table 657
Compounds of the formula Ia.15 in which $R^6$ is 2-(4-methylthiazol-2-yl)-3-oxo-isoxazolidin-4-yl, and the combination of $R^{2a}$, $R^{2b}$, $R^{2c}$ and $R^{4b}$ for a compound corresponds in each case to one row of Table A Table 658
Compounds of the formula Ia.15 in which $R^6$ is 2-(5-methylthiadiazol-2-yl)-3-oxo-isoxazolidin-4-yl, and the combination of $R^{2a}$, $R^{2b}$, $R^{2c}$ and $R^{4b}$ for a compound corresponds in each case to one row of Table A Table 659
Compounds of the formula Ia.15 in which $R^6$ is 2-(quinolin-2-yl)-3-oxo-isoxazolidin-4-yl, and the combination of $R^{2a}$, $R^{2b}$, $R^{2c}$ and $R^{4b}$ for a compound corresponds in each case to one row of Table A Table 660
Compounds of the formula Ia.15 in which $R^6$ is 2-(quinolin-5-yl)-3-oxo-isoxazolidin-4-yl, and the combination of $R^{2a}$, $R^{2b}$, $R^{2c}$ and $R^{4b}$ for a compound corresponds in each case to one row of Table A Table 661
Compounds of the formula Ia.15 in which $R^6$ is 2-(benzothiazol-6-yl)-3-oxo-isoxazolidin-4-yl, and the combination of $R^{2a}$, $R^{2b}$, $R^{2c}$ and $R^{4b}$ for a compound corresponds in each case to one row of Table A Table 662
Compounds of the formula Ia.15 in which $R^6$ is 2-(4-methylbenzothiazol-2-yl)-3-oxo-isoxazolidin-4-yl, and the combination of $R^{2a}$, $R^{2b}$, $R^{2c}$ and $R^{4b}$ for a compound corresponds in each case to one row of Table A Table 663
Compounds of the formula Ia.15 in which $R^6$ is 2-(thietan-3-yl)-3-oxo-isoxazolidin-4-yl, and the combination of $R^{2a}$, $R^{2b}$, $R^{2c}$ and $R^{4b}$ for a compound corresponds in each case to one row of Table A Table 664
Compounds of the formula Ia.15 in which $R^6$ is 2-(1-oxo-thietan-3-yl)-3-oxo-isoxazolidin-4-yl, and the combination of $R^{2a}$, $R^{2b}$, $R^{2c}$ and $R^{4b}$ for a compound corresponds in each case to one row of Table A Table 665
Compounds of the formula Ia.15 in which $R^6$ is 2-(1,1-dioxo-thietan-3-yl)-3-oxo-isoxazolidin-4-yl, and the combination of $R^{2a}$, $R^{2b}$, $R^{2c}$ and $R^{4b}$ for a compound corresponds in each case to one row of Table A Table 666
Compounds of the formula Ia.15 in which $R^6$ is 2-(3-methylthietan-3-yl)-3-oxo-isoxazolidin-4-yl, and the combination of $R^{2a}$, $R^{2b}$, $R^{2c}$ and $R^{4b}$ for a compound corresponds in each case to one row of Table A Table 667
Compounds of the formula Ia.15 in which $R^6$ is 2-(oxetan-3-yl)-3-oxo-isoxazolidin-4-yl, and the combination of $R^{2a}$, $R^{2b}$, $R^{2c}$ and $R^{4b}$ for a compound corresponds in each case to one row of Table A Table 668
Compounds of the formula Ia.15 in which $R^6$ is 2-(tetrahydropyran-4-yl)-3-oxo-isoxazolidin-4-yl, and the combination of $R^{2a}$, $R^{2b}$, $R^{2c}$ and $R^{4b}$ for a compound corresponds in each case to one row of Table A Tables 669 to 954
Compounds of the formula Ia.16 in which $R^6$ is as defined in tables 383 to 668 and the combination of $R^{2a}$, $R^{2b}$, $R^{2c}$ and $R^{4b}$ for a compound corresponds in each case to one row of Table A Tables 955 to 1240
Compounds of the formula Ia.17 in which $R^6$ is as defined in tables 383 to 668 and the combination of $R^{2a}$, $R^{2b}$, $R^{2c}$ and $R^{4b}$ for a compound corresponds in each case to one row of Table A Tables 1241 to 1526
Compounds of the formula Ia.18 in which $R^6$ is as defined in tables 383 to 668 and the combination of $R^{2a}$, $R^{2b}$, $R^{2c}$ and $R^{4b}$ for a compound corresponds in each case to one row of Table A Tables 1527 to 1812
Compounds of the formula Ia.19 in which $R^6$ is as defined in tables 383 to 668 and the combination of $R^{2a}$, $R^{2b}$, $R^{2c}$ and $R^{4b}$ for a compound corresponds in each case to one row of Table A Tables 1813 to 2098
Compounds of the formula Ia.20 in which $R^6$ is as defined in tables 383 to 668 and the combination of $R^{2a}$, $R^{2b}$, $R^{2c}$ and $R^{4b}$ for a compound corresponds in each case to one row of Table A Tables 2099 to 2384
Compounds of the formula Ia.21 in which $R^6$ is as defined in tables 383 to 668 and the combination of $R^{2a}$, $R^{2b}$, $R^{2c}$ and $R^{4b}$ for a compound corresponds in each case to one row of Table A Tables 2385 to 2670
Compounds of the formula Ia.22 in which $R^6$ is as defined in tables 383 to 668 and the combination of $R^{2a}$, $R^{2b}$, $R^{2c}$ and $R^{4b}$ for a compound corresponds in each case to one row of Table A Table 2671
Compounds of the formula Ia.23 in which $R^{9a}$ and $R^{9b}$ are methyl, and the combination of $R^{2a}$, $R^{2b}$, $R^{2c}$ and $R^{4b}$ for a compound corresponds in each case to one row of Table A Table 2672
Compounds of the formula Ia.23 in which $R^{9a}$ and $R^{9b}$ are ethyl, and the combination of $R^{2a}$, $R^{2b}$, $R^{2c}$ and $R^{4b}$ for a compound corresponds in each case to one row of Table A Table 2673
Compounds of the formula Ia.23 in which $R^{9a}$ and $R^{9b}$ are propyl, and the combination of $R^{2a}$, $R^{2b}$, $R^{2c}$ and $R^{4b}$ for a compound corresponds in each case to one row of Table A Table 2674
Compounds of the formula Ia.23 in which $R^{9a}$ and $R^{9b}$ are isopropyl, and the combination of $R^{2a}$, $R^{2b}$, $R^{2c}$ and $R^{4b}$ for a compound corresponds in each case to one row of Table A Table 2675 to 2678

Compounds of the formula Ia.24 in which $R^{9a}$ and $R^{9b}$ are as defined in tables 2671 to 2674, and the combination of $R^{2a}$, $R^{2b}$, $R^{2c}$ and $R^{4b}$ for a compound corresponds in each case to one row of Table A Table 2679

Compounds of the formula Ia.25 in which $R^8$ is hydrogen, and the combination of $R^{2a}$, $R^{2b}$, $R^{2c}$ and $R^{4b}$ for a compound corresponds in each case to one row of Table A Table 2680

Compounds of the formula Ia.25 in which $R^8$ is methyl, and the combination of $R^{2a}$, $R^{2b}$, $R^{2c}$ and $R^{4b}$ for a compound corresponds in each case to one row of Table A Table 2681

Compounds of the formula Ia.25 in which $R^8$ is ethyl, and the combination of $R^{2a}$, $R^{2b}$, $R^{2c}$ and $R^{4b}$ for a compound corresponds in each case to one row of Table A Table 2682

Compounds of the formula Ia.25 in which $R^8$ is propyl, and the combination of $R^{2a}$, $R^{2b}$, $R^{2c}$ and $R^{4b}$ for a compound corresponds in each case to one row of Table A Table 2683

Compounds of the formula Ia.25 in which $R^8$ is isopropyl, and the combination of $R^{2a}$, $R^{2b}$, $R^{2c}$ and $R^{4b}$ for a compound corresponds in each case to one row of Table A Table 2684

Compounds of the formula Ia.25 in which $R^8$ is n-butyl, and the combination of $R^{2a}$, $R^{2b}$, $R^{2c}$ and $R^{4b}$ for a compound corresponds in each case to one row of Table A Table 2685

Compounds of the formula Ia.25 in which $R^8$ is sec-butyl, and the combination of $R^{2a}$, $R^{2b}$, $R^{2c}$ and $R^{4b}$ for a compound corresponds in each case to one row of Table A Table 2686

Compounds of the formula Ia.25 in which $R^8$ is isobutyl, and the combination of $R^{2a}$, $R^{2b}$, $R^{2c}$ and $R^{4b}$ for a compound corresponds in each case to one row of Table A Table 2687

Compounds of the formula Ia.25 in which $R^8$ is tert-butyl, and the combination of $R^{2a}$, $R^{2b}$, $R^{2c}$ and $R^{4b}$ for a compound corresponds in each case to one row of Table A Table 2688

Compounds of the formula Ia.25 in which $R^8$ is $CH_2F$, and the combination of $R^{2a}$, $R^{2b}$, $R^{2c}$ and $R^{4b}$ for a compound corresponds in each case to one row of Table A Table 2689

Compounds of the formula Ia.25 in which $R^8$ is $CHF_2$, and the combination of $R^{2a}$, $R^{2b}$, $R^{2c}$ and $R^{4b}$ for a compound corresponds in each case to one row of Table A Table 2690

Compounds of the formula Ia.25 in which $R^8$ is $CF_3$, and the combination of $R^{2a}$, $R^{2b}$, $R^{2c}$ and $R^{4b}$ for a compound corresponds in each case to one row of Table A Table 2691

Compounds of the formula Ia.25 in which $R^8$ is $CH_2CHF_2$, and the combination of $R^{2a}$, $R^{2b}$, $R^{2c}$ and $R^{4b}$ for a compound corresponds in each case to one row of Table A Table 2692

Compounds of the formula Ia.25 in which $R^8$ is $CH_2CF_3$, and the combination of $R^{2a}$, $R^{2b}$, $R^{2c}$ and $R^{4b}$ for a compound corresponds in each case to one row of Table A Table 2693

Compounds of the formula Ia.25 in which $R^8$ is $CF_2CF_3$, and the combination of $R^{2a}$, $R^{2b}$, $R^{2c}$ and $R^{4b}$ for a compound corresponds in each case to one row of Table A Table 2694

Compounds of the formula Ia.25 in which $R^8$ is $CH_2CH_2CF_3$, and the combination of $R^{2a}$, $R^{2b}$, $R^{2c}$ and $R^{4b}$ for a compound corresponds in each case to one row of Table A Table 2695

Compounds of the formula Ia.25 in which $R^8$ is $CH(CH_3)CF_3$, and the combination of $R^{2a}$, $R^{2b}$, $R^{2c}$ and $R^{4b}$ for a compound corresponds in each case to one row of Table A Table 2696

Compounds of the formula Ia.25 in which $R^8$ is $CH(CF_3)_2$, and the combination of $R^{2a}$, $R^{2b}$, $R^{2c}$ and $R^{4b}$ for a compound corresponds in each case to one row of Table A Table 2697

Compounds of the formula Ia.25 in which $R^8$ is $CF(CF_3)_2$, and the combination of $R^{2a}$, $R^{2b}$, $R^{2b}$ and $R^{4b}$ for a compound corresponds in each case to one row of Table A Table 2698

Compounds of the formula Ia.25 in which $R^8$ is $CH_2CN$, and the combination of $R^{2a}$, $R^{2b}$, $R^{2c}$ and $R^{4b}$ for a compound corresponds in each case to one row of Table A Table 2699

Compounds of the formula Ia.25 in which $R^8$ is —CH=$CH_2$, and the combination of $R^{2a}$, $R^{2b}$, $R^{2c}$ and $R^{4b}$ for a compound corresponds in each case to one row of Table A Table 2700

Compounds of the formula Ia.25 in which $R^8$ is allyl, and the combination of $R^{2a}$, $R^{2b}$, $R^{2c}$ and $R^{4b}$ for a compound corresponds in each case to one row of Table A Table 2701

Compounds of the formula Ia.25 in which $R^8$ is —C≡CH, and the combination of $R^{2a}$, $R^{2b}$, $R^{2c}$ and $R^{4b}$ for a compound corresponds in each case to one row of Table A Table 2702

Compounds of the formula Ia.25 in which $R^8$ is propargyl, and the combination of $R^{2a}$, $R^{2b}$, $R^{2c}$ and $R^{4b}$ for a compound corresponds in each case to one row of Table A Table 2703

Compounds of the formula Ia.25 in which $R^8$ is CN, and the combination of $R^{2a}$, $R^{2b}$, $R^{2c}$ and $R^{4b}$ for a compound corresponds in each case to one row of Table A Table 2704

Compounds of the formula Ia.25 in which $R^8$ is —CH=CHF, and the combination of $R^{2a}$, $R^{2b}$, $R^{2c}$ and $R^{4b}$ for a compound corresponds in each case to one row of Table A Table 2705

Compounds of the formula Ia.25 in which $R^8$ is —CH=$CF_2$, and the combination of $R^{2a}$, $R^{2b}$, $R^{2c}$ and $R^{4b}$ for a compound corresponds in each case to one row of Table A Table 2706

Compounds of the formula Ia.25 in which $R^8$ is —CF=$CF_2$, and the combination of $R^{2a}$, $R^{2b}$, $R^{2c}$ and $R^{4b}$ for a compound corresponds in each case to one row of Table A Table 2707

Compounds of the formula Ia.25 in which $R^8$ is cyclopropyl, and the combination of $R^{2a}$, $R^{2b}$, $R^{2c}$ and $R^{4b}$ for a compound corresponds in each case to one row of Table A Table 2708

Compounds of the formula Ia.25 in which $R^8$ is 1-fluorocyclopropyl, and the combination of $R^{2a}$, $R^{2b}$, $R^{2c}$ and $R^{4b}$ for a compound corresponds in each case to one row of Table A Table 2709
Compounds of the formula Ia.25 in which $R^8$ is 1-cyanocyclopropyl, and the combination of $R^{2a}$, $R^{2b}$, $R^{2c}$ and $R^{4b}$ for a compound corresponds in each case to one row of Table A Table 2710
Compounds of the formula Ia.25 in which $R^8$ is cyclobutyl, and the combination of $R^{2a}$, $R^{2b}$, $R^{2c}$ and $R^{4b}$ for a compound corresponds in each case to one row of Table A Table 2711
Compounds of the formula Ia.25 in which $R^8$ is 1-fluorocyclobutyl, and the combination of $R^{2a}$, $R^{2b}$, $R^{2c}$ and $R^{4b}$ for a compound corresponds in each case to one row of Table A Table 2712
Compounds of the formula Ia.25 in which $R^8$ is 1-cyanocyclobutyl, and the combination of $R^{2a}$, $R^{2b}$, $R^{2c}$ and $R^{4b}$ for a compound corresponds in each case to one row of Table A Table 2713
Compounds of the formula Ia.25 in which $R^8$ is cyclobut-1-enyl, and the combination of $R^{2a}$, $R^{2b}$, $R^{2c}$ and $R^{4b}$ for a compound corresponds in each case to one row of Table A Table 2714
Compounds of the formula Ia.25 in which $R^8$ is —$CH_2$-cyclopropyl, and the combination of $R^{2a}$, $R^{2b}$, $R^{2c}$ and $R^{4b}$ for a compound corresponds in each case to one row of Table A Table 2715
Compounds of the formula Ia.25 in which $R^8$ is —$CH_2$-(1-cyanocyclopropyl), and the combination of $R^{2a}$, $R^{2b}$, $R^{2c}$ and $R^{4b}$ for a compound corresponds in each case to one row of Table A Table 2716
Compounds of the formula Ia.25 in which $R^8$ is —$CH_2$-cyclobutyl, and the combination of $R^{2a}$, $R^{2b}$, $R^{2c}$ and $R^{4b}$ for a compound corresponds in each case to one row of Table A Table 2717
Compounds of the formula Ia.25 in which $R^8$ is —$CH_2$-(1-cyanocyclobutyl), and the combination of $R^{2a}$, $R^{2b}$, $R^{2c}$ and $R^{4b}$ for a compound corresponds in each case to one row of Table A Table 2718
Compounds of the formula Ia.25 in which $R^8$ is oxetan-2-yl, and the combination of $R^{2a}$, $R^{2b}$, $R^{2b}$ and $R^{4b}$ for a compound corresponds in each case to one row of Table A Table 2719
Compounds of the formula Ia.25 in which $R^8$ is oxetan-3-yl, and the combination of $R^{2a}$, $R^{2b}$, $R^{2c}$ and $R^{4b}$ for a compound corresponds in each case to one row of Table A Table 2720
Compounds of the formula Ia.25 in which $R^8$ is tetrahydrofuran-2-yl, and the combination of $R^{2a}$, $R^{2b}$, $R^{2c}$ and $R^{4b}$ for a compound corresponds in each case to one row of Table A Table 2721
Compounds of the formula Ia.25 in which $R^8$ is tetrahydrofuran-3-yl, and the combination of $R^{2a}$, $R^{2b}$, $R^{2c}$ and $R^{4b}$ for a compound corresponds in each case to one row of Table A Table 2722
Compounds of the formula Ia.25 in which $R^8$ is thietan-3-yl, and the combination of $R^{2a}$, $R^{2b}$, $R^{2c}$ and $R^{4b}$ for a compound corresponds in each case to one row of Table A Table 2723
Compounds of the formula Ia.25 in which $R^8$ is 1-oxothietan-3-yl, and the combination of $R^{2a}$, $R^{2b}$, $R^{2c}$ and $R^{4b}$ for a compound corresponds in each case to one row of Table A Table 2724
Compounds of the formula Ia.25 in which $R^8$ is 1,1-dioxothietan-3-yl, and the combination of $R^{2a}$, $R^{2b}$, $R^{2c}$ and $R^{4b}$ for a compound corresponds in each case to one row of Table A Table 2725
Compounds of the formula Ia.25 in which $R^8$ is phenyl, and the combination of $R^{2a}$, $R^{2b}$, $R^{2c}$ and $R^{4b}$ for a compound corresponds in each case to one row of Table A Table 2726
Compounds of the formula Ia.25 in which $R^8$ is 2-fluorophenyl, and the combination of $R^{2a}$, $R^{2b}$, $R^{2c}$ and $R^{4b}$ for a compound corresponds in each case to one row of Table A Table 2727
Compounds of the formula Ia.25 in which $R^8$ is 3-fluorophenyl, and the combination of $R^{2a}$, $R^{2b}$, $R^{2c}$ and $R^{4b}$ for a compound corresponds in each case to one row of Table A Table 2728
Compounds of the formula Ia.25 in which $R^8$ is 4-fluorophenyl, and the combination of $R^{2a}$, $R^{2b}$, $R^{2c}$ and $R^{4b}$ for a compound corresponds in each case to one row of Table A Table 2729
Compounds of the formula Ia.25 in which $R^8$ is 2,3-difluorophenyl, and the combination of $R^{2a}$, $R^{2b}$, $R^{2c}$ and $R^{4b}$ for a compound corresponds in each case to one row of Table A Table 2730
Compounds of the formula Ia.25 in which $R^8$ is 2,4-difluorophenyl, and the combination of $R^{2a}$, $R^{2b}$, $R^{2c}$ and $R^{4b}$ for a compound corresponds in each case to one row of Table A Table 2731
Compounds of the formula Ia.25 in which $R^8$ is 2,5-difluorophenyl, and the combination of $R^{2a}$, $R^{2b}$, $R^{2c}$ and $R^{4b}$ for a compound corresponds in each case to one row of Table A Table 2732
Compounds of the formula Ia.25 in which $R^8$ is 2,6-difluorophenyl, and the combination of $R^{2a}$, $R^{2b}$, $R^{2c}$ and $R^{4b}$ for a compound corresponds in each case to one row of Table A Table 2733
Compounds of the formula Ia.25 in which $R^8$ is 3,4-difluorophenyl, and the combination of $R^{2a}$, $R^{2b}$, $R^{2c}$ and $R^{4b}$ for a compound corresponds in each case to one row of Table A Table 2734
Compounds of the formula Ia.25 in which $R^8$ is 3,5-difluorophenyl, and the combination of $R^{2a}$, $R^{2b}$, $R^{2c}$ and $R^{4b}$ for a compound corresponds in each case to one row of Table A Table 2735
Compounds of the formula Ia.25 in which $R^8$ is 2-chlorophenyl, and the combination of $R^{2a}$, $R^{2b}$, $R^{2c}$ and $R^{4b}$ for a compound corresponds in each case to one row of Table A Table 2736
Compounds of the formula Ia.25 in which $R^8$ is 3-chlorophenyl, and the combination of $R^{2a}$, $R^{2b}$, $R^{2c}$ and $R^{4b}$ for a compound corresponds in each case to one row of Table A Table 2737
Compounds of the formula Ia.25 in which $R^8$ is 4-chlorophenyl, and the combination of $R^{2a}$, $R^{2b}$, $R^{2c}$ and $R^{4b}$ for a compound corresponds in each case to one row of Table A Table 2738
Compounds of the formula Ia.25 in which $R^8$ is 2-methoxyphenyl, and the combination of $R^{2a}$, $R^{2b}$, $R^{2c}$ and $R^{4b}$ for a compound corresponds in each case to one row of Table A Table 2739
Compounds of the formula Ia.25 in which $R^8$ is 3-methoxyphenyl, and the combination of $R^{2a}$, $R^{2b}$, $R^{2c}$ and $R^{4b}$ for a compound corresponds in each case to one row of Table A Table 2740
Compounds of the formula Ia.25 in which $R^8$ is 4-methoxyphenyl, and the combination of $R^{2a}$, $R^{2b}$, $R^{2c}$ and $R^{4b}$ for a compound corresponds in each case to one row of Table A Table 2741
Compounds of the formula Ia.25 in which $R^8$ is pyridin-2-yl, and the combination of $R^{2a}$, $R^{2b}$, $R^{2c}$ and $R^{4b}$ for a compound corresponds in each case to one row of Table A Table 2742
Compounds of the formula Ia.25 in which $R^8$ is pyridin-3-yl, and the combination of $R^{2a}$, $R^{2b}$, $R^{2c}$ and $R^{4b}$ for a compound corresponds in each case to one row of Table A Table 2743
Compounds of the formula Ia.25 in which $R^8$ is pyridin-4-yl, and the combination of $R^{2a}$, $R^{2b}$, $R^{2c}$ and $R^{4b}$ for a compound corresponds in each case to one row of Table A Table 2744
Compounds of the formula Ia.25 in which $R^8$ is 4-chloropyridin-3-yl, and the combination of $R^{2a}$, $R^{2b}$, $R^{2c}$ and $R^{4b}$ for a compound corresponds in each case to one row of Table A Table 2745
Compounds of the formula Ia.25 in which $R^8$ is pyrimidin-2-yl, and the combination of $R^{2a}$, $R^{2b}$, $R^{2c}$ and $R^{4b}$ for a compound corresponds in each case to one row of Table A Table 2746
Compounds of the formula Ia.25 in which $R^8$ is methoxymethyl, and the combination of $R^{2a}$, $R^{2b}$, $R^{2c}$ and $R^{4b}$ for a compound corresponds in each case to one row of Table A Table 2747
Compounds of the formula Ia.25 in which $R^8$ is ethoxymethyl, and the combination of $R^{2a}$, $R^{2b}$, $R^{2c}$ and $R^{4b}$ for a compound corresponds in each case to one row of Table A Table 2748
Compounds of the formula Ia.25 in which $R^8$ is trifluoromethoxymethyl, and the combination of $R^{2a}$, $R^{2b}$, $R^{2c}$ and $R^{4b}$ for a compound corresponds in each case to one row of Table A Table 2749
Compounds of the formula Ia.25 in which $R^8$ is methylthiomethyl, and the combination of $R^{2a}$, $R^{2b}$, $R^{2c}$ and $R^{4b}$ for a compound corresponds in each case to one row of Table A Table 2750
Compounds of the formula Ia.25 in which $R^8$ is ethylthiomethyl, and the combination of $R^{2a}$, $R^{2b}$, $R^{2c}$ and $R^{4b}$ for a compound corresponds in each case to one row of Table A Table 2751
Compounds of the formula Ia.25 in which $R^8$ is trifluoromethylthiomethyl, and the combination of $R^{2a}$, $R^{2b}$, $R^{2c}$ and $R^{4b}$ for a compound corresponds in each case to one row of Table A Table 2752
Compounds of the formula Ia.25 in which $R^8$ is methylsulfinylmethyl, and the combination of $R^{2a}$, $R^{2b}$, $R^{2c}$ and $R^{4b}$ for a compound corresponds in each case to one row of Table A Table 2753
Compounds of the formula Ia.25 in which $R^8$ is ethylsulfinylmethyl, and the combination of $R^{2a}$, $R^{2b}$, $R^{2c}$ and $R^{4b}$ for a compound corresponds in each case to one row of Table A Table 2754
Compounds of the formula Ia.25 in which $R^8$ is trifluoromethylsulfinylmethyl, and the combination of $R^{2a}$, $R^{2b}$, $R^{2c}$ and $R^{4b}$ for a compound corresponds in each case to one row of Table A Table 2755
Compounds of the formula Ia.25 in which $R^8$ is methylsulfonylmethyl, and the combination of $R^{2a}$, $R^{2b}$, $R^{2c}$ and $R^{4b}$ for a compound corresponds in each case to one row of Table A Table 2756
Compounds of the formula Ia.25 in which $R^8$ is ethylsulfonylmethyl, and the combination of $R^{2a}$, $R^{2b}$, $R^{2c}$ and $R^{4b}$ for a compound corresponds in each case to one row of Table A Table 2757
Compounds of the formula Ia.25 in which $R^8$ is trifluoromethylsulfonylmethyl, and the combination of $R^{2a}$, $R^{2b}$, $R^{2c}$ and $R^{4b}$ for a compound corresponds in each case to one row of Table A Table 2758
Compounds of the formula Ia.25 in which $R^8$ is —CH(CH$_3$)—SO$_2$—CH$_3$, and the combination of $R^{2a}$, $R^{2b}$, $R^{2c}$ and $R^{4b}$ for a compound corresponds in each case to one row of Table A Table 2759
Compounds of the formula Ia.25 in which $R^8$ is —C(CH$_3$)$_2$—SO$_2$—CH$_3$, and the combination of $R^{2a}$, $R^{2b}$, $R^{2c}$ and $R^{4b}$ for a compound corresponds in each case to one row of Table A Table 2760
Compounds of the formula Ia.25 in which $R^8$ is —CH$_2$—N(CH$_3$)$_2$, and the combination of $R^{2a}$, $R^{2b}$, $R^{2c}$ and $R^{4b}$ for a compound corresponds in each case to one row of Table A Table 2761
Compounds of the formula Ia.25 in which $R^8$ is —CH$_2$—CH$_2$—N(CH$_3$)$_2$, and the combination of $R^{2a}$, $R^{2b}$, $R^{2c}$ and $R^{4b}$ for a compound corresponds in each case to one row of Table A Table 2762
Compounds of the formula Ia.25 in which $R^8$ is —N(H)CH$_3$, and the combination of $R^{2a}$, $R^{2b}$, $R^{2c}$ and $R^{4b}$ for a compound corresponds in each case to one row of Table A Table 2763
Compounds of the formula Ia.25 in which $R^8$ is —N(H)CH$_2$CH$_3$, and the combination of $R^{2a}$, $R^{2b}$, $R^{2c}$ and $R^{4b}$ for a compound corresponds in each case to one row of Table A Table 2764
Compounds of the formula Ia.25 in which $R^8$ is —N(H)CH$_2$CHF$_2$, and the combination of $R^{2a}$, $R^{2b}$, $R^{2c}$ and $R^{4b}$ for a compound corresponds in each case to one row of Table A Table 2765
Compounds of the formula Ia.25 in which $R^8$ is —N(H)CH$_2$CF$_3$, and the combination of $R^{2a}$, $R^{2b}$, $R^{2c}$ and $R^{4b}$ for a compound corresponds in each case to one row of Table A Table 2766
Compounds of the formula Ia.25 in which $R^8$ is —N(H)CH$_2$CH=CH$_2$, and the combination of $R^{2a}$, $R^{2b}$, $R^{2c}$ and $R^{4b}$ for a compound corresponds in each case to one row of Table A Table 2767
Compounds of the formula Ia.25 in which $R^8$ is —N(H)CH$_2$C≡CH, and the combination of $R^{2a}$, $R^{2b}$, $R^{2c}$ and $R^{4b}$ for a compound corresponds in each case to one row of Table A Table 2768
Compounds of the formula Ia.25 in which $R^8$ is —N(H)CH$_2$CN, and the combination of $R^{2a}$, $R^{2b}$, $R^{2c}$ and $R^{4b}$ for a compound corresponds in each case to one row of Table A Table 2769
Compounds of the formula Ia.25 in which $R^8$ is —N(H)-cyclopropyl, and the combination of $R^{2a}$, $R^{2b}$, $R^{2c}$ and $R^{4b}$ for a compound corresponds in each case to one row of Table A Table 2770
Compounds of the formula Ia.25 in which $R^8$ is —N(H)-(1-cyanocyclopropyl), and the combination of $R^{2a}$, $R^{2b}$, $R^{2c}$ and $R^{4b}$ for a compound corresponds in each case to one row of Table A Table 2771
Compounds of the formula Ia.25 in which $R^8$ is NH$_2$, and the combination of $R^{2a}$, $R^{2b}$, $R^{2b}$ and $R^{4b}$ for a compound corresponds in each case to one row of Table A Table 2772
Compounds of the formula Ia.25 in which $R^8$ is —N(H)—CH$_2$-cyclopropyl, and the combination of $R^{2a}$, $R^{2b}$, $R^{2c}$ and $R^{4b}$ for a compound corresponds in each case to one row of Table A Table 2773
Compounds of the formula Ia.25 in which $R^8$ is —N(H)—CH$_2$-(1-cyanocyclopropyl), and the combination of $R^{2a}$, $R^{2b}$, $R^{2c}$ and $R^{4b}$ for a compound corresponds in each case to one row of Table A Table 2774
Compounds of the formula Ia.25 in which $R^8$ is —C(O)—N(H)CH$_3$, and the combination of $R^{2a}$, $R^{2b}$, $R^{2c}$ and $R^{4b}$ for a compound corresponds in each case to one row of Table A Table 2775
Compounds of the formula Ia.25 in which $R^8$ is —C(O)—N(H)CH$_2$CH$_3$, and the combination of $R^{2a}$, $R^{2b}$, $R^{2c}$ and $R^{4b}$ for a compound corresponds in each case to one row of Table A Table 2776
Compounds of the formula Ia.25 in which $R^8$ is —C(O)—N(H)CH$_2$CHF$_2$, and the combination of $R^{2a}$, $R^{2b}$, $R^{2c}$ and $R^{4b}$ for a compound corresponds in each case to one row of Table A Table 2777
Compounds of the formula Ia.25 in which $R^8$ is —C(O)—N(H)CH$_2$CF$_3$, and the combination of $R^{2a}$, $R^{2b}$, $R^{2c}$ and $R^{4b}$ for a compound corresponds in each case to one row of Table A Table 2778
Compounds of the formula Ia.25 in which $R^8$ is —C(O)—N(H)CH$_2$CH=CH$_2$, and the combination of $R^{2a}$, $R^{2b}$, $R^{2c}$ and $R^{4b}$ for a compound corresponds in each case to one row of Table A Table 2779
Compounds of the formula Ia.25 in which $R^8$ is —C(O)—N(H)CH$_2$C≡CH, and the combination of $R^{2a}$, $R^{2b}$, $R^{2c}$ and $R^{4b}$ for a compound corresponds in each case to one row of Table A Table 2780
Compounds of the formula Ia.25 in which $R^8$ is —C(O)—N(H)CH$_2$CN, and the combination of $R^{2a}$, $R^{2b}$, $R^{2c}$ and $R^{4b}$ for a compound corresponds in each case to one row of Table A Table 2781
Compounds of the formula Ia.25 in which $R^8$ is —C(O)—N(H)-cyclopropyl, and the combination of $R^{2a}$, $R^{2b}$, $R^{2c}$ and $R^{4b}$ for a compound corresponds in each case to one row of Table A Table 2782
Compounds of the formula Ia.25 in which $R^8$ is —C(O)—N(H)-(1-cyanocyclopropyl), and the combination of $R^{2a}$, $R^{2b}$, $R^{2c}$ and $R^{4b}$ for a compound corresponds in each case to one row of Table A Table 2783
Compounds of the formula Ia.25 in which $R^8$ is —C(O)—N(H)—CH$_2$-cyclopropyl, and the combination of $R^{2a}$, $R^{2b}$, $R^{2c}$ and $R^{4b}$ for a compound corresponds in each case to one row of Table A Table 2784
Compounds of the formula Ia.25 in which $R^8$ is —C(O)—N(H)—CH$_2$-(1-cyanocyclopropyl), and the combination of $R^{2a}$, $R^{2b}$, $R^{2c}$ and $R^{4b}$ for a compound corresponds in each case to one row of Table A Table 2785
Compounds of the formula Ia.25 in which $R^8$ is —CH$_2$—C(O)—N(H)CH$_3$, and the combination of $R^{2a}$, $R^{2b}$, $R^{2c}$ and $R^{4b}$ for a compound corresponds in each case to one row of Table A Table 2786
Compounds of the formula Ia.25 in which $R^8$ is —CH$_2$—C(O)—N(H)CH$_2$CH$_3$, and the combination of $R^{2a}$, $R^{2b}$, $R^{2c}$ and $R^{4b}$ for a compound corresponds in each case to one row of Table A Table 2787
Compounds of the formula Ia.25 in which $R^8$ is —CH$_2$—C(O)—N(H)CH$_2$CHF$_2$, and the combination of $R^{2a}$, $R^{2b}$, $R^{2c}$ and $R^{4b}$ for a compound corresponds in each case to one row of Table A Table 2788
Compounds of the formula Ia.25 in which $R^8$ is —CH$_2$—C(O)—N(H)CH$_2$CF$_3$, and the combination of $R^{2a}$, $R^{2b}$, $R^{2c}$ and $R^{4b}$ for a compound corresponds in each case to one row of Table A Table 2789
Compounds of the formula Ia.25 in which $R^8$ is —CH$_2$—C(O)—N(H)CH$_2$CH=CH$_2$, and the combination of $R^{2a}$, $R^{2b}$, $R^{2c}$ and $R^{4b}$ for a compound corresponds in each case to one row of Table A Table 2790
Compounds of the formula Ia.25 in which $R^8$ is —CH$_2$—C(O)—N(H)CH$_2$C≡CH, and the combination of $R^{2a}$, $R^{2b}$, $R^{2c}$ and $R^{4b}$ for a compound corresponds in each case to one row of Table A Table 2791
Compounds of the formula Ia.25 in which $R^8$ is —CH$_2$—C(O)—N(H)CH$_2$CN, and the combination of $R^{2a}$, $R^{2b}$, $R^{2c}$ and $R^{4b}$ for a compound corresponds in each case to one row of Table A Table 2792
Compounds of the formula Ia.25 in which $R^8$ is —CH$_2$—C(O)—N(H)-cyclopropyl, and the combination of $R^{2a}$, $R^{2b}$, $R^{2c}$ and $R^{4b}$ for a compound corresponds in each case to one row of Table A Table 2793
Compounds of the formula Ia.25 in which $R^8$ is —$CH_2$—C(O)—N(H)-(1-cyanocyclopropyl), and the combination of $R^{2a}$, $R^{2b}$, $R^{2c}$ and $R^{4b}$ for a compound corresponds in each case to one row of Table A Table 2794
Compounds of the formula Ia.25 in which $R^8$ is —$CH_2$—C(O)—N(H)—$CH_2$-cyclopropyl, and the combination of $R^{2a}$, $R^{2b}$, $R^{2c}$ and $R^{4b}$ for a compound corresponds in each case to one row of Table A Table 2795
Compounds of the formula Ia.25 in which $R^8$ is —$CH_2$—C(O)—N(H)—$CH_2$-(1-cyanocyclopropyl), and the combination of $R^{2a}$, $R^{2b}$, $R^{2c}$ and $R^{4b}$ for a compound corresponds in each case to one row of Table A Table 2796
Compounds of the formula Ia.25 in which $R^8$ is —NH—C(O)—N(H)$CH_3$, and the combination of $R^{2a}$, $R^{2b}$, $R^{2c}$ and $R^{4b}$ for a compound corresponds in each case to one row of Table A Table 2797
Compounds of the formula Ia.25 in which $R^8$ is —NH—C(O)—N(H)$CH_2CH_3$, and the combination of $R^{2a}$, $R^{2b}$, $R^{2c}$ and $R^{4b}$ for a compound corresponds in each case to one row of Table A Table 2798
Compounds of the formula Ia.25 in which $R^8$ is —NH—C(O)—N(H)$CH_2CHF_2$, and the combination of $R^{2a}$, $R^{2b}$, $R^{2c}$ and $R^{4b}$ for a compound corresponds in each case to one row of Table A Table 2799
Compounds of the formula Ia.25 in which $R^8$ is —NH—C(O)—N(H)$CH_2CF_3$, and the combination of $R^{2a}$, $R^{2b}$, $R^{2c}$ and $R^{4b}$ for a compound corresponds in each case to one row of Table A Table 2800
Compounds of the formula Ia.25 in which $R^8$ is —NH—C(O)—N(H)$CH_2CH$=$CH_2$, and the combination of $R^{2a}$, $R^{2b}$, $R^{2c}$ and $R^{4b}$ for a compound corresponds in each case to one row of Table A Table 2801
Compounds of the formula Ia.25 in which $R^8$ is —NH—C(O)—N(H)$CH_2C$≡CH, and the combination of $R^{2a}$, $R^{2b}$, $R^{2c}$ and $R^{4b}$ for a compound corresponds in each case to one row of Table A Table 2802
Compounds of the formula Ia.25 in which $R^8$ is —NH—C(O)—N(H)$CH_2CN$, and the combination of $R^{2a}$, $R^{2b}$, $R^{2c}$ and $R^{4b}$ for a compound corresponds in each case to one row of Table A Table 2803
Compounds of the formula Ia.25 in which $R^8$ is —NH—C(O)—N(H)-cyclopropyl, and the combination of $R^{2a}$, $R^{2b}$, $R^{2c}$ and $R^{4b}$ for a compound corresponds in each case to one row of Table A Table 2804
Compounds of the formula Ia.25 in which $R^8$ is —NH—C(O)—N(H)-(1-cyanocyclopropyl), and the combination of $R^{2a}$, $R^{2b}$, $R^{2c}$ and $R^{4b}$ for a compound corresponds in each case to one row of Table A Table 2805
Compounds of the formula Ia.25 in which $R^8$ is —NH—C(O)—N(H)—$CH_2$-cyclopropyl, and the combination of $R^{2a}$, $R^{2b}$, $R^{2c}$ and $R^{4b}$ for a compound corresponds in each case to one row of Table A Table 2806
Compounds of the formula Ia.25 in which $R^8$ is —NH—C(O)—N(H)—$CH_2$-(1-cyanocyclopropyl), and the combination of $R^{2a}$, $R^{2b}$, $R^{2c}$ and $R^{4b}$ for a compound corresponds in each case to one row of Table A Table 2807
Compounds of the formula Ia.25 in which $R^8$ is —CH=N—$OCH_3$, and the combination of $R^{2a}$, $R^{2b}$, $R^{2c}$ and $R^{4b}$ for a compound corresponds in each case to one row of Table A Table 2808
Compounds of the formula Ia.25 in which $R^8$ is —CH=N—$OCH_2CH_3$, and the combination of $R^{2a}$, $R^{2b}$, $R^{2c}$ and $R^{4b}$ for a compound corresponds in each case to one row of Table A Table 2809
Compounds of the formula Ia.25 in which $R^8$ is —CH=N—$OCH_2CHF_2$, and the combination of $R^{2a}$, $R^{2b}$, $R^{2c}$ and $R^{4b}$ for a compound corresponds in each case to one row of Table A Table 2810
Compounds of the formula Ia.25 in which $R^8$ is —CH=N—$OCH_2CF_3$, and the combination of $R^{2a}$, $R^{2b}$, $R^{2c}$ and $R^{4b}$ for a compound corresponds in each case to one row of Table A Table 2811
Compounds of the formula Ia.25 in which $R^8$ is —CH=N—$OCH_2CH$=$CH_2$, and the combination of $R^{2a}$, $R^{2b}$, $R^{2c}$ and $R^{4b}$ for a compound corresponds in each case to one row of Table A Table 2812
Compounds of the formula Ia.25 in which $R^8$ is —CH=N—$OCH_2C$≡CH, and the combination of $R^{2a}$, $R^{2b}$, $R^{2c}$ and $R^{4b}$ for a compound corresponds in each case to one row of Table A Table 2813
Compounds of the formula Ia.25 in which $R^8$ is —CH=N—$OCH_2CN$, and the combination of $R^{2a}$, $R^{2b}$, $R^{2c}$ and $R^{4b}$ for a compound corresponds in each case to one row of Table A Table 2814
Compounds of the formula Ia.25 in which $R^8$ is —CH=N—O-cyclopropyl, and the combination of $R^{2a}$, $R^{2b}$, $R^{2c}$ and $R^{4b}$ for a compound corresponds in each case to one row of Table A Table 2815
Compounds of the formula Ia.25 in which $R^8$ is —CH=N—O-(1-cyanocyclopropyl), and the combination of $R^{2a}$, $R^{2b}$, $R^{2c}$ and $R^{4b}$ for a compound corresponds in each case to one row of Table A Table 2816
Compounds of the formula Ia.25 in which $R^8$ is —CH=N—O—$CH_2$-cyclopropyl, and the combination of $R^{2a}$, $R^{2b}$, $R^{2c}$ and $R^{4b}$ for a compound corresponds in each case to one row of Table A Table 2817
Compounds of the formula Ia.25 in which $R^8$ is —CH=N—O—$CH_2$-(1-cyanocyclopropyl), and the combination of $R^{2a}$, $R^{2b}$, $R^{2c}$ and $R^{4b}$ for a compound corresponds in each case to one row of Table A Tables 2818 to 2956
Compounds of the formula Ia.26 in which $R^8$ is as defined in tables 2679 to 2817, and the combination of $R^{2a}$, $R^{2b}$, $R^{2c}$ and $R^{4b}$ for a compound corresponds in each case to one row of Table A Tables 2957 to 3095
Compounds of the formula Ia.27 in which $R^8$ is as defined in tables 2679 to 2817, and the combination of $R^{2a}$, $R^{2b}$, $R^{2c}$ and $R^{4b}$ for a compound corresponds in each case to one row of Table A Tables 3096 to 3234
Compounds of the formula Ia.28 in which $R^8$ is as defined in tables 2679 to 2817, and the combination of $R^{2a}$, $R^{2b}$, $R^{2c}$ and $R^{4b}$ for a compound corresponds in each case to one row of Table A Tables 3235 to 3373
Compounds of the formula Ia.29 in which $R^8$ is as defined in tables 2679 to 2817, and the combination of $R^{2a}$, $R^{2b}$, $R^{2c}$ and $R^{4b}$ for a compound corresponds in each case to one row of Table A Tables 3374 to 3512
Compounds of the formula Ia.30 in which $R^8$ is as defined in tables 2679 to 2817, and the combination of $R^{2a}$, $R^{2b}$, $R^{2c}$ and $R^{4b}$ for a compound corresponds in each case to one row of Table A Tables 3513 to 3651
Compounds of the formula Ia.31 in which $R^8$ is as defined in tables 2679 to 2817, and the combination of $R^{2a}$, $R^{2b}$, $R^{2c}$ and $R^{4b}$ for a compound corresponds in each case to one row of Table A Tables 3652 to 3790
Compounds of the formula Ia.32 in which $R^8$ is as defined in tables 2679 to 2817, and the combination of $R^{2a}$, $R^{2b}$, $R^{2c}$ and $R^{4b}$ for a compound corresponds in each case to one row of Table A Tables 3791 to 3929
Compounds of the formula Ia.33 in which $R^8$ is as defined in tables 2679 to 2817, and the combination of $R^{2a}$, $R^{2b}$, $R^{2c}$ and $R^{4b}$ for a compound corresponds in each case to one row of Table A Tables 3930 to 4068
Compounds of the formula Ia.34 in which $R^8$ is as defined in tables 2679 to 2817, and the combination of $R^{2a}$, $R^{2b}$, $R^{2c}$ and $R^{4b}$ for a compound corresponds in each case to one row of Table A Tables 4069 to 4207
Compounds of the formula Ia.35 in which $R^8$ is as defined in tables 2679 to 2817, and the combination of $R^{2a}$, $R^{2b}$, $R^{2c}$ and $R^{4b}$ for a compound corresponds in each case to one row of Table A Tables 4208 to 4346
Compounds of the formula Ia.36 in which $R^8$ is as defined in tables 2679 to 2817, and the combination of $R^{2a}$, $R^{2b}$, $R^{2c}$ and $R^{4b}$ for a compound corresponds in each case to one row of Table A Table 4347
Compounds of the formula Ia.37 in which $A^4$ is 1H-pyrrol-1-yl, and the combination of $R^{2a}$, $R^{2b}$, $R^{2c}$ and $R^{4b}$ for a compound corresponds in each case to one row of Table A Table 4348
Compounds of the formula Ia.37 in which $A^4$ is 1H-3-chloro-pyrrol-1-yl, and the combination of $R^{2a}$, $R^{2b}$, $R^{2c}$ and $R^{4b}$ for a compound corresponds in each case to one row of Table A Table 4349
Compounds of the formula Ia.37 in which $A^4$ is 1H-3-cyano-pyrrol-1-yl, and the combination of $R^{2a}$, $R^{2b}$, $R^{2c}$ and $R^{4b}$ for a compound corresponds in each case to one row of Table A Table 4350
Compounds of the formula Ia.37 in which $A^4$ is 1H-pyrazol-1-yl, and the combination of $R^{2a}$, $R^{2b}$, $R^{2c}$ and $R^{4b}$ for a compound corresponds in each case to one row of Table A Table 4351
Compounds of the formula Ia.37 in which $A^4$ is 1H-4-cloro-pyrazol-1-yl, and the combination of $R^{2a}$, $R^{2b}$, $R^{2c}$ and $R^{4b}$ for a compound corresponds in each case to one row of Table A Table 4352
Compounds of the formula Ia.37 in which $A^4$ is 1H-4-cyano-pyrazol-1-yl, and the combination of $R^{2a}$, $R^{2b}$, $R^{2c}$ and $R^{4b}$ for a compound corresponds in each case to one row of Table A Table 4353
Compounds of the formula Ia.37 in which $A^4$ is 1H-imidazol-1-yl, and the combination of $R^{2a}$, $R^{2b}$, $R^{2c}$ and $R^{4b}$ for a compound corresponds in each case to one row of Table A Table 4354
Compounds of the formula Ia.37 in which $A^4$ is 1H-4-chloro-imidazol-1-yl, and the combination of $R^{2a}$, $R^{2b}$, $R^{2c}$ and $R^{4b}$ for a compound corresponds in each case to one row of Table A Table 4355
Compounds of the formula Ia.37 in which $A^4$ is 1H-4-cyano-imidazol-1-yl, and the combination of $R^{2a}$, $R^{2b}$, $R^{2c}$ and $R^{4b}$ for a compound corresponds in each case to one row of Table A Table 4356
Compounds of the formula Ia.37 in which $A^4$ is 1H-[1,2,4]-triazol-1-yl, and the combination of $R^{2a}$, $R^{2b}$, $R^{2c}$ and $R^{4b}$ for a compound corresponds in each case to one row of Table A Table 4357
Compounds of the formula Ia.37 in which $A^4$ is 1H-[1,2,4]-3-chloro-triazol-1-yl, and the combination of $R^{2a}$, $R^{2b}$, $R^{2c}$ and $R^{4b}$ for a compound corresponds in each case to one row of Table A Table 4358
Compounds of the formula Ia.37 in which $A^4$ is 1H-[1,2,4]-3-cyano-triazol-1-yl, and the combination of $R^{2a}$, $R^{2b}$, $R^{2c}$ and $R^{4b}$ for a compound corresponds in each case to one row of Table A Table 4359
Compounds of the formula Ia.37 in which $A^4$ is 1H-1-methyl-pyrrol-2-yl, and the combination of $R^{2a}$, $R^{2b}$, $R^{2c}$ and $R^{4b}$ for a compound corresponds in each case to one row of Table A Table 4360
Compounds of the formula Ia.37 in which $A^4$ is 1H-1-methyl-pyrrol-3-yl, and the combination of $R^{2a}$, $R^{2b}$, $R^{2c}$ and $R^{4b}$ for a compound corresponds in each case to one row of Table A Table 4361
Compounds of the formula Ia.37 in which $A^4$ is 1H-1-methyl-pyrazol-4-yl, and the combination of $R^{2a}$, $R^{2b}$, $R^{2c}$ and $R^{4b}$ for a compound corresponds in each case to one row of Table A Table 4362
Compounds of the formula Ia.37 in which $A^4$ is 1H-1-methyl-pyrazol-5-yl, and the combination of $R^{2a}$, $R^{2b}$, $R^{2c}$ and $R^{4b}$ for a compound corresponds in each case to one row of Table A Table 4363
Compounds of the formula Ia.37 in which $A^4$ is 1H-1,3-dimethyl-pyrazol-5-yl, and the combination of $R^{2a}$, $R^{2b}$, $R^{2c}$ and $R^{4b}$ for a compound corresponds in each case to one row of Table A Table 4364

Compounds of the formula Ia.37 in which $A^4$ is 1H-1-methyl-3-trifluoromethyl-pyrazol-5-yl, and the combination of $R^{2a}$, $R^{2b}$, $R^{2c}$ and $R^{4b}$ for a compound corresponds in each case to one row of Table A Table 4365

Compounds of the formula Ia.37 in which $A^4$ is 1H-1-[1,2,3]-triazol-5-yl, and the combination of $R^{2a}$, $R^{2b}$, $R^{2c}$ and $R^{4b}$ for a compound corresponds in each case to one row of Table A Table 4366

Compounds of the formula Ia.37 in which $A^4$ is pyridin-2-yl, and the combination of $R^{2a}$, $R^{2b}$, $R^{2c}$ and $R^{4b}$ for a compound corresponds in each case to one row of Table A Table 4367

Compounds of the formula Ia.37 in which $A^4$ is pyridin-3-yl, and the combination of $R^{2a}$, $R^{2b}$, $R^{2c}$ and $R^{4b}$ for a compound corresponds in each case to one row of Table A Table 4368

Compounds of the formula Ia.37 in which $A^4$ is pyridin-4-yl, and the combination of $R^{2a}$, $R^{2b}$, $R^{2c}$ and $R^{4b}$ for a compound corresponds in each case to one row of Table A Table 4369

Compounds of the formula Ia.37 in which $A^4$ is pyrimidin-2-yl, and the combination of $R^{2a}$, $R^{2b}$, $R^{2c}$ and $R^{4b}$ for a compound corresponds in each case to one row of Table A Table 4370

Compounds of the formula Ia.37 in which $A^4$ is pyrimidin-4-yl, and the combination of $R^{2a}$, $R^{2b}$, $R^{2c}$ and $R^{4b}$ for a compound corresponds in each case to one row of Table A Table 4371

Compounds of the formula Ia.37 in which $A^4$ is pyrimidin-5-yl, and the combination of $R^{2a}$, $R^{2b}$, $R^{2c}$ and $R^{4b}$ for a compound corresponds in each case to one row of Table A Table 4372

Compounds of the formula Ia.37 in which $A^4$ is pyrazin-2-yl, and the combination of $R^{2a}$, $R^{2b}$, $R^{2c}$ and $R^{4b}$ for a compound corresponds in each case to one row of Table A

TABLE A

| No. | $R^{2a}$ | $R^{2b}$ | $R^{2c}$ | $R^{4b}$ |
|---|---|---|---|---|
| A-1 | F | H | F | H |
| A-2 | F | F | F | H |
| A-3 | F | Cl | F | H |
| A-4 | F | Br | F | H |
| A-5 | F | H | Cl | H |
| A-6 | F | H | Br | H |
| A-7 | Cl | H | Cl | H |
| A-8 | Cl | Cl | Cl | H |
| A-9 | Cl | F | Cl | H |
| A-10 | Cl | Br | Cl | H |
| A-11 | Cl | H | Br | H |
| A-12 | Br | H | Br | H |
| A-13 | Br | F | Br | H |
| A-14 | Br | Cl | Br | H |
| A-15 | $CF_3$ | H | F | H |
| A-16 | $CF_3$ | H | Cl | H |
| A-17 | $CF_3$ | H | Br | H |
| A-18 | $CF_3$ | H | $CF_3$ | H |
| A-19 | $CF_3$ | F | F | H |
| A-20 | $CF_3$ | Cl | Cl | H |
| A-21 | $CF_3$ | Br | Br | H |
| A-22 | $SF_5$ | H | F | H |
| A-23 | $SF_5$ | H | Cl | H |
| A-24 | $SF_5$ | H | Br | H |
| A-25 | $SF_5$ | H | $CF_3$ | H |
| A-26 | $SF_5$ | H | H | H |
| A-27 | $CF_3$ | H | H | H |
| A-28 | Br | H | H | H |
| A-29 | Cl | H | H | H |
| A-30 | F | H | H | H |
| A-31 | F | H | F | $CH_3$ |
| A-32 | F | F | F | $CH_3$ |
| A-33 | F | Cl | F | $CH_3$ |
| A-34 | F | Br | F | $CH_3$ |
| A-35 | F | H | Cl | $CH_3$ |
| A-36 | F | H | Br | $CH_3$ |
| A-37 | Cl | H | Cl | $CH_3$ |
| A-38 | Cl | Cl | Cl | $CH_3$ |
| A-39 | Cl | F | Cl | $CH_3$ |
| A-40 | Cl | Br | Cl | $CH_3$ |
| A-41 | Cl | H | Br | $CH_3$ |
| A-42 | Br | H | Br | $CH_3$ |
| A-43 | Br | F | Br | $CH_3$ |
| A-44 | Br | Cl | Br | $CH_3$ |
| A-45 | $CF_3$ | H | F | $CH_3$ |
| A-46 | $CF_3$ | H | Cl | $CH_3$ |
| A-47 | $CF_3$ | H | Br | $CH_3$ |
| A-48 | $CF_3$ | H | $CF_3$ | $CH_3$ |
| A-49 | $CF_3$ | F | F | $CH_3$ |
| A-50 | $CF_3$ | Cl | Cl | $CH_3$ |
| A-51 | $CF_3$ | Br | Br | $CH_3$ |
| A-52 | $SF_5$ | H | F | $CH_3$ |
| A-53 | $SF_5$ | H | Cl | $CH_3$ |
| A-54 | $SF_5$ | H | Br | $CH_3$ |
| A-55 | $SF_5$ | H | $CF_3$ | $CH_3$ |
| A-56 | $SF_5$ | H | H | $CH_3$ |
| A-57 | $CF_3$ | H | H | $CH_3$ |
| A-58 | Br | H | H | $CH_3$ |
| A-59 | Cl | H | H | $CH_3$ |
| A-60 | F | H | H | $CH_3$ |
| A-61 | F | H | F | $CH_2CH_3$ |
| A-62 | F | F | F | $CH_2CH_3$ |
| A-63 | F | Cl | F | $CH_2CH_3$ |
| A-64 | F | Br | F | $CH_2CH_3$ |
| A-65 | F | H | Cl | $CH_2CH_3$ |
| A-66 | F | H | Br | $CH_2CH_3$ |
| A-67 | Cl | H | Cl | $CH_2CH_3$ |
| A-68 | Cl | Cl | Cl | $CH_2CH_3$ |
| A-69 | Cl | F | Cl | $CH_2CH_3$ |
| A-70 | Cl | Br | Cl | $CH_2CH_3$ |
| A-71 | Cl | H | Br | $CH_2CH_3$ |
| A-72 | Br | H | Br | $CH_2CH_3$ |
| A-73 | Br | F | Br | $CH_2CH_3$ |
| A-74 | Br | Cl | Br | $CH_2CH_3$ |
| A-75 | $CF_3$ | H | F | $CH_2CH_3$ |
| A-76 | $CF_3$ | H | Cl | $CH_2CH_3$ |
| A-77 | $CF_3$ | H | Br | $CH_2CH_3$ |
| A-78 | $CF_3$ | H | $CF_3$ | $CH_2CH_3$ |
| A-79 | $CF_3$ | F | F | $CH_2CH_3$ |
| A-80 | $CF_3$ | Cl | Cl | $CH_2CH_3$ |
| A-81 | $CF_3$ | Br | Br | $CH_2CH_3$ |
| A-82 | $SF_5$ | H | F | $CH_2CH_3$ |
| A-83 | $SF_5$ | H | Cl | $CH_2CH_3$ |
| A-84 | $SF_5$ | H | Br | $CH_2CH_3$ |
| A-85 | $SF_5$ | H | $CF_3$ | $CH_2CH_3$ |
| A-86 | $SF_5$ | H | H | $CH_2CH_3$ |
| A-87 | $CF_3$ | H | H | $CH_2CH_3$ |
| A-88 | Br | H | H | $CH_2CH_3$ |
| A-89 | Cl | H | H | $CH_2CH_3$ |
| A-90 | F | H | H | $CH_2CH_3$ |
| A-91 | F | H | F | $CH(CH_3)_2$ |
| A-92 | F | F | F | $CH(CH_3)_2$ |
| A-93 | F | Cl | F | $CH(CH_3)_2$ |
| A-94 | F | Br | F | $CH(CH_3)_2$ |
| A-95 | F | H | Cl | $CH(CH_3)_2$ |
| A-96 | F | H | Br | $CH(CH_3)_2$ |
| A-97 | Cl | H | Cl | $CH(CH_3)_2$ |
| A-98 | Cl | Cl | Cl | $CH(CH_3)_2$ |
| A-99 | Cl | F | Cl | $CH(CH_3)_2$ |
| A-100 | Cl | Br | Cl | $CH(CH_3)_2$ |
| A-101 | Cl | H | Br | $CH(CH_3)_2$ |
| A-102 | Br | H | Br | $CH(CH_3)_2$ |
| A-103 | Br | F | Br | $CH(CH_3)_2$ |
| A-104 | Br | Cl | Br | $CH(CH_3)_2$ |
| A-105 | $CF_3$ | H | F | $CH(CH_3)_2$ |
| A-106 | $CF_3$ | H | Cl | $CH(CH_3)_2$ |
| A-107 | $CF_3$ | H | Br | $CH(CH_3)_2$ |

TABLE A-continued

| No. | $R^{2a}$ | $R^{2b}$ | $R^{2c}$ | $R^{4b}$ |
|---|---|---|---|---|
| A-108 | $CF_3$ | H | $CF_3$ | $CH(CH_3)_2$ |
| A-109 | $CF_3$ | F | F | $CH(CH_3)_2$ |
| A-110 | $CF_3$ | Cl | Cl | $CH(CH_3)_2$ |
| A-111 | $CF_3$ | Br | Br | $CH(CH_3)_2$ |
| A-112 | $SF_5$ | H | F | $CH(CH_3)_2$ |
| A-113 | $SF_5$ | H | Cl | $CH(CH_3)_2$ |
| A-114 | $SF_5$ | H | Br | $CH(CH_3)_2$ |
| A-115 | $SF_5$ | H | $CF_3$ | $CH(CH_3)_2$ |
| A-116 | $SF_5$ | H | H | $CH(CH_3)_2$ |
| A-117 | $CF_3$ | H | H | $CH(CH_3)_2$ |
| A-118 | Br | H | H | $CH(CH_3)_2$ |
| A-119 | Cl | H | H | $CH(CH_3)_2$ |
| A-120 | F | H | H | $CH(CH_3)_2$ |
| A-121 | F | H | F | $CHF_2$ |
| A-122 | F | F | F | $CHF_2$ |
| A-123 | F | Cl | F | $CHF_2$ |
| A-124 | F | Br | F | $CHF_2$ |
| A-125 | F | H | Cl | $CHF_2$ |
| A-126 | F | H | Br | $CHF_2$ |
| A-127 | Cl | H | Cl | $CHF_2$ |
| A-128 | Cl | Cl | Cl | $CHF_2$ |
| A-129 | Cl | F | Cl | $CHF_2$ |
| A-130 | Cl | Br | Cl | $CHF_2$ |
| A-131 | Cl | H | Br | $CHF_2$ |
| A-132 | Br | H | Br | $CHF_2$ |
| A-133 | Br | F | Br | $CHF_2$ |
| A-134 | Br | Cl | Br | $CHF_2$ |
| A-135 | $CF_3$ | H | F | $CHF_2$ |
| A-136 | $CF_3$ | H | Cl | $CHF_2$ |
| A-137 | $CF_3$ | H | Br | $CHF_2$ |
| A-138 | $CF_3$ | H | $CF_3$ | $CHF_2$ |
| A-139 | $CF_3$ | F | F | $CHF_2$ |
| A-140 | $CF_3$ | Cl | Cl | $CHF_2$ |
| A-141 | $CF_3$ | Br | Br | $CHF_2$ |
| A-142 | $SF_5$ | H | F | $CHF_2$ |
| A-143 | $SF_5$ | H | Cl | $CHF_2$ |
| A-144 | $SF_5$ | H | Br | $CHF_2$ |
| A-145 | $SF_5$ | H | $CF_3$ | $CHF_2$ |
| A-146 | $SF_5$ | H | H | $CHF_2$ |
| A-147 | $CF_3$ | H | H | $CHF_2$ |
| A-148 | Br | H | H | $CHF_2$ |
| A-149 | Cl | H | H | $CHF_2$ |
| A-150 | F | H | H | $CHF_2$ |
| A-151 | F | H | F | $CF_3$ |
| A-152 | F | F | F | $CF_3$ |
| A-153 | F | Cl | F | $CF_3$ |
| A-154 | F | Br | F | $CF_3$ |
| A-155 | F | H | Cl | $CF_3$ |
| A-156 | F | H | Br | $CF_3$ |
| A-157 | Cl | H | Cl | $CF_3$ |
| A-158 | Cl | Cl | Cl | $CF_3$ |
| A-159 | Cl | F | Cl | $CF_3$ |
| A-160 | Cl | Br | Cl | $CF_3$ |
| A-161 | Cl | H | Br | $CF_3$ |
| A-162 | Br | H | Br | $CF_3$ |
| A-163 | Br | F | Br | $CF_3$ |
| A-164 | Br | Cl | Br | $CF_3$ |
| A-165 | $CF_3$ | H | F | $CF_3$ |
| A-166 | $CF_3$ | H | Cl | $CF_3$ |
| A-167 | $CF_3$ | H | Br | $CF_3$ |
| A-168 | $CF_3$ | H | $CF_3$ | $CF_3$ |
| A-169 | $CF_3$ | F | F | $CF_3$ |
| A-170 | $CF_3$ | Cl | Cl | $CF_3$ |
| A-171 | $CF_3$ | Br | Br | $CF_3$ |
| A-172 | $SF_5$ | H | F | $CF_3$ |
| A-173 | $SF_5$ | H | Cl | $CF_3$ |
| A-174 | $SF_5$ | H | Br | $CF_3$ |
| A-175 | $SF_5$ | H | $CF_3$ | $CF_3$ |
| A-176 | $SF_5$ | H | H | $CF_3$ |
| A-177 | $CF_3$ | H | H | $CF_3$ |
| A-178 | Br | H | H | $CF_3$ |
| A-179 | Cl | H | H | $CF_3$ |
| A-180 | F | H | H | $CF_3$ |
| A-181 | F | H | F | $CH_2\text{—}CH\text{=}CH_2$ |
| A-182 | F | F | F | $CH_2\text{—}CH\text{=}CH_2$ |
| A-183 | F | Cl | F | $CH_2\text{—}CH\text{=}CH_2$ |
| A-184 | F | Br | F | $CH_2\text{—}CH\text{=}CH_2$ |
| A-185 | F | H | Cl | $CH_2\text{—}CH\text{=}CH_2$ |
| A-186 | F | H | Br | $CH_2\text{—}CH\text{=}CH_2$ |
| A-187 | Cl | H | Cl | $CH_2\text{—}CH\text{=}CH_2$ |
| A-188 | Cl | Cl | Cl | $CH_2\text{—}CH\text{=}CH_2$ |
| A-189 | Cl | F | Cl | $CH_2\text{—}CH\text{=}CH_2$ |
| A-190 | Cl | Br | Cl | $CH_2\text{—}CH\text{=}CH_2$ |
| A-191 | Cl | H | Br | $CH_2\text{—}CH\text{=}CH_2$ |
| A-192 | Br | H | Br | $CH_2\text{—}CH\text{=}CH_2$ |
| A-193 | Br | F | Br | $CH_2\text{—}CH\text{=}CH_2$ |
| A-194 | Br | Cl | Br | $CH_2\text{—}CH\text{=}CH_2$ |
| A-195 | $CF_3$ | H | F | $CH_2\text{—}CH\text{=}CH_2$ |
| A-196 | $CF_3$ | H | Cl | $CH_2\text{—}CH\text{=}CH_2$ |
| A-197 | $CF_3$ | H | Br | $CH_2\text{—}CH\text{=}CH_2$ |
| A-198 | $CF_3$ | H | $CF_3$ | $CH_2\text{—}CH\text{=}CH_2$ |
| A-199 | $CF_3$ | F | F | $CH_2\text{—}CH\text{=}CH_2$ |
| A-200 | $CF_3$ | Cl | Cl | $CH_2\text{—}CH\text{=}CH_2$ |
| A-201 | $CF_3$ | Br | Br | $CH_2\text{—}CH\text{=}CH_2$ |
| A-202 | $SF_5$ | H | F | $CH_2\text{—}CH\text{=}CH_2$ |
| A-203 | $SF_5$ | H | Cl | $CH_2\text{—}CH\text{=}CH_2$ |
| A-204 | $SF_5$ | H | Br | $CH_2\text{—}CH\text{=}CH_2$ |
| A-205 | $SF_5$ | H | $CF_3$ | $CH_2\text{—}CH\text{=}CH_2$ |
| A-206 | $SF_5$ | H | H | $CH_2\text{—}CH\text{=}CH_2$ |
| A-207 | $CF_3$ | H | H | $CH_2\text{—}CH\text{=}CH_2$ |
| A-208 | Br | H | H | $CH_2\text{—}CH\text{=}CH_2$ |
| A-209 | Cl | H | H | $CH_2\text{—}CH\text{=}CH_2$ |
| A-210 | F | H | H | $CH_2\text{—}CH\text{=}CH_2$ |
| A-211 | F | H | F | $CH\text{=}CH_2$ |
| A-212 | F | F | F | $CH\text{=}CH_2$ |
| A-213 | F | Cl | F | $CH\text{=}CH_2$ |
| A-214 | F | Br | F | $CH\text{=}CH_2$ |
| A-215 | F | H | Cl | $CH\text{=}CH_2$ |
| A-216 | F | H | Br | $CH\text{=}CH_2$ |
| A-217 | Cl | H | Cl | $CH\text{=}CH_2$ |
| A-218 | Cl | Cl | Cl | $CH\text{=}CH_2$ |
| A-219 | Cl | F | Cl | $CH\text{=}CH_2$ |
| A-220 | Cl | Br | Cl | $CH\text{=}CH_2$ |
| A-221 | Cl | H | Br | $CH\text{=}CH_2$ |
| A-222 | Br | H | Br | $CH\text{=}CH_2$ |
| A-223 | Br | F | Br | $CH\text{=}CH_2$ |
| A-224 | Br | Cl | Br | $CH\text{=}CH_2$ |
| A-225 | $CF_3$ | H | F | $CH\text{=}CH_2$ |
| A-226 | $CF_3$ | H | Cl | $CH\text{=}CH_2$ |
| A-227 | $CF_3$ | H | Br | $CH\text{=}CH_2$ |
| A-228 | $CF_3$ | H | $CF_3$ | $CH\text{=}CH_2$ |
| A-229 | $CF_3$ | F | F | $CH\text{=}CH_2$ |
| A-230 | $CF_3$ | Cl | Cl | $CH\text{=}CH_2$ |
| A-231 | $CF_3$ | Br | Br | $CH\text{=}CH_2$ |
| A-232 | $SF_5$ | H | F | $CH\text{=}CH_2$ |
| A-233 | $SF_5$ | H | Cl | $CH\text{=}CH_2$ |
| A-234 | $SF_5$ | H | Br | $CH\text{=}CH_2$ |
| A-235 | $SF_5$ | H | $CF_3$ | $CH\text{=}CH_2$ |
| A-236 | $SF_5$ | H | H | $CH\text{=}CH_2$ |
| A-237 | $CF_3$ | H | H | $CH\text{=}CH_2$ |
| A-238 | Br | H | H | $CH\text{=}CH_2$ |
| A-239 | Cl | H | H | $CH\text{=}CH_2$ |
| A-240 | F | H | H | $CH\text{=}CH_2$ |
| A-241 | F | H | F | $C\text{≡}CH$ |
| A-242 | F | F | F | $C\text{≡}CH$ |
| A-243 | F | Cl | F | $C\text{≡}CH$ |
| A-244 | F | Br | F | $C\text{≡}CH$ |
| A-245 | F | H | Cl | $C\text{≡}CH$ |
| A-246 | F | H | Br | $C\text{≡}CH$ |
| A-247 | Cl | H | Cl | $C\text{≡}CH$ |
| A-248 | Cl | Cl | Cl | $C\text{≡}CH$ |
| A-249 | Cl | F | Cl | $C\text{≡}CH$ |
| A-250 | Cl | Br | Cl | $C\text{≡}CH$ |
| A-251 | Cl | H | Br | $C\text{≡}CH$ |
| A-252 | Br | H | Br | $C\text{≡}CH$ |
| A-253 | Br | F | Br | $C\text{≡}CH$ |
| A-254 | Br | Cl | Br | $C\text{≡}CH$ |
| A-255 | $CF_3$ | H | F | $C\text{≡}CH$ |
| A-256 | $CF_3$ | H | Cl | $C\text{≡}CH$ |
| A-257 | $CF_3$ | H | Br | $C\text{≡}CH$ |
| A-258 | $CF_3$ | H | $CF_3$ | $C\text{≡}CH$ |
| A-259 | $CF_3$ | F | F | $C\text{≡}CH$ |
| A-260 | $CF_3$ | Cl | Cl | $C\text{≡}CH$ |
| A-261 | $CF_3$ | Br | Br | $C\text{≡}CH$ |
| A-262 | $SF_5$ | H | F | $C\text{≡}CH$ |
| A-263 | $SF_5$ | H | Cl | $C\text{≡}CH$ |

TABLE A-continued

| No. | $R^{2a}$ | $R^{2b}$ | $R^{2c}$ | $R^{4b}$ |
|---|---|---|---|---|
| A-264 | $SF_5$ | H | Br | C≡CH |
| A-265 | $SF_5$ | H | $CF_3$ | C≡CH |
| A-266 | $SF_5$ | H | H | C≡CH |
| A-267 | $CF_3$ | H | H | C≡CH |
| A-268 | Br | H | H | C≡CH |
| A-269 | Cl | H | H | C≡CH |
| A-270 | F | H | H | C≡CH |
| A-271 | F | H | F | $^cC_3H_5$* |
| A-272 | F | F | F | $^cC_3H_5$* |
| A-273 | F | Cl | F | $^cC_3H_5$* |
| A-274 | F | Br | F | $^cC_3H_5$* |
| A-275 | F | H | Cl | $^cC_3H_5$* |
| A-276 | F | H | Br | $^cC_3H_5$* |
| A-277 | Cl | H | Cl | $^cC_3H_5$* |
| A-278 | Cl | Cl | Cl | $^cC_3H_5$* |
| A-279 | Cl | F | Cl | $^cC_3H_5$* |
| A-280 | Cl | Br | Cl | $^cC_3H_5$* |
| A-281 | Cl | H | Br | $^cC_3H_5$* |
| A-282 | Br | H | Br | $^cC_3H_5$* |
| A-283 | Br | F | Br | $^cC_3H_5$* |
| A-284 | Br | Cl | Br | $^cC_3H_5$* |
| A-285 | $CF_3$ | H | F | $^cC_3H_5$* |
| A-286 | $CF_3$ | H | Cl | $^cC_3H_5$* |
| A-287 | $CF_3$ | H | Br | $^cC_3H_5$* |
| A-288 | $CF_3$ | H | $CF_3$ | $^cC_3H_5$* |
| A-289 | $CF_3$ | F | F | $^cC_3H_5$* |
| A-290 | $CF_3$ | Cl | Cl | $^cC_3H_5$* |
| A-291 | $CF_3$ | Br | Br | $^cC_3H_5$* |
| A-292 | $SF_5$ | H | F | $^cC_3H_5$* |
| A-293 | $SF_5$ | H | Cl | $^cC_3H_5$* |
| A-294 | $SF_5$ | H | Br | $^cC_3H_5$* |
| A-295 | $SF_5$ | H | $CF_3$ | $^cC_3H_5$* |
| A-296 | $SF_5$ | H | H | $^cC_3H_5$* |
| A-297 | $CF_3$ | H | H | $^cC_3H_5$* |
| A-298 | Br | H | H | $^cC_3H_5$* |
| A-299 | Cl | H | H | $^cC_3H_5$* |
| A-300 | F | H | H | $^cC_3H_5$* |
| A-301 | F | H | F | F |
| A-302 | F | F | F | F |
| A-303 | F | Cl | F | F |
| A-304 | F | Br | F | F |
| A-305 | F | H | Cl | F |
| A-306 | F | H | Br | F |
| A-307 | Cl | H | Cl | F |
| A-308 | Cl | Cl | Cl | F |
| A-309 | Cl | F | Cl | F |
| A-310 | Cl | Br | Cl | F |
| A-311 | Cl | H | Br | F |
| A-312 | Br | H | Br | F |
| A-313 | Br | F | Br | F |
| A-314 | Br | Cl | Br | F |
| A-315 | $CF_3$ | H | F | F |
| A-316 | $CF_3$ | H | Cl | F |
| A-317 | $CF_3$ | H | Br | F |
| A-318 | $CF_3$ | H | $CF_3$ | F |
| A-319 | $CF_3$ | F | F | F |
| A-320 | $CF_3$ | Cl | Cl | F |
| A-321 | $CF_3$ | Br | Br | F |
| A-322 | $SF_5$ | H | F | F |
| A-323 | $SF_5$ | H | Cl | F |
| A-324 | $SF_5$ | H | Br | F |
| A-325 | $SF_5$ | H | $CF_3$ | F |
| A-326 | $SF_5$ | H | H | F |
| A-327 | $CF_3$ | H | H | F |
| A-328 | Br | H | H | F |
| A-329 | Cl | H | H | F |
| A-330 | F | H | H | F |
| A-331 | F | H | F | Cl |
| A-332 | F | F | F | Cl |
| A-333 | F | Cl | F | Cl |
| A-334 | F | Br | F | Cl |
| A-335 | F | H | Cl | Cl |
| A-336 | F | H | Br | Cl |
| A-337 | Cl | H | Cl | Cl |
| A-338 | Cl | Cl | Cl | Cl |
| A-339 | Cl | F | Cl | Cl |
| A-340 | Cl | Br | Cl | Cl |
| A-341 | Cl | H | Br | Cl |
| A-342 | Br | H | Br | Cl |
| A-343 | Br | F | Br | Cl |
| A-344 | Br | Cl | Br | Cl |
| A-345 | $CF_3$ | H | F | Cl |
| A-346 | $CF_3$ | H | Cl | Cl |
| A-347 | $CF_3$ | H | Br | Cl |
| A-348 | $CF_3$ | H | $CF_3$ | Cl |
| A-349 | $CF_3$ | F | F | Cl |
| A-350 | $CF_3$ | Cl | Cl | Cl |
| A-351 | $CF_3$ | Br | Br | Cl |
| A-352 | $SF_5$ | H | F | Cl |
| A-353 | $SF_5$ | H | Cl | Cl |
| A-354 | $SF_5$ | H | Br | Cl |
| A-355 | $SF_5$ | H | $CF_3$ | Cl |
| A-356 | $SF_5$ | H | H | Cl |
| A-357 | $CF_3$ | H | H | Cl |
| A-358 | Br | H | H | Cl |
| A-359 | Cl | H | H | Cl |
| A-360 | F | H | H | Cl |
| A-361 | F | H | F | Br |
| A-362 | F | F | F | Br |
| A-363 | F | Cl | F | Br |
| A-364 | F | Br | F | Br |
| A-365 | F | H | Cl | Br |
| A-366 | F | H | Br | Br |
| A-367 | Cl | H | Cl | Br |
| A-368 | Cl | Cl | Cl | Br |
| A-369 | Cl | F | Cl | Br |
| A-370 | Cl | Br | Cl | Br |
| A-371 | Cl | H | Br | Br |
| A-372 | Br | H | Br | Br |
| A-373 | Br | F | Br | Br |
| A-374 | Br | Cl | Br | Br |
| A-375 | $CF_3$ | H | F | Br |
| A-376 | $CF_3$ | H | Cl | Br |
| A-377 | $CF_3$ | H | Br | Br |
| A-378 | $CF_3$ | H | $CF_3$ | Br |
| A-379 | $CF_3$ | F | F | Br |
| A-380 | $CF_3$ | Cl | Cl | Br |
| A-381 | $CF_3$ | Br | Br | Br |
| A-382 | $SF_5$ | H | F | Br |
| A-383 | $SF_5$ | H | Cl | Br |
| A-384 | $SF_5$ | H | Br | Br |
| A-385 | $SF_5$ | H | $CF_3$ | Br |
| A-386 | $SF_5$ | H | H | Br |
| A-387 | $CF_3$ | H | H | Br |
| A-388 | Br | H | H | Br |
| A-389 | Cl | H | H | Br |
| A-390 | F | H | H | Br |
| A-391 | F | H | F | CN |
| A-392 | F | F | F | CN |
| A-393 | F | Cl | F | CN |
| A-394 | F | Br | F | CN |
| A-395 | F | H | Cl | CN |
| A-396 | F | H | Br | CN |
| A-397 | Cl | H | Cl | CN |
| A-398 | Cl | Cl | Cl | CN |
| A-399 | Cl | F | Cl | CN |
| A-400 | Cl | Br | Cl | CN |
| A-401 | Cl | H | Br | CN |
| A-402 | Br | H | Br | CN |
| A-403 | Br | F | Br | CN |
| A-404 | Br | Cl | Br | CN |
| A-405 | $CF_3$ | H | F | CN |
| A-406 | $CF_3$ | H | Cl | CN |
| A-407 | $CF_3$ | H | Br | CN |
| A-408 | $CF_3$ | H | $CF_3$ | CN |
| A-409 | $CF_3$ | F | F | CN |
| A-410 | $CF_3$ | Cl | Cl | CN |
| A-411 | $CF_3$ | Br | Br | CN |
| A-412 | $SF_5$ | H | F | CN |
| A-413 | $SF_5$ | H | Cl | CN |
| A-414 | $SF_5$ | H | Br | CN |
| A-415 | $SF_5$ | H | $CF_3$ | CN |
| A-416 | $SF_5$ | H | H | CN |
| A-417 | $CF_3$ | H | H | CN |
| A-418 | Br | H | H | CN |
| A-419 | Cl | H | H | CN |

TABLE A-continued

| No. | $R^{2a}$ | $R^{2b}$ | $R^{2c}$ | $R^{4b}$ |
|---|---|---|---|---|
| A-420 | F | H | H | CN |
| A-421 | F | H | F | OCH$_3$ |
| A-422 | F | F | F | OCH$_3$ |
| A-423 | F | Cl | F | OCH$_3$ |
| A-424 | F | Br | F | OCH$_3$ |
| A-425 | F | H | Cl | OCH$_3$ |
| A-426 | F | H | Br | OCH$_3$ |
| A-427 | Cl | H | Cl | OCH$_3$ |
| A-428 | Cl | Cl | Cl | OCH$_3$ |
| A-429 | Cl | F | Cl | OCH$_3$ |
| A-430 | Cl | Br | Cl | OCH$_3$ |
| A-431 | Cl | H | Br | OCH$_3$ |
| A-432 | Br | H | Br | OCH$_3$ |
| A-433 | Br | F | Br | OCH$_3$ |
| A-434 | Br | Cl | Br | OCH$_3$ |
| A-435 | CF$_3$ | H | F | OCH$_3$ |
| A-436 | CF$_3$ | H | Cl | OCH$_3$ |
| A-437 | CF$_3$ | H | Br | OCH$_3$ |
| A-438 | CF$_3$ | H | CF$_3$ | OCH$_3$ |
| A-439 | CF$_3$ | F | F | OCH$_3$ |
| A-440 | CF$_3$ | Cl | Cl | OCH$_3$ |
| A-441 | CF$_3$ | Br | Br | OCH$_3$ |
| A-442 | SF$_5$ | H | F | OCH$_3$ |
| A-443 | SF$_5$ | H | Cl | OCH$_3$ |
| A-444 | SF$_5$ | H | Br | OCH$_3$ |
| A-445 | SF$_5$ | H | CF$_3$ | OCH$_3$ |
| A-446 | SF$_5$ | H | H | OCH$_3$ |
| A-447 | CF$_3$ | H | H | OCH$_3$ |
| A-448 | Br | H | H | OCH$_3$ |
| A-449 | Cl | H | H | OCH$_3$ |
| A-450 | F | H | H | OCH$_3$ |
| A-451 | F | H | F | OCH$_2$CH$_3$ |
| A-452 | F | F | F | OCH$_2$CH$_3$ |
| A-453 | F | Cl | F | OCH$_2$CH$_3$ |
| A-454 | F | Br | F | OCH$_2$CH$_3$ |
| A-455 | F | H | Cl | OCH$_2$CH$_3$ |
| A-456 | F | H | Br | OCH$_2$CH$_3$ |
| A-457 | Cl | H | Cl | OCH$_2$CH$_3$ |
| A-458 | Cl | Cl | Cl | OCH$_2$CH$_3$ |
| A-459 | Cl | F | Cl | OCH$_2$CH$_3$ |
| A-460 | Cl | Br | Cl | OCH$_2$CH$_3$ |
| A-461 | Cl | H | Br | OCH$_2$CH$_3$ |
| A-462 | Br | H | Br | OCH$_2$CH$_3$ |
| A-463 | Br | F | Br | OCH$_2$CH$_3$ |
| A-464 | Br | Cl | Br | OCH$_2$CH$_3$ |
| A-465 | CF$_3$ | H | F | OCH$_2$CH$_3$ |
| A-466 | CF$_3$ | H | Cl | OCH$_2$CH$_3$ |
| A-467 | CF$_3$ | H | Br | OCH$_2$CH$_3$ |
| A-468 | CF$_3$ | H | CF$_3$ | OCH$_2$CH$_3$ |
| A-469 | CF$_3$ | F | F | OCH$_2$CH$_3$ |
| A-470 | CF$_3$ | Cl | Cl | OCH$_2$CH$_3$ |
| A-471 | CF$_3$ | Br | Br | OCH$_2$CH$_3$ |
| A-472 | SF$_5$ | H | F | OCH$_2$CH$_3$ |
| A-473 | SF$_5$ | H | Cl | OCH$_2$CH$_3$ |
| A-474 | SF$_5$ | H | Br | OCH$_2$CH$_3$ |
| A-475 | SF$_5$ | H | CF$_3$ | OCH$_2$CH$_3$ |
| A-476 | SF$_5$ | H | H | OCH$_2$CH$_3$ |
| A-477 | CF$_3$ | H | H | OCH$_2$CH$_3$ |
| A-478 | Br | H | H | OCH$_2$CH$_3$ |
| A-479 | Cl | H | H | OCH$_2$CH$_3$ |
| A-480 | F | H | H | OCH$_2$CH$_3$ |
| A-481 | F | H | F | OCH(CH$_3$)$_2$ |
| A-482 | F | F | F | OCH(CH$_3$)$_2$ |
| A-483 | F | Cl | F | OCH(CH$_3$)$_2$ |
| A-484 | F | Br | F | OCH(CH$_3$)$_2$ |
| A-485 | F | H | Cl | OCH(CH$_3$)$_2$ |
| A-486 | F | H | Br | OCH(CH$_3$)$_2$ |
| A-487 | Cl | H | Cl | OCH(CH$_3$)$_2$ |
| A-488 | Cl | Cl | Cl | OCH(CH$_3$)$_2$ |
| A-489 | Cl | F | Cl | OCH(CH$_3$)$_2$ |
| A-490 | Cl | Br | Cl | OCH(CH$_3$)$_2$ |
| A-491 | Cl | H | Br | OCH(CH$_3$)$_2$ |
| A-492 | Br | H | Br | OCH(CH$_3$)$_2$ |
| A-493 | Br | F | Br | OCH(CH$_3$)$_2$ |
| A-494 | Br | Cl | Br | OCH(CH$_3$)$_2$ |
| A-495 | CF$_3$ | H | F | OCH(CH$_3$)$_2$ |
| A-496 | CF$_3$ | H | Cl | OCH(CH$_3$)$_2$ |
| A-497 | CF$_3$ | H | Br | OCH(CH$_3$)$_2$ |
| A-498 | CF$_3$ | H | CF$_3$ | OCH(CH$_3$)$_2$ |
| A-499 | CF$_3$ | F | F | OCH(CH$_3$)$_2$ |
| A-500 | CF$_3$ | Cl | Cl | OCH(CH$_3$)$_2$ |
| A-501 | CF$_3$ | Br | Br | OCH(CH$_3$)$_2$ |
| A-502 | SF$_5$ | H | F | OCH(CH$_3$)$_2$ |
| A-503 | SF$_5$ | H | Cl | OCH(CH$_3$)$_2$ |
| A-504 | SF$_5$ | H | Br | OCH(CH$_3$)$_2$ |
| A-505 | SF$_5$ | H | CF$_3$ | OCH(CH$_3$)$_2$ |
| A-506 | SF$_5$ | H | H | OCH(CH$_3$)$_2$ |
| A-507 | CF$_3$ | H | H | OCH(CH$_3$)$_2$ |
| A-508 | Br | H | H | OCH(CH$_3$)$_2$ |
| A-509 | Cl | H | H | OCH(CH$_3$)$_2$ |
| A-510 | F | H | H | OCH(CH$_3$)$_2$ |
| A-511 | F | H | F | OCH$_2$CH=CH$_2$ |
| A-512 | F | F | F | OCH$_2$CH=CH$_2$ |
| A-513 | F | Cl | F | OCH$_2$CH=CH$_2$ |
| A-514 | F | Br | F | OCH$_2$CH=CH$_2$ |
| A-515 | F | H | Cl | OCH$_2$CH=CH$_2$ |
| A-516 | F | H | Br | OCH$_2$CH=CH$_2$ |
| A-517 | Cl | H | Cl | OCH$_2$CH=CH$_2$ |
| A-518 | Cl | Cl | Cl | OCH$_2$CH=CH$_2$ |
| A-519 | Cl | F | Cl | OCH$_2$CH=CH$_2$ |
| A-520 | Cl | Br | Cl | OCH$_2$CH=CH$_2$ |
| A-521 | Cl | H | Br | OCH$_2$CH=CH$_2$ |
| A-522 | Br | H | Br | OCH$_2$CH=CH$_2$ |
| A-523 | Br | F | Br | OCH$_2$CH=CH$_2$ |
| A-524 | Br | Cl | Br | OCH$_2$CH=CH$_2$ |
| A-525 | CF$_3$ | H | F | OCH$_2$CH=CH$_2$ |
| A-526 | CF$_3$ | H | Cl | OCH$_2$CH=CH$_2$ |
| A-527 | CF$_3$ | H | Br | OCH$_2$CH=CH$_2$ |
| A-528 | CF$_3$ | H | CF$_3$ | OCH$_2$CH=CH$_2$ |
| A-529 | CF$_3$ | F | F | OCH$_2$CH=CH$_2$ |
| A-530 | CF$_3$ | Cl | Cl | OCH$_2$CH=CH$_2$ |
| A-531 | CF$_3$ | Br | Br | OCH$_2$CH=CH$_2$ |
| A-532 | SF$_5$ | H | F | OCH$_2$CH=CH$_2$ |
| A-533 | SF$_5$ | H | Cl | OCH$_2$CH=CH$_2$ |
| A-534 | SF$_5$ | H | Br | OCH$_2$CH=CH$_2$ |
| A-535 | SF$_5$ | H | CF$_3$ | OCH$_2$CH=CH$_2$ |
| A-536 | SF$_5$ | H | H | OCH$_2$CH=CH$_2$ |
| A-537 | CF$_3$ | H | H | OCH$_2$CH=CH$_2$ |
| A-538 | Br | H | H | OCH$_2$CH=CH$_2$ |
| A-539 | Cl | H | H | OCH$_2$CH=CH$_2$ |
| A-540 | F | H | H | OCH$_2$CH=CH$_2$ |
| A-541 | F | H | F | O—$^c$C$_3$H$_5$* |
| A-542 | F | F | F | O—$^c$C$_3$H$_5$* |
| A-543 | F | Cl | F | O—$^c$C$_3$H$_5$* |
| A-544 | F | Br | F | O—$^c$C$_3$H$_5$* |
| A-545 | F | H | Cl | O—$^c$C$_3$H$_5$* |
| A-546 | F | H | Br | O—$^c$C$_3$H$_5$* |
| A-547 | Cl | H | Cl | O—$^c$C$_3$H$_5$* |
| A-548 | Cl | Cl | Cl | O—$^c$C$_3$H$_5$* |
| A-549 | Cl | F | Cl | O—$^c$C$_3$H$_5$* |
| A-550 | Cl | Br | Cl | O—$^c$C$_3$H$_5$* |
| A-551 | Cl | H | Br | O—$^c$C$_3$H$_5$* |
| A-552 | Br | H | Br | O—$^c$C$_3$H$_5$* |
| A-553 | Br | F | Br | O—$^c$C$_3$H$_5$* |
| A-554 | Br | Cl | Br | O—$^c$C$_3$H$_5$* |
| A-555 | CF$_3$ | H | F | O—$^c$C$_3$H$_5$* |
| A-556 | CF$_3$ | H | Cl | O—$^c$C$_3$H$_5$* |
| A-557 | CF$_3$ | H | Br | O—$^c$C$_3$H$_5$* |
| A-558 | CF$_3$ | H | CF$_3$ | O—$^c$C$_3$H$_5$* |
| A-559 | CF$_3$ | F | F | O—$^c$C$_3$H$_5$* |
| A-560 | CF$_3$ | Cl | Cl | O—$^c$C$_3$H$_5$* |
| A-561 | CF$_3$ | Br | Br | O—$^c$C$_3$H$_5$* |
| A-562 | SF$_5$ | H | F | O—$^c$C$_3$H$_5$* |
| A-563 | SF$_5$ | H | Cl | O—$^c$C$_3$H$_5$* |
| A-564 | SF$_5$ | H | Br | O—$^c$C$_3$H$_5$* |
| A-565 | SF$_5$ | H | CF$_3$ | O—$^c$C$_3$H$_5$* |
| A-566 | SF$_5$ | H | H | O—$^c$C$_3$H$_5$* |
| A-567 | CF$_3$ | H | H | O—$^c$C$_3$H$_5$* |
| A-568 | Br | H | H | O—$^c$C$_3$H$_5$* |
| A-569 | Cl | H | H | O—$^c$C$_3$H$_5$* |
| A-570 | F | H | H | O—$^c$C$_3$H$_5$* |
| A-571 | F | H | F | OCHF$_2$ |
| A-572 | F | F | F | OCHF$_2$ |
| A-573 | F | Cl | F | OCHF$_2$ |
| A-574 | F | Br | F | OCHF$_2$ |
| A-575 | F | H | Cl | OCHF$_2$ |

TABLE A-continued

| No. | $R^{2a}$ | $R^{2b}$ | $R^{2c}$ | $R^{4b}$ |
| --- | --- | --- | --- | --- |
| A-576 | F | H | Br | $OCHF_2$ |
| A-577 | Cl | H | Cl | $OCHF_2$ |
| A-578 | Cl | Cl | Cl | $OCHF_2$ |
| A-579 | Cl | F | Cl | $OCHF_2$ |
| A-580 | Cl | Br | Cl | $OCHF_2$ |
| A-581 | Cl | H | Br | $OCHF_2$ |
| A-582 | Br | H | Br | $OCHF_2$ |
| A-583 | Br | F | Br | $OCHF_2$ |
| A-584 | Br | Cl | Br | $OCHF_2$ |
| A-585 | $CF_3$ | H | F | $OCHF_2$ |
| A-586 | $CF_3$ | H | Cl | $OCHF_2$ |
| A-587 | $CF_3$ | H | Br | $OCHF_2$ |
| A-588 | $CF_3$ | H | $CF_3$ | $OCHF_2$ |
| A-589 | $CF_3$ | F | F | $OCHF_2$ |
| A-590 | $CF_3$ | Cl | Cl | $OCHF_2$ |
| A-591 | $CF_3$ | Br | Br | $OCHF_2$ |
| A-592 | $SF_5$ | H | F | $OCHF_2$ |
| A-593 | $SF_5$ | H | Cl | $OCHF_2$ |
| A-594 | $SF_5$ | H | Br | $OCHF_2$ |
| A-595 | $SF_5$ | H | $CF_3$ | $OCHF_2$ |
| A-596 | $SF_5$ | H | H | $OCHF_2$ |
| A-597 | $CF_3$ | H | H | $OCHF_2$ |
| A-598 | Br | H | H | $OCHF_2$ |
| A-599 | Cl | H | H | $OCHF_2$ |
| A-600 | F | H | H | $OCHF_2$ |
| A-601 | F | H | F | $OCF_3$ |
| A-602 | F | F | F | $OCF_3$ |
| A-603 | F | Cl | F | $OCF_3$ |
| A-604 | F | Br | F | $OCF_3$ |
| A-605 | F | H | Cl | $OCF_3$ |
| A-606 | F | H | Br | $OCF_3$ |
| A-607 | Cl | H | Cl | $OCF_3$ |
| A-608 | Cl | Cl | Cl | $OCF_3$ |
| A-609 | Cl | F | Cl | $OCF_3$ |
| A-610 | Cl | Br | Cl | $OCF_3$ |
| A-611 | Cl | H | Br | $OCF_3$ |
| A-612 | Br | H | Br | $OCF_3$ |
| A-613 | Br | F | Br | $OCF_3$ |
| A-614 | Br | Cl | Br | $OCF_3$ |
| A-615 | $CF_3$ | H | F | $OCF_3$ |
| A-616 | $CF_3$ | H | Cl | $OCF_3$ |
| A-617 | $CF_3$ | H | Br | $OCF_3$ |
| A-618 | $CF_3$ | H | $CF_3$ | $OCF_3$ |
| A-619 | $CF_3$ | F | F | $OCF_3$ |
| A-620 | $CF_3$ | Cl | Cl | $OCF_3$ |
| A-621 | $CF_3$ | Br | Br | $OCF_3$ |
| A-622 | $SF_5$ | H | F | $OCF_3$ |
| A-623 | $SF_5$ | H | Cl | $OCF_3$ |
| A-624 | $SF_5$ | H | Br | $OCF_3$ |
| A-625 | $SF_5$ | H | $CF_3$ | $OCF_3$ |
| A-626 | $SF_5$ | H | H | $OCF_3$ |
| A-627 | $CF_3$ | H | H | $OCF_3$ |
| A-628 | Br | H | H | $OCF_3$ |
| A-629 | Cl | H | H | $OCF_3$ |
| A-630 | F | H | H | $OCF_3$ |
| A-631 | F | H | F | $OCH_2CF_3$ |
| A-632 | F | F | F | $OCH_2CF_3$ |
| A-633 | F | Cl | F | $OCH_2CF_3$ |
| A-634 | F | Br | F | $OCH_2CF_3$ |
| A-635 | F | H | Cl | $OCH_2CF_3$ |
| A-636 | F | H | Br | $OCH_2CF_3$ |
| A-637 | Cl | H | Cl | $OCH_2CF_3$ |
| A-638 | Cl | Cl | Cl | $OCH_2CF_3$ |
| A-639 | Cl | F | Cl | $OCH_2CF_3$ |
| A-640 | Cl | Br | Cl | $OCH_2CF_3$ |
| A-641 | Cl | H | Br | $OCH_2CF_3$ |
| A-642 | Br | H | Br | $OCH_2CF_3$ |
| A-643 | Br | F | Br | $OCH_2CF_3$ |
| A-644 | Br | Cl | Br | $OCH_2CF_3$ |
| A-645 | $CF_3$ | H | F | $OCH_2CF_3$ |
| A-646 | $CF_3$ | H | Cl | $OCH_2CF_3$ |
| A-647 | $CF_3$ | H | Br | $OCH_2CF_3$ |
| A-648 | $CF_3$ | H | $CF_3$ | $OCH_2CF_3$ |
| A-649 | $CF_3$ | F | F | $OCH_2CF_3$ |
| A-650 | $CF_3$ | Cl | Cl | $OCH_2CF_3$ |
| A-651 | $CF_3$ | Br | Br | $OCH_2CF_3$ |
| A-652 | $SF_5$ | H | F | $OCH_2CF_3$ |
| A-653 | $SF_5$ | H | Cl | $OCH_2CF_3$ |
| A-654 | $SF_5$ | H | Br | $OCH_2CF_3$ |
| A-655 | $SF_5$ | H | $CF_3$ | $OCH_2CF_3$ |
| A-656 | $SF_5$ | H | H | $OCH_2CF_3$ |
| A-657 | $CF_3$ | H | H | $OCH_2CF_3$ |
| A-658 | Br | H | H | $OCH_2CF_3$ |
| A-659 | Cl | H | H | $OCH_2CF_3$ |
| A-660 | F | H | H | $OCH_2CF_3$ |
| A-661 | F | H | F | $SCH_3$ |
| A-662 | F | F | F | $SCH_3$ |
| A-663 | F | Cl | F | $SCH_3$ |
| A-664 | F | Br | F | $SCH_3$ |
| A-665 | F | H | Cl | $SCH_3$ |
| A-666 | F | H | Br | $SCH_3$ |
| A-667 | Cl | H | Cl | $SCH_3$ |
| A-668 | Cl | Cl | Cl | $SCH_3$ |
| A-669 | Cl | F | Cl | $SCH_3$ |
| A-670 | Cl | Br | Cl | $SCH_3$ |
| A-671 | Cl | H | Br | $SCH_3$ |
| A-672 | Br | H | Br | $SCH_3$ |
| A-673 | Br | F | Br | $SCH_3$ |
| A-674 | Br | Cl | Br | $SCH_3$ |
| A-675 | $CF_3$ | H | F | $SCH_3$ |
| A-676 | $CF_3$ | H | Cl | $SCH_3$ |
| A-677 | $CF_3$ | H | Br | $SCH_3$ |
| A-678 | $CF_3$ | H | $CF_3$ | $SCH_3$ |
| A-679 | $CF_3$ | F | F | $SCH_3$ |
| A-680 | $CF_3$ | Cl | Cl | $SCH_3$ |
| A-681 | $CF_3$ | Br | Br | $SCH_3$ |
| A-682 | $SF_5$ | H | F | $SCH_3$ |
| A-683 | $SF_5$ | H | Cl | $SCH_3$ |
| A-684 | $SF_5$ | H | Br | $SCH_3$ |
| A-685 | $SF_5$ | H | $CF_3$ | $SCH_3$ |
| A-686 | $SF_5$ | H | H | $SCH_3$ |
| A-687 | $CF_3$ | H | H | $SCH_3$ |
| A-688 | Br | H | H | $SCH_3$ |
| A-689 | Cl | H | H | $SCH_3$ |
| A-690 | F | H | H | $SCH_3$ |
| A-691 | F | H | F | $SCH_2CH_3$ |
| A-692 | F | F | F | $SCH_2CH_3$ |
| A-693 | F | Cl | F | $SCH_2CH_3$ |
| A-694 | F | Br | F | $SCH_2CH_3$ |
| A-695 | F | H | Cl | $SCH_2CH_3$ |
| A-696 | F | H | Br | $SCH_2CH_3$ |
| A-697 | Cl | H | Cl | $SCH_2CH_3$ |
| A-698 | Cl | Cl | Cl | $SCH_2CH_3$ |
| A-699 | Cl | F | Cl | $SCH_2CH_3$ |
| A-700 | Cl | Br | Cl | $SCH_2CH_3$ |
| A-701 | Cl | H | Br | $SCH_2CH_3$ |
| A-702 | Br | H | Br | $SCH_2CH_3$ |
| A-703 | Br | F | Br | $SCH_2CH_3$ |
| A-704 | Br | Cl | Br | $SCH_2CH_3$ |
| A-705 | $CF_3$ | H | F | $SCH_2CH_3$ |
| A-706 | $CF_3$ | H | Cl | $SCH_2CH_3$ |
| A-707 | $CF_3$ | H | Br | $SCH_2CH_3$ |
| A-708 | $CF_3$ | H | $CF_3$ | $SCH_2CH_3$ |
| A-709 | $CF_3$ | F | F | $SCH_2CH_3$ |
| A-710 | $CF_3$ | Cl | Cl | $SCH_2CH_3$ |
| A-711 | $CF_3$ | Br | Br | $SCH_2CH_3$ |
| A-712 | $SF_5$ | H | F | $SCH_2CH_3$ |
| A-713 | $SF_5$ | H | Cl | $SCH_2CH_3$ |
| A-714 | $SF_5$ | H | Br | $SCH_2CH_3$ |
| A-715 | $SF_5$ | H | $CF_3$ | $SCH_2CH_3$ |
| A-716 | $SF_5$ | H | H | $SCH_2CH_3$ |
| A-717 | $CF_3$ | H | H | $SCH_2CH_3$ |
| A-718 | Br | H | H | $SCH_2CH_3$ |
| A-719 | Cl | H | H | $SCH_2CH_3$ |
| A-720 | F | H | H | $SCH_2CH_3$ |
| A-721 | F | H | F | $SCH(CH_3)_2$ |
| A-722 | F | F | F | $SCH(CH_3)_2$ |
| A-723 | F | Cl | F | $SCH(CH_3)_2$ |
| A-724 | F | Br | F | $SCH(CH_3)_2$ |
| A-725 | F | H | Cl | $SCH(CH_3)_2$ |
| A-726 | F | H | Br | $SCH(CH_3)_2$ |
| A-727 | Cl | H | Cl | $SCH(CH_3)_2$ |
| A-728 | Cl | Cl | Cl | $SCH(CH_3)_2$ |
| A-729 | Cl | F | Cl | $SCH(CH_3)_2$ |
| A-730 | Cl | Br | Cl | $SCH(CH_3)_2$ |
| A-731 | Cl | H | Br | $SCH(CH_3)_2$ |

TABLE A-continued

| No. | $R^{2a}$ | $R^{2b}$ | $R^{2c}$ | $R^{4b}$ |
|---|---|---|---|---|
| A-732 | Br | H | Br | $SCH(CH_3)_2$ |
| A-733 | Br | F | Br | $SCH(CH_3)_2$ |
| A-734 | Br | Cl | Br | $SCH(CH_3)_2$ |
| A-735 | $CF_3$ | H | F | $SCH(CH_3)_2$ |
| A-736 | $CF_3$ | H | Cl | $SCH(CH_3)_2$ |
| A-737 | $CF_3$ | H | Br | $SCH(CH_3)_2$ |
| A-738 | $CF_3$ | H | $CF_3$ | $SCH(CH_3)_2$ |
| A-739 | $CF_3$ | F | F | $SCH(CH_3)_2$ |
| A-740 | $CF_3$ | Cl | Cl | $SCH(CH_3)_2$ |
| A-741 | $CF_3$ | Br | Br | $SCH(CH_3)_2$ |
| A-742 | $SF_5$ | H | F | $SCH(CH_3)_2$ |
| A-743 | $SF_5$ | H | Cl | $SCH(CH_3)_2$ |
| A-744 | $SF_5$ | H | Br | $SCH(CH_3)_2$ |
| A-745 | $SF_5$ | H | $CF_3$ | $SCH(CH_3)_2$ |
| A-746 | $SF_5$ | H | H | $SCH(CH_3)_2$ |
| A-747 | $CF_3$ | H | H | $SCH(CH_3)_2$ |
| A-748 | Br | H | H | $SCH(CH_3)_2$ |
| A-749 | Cl | H | H | $SCH(CH_3)_2$ |
| A-750 | F | H | H | $SCH(CH_3)_2$ |
| A-751 | F | H | F | $SCH_2CH=CH_2$ |
| A-752 | F | F | F | $SCH_2CH=CH_2$ |
| A-753 | F | Cl | F | $SCH_2CH=CH_2$ |
| A-754 | F | Br | F | $SCH_2CH=CH_2$ |
| A-755 | F | H | Cl | $SCH_2CH=CH_2$ |
| A-756 | F | H | Br | $SCH_2CH=CH_2$ |
| A-757 | Cl | H | Cl | $SCH_2CH=CH_2$ |
| A-758 | Cl | Cl | Cl | $SCH_2CH=CH_2$ |
| A-759 | Cl | F | Cl | $SCH_2CH=CH_2$ |
| A-760 | Cl | Br | Cl | $SCH_2CH=CH_2$ |
| A-761 | Cl | H | Br | $SCH_2CH=CH_2$ |
| A-762 | Br | H | Br | $SCH_2CH=CH_2$ |
| A-763 | Br | F | Br | $SCH_2CH=CH_2$ |
| A-764 | Br | Cl | Br | $SCH_2CH=CH_2$ |
| A-765 | $CF_3$ | H | F | $SCH_2CH=CH_2$ |
| A-766 | $CF_3$ | H | Cl | $SCH_2CH=CH_2$ |
| A-767 | $CF_3$ | H | Br | $SCH_2CH=CH_2$ |
| A-768 | $CF_3$ | H | $CF_3$ | $SCH_2CH=CH_2$ |
| A-769 | $CF_3$ | F | F | $SCH_2CH=CH_2$ |
| A-770 | $CF_3$ | Cl | Cl | $SCH_2CH=CH_2$ |
| A-771 | $CF_3$ | Br | Br | $SCH_2CH=CH_2$ |
| A-772 | $SF_5$ | H | F | $SCH_2CH=CH_2$ |
| A-773 | $SF_5$ | H | Cl | $SCH_2CH=CH_2$ |
| A-774 | $SF_5$ | H | Br | $SCH_2CH=CH_2$ |
| A-775 | $SF_5$ | H | $CF_3$ | $SCH_2CH=CH_2$ |
| A-776 | $SF_5$ | H | H | $SCH_2CH=CH_2$ |
| A-777 | $CF_3$ | H | H | $SCH_2CH=CH_2$ |
| A-778 | Br | H | H | $SCH_2CH=CH_2$ |
| A-779 | Cl | H | H | $SCH_2CH=CH_2$ |
| A-780 | F | H | H | $SCH_2CH=CH_2$ |
| A-781 | F | H | F | $S-{}^cC_3H_5{}^*$ |
| A-782 | F | F | F | $S-{}^cC_3H_5{}^*$ |
| A-783 | F | Cl | F | $S-{}^cC_3H_5{}^*$ |
| A-784 | F | Br | F | $S-{}^cC_3H_5{}^*$ |
| A-785 | F | H | Cl | $S-{}^cC_3H_5{}^*$ |
| A-786 | F | H | Br | $S-{}^cC_3H_5{}^*$ |
| A-787 | Cl | H | Cl | $S-{}^cC_3H_5{}^*$ |
| A-788 | Cl | Cl | Cl | $S-{}^cC_3H_5{}^*$ |
| A-789 | Cl | F | Cl | $S-{}^cC_3H_5{}^*$ |
| A-790 | Cl | Br | Cl | $S-{}^cC_3H_5{}^*$ |
| A-791 | Cl | H | Br | $S-{}^cC_3H_5{}^*$ |
| A-792 | Br | H | Br | $S-{}^cC_3H_5{}^*$ |
| A-793 | Br | F | Br | $S-{}^cC_3H_5{}^*$ |
| A-794 | Br | Cl | Br | $S-{}^cC_3H_5{}^*$ |
| A-795 | $CF_3$ | H | F | $S-{}^cC_3H_5{}^*$ |
| A-796 | $CF_3$ | H | Cl | $S-{}^cC_3H_5{}^*$ |
| A-797 | $CF_3$ | H | Br | $S-{}^cC_3H_5{}^*$ |
| A-798 | $CF_3$ | H | $CF_3$ | $S-{}^cC_3H_5{}^*$ |
| A-799 | $CF_3$ | F | F | $S-{}^cC_3H_5{}^*$ |
| A-800 | $CF_3$ | Cl | Cl | $S-{}^cC_3H_5{}^*$ |
| A-801 | $CF_3$ | Br | Br | $S-{}^cC_3H_5{}^*$ |
| A-802 | $SF_5$ | H | F | $S-{}^cC_3H_5{}^*$ |
| A-803 | $SF_5$ | H | Cl | $S-{}^cC_3H_5{}^*$ |
| A-804 | $SF_5$ | H | Br | $S-{}^cC_3H_5{}^*$ |
| A-805 | $SF_5$ | H | $CF_3$ | $S-{}^cC_3H_5{}^*$ |
| A-806 | $SF_5$ | H | H | $S-{}^cC_3H_5{}^*$ |
| A-807 | $CF_3$ | H | H | $S-{}^cC_3H_5{}^*$ |
| A-808 | Br | H | H | $S-{}^cC_3H_5{}^*$ |
| A-809 | Cl | H | H | $S-{}^cC_3H_5{}^*$ |
| A-810 | F | H | H | $S-{}^cC_3H_5{}^*$ |
| A-811 | F | H | F | $SCF_3$ |
| A-812 | F | F | F | $SCF_3$ |
| A-813 | F | Cl | F | $SCF_3$ |
| A-814 | F | Br | F | $SCF_3$ |
| A-815 | F | H | Cl | $SCF_3$ |
| A-816 | F | H | Br | $SCF_3$ |
| A-817 | Cl | H | Cl | $SCF_3$ |
| A-818 | Cl | Cl | Cl | $SCF_3$ |
| A-819 | Cl | F | Cl | $SCF_3$ |
| A-820 | Cl | Br | Cl | $SCF_3$ |
| A-821 | Cl | H | Br | $SCF_3$ |
| A-822 | Br | H | Br | $SCF_3$ |
| A-823 | Br | F | Br | $SCF_3$ |
| A-824 | Br | Cl | Br | $SCF_3$ |
| A-825 | $CF_3$ | H | F | $SCF_3$ |
| A-826 | $CF_3$ | H | Cl | $SCF_3$ |
| A-827 | $CF_3$ | H | Br | $SCF_3$ |
| A-828 | $CF_3$ | H | $CF_3$ | $SCF_3$ |
| A-829 | $CF_3$ | F | F | $SCF_3$ |
| A-830 | $CF_3$ | Cl | Cl | $SCF_3$ |
| A-831 | $CF_3$ | Br | Br | $SCF_3$ |
| A-832 | $SF_5$ | H | F | $SCF_3$ |
| A-833 | $SF_5$ | H | Cl | $SCF_3$ |
| A-834 | $SF_5$ | H | Br | $SCF_3$ |
| A-835 | $SF_5$ | H | $CF_3$ | $SCF_3$ |
| A-836 | $SF_5$ | H | H | $SCF_3$ |
| A-837 | $CF_3$ | H | H | $SCF_3$ |
| A-838 | Br | H | H | $SCF_3$ |
| A-839 | Cl | H | H | $SCF_3$ |
| A-840 | F | H | H | $SCF_3$ |
| A-841 | F | H | F | $SCH_2CF_3$ |
| A-842 | F | F | F | $SCH_2CF_3$ |
| A-843 | F | Cl | F | $SCH_2CF_3$ |
| A-844 | F | Br | F | $SCH_2CF_3$ |
| A-845 | F | H | Cl | $SCH_2CF_3$ |
| A-846 | F | H | Br | $SCH_2CF_3$ |
| A-847 | Cl | H | Cl | $SCH_2CF_3$ |
| A-848 | Cl | Cl | Cl | $SCH_2CF_3$ |
| A-849 | Cl | F | Cl | $SCH_2CF_3$ |
| A-850 | Cl | Br | Cl | $SCH_2CF_3$ |
| A-851 | Cl | H | Br | $SCH_2CF_3$ |
| A-852 | Br | H | Br | $SCH_2CF_3$ |
| A-853 | Br | F | Br | $SCH_2CF_3$ |
| A-854 | Br | Cl | Br | $SCH_2CF_3$ |
| A-855 | $CF_3$ | H | F | $SCH_2CF_3$ |
| A-856 | $CF_3$ | H | Cl | $SCH_2CF_3$ |
| A-857 | $CF_3$ | H | Br | $SCH_2CF_3$ |
| A-858 | $CF_3$ | H | $CF_3$ | $SCH_2CF_3$ |
| A-859 | $CF_3$ | F | F | $SCH_2CF_3$ |
| A-860 | $CF_3$ | Cl | Cl | $SCH_2CF_3$ |
| A-861 | $CF_3$ | Br | Br | $SCH_2CF_3$ |
| A-862 | $SF_5$ | H | F | $SCH_2CF_3$ |
| A-863 | $SF_5$ | H | Cl | $SCH_2CF_3$ |
| A-864 | $SF_5$ | H | Br | $SCH_2CF_3$ |
| A-865 | $SF_5$ | H | $CF_3$ | $SCH_2CF_3$ |
| A-866 | $SF_5$ | H | H | $SCH_2CF_3$ |
| A-867 | $CF_3$ | H | H | $SCH_2CF_3$ |
| A-868 | Br | H | H | $SCH_2CF_3$ |
| A-869 | Cl | H | H | $SCH_2CF_3$ |
| A-870 | F | H | H | $SCH_2CF_3$ |

*${}^cC_3H_5$ = cyclopropyl

Among the above compounds, preference is given to compounds of formula Ia.1, Ia.13, Ia.15, Ia.25, Ia.26, and Ia.27, and especially to Ia.15.

The compounds of the formula (I) can be prepared by the methods as described in the below schemes or and in the synthesis descriptions of the working examples, or by standard methods of organic chemistry. The substituents, variables and indices are as defined above for formula (I), if not otherwise specified.

Compounds of formula I can be prepared by dehydrating a compound of formula 1 as shown in scheme 1 below. X' corresponds to a heterocyclic radical X, which however either carries a group A or a group A', where A' is a precursor of A. Typical precursors of A are a halogen atom, CN, carboxy, tert-butoxycarbonyl, an acetale group, a protected aldehyde group or —OSO$_2$—R$^{z1}$, where R$^{z1}$ is C$_1$-C$_4$-alkyl, C$_1$-C$_4$-haloalkyl or phenyl which may be substituted by 1, 2 or 3 radicals selected from C$_1$-C$_4$-alkyl, C$_1$-C$_4$-haloalkyl C$_1$-C$_4$-alkoxy or C$_1$-C$_4$-haloalkoxy. Compounds I' correspond to compounds I when A' is A (or X' is X). Dehydration either occurs spontaneously or with the help of dehydrating agents, such as molecular sieves, acid-washed molecular sieves, magnesium sulfate, sodium sulfate, silica gel, SOCl$_2$, POCl$_3$, Burgess reagent, trifluoroacetic anhydride, p-toluene sulfonic acid, anhydrous HCl or sulfuric acid. Preferably, p-toluene sulfonic acid or acid-washed molecular sieves are used. The water formed may alternatively be removed, e.g. by azeotropic distillation, e.g. with benzene/toluene as entrainer, e.g. using a Dean Stark trap. If necessary (i.e. if A' is a precursor of A), A' is then converted into a group A.

Scheme 1

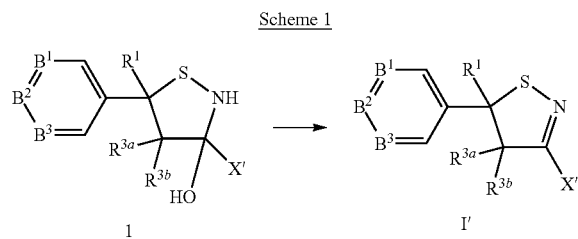

Compounds 1 wherein R$^{3b}$ is hydrogen can be prepared by reacting a compound 3 with an amination agent to give a compound of formula 2, which reacts spontaneously to the compound 1, as shown in scheme 2. Depending on the amination agents used, amination can the carried out in a one step reaction, wherein compound 3 reacts directly to compound 2, or as a two step reaction, wherein the SH group of compound 3 is first oxidized to a S—Cl group, which then further reacts to a S—NH$_2$ group, thus giving compound 2.

Suitable amination agents for the one step reaction are for example HOSA (hydroxylamine-O-sulfonic acid), which is generally used in the presence of a base (suitable bases being for example sodium hydrogen phosphate, potassium hydrogen phosphate, sodium hydroxide, potassium hydroxide, sodium carbonate, potassium carbonate, sodium methanolate, triethylamine and the like), O-(diphenylphosphoryl)hydroxyl amine, which is generally also used in the presence of a base (suitable bases being for example sodium hydrogen phosphate, potassium hydrogen phosphate, sodium hydroxide, potassium hydroxide, sodium carbonate, potassium carbonate, sodium methanolate, triethylamine and the like), 2,4-dinitrophenylhydroxyl amine, O-mesitylensulfonylhydroxylamine and 2-oxa-1-azaspiro[2.5]octane, among which HOSA and O-(diphenylphosphoryl)hydroxyl amine are preferred. The amination is generally carried out in a solvent, suitable solvents being for example chlorinated alkanes, such as methylene chloride or chloroform, aromatic solvents, such as benzene, toluene, the xylenes, chlorobenzene or dichlorobenzene, and ethers, such as diethylether, dipropylether, methyl tert-butylether, methyl isobutylether, ethylenegylcol dimethylether, tetrahydrofuran (THF) or dioxane and the like. The reaction is suitably carried out low temperature, e.g. at from −100 to 0° C. or −78 to 0° C. Generally, the compound 3 is dispersed in a solvent and cooled to the desired temperature and the base is added followed by the amination agent, or the amination agent is added followed by the base, or base and amination agent are added simultaneously. HOSA is suitably used in combination with an amine base, such as triethylamine. In this case, it is preferred to cool compound 3 to −30 to 0° C., preferably −20 to −10° C., to add the amine base at this temperature and then HOSA and keep the reaction at approximately −10 to 0° C.

Alternatively, O-(diphenylphosphoryl)hydroxyl amine can be used in combination with a base, e.g. with an inorganic base, such as sodium hydrogen phosphate, potassium hydrogen phosphate, sodium hydroxide, potassium hydroxide, sodium carbonate or potassium carbonate and specifically sodium hydrogen phosphate. In this case, it is suitable to cool compound 3 to −80 to −30° C., especially −80 to −70° C., to add the base at this temperature and then O-(diphenylphosphoryl)hydroxyl amine and keep the reaction at approximately 0° C. to room temperature.

In the two step reaction, the compound 3 is first reacted with a chlorination agent which converts the SH group into an S—Cl group. Suitable chlorination agents are for example sulfurylchloride, N-chloro succinimide (NCS), sodium hypochlorite, monochloroamine (NH$_2$Cl) or chlorine, which is preferably used in the presence of FeCl$_3$. The chlorination can be carried out in analogy to the method described in Synthesis 1987, 1987, 683-688, Tetrahedron 66(36), 2010, 7279-7287, J. Org. Chem. 59(4), 1994, 914-921, J. Org. Chem. 63, 1998, 4878-4888 or J. Chem Soc. 1938, 2114-2117. The chlorination is generally carried out in a solvent. Suitable solvents are for example ethers, such as diethylether, dipropylether, methyl tert-butylether, methyl isobutylether, ethylenegylcol dimethylether, tetrahydrofuran or dioxane. The reaction temperature can vary over wide ranges and is generally from 0° C. to the boiling point of the reaction mixture (if a solvent is used). The chlorinated compound is then reacted without isolation with ammonia or ammonium hydroxide. If anhydrous ammonia is used, the reaction is generally carried out at from −78 to −33° C. If aqueous ammonia or ammonium hydroxide is used, the reaction can also be carried out at higher temperatures, such as 0 to 25° C. The reaction is generally carried out in a solvent. Suitable solvents are for example the above-listed ethers, among which the water-miscible ethers, such as THF and dioxane, are preferred. In general, the chlorinated compound is dissolved in a solvent to which ammonia or ammonium hydroxide is added. The reaction can be carried out as described, for example, in Synthesis, 1987, 8, 683-688. The chlorination/amination can also be carried as a one pot reaction. For example, the thiol 3 is reacted simultaneously with a chlorinating agent (such as NCS or aqueous sodium hypochlorite) and anhydrous or aqueous ammonia in ethereal solvents (such as THF or Et$_2$O) or water. Preferred is the reaction with NCS in a mixture of THF and anhydrous liquid ammonia at −33° C. For instance, a solution of the thiol 3 in THF is added to a solution of NCS (N-chlorosuccinimide) in THF/liquid ammonia at −78° C. The solution is warmed to −30° C. and stirred until the ammonia has evaporated. Alternatively, at 0° C., a solution of the sodium thiolate (NaSR) in water is added to a mixture of aqueous ammonia (25%) and aqueous sodium hypochlorite (1 N). The one pot chlorination/amination reaction can be carried out as described, for example, in Tetrahedron 2010, 66, 7279-7287 or in J. Org. Chem. 1994, 59, 914-921.

Compound 2 can virtually not be isolated as it generally reacts spontaneously in a ring-closing reaction to compound 1.

Scheme 2

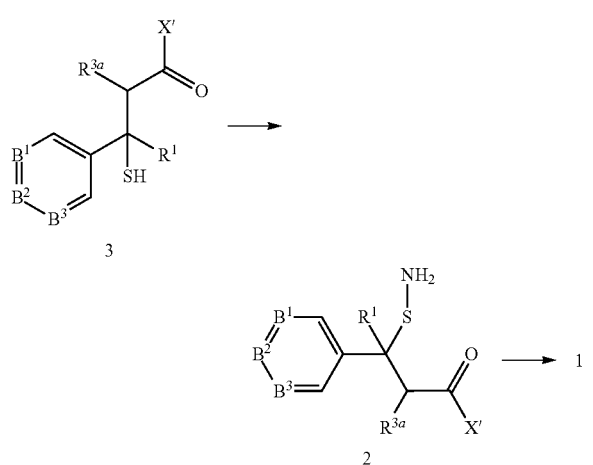

The compound of formula 3 can be prepared by reacting a compound of formula 4

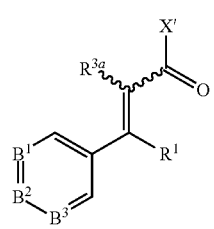

with a sulfur source. Suitable sulfur sources are for example $H_2S$, metal hydrogen sulfides, such as NaSH or KSH, metal sulfides, such as $Na_2S$, $K_2S$ $Li_2S$, $Cu_2S$, MgS, CaS, CuS, FeS and the like, ammonium sulfide [$(NH_4)_2S$], tetraalkylammonium sulfides ($R_4NSH$), such as tetramethylammonium sulfide, tetraethylammonium sulfide, tetrapropylammonium sulfide and the like, or bistrimethylsilyl sulfide. $H_2S$ as a sulfur source is generally used in the presence of a base, such as $Na_2CO_3$, $K_2CO_3$, $Cs_2CO_3$, sodium acetate, potassium acetate, cesium acetate, amines, such as diethylamine, dipropylamine, triethylamine, diisopropylethylamine and the like, or basic nitrogen-containing heterocycles, such as pyrrolidine, piperidine, piperazine, pyridine, lutidine and the like. Alternatively, $H_2S$ as a sulfur source can be used in the presence of a Lewis acid, such as $AlCl_3$ or $FeCl_3$. The reaction of compound 4 with a sulfur source is generally carried out in a solvent, suitable solvents being for example chlorinated alkanes, such as methylene chloride or chloroform, and aromatic solvents, such as benzene, toluene, the xylenes, chlorobenzene or dichlorobenzene. The reaction temperature can vary over a wide range, such as −78° C. to room temperature. In general, compound 4 is dissolved in a solvent, optionally cooled, then the base (if used) and subsequently the sulfur source is added. The compound 4 can alternatively be reacted with a sulfur source which provides a compound 3 which is protected at the thiol group SH by a protective group (S-PG). This is advantageous if compound 3 is for example subjected to harsher purification conditions or is derivatized, e.g. for converting the precursor group A' into a group A or for modifying group A' at this stage. Moreover, purification of the protected product is easier. Suitable sulfuration reagents which give such protected thiols are for example thiourea ($NH_2$—C(=S)—$NH_2$), optionally substituted benzyl thiols, such as benzylthiol, o- or p-methoxy-benzylthiol, o- or p-hydroxybenzylthiol, o- or p-acetoxybenzylthiol, o- or p-nitrobenzylthiol or 2,4,6-trimethylbenzylthiol, pyridin-4-yl-methylthiol, quinolin-2-yl-methylthiol, benzyl metal sulfides, such as sodium benzyl-sulfide, phenylthiol, 2,4-dinitrophenylthiol, tritylthiol, tert-butylthiol, compounds of formula R—C(=O)—NH—$CH_3$—SH, wherein R is methyl, tert-butyl, allyl, phenyl or benzyl, 2-trimethylsilanyl-ethanethiol, 2-(2,4-dinitrophenyl)-ethanethiol, 2-phenylsulfonyl-ethanethiol, acylated thiols, such as methylcarbonylthiol or phenylcarbonylthiol, and thiocarbamates R—NH—C(=O)—SH, wherein R is e.g. methyl or ethyl. The benzyl and alkyl thiols are generally used in the presence of a base, such as sodium hydroxide, potassium hydroxide, sodium phosphate, potassium phosphate, sodium hydrogenphosphate, potassium hydrogenphosphate, sodium carbonate, potassium carbonate, caesium carbonate, sodium hydride, potassium hydride, lithium diisopropyl amide (LDA), sodium methanolate, sodium ethanolate, potassium tert-butoxide, aqueous sodium tetraborate, n-butyllithium, tert-butyllithium, tetrabutylammoniumfluoride (TBAF), NaHMDS and the like, or in the presence of a Lewis or Bronsted acid, such as $FeCl_3$, $Zn(ClO_4)_2$, $Cu(BF_4)_2$, $HBF_4$ or $HClO_4$. The reaction is generally carried out in a solvent, suitable solvents being for example chlorinated alkanes, such as methylene chloride or chloroform, and ethers, such as diethylether, dipropylether, methyl tert-butylether, methyl isobutylether, ethylenegylcol dimethylether, tetrahydrofuran (THF) or dioxane and the like. The reaction temperature can vary over a wide range, such as from −25° C. to the boiling point of the reaction mixture. The acylated thiols can be reacted neat or in a solvent, suitable solvents being for example chlorinated alkanes, such as methylene chloride or chloroform, and ethers, such as diethylether, dipropylether, methyl tert-butylether, methyl isobutylether, ethylenegylcol dimethylether, tetrahydrofuran (THF) or dioxane and the like. They can be used with or without a base. The S-protected compound 3 can then be deprotected to the free thiol 3 under conditions generally known for the respective protective group, such as described, for example, in Peter G. M. Wuts, Theodora Greene, Protective Groups in Organic Synthesis, 4th edition, John Wiley & Sons, Inc., 2007, Chapter 6.

Compound 4 can be prepared in analogy to the method described in EP-A-2172462.

Compounds 1 (in which $R^{3b}$ is not necessarily hydrogen) can be prepared alternatively by reacting a compound of formula 6 with an amination agent to a compound of formula 5, which reacts spontaneously to the compound 1, as shown in scheme 3. The reaction can be carried out in analogy to that of compounds 3 and 2.

Scheme 3

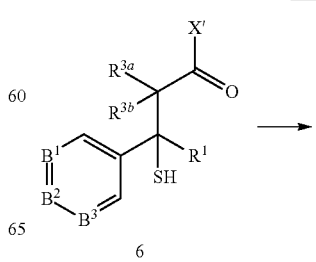

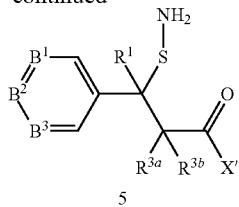

5

The compound of formula 6 can be obtained by reacting a compound of formula 7 with a compound of formula 8.

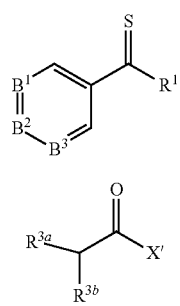

7

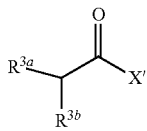

8

The reaction is preferably carried out as a Mukaiyama aldol reaction. To this purpose, the trialklysilyl-enolate derivative of 8 is reacted with 7 in the presence of a Lewis acid, such as TiCl$_4$ or BF$_3$[O(C$_2$H$_5$)$_2$]. Alternatively, the reaction can be carried out in the presence of a strong base, such as lithium diisopropylamide (LDA), sodium bistrimethylsilylamide (sodium hexamethyldisilazide; NaHMDS) and amines, such as triethylamine, tripropylamine or diisopropylethylamine. The reaction is generally carried out in a solvent. If a lithium or sodium base is used, the solvent is suitably an ether, such as diethylether, dipropylether, methyl tert-butylether, methyl isobutylether, ethylenegylcol dimethylether, tetrahydrofuran (THF) or dioxane and the like. Suitable reaction temperatures range from −78 to 25° C. If an amine base is used, the solvent is suitably an ether, such as diethylether, dipropylether, methyl tert-butylether, methyl isobutylether, ethylenegylcol dimethylether, tetrahydrofuran (THF) or dioxane, or an alkane, such as pentane, hexane or heptane. Suitable reaction temperatures range from 25 to 100° C.

The compound of formula 7 can be obtained by reacting a compound of formula 9 with a sulfuration agent, such as Lawesson's reagent or P$_2$S$_5$.

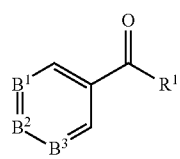

9

The reaction is generally carried out in a solvent, suitable solvents being for example aromatic solvents, such as benzene, toluene, the xylenes, chlorobenzene or dichlorobenzene, ethers, such as diethylether, dipropylether, methyl tert-butylether, methyl isobutylether, ethylenegylcol dimethylether, tetrahydrofuran (THF) or dioxane, and hexamethyl phosphoric acid triamide (HMPA). The reaction is generally carried out at a temperature of from 25° C. to the boiling point of the reaction mixture.

Compounds of formula I wherein R$^1$ is CF$_3$ can moreover be prepared by reacting a compound of formula 10 with a fluorinating agent and, if necessary (i.e. if A' is a precursor of A), converting the group A' into a group A.

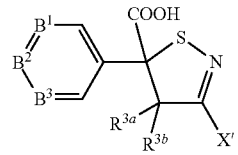

10

Suitable fluorinating agents are, for example, SF$_4$, preferably in combination with HF or BF$_3$[O(C$_2$H$_5$)$_2$], phenyl-sulfur trifluoride (Ph-SF$_3$), preferably in combination with HF and pyridine, 4-tert-butyl-2,6-dimethylphenylsulfur trifluoride ("Fluoled"), and bis(2-methoxyethyl)aminosulfur trifluoride [(CH$_3$OCH$_2$CH$_2$)$_2$NSF$_3$]. Among these, preference is given to SF$_4$ in combination with HF. If SF$_4$ in combination with HF is used, the reaction is carried out neat, i.e. without any further solvent. The reaction is generally carried out under elevated pressure stemming from the reactants, e.g. at a pressure of from 2 to 10 bar, preferably from 5 to 8 bar. The reaction temperature can vary over wide ranges, such as from 25 to 120° C., preferably from 60 to 100° C.

Alternatively, fluorination can be carried out by a two step method, in which the carboxyl group on the isothiazoline ring is first converted into a CCl$_3$ group, and this is subsequently fluorinated to the CF$_3$ group. The conversion of the COOH group to the CCl$_3$ group is preferably carried out by reacting the compound VI with PCl$_5$ and phenyl-phosphoroxy dichloride (Ph-P(=O)Cl$_2$). The reaction can be carried out neat, i.e. without any further solvent. Suitably, the reaction is carried out at elevated temperatures, for example at from 50° C. to reflux and preferably at reflux. Fluorination agents for converting the CCl$_3$ group into a CF$_3$ group are those mentioned above, and further HF and HF in combination with SbCl$_5$ and HF in combination with Cl$_2$ and SbF$_3$. The reaction can be carried out neat, i.e. without any further solvent. The reaction temperature can vary over wide ranges, for examples from 25 to 300° C., preferably from 50 to 200° C. and in particular from 80 to 120° C. If the fluorination agent is HF or HF in combination with a further agent, the reaction generally takes place at the pressure stemming from HF and ranging generally from 2 to 10 bar, preferably from 5 to 8 bar.

The compound of formula 10 is preferably obtained by hydrolyzing a compound of formula 11, wherein R is C$_1$-C$_4$-alkyl.

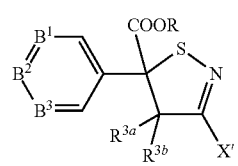

11

Hydrolysis can be carried out by any suitable means known for hydrolyzing ester groups, such as acidic conditions, e.g. using hydrochloric acid, hydrobromic acid, sulfuric acid, trifluoroacetic acid, etc., or by basic conditions, e.g. using an alkali metal hydroxide, such as LiOH, NaOH or KOH, or an alkali metal carbonate, such as sodium or potassium carbonate.

The compound of formula 11 can in turn be obtained by reacting a compound 12 with a compound 13

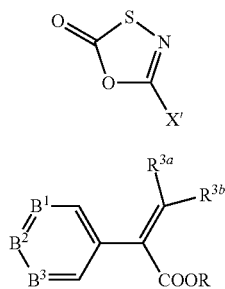

12

13

The reaction is carried out at elevated temperature, e.g. at from 90 to 200° C., preferably from 100 to 180° C. and in particular from 120 to 160° C., e.g. at about 140° C.

The compound of formula 12 can in turn be obtained by reacting a compound 15 with a compound 16

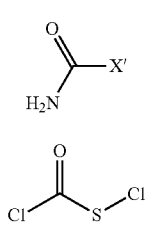

15

16

The reaction is generally carried out in a solvent, suitable solvents being for example aromatic solvents, such as benzene, toluene, the xylenes, chlorobenzene and dichlorobenzene. The reaction temperature is preferably from 80 to 140° C., more preferably from 100 to 120° C.

Compounds of formula I wherein however $R^1$ is $CF_3$ can moreover be prepared by reacting a compound of formula 12 as defined above with a compound of formula 14 and, if necessary, converting the group A' into a group A.

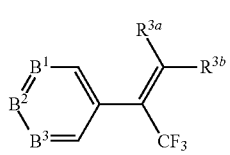

14

The reaction is carried out at elevated temperature, e.g. at from 90 to 200° C., preferably from 100 to 180° C. and in particular from 120 to 160° C., e.g. at about 140° C.

Compounds I', in which A' is a precursor of A can be converted as shown below into the different groups $A^1$ to $A^3$.

Compounds I', in which A' is Cl, Br, I or —$OSO_2$—$R^{z1}$, where $R^{z1}$ is as defined above, can be converted to compounds I wherein A is a group $A^1$, wherein $A^1$ is an imino group —C(=$NR^6$)$R^8$, by reaction with carbon monoxide and a hydride source, such as triethylsilane, in the presence of a transition metal complex catalyst, preferably a palladium catalyst, to a carbonyl compound 17. This reaction converts the starting group A' into a carbonyl group —C(=O)H.

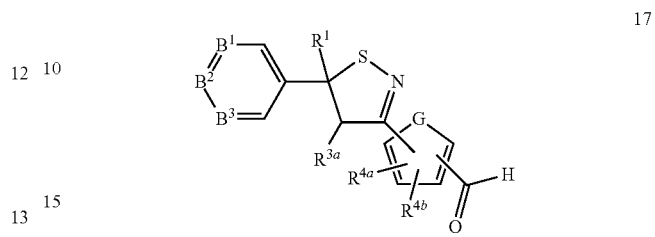

17

The aldehyde 17 can also be obtained by reducing the ester 20 (see below; R=$C_1$-$C_4$-alkyl) with diisobutylaluminium hydride (DIBAL-H) either directly to the aldehyde 17 or via the corresponding alcohol, which is then oxidized to the aldehyde.

For obtaining compounds in which $R^8$ in the imino group is H, such carbonyl compounds 17 are then reacted with an amine (derivative) $NH_2R^6$. Alternatively, the compound I', in which A' is Cl, Br, I or —$OSO_2$—$R^{z1}$, where $R^{z1}$ is as defined above, can be reacted in a one pot reaction with carbon monoxide and hydrogen in the presence of a transition metal complex catalyst and the amine $NH_2R^6$.

For obtaining compounds in which $R^8$ in the imino group is not H, the carbonyl compounds are reacted with a Grignard reagent $R^8$—MgHal, where Hal is Cl, Br or I, or an organolithium compound $R^8$—Li to obtain an alcohol of formula 18, which is then oxidized to a carbonyl compound of the formula 19, as shown in scheme 4. This is then reacted with an amine $NH_2R^6$ to the respective imine compound.

Scheme 4

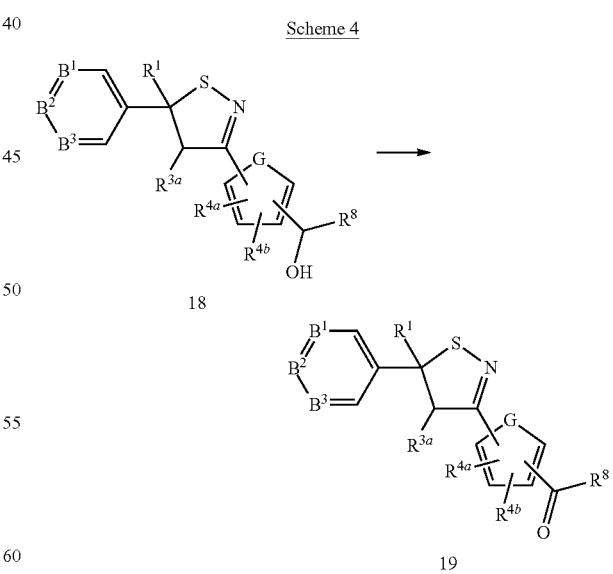

These reactions can be carried out in analogy to the methods described in PCT/EP 2011/060388 or in WO 2010/072781 and the references cited therein, especially WO 2006135763, Fattorusso et al, J. Med. Chem. 2008, 51, 1333-1343 and WO 2008/122375.

Compounds I wherein A is a group $A^1$, wherein $A^1$ is —S(O)$_n$R$^9$ or —N(R$^5$)R$^6$, can for example be prepared by reacting a compound I' wherein A' is Cl, Br or I in a Ullmann-type reaction with an amine NHR$^5$R$^6$ or a thiol SHR$^9$ in the presence of a Cu(I) catalyst. To obtain a compound wherein $A^1$ is —S(O)$_n$R$^9$ wherein n is not 0 the thiol can then be oxidized, e.g. with hydrogen peroxide. Amine and thiol groups can further be introduced in a Buchwald-Hartwig reaction by reacting a compound I' wherein A' is Cl, Br or I with an amine NHR$^5$R$^6$ or a thiol HSR$^9$ in the presence of a palladium catalyst, such as PdCl$_2$(dppf) in the presence of a base, such as cesium carbonate or N,N-diisopropylethyl amine, and optionally in the presence of a phosphine ligand, such as Xantphos ("4,5-Bis(diphenylphosphino)-9,9-dimethylxanthene").

Thioethers ($A^1$=SR$^9$) can further be introduced by reacting a compound I' wherein A' is F in an S$_N$Ar reaction (nucleophilic aromatic substitution reaction) with a thiol HSR$^9$ in the presence of a base, such as potassium carbonate (K$_2$CO$_3$), or with a thiolate (e.g. NaSR$^9$).

Compounds I wherein A is a group $A^2$, wherein W is O can be prepared by reacting a compound I' wherein A' is Cl, Br, I or triflate with carbon monoxide in the presence of a palladium catalyst and an alcohol ROH, wherein R is C$_1$-C$_4$-alkyl, to a compound of formula 20. Suitable palladium catalysts are for example those described in PCT/EP 2011/060388.

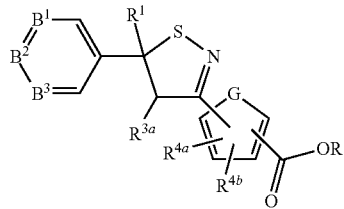

20

This ester is then hydrolyzed to the respective carboxylic acid, which is the reacted under standard amidation conditions with an amine NHR$^5$R$^6$. Hydrolyzation can be carried out under standard conditions, e.g. under acidic conditions using for example hydrochloric acid, sulfuric acid or trifluoroacetic acid, or under basic conditions using for example an alkali metal hydroxide, such as LiOH, NaOH or KOH. Amidation is preferably carried out by activation of the carboxylic acids with oxalylchloride [(COCl)$_2$] or thionylchloride (SOCl$_2$) to the respective acid chlorides, followed by reaction with an amine NHR$^5$R$^6$. Alternatively, amidation is carried out in the presence of a coupling reagent. Suitable coupling reagent (activators) are well known and are for instance selected from carbodiimides, such as DCC (dicyclohexylcarbodiimide) and DCI (diisopropylcarbodiimide), benzotriazol derivatives, such as HATU (O-(7-azabenzotriazol-1-yl)N,N,N',N'-tetramethyluronium hexafluorophosphate), HBTU ((0-benzotriazol-1-yl)N,N,N',N'-tetramethyluronium hexafluorophosphate) and HCTU (1H-benzotriazolium-1-[bis(dimethylamino)methylene]-5-chloro tetrafluoroborate) and phosphonium-derived activators, such as BOP ((benzotriazol-1-yloxy)-tris(dimethylamino)phosphonium hexafluorophosphate), Py-BOP ((benzotriazol-1-yloxy)-tripyrrolidinphosphonium hexafluorophosphate) and Py-BrOP (bromotripyrrolidinphosphonium hexafluorophosphate).

Generally, the activator is used in excess. The benzotriazol and phosphonium coupling reagents are generally used in a basic medium.

Compounds I wherein A is a group $A^2$, wherein W is S, can be prepared by reacting the corresponding oxo-compound (W is O) with Lawesson's reagent (CAS 19172-47-5), see for example Jesberger et al., Synthesis, 2003, 1929-1958 and references therein. Solvents such as HMPA or THF at an elevated temperature such as 60° C. to 100° C. can be used. Preferred reaction conditions are THF at 65° C.

Compounds I wherein A is a group $A^3$, wherein $R^{7a}$ and $R^{7b}$ are hydrogen, can be prepared by reducing a compound 20 or 17 for example with LAH (lithium aluminium hydride) or DIBAL-H (diisobutyl aluminium hydride) to a compound 21.

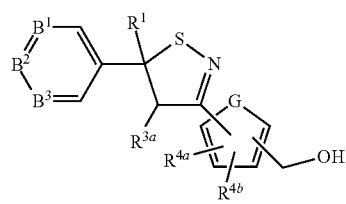

21

This is then reacted in an SN reaction with an amine NHR$^5$R$^6$. For this purpose, the OH group can first be converted into a better leaving group, e.g. into a sulfonate (for example mesylate, tosylate or a triflate group). If $R^6$ is a group —C(O)R$^8$, it is alternatively possible to react compound 21 with an amine NH$_2$R$^5$ and react then the resulting benzylic amine with an acid R$^8$—COOH or a derivative thereof, such as its acid chloride R$^3$—COCl, in an amidation reaction.

Compounds I wherein A is a group $A^3$, wherein $R^{7a}$ is optionally substituted alkyl or optionally substituted cycloalkyl and $R^{7b}$ is hydrogen, can be prepared by subjecting a ketone 19, in which $R^8$ corresponds to $R^{7a}$ which is optionally substituted C$_1$-C$_6$-alkyl or optionally substituted C$_3$-C$_8$-cycloalkyl, to a reductive amination to furnish compounds 22. Typical conditions for the reductive amination are: Reacting ketone 19 with an amine H$_2$NR$^5$ to yield the corresponding imine which is reduced to amine 22 with a reducing agent reagent such as Na(CN)BH$_3$. The reaction from ketone 19 to amine 22 may also be carried out as a one pot procedure.

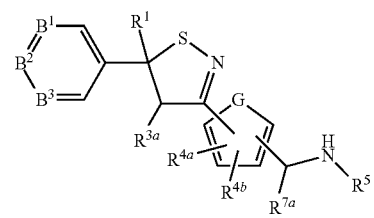

22

For obtaining compounds in which $R^{7a}$ and $R^{4b}$ are optionally substituted alkyl, optionally substituted cycloalkyl, optionally substituted alkenyl or optionally substituted alkynyl, carbonyl compounds such as 19, in which $R^8$ corresponds to $R^{7a}$ which is optionally substituted C$_1$-C$_6$-alkyl, optionally substituted C$_3$-C$_8$-cycloalkyl, optionally substituted C$_2$-C$_6$-alkenyl or optionally substituted C$_2$-C$_6$- alkynyl, is reacted with a Grignard reagent R$^{7b}$-MgHal, where Hal is Cl, Br or I, or an organolithium compound R$^{7b}$—Li, where R$^{4b}$ is optionally substituted C$_1$-C$_6$-alkyl, optionally substituted C$_3$-C$_8$-cycloalkyl, optionally substituted C$_2$-C$_6$-alkenyl or optionally substituted C$_2$-C$_6$-alkynyl, to obtain an alcohol of formula 23.

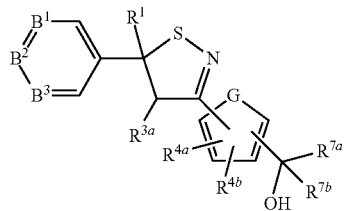

23

Alcohol 23 can then be converted into amine 24 via the corresponding azide, as described, for example, in Organic Letters, 2001, 3(20), 3145-3148.

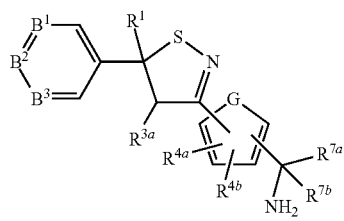

24

If desired, this can be converted into compounds I wherein R$^5$ and R$^6$ are different from hydrogen, for example by standard alkylation or acylation reactions.

Compounds I wherein A is a group A$^3$, wherein R$^{7a}$ is optionally substituted alkyl, alkenyl, alkynyl, cycloalkyl or CN and R$^{7b}$ is hydrogen, can be prepared by converting an aldehyde 17 into an imine 25 by reaction with an amine derivative NH$_2$R$^6$, wherein R$^6$ is tert-butyl sulfinyl, or, for preparing a compound with R$^{7a}$=CN, tosylate.

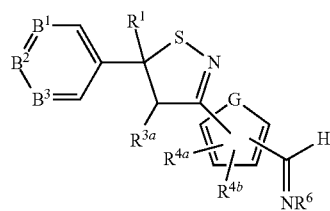

25

This imine is then reacted with a compound H—R$^{7a}$ in an addition reaction under conditions as described for example in J. Am. Chem. Soc. 2009, 3850-3851 and the references cited therein, or, for introducing CN as a group R$^{7a}$, Chemistry—A European Journal 2009, 15, 11642-11659.

Compounds I wherein A is a group A$^3$, wherein both R$^{7a}$ and R$^{7b}$ are optionally substituted alkyl, alkenyl, alkynyl, cycloalkyl or CN, can be prepared analogously by converting a ketone 19, wherein R$^8$ is has the meaning desired for R$^{7b}$ and is optionally substituted alkyl, alkenyl, alkynyl, cycloalkyl or CN, into an imine by reaction with an amine derivative NH$_2$R$^6$, wherein R$^6$ is tert-butyl sulfinyl, or, for preparing a compound 26 with R$^{7a}$=CN, tosylate.

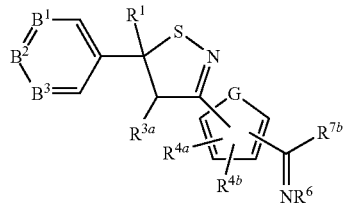

26

This imine is then reacted with a compound H—R$^{7a}$ in an addition reaction under conditions as described for example in J. Org. Chem 2002, 67, 7819-7832 and the references cited therein, or, for introducing CN as a group R$^{7a}$, Chemistry—A European Journal 2009, 15, 11642-11659. If desired, R$^6$ can then be removed to yield an amino group NH$_2$.

Compounds I wherein A is A$^4$ can be prepared by standard ring coupling reactions. For example, compounds, wherein A$^4$ is an N-bound heterocyclic ring can be prepared by reacting a compound I' wherein A' is Cl, Br or I with the respective ring A$^4$-H (H being on the nitrogen ring atom to be coupled) under Ullmann coupling conditions, such as described, for example, in WO 2007/075459. Typically, copper(I) iodide or copper(I) oxide and a ligand such as 1,2-cyclohexyldiamine is used, see for example Kanemasa et al., European Journal of Organic Chemistry, 2004, 695-709. If A' is F, the reaction is typically run in a polar aprotic solvent such as N,N-dimethylformamide, N,N-dimethylacetamide or N-methylpyrrolidone, and in the presence of an inorganic base such as sodium, potassium or cesium carbonate.

Compounds, wherein A$^4$ is a C-bound heterocyclic ring can be prepared by reacting a compound I' wherein A' is Br or I with the boronic acid of the respective ring A$^4$-B(OH)$_2$ or the boronate ester of the respective ring A$^4$-B(OR$_2$) under Suzuki reaction conditions via Pd-catalyzed cross coupling, such as described, for example, in WO 2007/075459. A typical catalyst is tetrakis(triphenylphosphine)palladium(0). Solvents such as tetrahydrofuran, acetonitrile, diethyl ether and dioxane are suitable. The boronic acids A$^4$-B(OH)$_2$ are either commercially available or can be prepared by known methods. Other methods for introduction of the heterocyclic groups A$^4$ are the Heck, Stille, Kumada and Buchwald-Hartwig coupling procedures; see for example Tetrahedron, 2004, 60, 8991-9016.

As a rule, the compounds of formula (I) including their stereoisomers, salts, and N-oxides, and their precursors in the synthesis process, can be prepared by the methods described above. If individual compounds can not be prepared via the above-described routes, they can be prepared by derivatization of other compounds (I) or the respective precursor or by customary modifications of the synthesis routes described. For example, in individual cases, certain compounds of formula (I) can advantageously be prepared from other compounds of formula (I) by derivatization, e.g. by ester hydrolysis, amidation, esterification, ether cleavage, olefination, reduction, oxidation and the like, or by customary modifications of the synthesis routes described.

The reaction mixtures are worked up in the customary manner, for example by mixing with water, separating the phases, and, if appropriate, purifying the crude products by chromatography, for example on alumina or on silica gel. Some of the intermediates and end products may be obtained in the form of colorless or pale brown viscous oils which are freed or purified from volatile components under reduced pressure and at moderately elevated temperature. If the intermediates and end products are obtained as solids, they may be purified by recrystallization or trituration.

Due to their excellent activity, the compounds of the present invention may be used for controlling invertebrate pests.

Accordingly, the present invention also provides a method for controlling invertebrate pests which method comprises treating the pests, their food supply, their habitat or their breeding ground or a cultivated plant, plant propagation materials (such as seed), soil, area, material or environment in which the pests are growing or may grow, or the materials, cultivated plants, plant propagation materials (such as seed), soils, surfaces or spaces to be protected from pest attack or infestation with a pesticidally effective amount of a compound of the present invention or a composition as defined above. The invention also relates to the use of a compound of the invention, of a stereoisomer and/or of an agriculturally or veterinarily acceptable salt thereof for combating invertebrate pests Preferably, the method of the invention serves for protecting plant propagation material (such as seed) and the plant which grows therefrom from invertebrate pest attack or infestation and comprises treating the plant propagation material (such as seed) with a pesticidally effective amount of a compound of the present invention as defined above or with a pesticidally effective amount of an agricultural composition as defined above and below. The method of the invention is not limited to the protection of the "substrate" (plant, plant propagation materials, soil material etc.) which has been treated according to the invention, but also has a preventive effect, thus, for example, according protection to a plant which grows from a treated plant propagation materials (such as seed), the plant itself not having been treated.

Alternatively preferably, the method of the invention serves for protecting plants from attack or infestation by invertebrate pests, which method comprises treating the plants with a pesticidally effective amount of at least one compound of the invention, a stereoisomer thereof and/or at least one agriculturally acceptable salt thereof.

In the sense of the present invention, "invertebrate pests" are preferably selected from arthropods and nematodes, more preferably from harmful insects, arachnids and nematodes, and even more preferably from insects, acarids and nematodes. In the sense of the present invention, "invertebrate pests" are most preferably insects.

The invention further provides an agricultural composition for combating invertebrate pests, which comprises such an amount of at least one compound according to the invention and at least one inert liquid and/or solid agronomically acceptable carrier that has a pesticidal action and, if desired, at least one surfactant.

Such a composition may comprise a single active compound of the present invention or a mixture of several active compounds of the present invention. The composition according to the present invention may comprise an individual isomer or mixtures of isomers or a salt as well as individual tautomers or mixtures of tautomers.

The compounds of the present invention, including their salts, stereoisomers and tautomers, are in particular suitable for efficiently controlling arthropodal pests such as arachnids, myriapedes and insects as well as nematodes. They are especially suitable for efficiently combating or controlling the following pests:
insects from the order of the lepidopterans (Lepidoptera), for example *Acronicta major, Adoxophyes orana, Aedia leucomelas, Agrotis* spp. such as *Agrotis fucosa, Agrotis segetum, Agrotis ipsilon; Alabama argillacea, Anticarsia gemmatalis, Anticarsia* spp., *Argyresthia conjugella, Autographa gamma, Barathra brassicae, Bucculatrix thurberiella, Bupalus piniarius, Cacoecia murinana, Cacoecia podana, Capua reticulana, Carpocapsa pomonella, Cheimatobia brumata, Chilo* spp. such as *Chilo suppressalis; Choristoneura fumiferana, Choristoneura occidentalis, Cirphis unipuncta, Clysia ambiguella, Cnaphalocerus* spp., *Cydia pomonella, Dendrolimus pini, Diaphania nitidalis, Diatraea grandiosella, Earias insulana, Elasmopalpus lignosellus, Ephestia cautella, Ephestia kuehniella, Eupoecilia ambiguella, Euproctis chrysorrhoea, Euxoa* spp., *Evetria bouliana, Feltia* spp. such as *Feltia subterranean; Galleria mellonella, Grapholitha funebrana, Grapholitha molesta, Helicoverpa* spp. such as *Helicoverpa armigera, Helicoverpa zea; Heliothis* spp. such as *Heliothis armigera, Heliothis virescens, Heliothis zea; Hellula undalis, Hibernia defoliaria, Hofmannophila pseudospretella, Homona magnanima, Hyphantria cunea, Hyponomeuta padella, Hyponomeuta malinellus, Keiferia lycopersicella, Lambdina fiscellaria, Laphygma* spp. such as *Laphygma exigua; Leucoptera coffeella, Leucoptera scitella, Lithocolletis blancardella, Lithophane antennata, Lobesia botrana, Loxagrotis albicosta, Loxostege sticticalis, Lymantria* spp. such as *Lymantria dispar, Lymantria monacha; Lyonetia clerkella, Malacosoma neustria, Mamestra* spp. such as *Mamestra brassicae; Mocis repanda, Mythimna separata, Orgyia pseudotsugata, Oria* spp., *Ostrinia* spp. such as *Ostrinia nubilalis; Oulema oryzae, Panolis flammea, Pectinophora* spp. such as *Pectinophora gossypiella; Peridroma saucia, Phalera bucephala, Phthorimaea* spp. such as *Phthorimaea operculella; Phyllocnistis citrella, Pieris* spp. such as *Pieris brassicae, Pieris rapae; Plathypena scabra, Plutella maculipennis, Plutella xylostella, Prodenia* spp., *Pseudaletia* spp., *Pseudoplusia includens, Pyrausta nubilalis, Rhyacionia frustrana, Scrobipalpula absoluta, Sitotroga cerealella, Sparganothis pilleriana, Spodoptera* spp. such as *Spodoptera frugiperda, Spodoptera littoralis, Spodoptera litura; Thaumatopoea pityocampa, Thermesia gemmatalis, Tinea pellionella, Tineola bisselliella, Tortrix viridana, Trichoplusia* spp. such as *Trichoplusia ni; Tuta absoluta*, and *Zeiraphera canadensis*, beetles (Coleoptera), for example *Acanthoscehdes obtectus, Adoretus* spp., *Agelastica alni, Agrilus sinuatus, Agriotes* spp. such as *Agriotes fuscicollis, Agriotes lineatus, Agriotes obscurus; Amphimallus solstitialis, Anisandrus dispar, Anobium punctatum, Anomala rufocuprea, Anoplophora* spp. such as *Anoplophora glabripennis; Anthonomus* spp. such as *Anthonomus grandis, Anthonomus pomorum; Anthrenus* spp., *Aphthona euphoridae, Apogonia* spp., *Athous haemorrhoidalis, Atomaria* spp. such as *Atomaria linearis; Attagenus* spp., *Aulacophora femoralis, Blastophagus piniperda, Blitophaga undata, Bruchidius obtectus, Bruchus* spp. such as *Bruchus lentis, Bruchus pisorum, Bruchus rufimanus; Byctiscus betulae, Callosobruchus chinensis, Cassida nebulosa, Cerotoma trifurcata, Cetonia aurata, Ceuthorhynchus* spp. such as *Ceuthorrhynchus assimilis, Ceuthorrhynchus napi; Chaetocnema tibialis, Cleonus mendicus, Conoderus* spp. such as *Conoderus vespertinus; Cosmopolites* spp., *Costelytra zea-landica, Crioceris asparagi, Cryptorhynchus lapathi, Ctenicera* ssp. such as *Ctenicera destructor; Curculio* spp., *Dectes texanus, Dermestes* spp., *Diabrotica* spp. such as *Diabrotica 12-punctata Diabrotica speciosa, Diabrotica longicornis, Diabrotica semi-punctata, Diabrotica virgifera; Epilachna* spp. such as *Epilachna varivestis, Epilachna vigintioctomaculata; Epitrix* spp. such as *Epitrix hirtipennis; Eutinobothrus brasiliensis, Faustinus cubae, Gibbium psylloides, Heteronychus arator, Hylamorpha elegans, Hylobius abietis, Hylotrupes bajulus, Hypera brunneipennis, Hypera postica, Hypothenemus* spp., *Ips typographus, Lachnosterna consanguinea, Lema bilineata, Lema melanopus, Leptinotarsa* spp. such as *Leptinotarsa decemlineata; Limonius californicus, Lissorhoptrus oryzophilus, Lissorhoptrus oryzophilus, Lixus* spp., *Lyctus* spp. such as *Lyctus bruneus; Melanotus communis, Meligethes* spp. such as *Meligethes aeneus; Melolontha hippocastani, Melolontha melolontha, Migdolus* spp., *Monochamus* spp. such as *Monochamus alternatus; Naupactus xanthographus, Niptus hololeucus, Oryctes rhinoceros, Oryzaephilus surinamensis, Otiorrhynchus sulcatus, Otiorrhynchus ovatus, Otiorrhynchus sulcatus, Oulema oryzae, Oxycetonia jucunda, Phaedon cochleariae, Phyllobius pyri, Phyllopertha horticola, Phyllophaga* spp., *Phyllotreta* spp. such as *Phyllotreta chrysocephala, Phyllotreta nemorum, Phyllotreta striolata; Phyllophaga* spp., *Phyllopertha horticola, Popillia japonica, Premnotrypes* spp., *Psylliodes chrysocephala, Ptinus* spp., *Rhizobius ventralis, Rhizopertha dominica, Sitona lineatus, Sitophilus* spp. such as *Sitophilus granaria, Sitophilus zeamais; Sphenophorus* spp. such as *Sphenophorus levis; Sternechus* spp. such as *Sternechus subsignatus; Symphyletes* spp., *Tenebrio molitor, Tribolium* spp. such as *Tribolium castaneum; Trogoderma* spp., *Tychius* spp., *Xylotrechus* spp., and *Zabrus* spp. such as *Zabrus tenebrioides*, flies, mosquitoes (Diptera), e.g. *Aedes* spp. such as *Aedes aegypti, Aedes albopictus, Aedes vexans; Anastrepha ludens, Anopheles* spp. such as *Anopheles albimanus, Anopheles crucians, Anopheles freeborni, Anopheles gambiae, Anopheles leucosphyrus, Anopheles maculipennis, Anopheles minimus, Anopheles quadrimaculatus, Anopheles sinensis; Bibio hortulanus, Calliphora erythrocephala, Calliphora vicina, Cerafitis capitata, Ceratitis capitata, Chrysomyia* spp. such as *Chrysomya bezziana, Chrysomya hominivorax, Chrysomya macellaria; Chrysops atlanticus, Chrysops discalis, Chrysops silacea, Cochliomyia* spp. such as *Cochliomyia hominivorax; Contarinia* spp. such as *Contarinia sorghicola; Cordylobia anthropophaga, Culex* spp. such as *Culex nigripalpus, Culex pipiens, Culex quinquefasciatus, Culex tarsalis, Culex tritaeniorhynchus; Culicoides furens, Culiseta inornata, Culiseta melanura, Cuterebra* spp., *Dacus cucurbitae, Dacus oleae, Dasineura brassicae, Delia* spp. such as *Delia antique, Delia coarctata, Delia platura, Delia radicum; Dermatobia hominis, Drosophila* spp., *Fannia* spp. such as *Fannia canicularis; Gastraphilus* spp. such as *Gasterophilus intestinalis; Geomyza Tripunctata, Glossina fuscipes, Glossina morsitans, Glossina palpalis, Glossina tachinoides, Haematobia irritans, Haplodiplosis equestris, Hippelates* spp., *Hylemyia* spp. such as *Hylemyia platura; Hypoderma* spp. such as *Hypoderma lineata; Hyppobosca* spp., *Leptoconops torrens, Liriomyza* spp. such as *Liriomyza sativae, Liriomyza trifolii; Lucilia* spp. such as *Lucilia caprina, Lucilia cuprina, Lucilia sericata; Lycoria pectoralis, Mansonia titillanus, Mayetiola* spp. such as *Mayetiola destructor; Musca* spp. such as *Musca autumnalis, Musca domestica; Muscina stabulans, Oestrus* spp. such as *Oestrus ovis; Opomyza florum, Oscinella* spp. such as *Oscinella frit; Pegomya hysocyami, Phlebotomus argentipes, Phorbia* spp. such as *Phorbia antiqua, Phorbia brassicae, Phorbia coarctata; Prosimulium mixtum, Psila rosae, Psorophora columbiae, Psorophora discolor, Rhagoletis cerasi, Rhagoletis pomonella, Sarcophaga* spp. such as *Sarcophaga haemorrhoidalis; Simulium vittatum, Stomoxys* spp. such as *Stomoxys calcitrans; Tabanus* spp. such as *Tabanus atratus, Tabanus bovinus, Tabanus lineola, Tabanus similis; Tannia* spp., *Tipula oleracea, Tipula paludosa,* and *Wohlfahrtia* spp., thrips (Thysanoptera), e.g. *Baliothrips biformis, Dichromothrips corbetti, Dichromothrips* ssp., *Enneothrips flavens, Frankliniella* spp. such as *Frankliniella fusca, Frankliniella occidentalis, Frankliniella tritici; Heliothrips* spp., *Hercinothrips femoralis, Kakothrips* spp., *Rhipiphorothrips cruentatus, Scirtothrips* spp. such as *Scirtothrips citri; Taeniothrips cardamoni, Thrips* spp. such as *Thrips oryzae, Thrips palmi, Thrips tabaci*;

termites (Isoptera), e.g. *Calotermes flavicollis, Coptotermes formosanus, Heterotermes aureus, Heterotermes longiceps, Heterotermes tenuis, Leucotermes flavipes, Odontotermes* spp., *Reticulitermes* spp. such as *Reticulitermes speratus, Reticulitermes flavipes, Reticulitermes grassei, Reticulitermes lucifugus, Reticulitermes santonensis, Reticulitermes virginicus; Termes natalensis*, cockroaches (Blattaria—Blattodea), e.g. *Acheta domesticus, Blatta orientalis, Blattella asahinae, Blattella germanica, Gryllotalpa* spp., *Leucophaea maderae, Locusta* spp., *Melanoplus* spp., *Periplaneta americana, Periplaneta australasiae, Periplaneta brunnea, Periplaneta fuligginosa, Periplaneta japonica*, bugs, aphids, leafhoppers, whiteflies, scale insects, cicadas (Hemiptera), e.g. *Acrosternum* spp. such as *Acrosternum hilare; Acyrthosipon* spp. such as *Acyrthosiphon onobrychis, Acyrthosiphon pisum; Adelges laricis, Aeneolamia* spp., *Agonoscena* spp., *Aleurodes* spp., *Aleurolobus barodensis, Aleurothrixus* spp., *Amrasca* spp., *Anasa tristis, Antestiopsis* spp., *Anuraphis cardui, Aonidiella* spp., *Aphanostigma piri, Aphidula nasturtii, Aphis* spp. such as *Aphis fabae, Aphis forbesi, Aphis gossypii, Aphis grossulariae, Aphis pomi, Aphis sambuci, Aphis schneideri, Aphis spiraecola; Arboridia apicalis, Arilus critatus, Aspidiella* spp., *Aspidiotus* spp., *Atanus* spp., *Aulacorthum solani, Bemisia* spp. such as *Bemisia argentifolii, Bemisia tabaci; Blissus* spp. such as *Blissus leucopterus; Brachycaudus cardui, Brachycaudus helichrysi, Brachycaudus persicae, Brachycaudus prunicola, Brachycolus* spp., *Brevicoryne brassicae, Calligypona marginate, Calocoris* spp., *Campylomma livida, Capitophorus horni, Carneocephala fulgida, Cavelerius* spp., *Ceraplastes* spp., *Ceratovacuna lanigera, Cercopidae, Cerosipha gossypii, Chaetosiphon fragaefolii, Chionaspis tegalensis, Chlorita onukii, Chromaphis juglandicola, Chrysomphalus ficus, Cicadulina mbila, Cimex* spp. such as *Cimex hemipterus, Cimex lectularius; Coccomytilus halli, Coccus* spp., *Creontiades dilutus, Cryptomyzus ribis, Cryptomyzus ribis, Cyrtopeltis notatus, Dalbulus* spp., *Dasynus piperis, Dialeurades* spp., *Diaphorina* spp., *Diaspis* spp., *Dichelops furcatus, Diconocoris hewetti, Doralis* spp., *Dreyfusia nordmannianae, Dreyfusia piceae, Drosicha* spp., *Dysaphis* spp. such as *Dysaphis plantaginea, Dysaphis pyri, Dysaphis radicula; Dysaulacorthum pseudosolani, Dysdercus* spp. such as *Dysdercus cingulatus, Dysdercus intermedius; Dysmicoccus* spp., *Empoasca* spp. such as *Empoasca fabae, Empoasca solana; Eriosoma* spp., *Erythroneura* spp., *Eurygaster* spp. such as *Eurygaster integriceps; Euscelis bilobatus, Euschistus* spp. such as *Euschistuos heros, Euschistus impictiventris, Euschistus servus; Geococcus coffeae, Halyomorpha* spp. such as *Halyomorpha halys; Heliopeltis* spp., *Homalodisca coagulata, Horcias nobilellus, Hyalopterus pruni, Hyperomyzus lactucae, Icerya* spp., *Idiocerus* spp., *Idioscopus* spp., *Laodelphax striatellus, Lecanium* spp., *Lepidosaphes* spp., *Leptocorisa* spp., *Leptoglossus phyllopus, Lipaphis erysimi, Lygus* spp. such as *Lygus hesperus, Lygus lineolaris, Lygus*

*pratensis; Macropes excavatus, Macrosiphum* spp. such as *Macrosiphum rosae, Macrosiphum avenae, Macrosiphum euphorbiae; Mahanarva fimbriolata, Megacopta cribraria, Megoura viciae, Melanaphis pyrarius, Melanaphis sacchari, Metcafiella* spp., *Metopolophium dirhodum, Miridae* spp., *Monellia costalis, Monelliopsis pecanis, Myzus* spp. such as *Myzus ascalonicus, Myzus cerasi, Myzus persicae, Myzus varians; Nasonovia ribis-nigri, Nephotettix* spp. such as *Nephotettix malayanus, Nephotettix nigropictus, Nephotettix parvus, Nephotettix virescens; Nezara* spp. such as *Nezara viridula; Nilaparvata lugens, Oebalus* spp., *Oncometopia* spp., *Orthezia praelonga, Parabemisia myricae, Paratrioza* spp., *Parlatoria* spp., *Pemphigus* spp. such as *Pemphigus bursarius; Pentomidae, Peregrinus maidis, Perkinsiella saccharicida, Phenacoccus* spp., *Phloeomyzus passerinii, Phorodon humuli, Phylloxera* spp., *Piesma quadrata, Piezodorus* spp. such as *Piezodorus guildinii, Pinnaspis aspidistrae, Planococcus* spp., *Protopulvinaria pyriformis, Psallus seriatus, Pseudacysta persea, Pseudaulacaspis pentagona, Pseudococcus* spp. such as *Pseudococcus comstocki; Psylla* spp. such as *Psylla mall, Psylla piri; Pteromalus* spp., *Pyrilla* spp., *Quadraspidiotus* spp., *Quesada gigas, Rastrococcus* spp., *Reduvius senilis, Rhodnius* spp., *Rhopalomyzus ascalonicus, Rhopalosiphum* spp. such as *Rhopalosiphum pseudobrassicas, Rhopalosiphum insertum, Rhopalosiphum maidis, Rhopalosiphum padi; Sagatodes* spp., *Sahlbergella singularis, Saissetia* spp., *Sappaphis mala, Sappaphis mali, Scaphoides titanus, Schizaphis graminum, Schizoneura lanuginosa, Scotinophora* spp., *Selenaspidus articulatus, Sitobion avenae, Sogata* spp., *Sogatella furcifera, Solubea insularis, Stephanitis nashi, Stictocephala festina, Tenalaphara malayensis, Thyanta* spp. such as *Thyanta perditor; Tibraca* spp., *Tinocallis caryaefoliae, Tomaspis* spp., *Toxoptera* spp. such as *Toxoptera aurantii; Trialeurodes* spp. such as *Trialeurodes vaporariorum; Triatoma* spp., *Trioza* spp., *Typhlocyba* spp., *Unaspis* spp. such as *Unaspis yanonensis; and Viteus vitifolii,* ants, bees, wasps, sawflies (Hymenoptera), e.g. *Athalia rosae, Atta capiguara, Atta cephalotes, Atta cephalotes, Atta laevigata, Atta robusta, Atta sexdens, Atta texana, Bombus* spp., *Camponotus floridanus, Crematogaster* spp., *Dasymutilla occidentalis*, Diprion spp., *Dolichovespula maculata, Hoplocampa* spp. such as *Hoplocampa minuta, Hoplocampa testudinea; Lasius* spp. such as *Lasius niger, Linepithema humile, Monomorium pharaonis, Paravespula germanica, Paravespula pennsylvanica, Paravespula vulgaris, Pheidole megacephala, Pogonomyrmex barbatus, Pogonomyrmex californicus, Polistes rubiginosa, Solenopsis geminata, Solenopsis invicta, Solenopsis richteri, Solenopsis xyloni, Vespa* spp. such as *Vespa crabro*, and *Vespula squamosa,* crickets, grasshoppers, locusts (Orthoptera), e.g. *Acheta domestica, Calliptamus italicus, Chortoicetes terminifera, Dociostaurus maroccanus, Gryllotalpa africana, Gryllotalpa gryllotalpa, Hieroglyphus daganensis, Kraussaria angulifera, Locusta migratoria, Locustana pardalina, Melanoplus bivittatus, Melanoplus femurrubrum, Melanoplus mexicanus, Melanoplus sanguinipes, Melanoplus spretus, Nomadacris septemfasciata, Oedaleus senegalensis, Schistocerca americana, Schistocerca gregaria, Tachycines asynamorus*, and *Zonozerus variegatus,* arachnids (Arachnida), such as acari, e.g. of the families Argasidae, Ixodidae and Sarcoptidae, such as *Amblyomma* spp. (e.g. *Amblyomma americanum, Amblyomma variegatum, Amblyomma maculatum*), *Argas* spp. (e.g. *Argas persicus*), *Boophilus* spp. (e.g. *Boophilus annulatus, Boophilus decoloratus, Boophilus microplus*), *Dermacentor silvarum,* *Dermacentor andersoni, Dermacentor variabilis, Hyalomma* spp. (e.g. *Hyalomma truncatum*), *Ixodes* spp. (e.g. *Ixodes ricinus, Ixodes rubicundus, Ixodes scapularis, Ixodes holocyclus, Ixodes pacificus*), *Ornithodorus* spp. (e.g. *Ornithodorus moubata, Ornithodorus hermsi, Ornithodorus turicata*), *Ornithonyssus bacoti, Otobius megnini, Dermanyssus gallinae, Psoroptes* spp. (e.g. *Psoroptes ovis*), *Rhipicephalus* spp. (e.g. *Rhipicephalus sanguineus, Rhipicephalus appendiculatus, Rhipicephalus evertsi*), *Rhizoglyphus* spp., *Sarcoptes* spp. (e.g. *Sarcoptes scabiei*), and *Eriophyidae* spp. such as *Acaria sheldoni, Aculops* spp. (e.g. *Aculops pelekassi*) *Aculus* spp. (e.g. *Aculus schlechtendali*), *Epitrimerus pyri, Phyllocoptruta oleivora* and *Eriophyes* spp. (e.g. *Eriophyes sheldoni*); *Tarsonemidae* spp. such as *Hemitarsonemus* spp., *Phytonemus pallidus* and *Polyphagotarsonemus latus, Stenotarsonemus* spp.; *Tenuipalpidae* spp. such as *Brevipalpus* spp. (e.g. *Brevipalpus phoenicis*); *Tetranychidae* spp. such as *Eotetranychus* spp., *Eutetranychus* spp., *Oligonychus* spp., *Tetranychus cinnabarinus, Tetranychus kanzawai, Tetranychus pacificus, Tetranychus telarius* and *Tetranychus urticae; Bryobia praetiosa, Panonychus* spp. (e.g. *Panonychus ulmi, Panonychus citri*), *Metatetranychus* spp. and *Oligonychus* spp. (e.g. *Oligonychus pratensis*), *Vasates lycopersici; Araneida*, e.g. *Latrodectus mactans*, and *Loxosceles reclusa*. And *Acarus siro, Chorioptes* spp., *Scorpio maurus* fleas (Siphonaptera), e.g. *Ceratophyllus* spp., *Ctenocephalides felis, Ctenocephalides canis, Xenopsylla cheopis, Pulex irritans, Tunga penetrans*, and *Nosopsyllus fasciatus,* silverfish, firebrat (Thysanura), e.g. *Lepisma saccharina* and *Thermobia domestica,* centipedes (Chilopoda), e.g. *Geophilus* spp., *Scutigera* spp. such as *Scutigera coleoptrata;* millipedes (Diplopoda), e.g. *Blaniulus guttulatus, Narceus* spp.,

Earwigs (Dermaptera), e.g. *forficula auricularia,* lice (Phthiraptera), e.g. *Damalinia* spp., *Pediculus* spp. such as *Pediculus humanus capitis, Pediculus humanus corporis; Pthirus pubis, Haematopinus* spp. such as *Haematopinus eurysternus, Haematopinus suis; Linognathus* spp. such as *Linognathus vituli; Bovicola bovis, Menopon gallinae, Menacanthus stramineus* and *Solenopotes capillatus, Trichodectes* spp., springtails (Collembola), e.g. *Onychiurus* ssp. such as *Onychiurus armatus,*

They are also suitable for controlling nematodes: plant parasitic nematodes such as root knot nematodes, *Meloidogyne hapla, Meloidogyne incognita, Meloidogyne javanica*, and other *Meloidogyne* species; cyst-forming nematodes, *Globodera rostochiensis* and other *Globodera* species; *Heterodera avenae, Heterodera glycines, Heterodera schachtii, Heterodera trifolii*, and other *Heterodera* species; Seed gall nematodes, *Anguina* species; Stem and foliar nematodes, *Aphelenchoides* species such as *Aphelenchoides besseyi*; Sting nematodes, *Belonolaimus longicaudatus* and other *Belonolaimus* species; Pine nematodes, *Bursaphelenchus lignicolus Mamiya* et *Kiyohara, Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes,

*Nacobbus* species; Needle nematodes, *Longidorus elongatus* and other *Longidorus* species; Lesion nematodes, *Pratylenchus brachyurus, Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus, Rotylenchus reniformis* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species such as *Tylenchulus semi-penetrans*; Dagger nematodes, *Xiphinema* species; and other plant parasitic nematode species.

Examples of further pest species which may be controlled by compounds of formula (I) include: from the class of the Bivalva, for example, *Dreissena* spp.; from the class of the Gastropoda, for example, *Anion* spp., *Biomphalaria* spp., *Bulinus* spp., *Deroceras* spp., *Galba* spp., *Lymnaea* spp., *Oncomelania* spp., *Succinea* spp.; from the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp., *Dictyocaulus filaria, Diphyllobothrium latum, Dracunculus medinensis, Echinococcus granulosus, Echinococcus multilocularis, Enterobius vermicularis, Faciola* spp., *Haemonchus* spp. such as *Haemonchus contortus; Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercora lis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichiura, Wuchereria bancrofti*; from the order of the Isopoda, for example, *Armadillidium vulgare, Oniscus asellus, Porcellio scaber*; from the order of the Symphyla, for example, *Scutigerella immaculata;*

Further examples of pest species which may be controlled by compounds of formula (I) include: *Anisoplia austriaca, Apamea* spp., *Austroasca viridigrisea, Baliothrips biformis, Caenorhabditis elegans, Cephus* spp., *Ceutorhynchus napi, Chaetocnema aridula, Chilo auricilius, Chilo indicus, Chilo polychrysus, Chortiocetes terminifera, Cnaphalocroci medinalis, Cnaphalocrosis* spp., *Colias eurytheme, Collops* spp., *Cornitermes cumulans, Creontiades* spp., *Cyclocephala* spp., *Dalbulus maidis, Deraceras reticulaturn, Diatrea saccharalis, Dichelops furcatus, Dicladispa armigera, Diloboderus* spp. such as *Diloboderus abderus; Edessa* spp., *Epinotia* spp., *Formicidae, Geocoris* spp., *Globitermes sulfureus, Gryllotalpidae, Halotydeus destructor, Hipnodes bicolor, Hydrellia philippina, Julus* spp., *Laodelphax* spp., *Leptocorsia acuta, Leptocorsia oratorius, Liogenys fuscus, Lucillia* spp., *Lyogenys fuscus, Mahanarva* spp., *Maladera matrida, Marasmia* spp., *Mastotermes* spp., *Mealybugs, Megascelis* ssp, *Metamasius hemipterus, Microtheca* spp., *Mocis latipes, Murgantia* spp., *Mythemina separata, Neocapritermes opacus, Neocapritermes parvus, Neomegalotomus* spp., *Neotermes* spp., *Nymphula depunctalis, Oebalus pugnax, Orseolia* spp. such as *Orseolia oryzae; Oxycaraenus hyalinipennis, Plusia* spp., *Pomacea canaliculata, Procornitermes* ssp, *Procornitermes triacifer, Psylloides* spp., *Rachiplusia* spp., *Rhodopholus* spp., *Scaptocoris castanea, Scaptocoris* spp., *Scirpophaga* spp. such as *Scirpophaga incertulas, Scirpophaga innotata; Scotinophara* spp. such as *Scotinophara coarctata; Sesamia* spp. such as *Sesamia inferens, Sogaella frucifera, Solenapsis geminata, Spississtilus* spp., Stalk borer, *Stenchaetothrips biformis, Steneotarsonemus spinki, Sylepta derogata, Telehin licus, Trichostrongylus* spp.

The compounds of the present invention, including their salts, stereoisomers and tautomers, are particularly useful for controlling insects, preferably sucking or piercing and chewing and biting insects such as insects from the genera *Lepidoptera, Coleoptera* and *Hemiptera*, in particular *Lepidoptera, Coleoptera* and true bugs.

The compounds of the present invention, including their salts, stereoisomers and tautomers, are moreover useful for controlling insects of the orders Thysanoptera, Diptera (especially flies, mosquitos), Hymenoptera (especially ants) and Isoptera (especially termites.

The compounds of the present invention, including their salts, stereoisomers and tautomers, are particularly useful for controlling insects of the orders Lepidoptera and Coleoptera.

The invention also relates to agrochemical compositions comprising an auxiliary and at least one compound I according to the invention.

An agrochemical composition comprises a pesticidally effective amount of a compound I. The term "effective amount" denotes an amount of the composition or of the compounds I, which is sufficient for controlling harmful fungi on cultivated plants or in the protection of materials and which does not result in a substantial damage to the treated plants. Such an amount can vary in a broad range and is dependent on various factors, such as the species to be controlled, the treated cultivated plant or material, the climatic conditions and the specific compound I used.

The compounds I, their N-oxides and salts can be converted into customary types of agrochemical compositions, e.g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Monograph No. 2, 6th Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e.g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emusifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinyl-alcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compound I on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for composition types and their preparation are:
i) Water-soluble concentrates (SL, LS)
10-60 wt % of a compound I according to the invention and 5-15 wt % wetting agent (e.g. alcohol alkoxylates) are dissolved in water and/or in a water-soluble solvent (e.g. alcohols) ad 100 wt %. The active substance dissolves upon dilution with water.
ii) Dispersible concentrates (DC)
5-25 wt % of a compound I according to the invention and 1-10 wt % dispersant (e.g. polyvinylpyrrolidone) are dissolved in organic solvent (e.g. cyclohexanone) ad 100 wt %. Dilution with water gives a dispersion.
iii) Emulsifiable concentrates (EC)
15-70 wt % of a compound I according to the invention and 5-10 wt % emulsifiers (e.g. calcium dodecylbenzenesulfonate and castor oil ethoxylate) are dissolved in water-insoluble organic solvent (e.g. aromatic hydrocarbon) ad 100 wt %. Dilution with water gives an emulsion.
iv) Emulsions (EW, EO, ES)
5-40 wt % of a compound I according to the invention and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into water ad 100 wt % by means of an emulsifying machine and made into a homogeneous emulsion. Dilution with water gives an emulsion.
v) Suspensions (SC, OD, FS)
In an agitated ball mill, 20-60 wt % of a compound I according to the invention are comminuted with addition of 2-10 wt % dispersants and wetting agents (e.g. sodium lignosulfonate and alcohol ethoxylate), 0.1-2 wt % thickener (e.g. xanthan gum) and water ad 100 wt % to give a fine active substance suspension. Dilution with water gives a stable suspension of the active substance. For FS type composition up to 40 wt % binder (e.g. polyvinylalcohol) is added.
vi) Water-dispersible granules and water-soluble granules (WG, SG)
50-80 wt % of a compound I according to the invention are ground finely with addition of dispersants and wetting agents (e.g. sodium lignosulfonate and alcohol ethoxylate) ad 100 wt % and prepared as water-dispersible or water-soluble granules by means of technical appliances (e.g.

extrusion, spray tower, fluidized bed). Dilution with water gives a stable dispersion or solution of the active substance.

vii) Water-dispersible powders and water-soluble powders (WP, SP, WS)

50-80 wt % of a compound I according to the invention are ground in a rotor-stator mill with addition of 1-5 wt % dispersants (e.g. sodium lignosulfonate), 1-3 wt % wetting agents (e.g. alcohol ethoxylate) and solid carrier (e.g. silica gel) ad 100 wt %. Dilution with water gives a stable dispersion or solution of the active substance.

viii) Gel (GW, GF)

In an agitated ball mill, 5-25 wt % of a compound I according to the invention are comminuted with addition of 3-10 wt % dispersants (e.g. sodium lignosulfonate), 1-5 wt % thickener (e.g. carboxymethylcellulose) and water ad 100 wt % to give a fine suspension of the active substance. Dilution with water gives a stable suspension of the active substance.

iv) Microemulsion (ME)

5-20 wt % of a compound I according to the invention are added to 5-30 wt % organic solvent blend (e.g. fatty acid dimethylamide and cyclohexanone), 10-25 wt % surfactant blend (e.g. alkohol ethoxylate and arylphenol ethoxylate), and water ad 100%. This mixture is stirred for 1 h to produce spontaneously a thermodynamically stable microemulsion.

iv) Microcapsules (CS)

An oil phase comprising 5-50 wt % of a compound I according to the invention, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of a compound I according to the invention, 0-40 wt % water insoluble organic solvent (e.g. aromatic hydrocarbon), and an isocyanate monomer (e.g. diphenylmethene-4,4'-diisocyanatae) are dispersed into an aqueous solution of a protective colloid (e.g. polyvinyl alcohol). The addition of a polyamine (e.g. hexamethylenediamine) results in the formation of a polyurea microcapsules. The monomers amount to 1-10 wt %. The wt % relate to the total CS composition.

ix) Dustable powders (DP, DS)

1-10 wt % of a compound I according to the invention are ground finely and mixed intimately with solid carrier (e.g. finely divided kaolin) ad 100 wt %.

x) Granules (GR, FG)

0.5-30 wt % of a compound I according to the invention is ground finely and associated with solid carrier (e.g. silicate) ad 100 wt %. Granulation is achieved by extrusion, spray-drying or the fluidized bed.

xi) Ultra-low volume liquids (UL)

1-50 wt % of a compound I according to the invention are dissolved in organic solvent (e.g. aromatic hydrocarbon) ad 100 wt %.

The compositions types i) to xi) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, and in particular between 0.5 and 75%, by weight of active substance. The active substances are employed in a purity of from 90% to 100%, preferably from 95% to 100% (according to NMR spectrum).

Solutions for seed treatment (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The compositions in question give, after two-to-tenfold dilution, active substance concentrations of from 0.01 to 60% by weight, preferably from 0.1 to 40% by weight, in the ready-to-use preparations. Application can be carried out before or during sowing. Methods for applying compound I and compositions thereof, respectively, on to plant propagation material, especially seeds include dressing, coating, pelleting, dusting, soaking and in-furrow application methods of the propagation material. Preferably, compound I or the compositions thereof, respectively, are applied on to the plant propagation material by a method such that germination is not induced, e.g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, and in particular from 0.1 to 0.75 kg per ha.

In treatment of plant propagation materials such as seeds, e.g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seeds) are generally required. When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and further pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank and further auxiliaries may be added, if appropriate. In a further embodiment, either individual components of the composition according to the invention or partially premixed components, e.g. components comprising compounds I and/or active substances from the groups M) or F) (see below), may be mixed by the user in a spray tank and further auxiliaries and additives may be added, if appropriate.

In a further embodiment, either individual components of the composition according to the invention or partially premixed components, e. g. components comprising compounds I and/or active substances from the groups M.1 to M.UN.X or F.I to F.XII, can be applied jointly (e.g. after tank mix) or consecutively.

The following list M of pesticides, grouped according the Mode of Action Classification of the Insecticide Resistance Action Committee (IRAC), together with which the compounds according to the invention can be used and with which potential synergistic effects might be produced, is intended to illustrate the possible combinations, but not to impose any limitation:

M.1 Acetylcholine esterase (AChE) inhibitors from the class of

M.1A carbamates, for example aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb and triazamate; or from the class of M.1B organophosphates, for example acephate, azamethiphos, azinphos-ethyl, azinphosmethyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothio-phosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon and vamidothion;

M.2. GABA-gated chloride channel antagonists such as:

M.2A cyclodiene organochlorine compounds, as for example endosulfan or chlordane; or M.2B fiproles (phenylpyrazoles), as for example ethiprole, fipronil, flufiprole, pyrafluprole and pyriprole;

M.3 Sodium channel modulators from the class of

M.3A pyrethroids, for example acrinathrin, allethrin, d-cis-trans allethrin, d-trans allethrin, bifenthrin, bioallethrin, bioallethrin S-cylclopentenyl, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zetacypermethrin, cyphenothrin, deltamethrin, empenthrin, esfenvalerate, etofenprox, fenpropathrin, fenvalerate, flucythrinate, flumethrin, tau-fluvalinate, halfenprox, imiprothrin, meperfluthrin, metofluthrin, momfluorothrin, permethrin, phenothrin, prallethrin, profluthrin, pyrethrin (pyrethrum), resmethrin, silafluofen, tefluthrin, tetramethylfluthrin, tetramethrin, tralomethrin and transfluthrin; or M.3B sodium channel modulators such as DDT or methoxychlor;

M.4 Nicotinic acetylcholine receptor agonists (nAChR) from the class of

M.4A neonicotinoids, for example acteamiprid, chlothianidin, dinotefuran, imidacloprid, nitenpyram, thiacloprid and thiamethoxam; or the compounds M.4A.1: 1-[(6-chloro-3-pyridinyl)methyl]-2,3,5,6,7,8-hexahydro-9-nitro-(5S,8R)-5,8-Epoxy-1H-imidazo[1,2-a]azepine; or M.4A.2: 1-[(6-chloro-3-pyridyl)methyl]-2-nitro-1-[(E)-pentylideneamino]guanidine; or M4.A.3: 1-[(6-chloro-3-pyridyl)methyl]-7-methyl-8-nitro-5-propoxy-3,5,6,7-tetrahydro-2H-imidazo[1,2-a]pyridine; or M.4B nicotine.

M.5 Nicotinic acetylcholine receptor allosteric activators from the class of spinosyns, for example spinosad or spinetoram;

M.6 Chloride channel activators from the class of avermectins and milbemycins, for example abamectin, emamectin benzoate, ivermectin, lepimectin or milbemectin;

M.7 Juvenile hormone mimics, such as

M.7A juvenile hormone analogues as hydroprene, kinoprene and methoprene; or others as M.7B fenoxycarb or M.7C pyriproxyfen;

M.8 miscellaneous non-specific (multi-site) inhibitors, for example

M.8A alkyl halides as methyl bromide and other alkyl halides, or

M.8B chloropicrin, or M.8C sulfuryl fluoride, or M.8D borax, or M.8E tartar emetic;

M.9 Selective homopteran feeding blockers, for example M.9B pymetrozine, or M.9C flonicamid;

M.10 Mite growth inhibitors, for example

M.10A clofentezine, hexythiazox and diflovidazin, or M.10B etoxazole;

M.11 Microbial disruptors of insect midgut membranes, for example *Bacillus thuringiensis* or *Bacillus sphaericus* and the insecticdal proteins they produce such as *Bacillus thuringiensis* subsp. *israelensis, Bacillus sphaericus, Bacillus thuringiensis* subsp. *aizawai, Bacillus thuringiensis* subsp. *kurstaki* and *Bacillus thuringiensis* subsp. *tenebrionis*, or the Bt crop proteins: Cry1Ab, Cry1Ac, Cry1Fa, Cry2Ab, mCry3A, Cry3Ab, Cry3Bb and Cry34/35Ab1;

M.12 Inhibitors of mitochondrial ATP synthase, for example M.12A diafenthiuron, or M.12B organotin miticides such as azocyclotin, cyhexatin or fenbutatin oxide, or M.12C propargite, or M.12D tetradifon;

M.13 Uncouplers of oxidative phosphorylation via disruption of the proton gradient, for example chlorfenapyr, DNOC or sulfluramid;

M.14 Nicotinic acetylcholine receptor (nAChR) channel blockers, for example nereistoxin analogues as bensultap, cartap hydrochloride, thiocyclam or thiosultap sodium;

M.15 Inhibitors of the chitin biosynthesis type 0, such as benzoylureas as for example bistrifluron, chlorfluazuron, diflubenzuron, flucycloxuron, flufenoxuron, hexaflumuron, lufenuron, novaluron, noviflumuron, teflubenzuron or triflumuron;

M.16 Inhibitors of the chitin biosynthesis type 1, as for example buprofezin;

M.17 Moulting disruptors, Dipteran, as for example cyromazine;

M.18 Ecdyson receptor agonists such as diacylhydrazines, for example methoxyfenozide, tebufenozide, halofenozide, fufenozide or chromafenozide;

M.19 Octopamin receptor agonists, as for example amitraz;

M.20 Mitochondrial complex III electron transport inhibitors, for example

M.20A hydramethylnon, or M.20B acequinocyl, or M.20C fluacrypyrim;

M.21 Mitochondrial complex I electron transport inhibitors, for example

M.21A METI acaricides and insecticides such as fenazaquin, fenpyroximate, pyrimidifen, pyridaben, tebupyrad or tolfenpyrad, or M.21B rotenone;

M.22 Voltage-dependent sodium channel blockers, for example
M.22A indoxacarb, or M.22B metaflumizone, or M.22C 1-[(E)-[2-(4-cyanophenyl)-1-[3-(trifluoromethyl)phenyl]ethylidene]amino]-3-[4-(difluoromethoxy)phenyl]urea;
M.23 Inhibitors of the of acetyl CoA carboxylase, such as Tetronic and Tetramic acid derivatives, for example spirodiclofen, spiromesifen or spirotetramat;
M.24 Mitochondrial complex IV electron transport inhibitors, for example
M.24A phosphine such as aluminium phosphide, calcium phosphide, phosphine or zinc phosphide, or M.24B cyanide.
M.25 Mitochondrial complex II electron transport inhibitors, such as beta-ketonitrile derivatives, for example cyenopyrafen or cyflumetofen;
M.28 Ryanodine receptor-modulators from the class of diamides, as for example flubendiamide, chlorantraniliprole (Rynaxypyr®), cyantraniliprole (Cyazypyr®), or the phthalamide compounds
M.28.1: (R)-3-Chlor-N1-{2-methyl-4-[1,2,2,2-tetrafluor-1-(trifluormethyl)ethyl]phenyl}-N2-(1-methyl-2-methylsulfonylethyl)phthalamid and
M.28.2: (S)-3-Chlor-N1-{2-methyl-4-[1,2,2,2-tetrafluor-1-(trifluormethyl)ethyl]phenyl}-N2-(1-methyl-2-methylsulfonylethyl)phthalamid, or the compound
M.28.3: 3-bromo-N-{2-bromo-4-chloro-6-[(1-cyclopropylethyl)carbamoyl]phenyl}-1-(3-chlorpyridin-2-yl)-1H-pyrazole-5-carboxamide (proposed ISO name: cyclaniliprole), or the compound
M.28.4: methyl-2-[3,5-dibromo-2-({[3-bromo-1-(3-chlorpyridin-2-yl)-1H-pyrazol-5-yl]carbonyl}amino)benzoyl]-1,2-dimethylhydrazinecarboxylate; or a compound selected from M.28.5a) to M.28.5l):
M.28.5a) N-[4,6-dichloro-2-[(diethyl-lambda-4-sulfanylidene)carbamoyl]-phenyl]-2-(3-chloro-2-pyridyl)-5-(trifluoromethyl)pyrazole-3-carboxamide;
M.28.5b) N-[4-chloro-2-[(diethyl-lambda-4-sulfanylidene)carbamoyl]-6-methyl-phenyl]-2-(3-chloro-2-pyridyl)-5-(trifluoromethyl)pyrazole-3-carboxamide;
M.28.5c) N-[4-chloro-2-[(di-2-propyl-lambda-4-sulfanylidene)carbamoyl]-6-methyl-phenyl]-2-(3-chloro-2-pyridyl)-5-(trifluoromethyl)pyrazole-3-carboxamide;
M.28.5d) N-[4,6-dichloro-2-[(di-2-propyl-lambda-4-sulfanylidene)carbamoyl]-phenyl]-2-(3-chloro-2-pyridyl)-5-(trifluoromethyl)pyrazole-3-carboxamide;
M.28.5e) N-[4,6-dichloro-2-[(diethyl-lambda-4-sulfanylidene)carbamoyl]-phenyl]-2-(3-chloro-2-pyridyl)-5-(difluoromethyl)pyrazole-3-carboxamide;
M.28.5f) N-[4,6-dibromo-2-[(di-2-propyl-lambda-4-sulfanylidene)carbamoyl]-phenyl]-2-(3-chloro-2-pyridyl)-5-(trifluoromethyl)pyrazole-3-carboxamide;
M.28.5g) N-[4-chloro-2-[(di-2-propyl-lambda-4-sulfanylidene)carbamoyl]-6-cyano-phenyl]-2-(3-chloro-2-pyridyl)-5-(trifluoromethyl)pyrazole-3-carboxamide;
M.28.5h) N-[4,6-dibromo-2-[(diethyl-lambda-4-sulfanylidene)carbamoyl]-phenyl]-2-(3-chloro-2-pyridyl)-5-(trifluoromethyl)pyrazole-3-carboxamide;
M.28.5i) N-[2-(5-amino-1,3,4-thiadiazol-2-yl)-4-chloro-6-methyl-phenyl]-5-bromo-2-(3-chloro-2-pyridyl)pyrazole-3-carboxamide;
M.28.5j) 5-chloro-2-(3-chloro-2-pyridyl)-N-[2,4-dichloro-6-[(1-cyano-1-methyl-ethyl)carbamoyl]phenyl]pyrazole-3-carboxamide;
M.28.5k) 5-bromo-N-[2,4-dichloro-6-(methylcarbamoyl)phenyl]-2-(3,5-dichloro-2-pyridyl)pyrazole-3-carboxamide;
M.28.5l) N-[2-(tert-butylcarbamoyl)-4-chloro-6-methylphenyl]-2-(3-chloro-2-pyridyl)-5-(fluoromethoxy)pyrazole-3-carboxamide; or a compound selected from
M.28.6 N2-(1-cyano-1-methyl-ethyl)-N1-(2,4-dimethylphenyl)-3-iodo-phthalamide; or
M.28.7 3-chloro-N2-(1-cyano-1-methyl-ethyl)-N1-(2,4-dimethylphenyl)phthalamide;
M.UN.X insecticidal active compounds of unknown or uncertain mode of action, as for example azadirachtin, amidoflumet, benzoximate, bifenazate, bromopropylate, chinomethionat, cryolite, dicofol, flufenerim, flometoquin, fluensulfone, flupyradifurone, piperonyl butoxide, pyridalyl, pyrifluquinazon, sulfoxaflor, pyflubumide or the compounds
M.UN.X.1: 4-[5-(3,5-Dichloro-phenyl)-5-trifluoromethyl-4,5-dihydro-isoxazol-3-yl]-2-methyl-N-[(2,2,2-trifluoro-ethylcarbamoyl)-methyl]-benzamide, or the compound
M.UN.X.2: cyclopropaneacetic acid, 1,1'-[(3S,4R,4aR,6S,6aS,12R,12aS,12bS)-4-[[(2-cyclopropylacetyl)oxy]methyl]-1,3,4,4a,5,6,6a,12,12a,12b-decahydro-12-hydroxy-4,6a,12b-trimethyl-11-oxo-9-(3-pyridinyl)-2H,11H-naphtho[2,1-b]pyrano[3,4-e]pyran-3,6-diyl] ester, or the compound
M.UN.X.3: 11-(4-chloro-2,6-dimethylphenyl)-12-hydroxy-1,4-dioxa-9-azadispiro[4.2.4.2]-tetradec-11-en-10-one, or the compound
M.UN.X.4: 3-(4'-fluoro-2,4-dimethylbiphenyl-3-yl)-4-hydroxy-8-oxa-1-azaspiro[4.5]dec-3-en-2-one, or the compound
M.UN.X.5: 1-[2-fluoro-4-methyl-5-[(2,2,2-trifluoroethyl)sulfinyl]phenyl]-3-(trifluoromethyl)-1H-1,2,4-triazole-5-amine, or actives on basis of *Bacillus firmus* (Votivo, 1-1582); or
M.UN.X.6; a compound selected from the group of
M.UN.X.6a) (E/Z)-N-[1-[(6-chloro-3-pyridyl)methyl]-2-pyridylidene]-2,2,2-trifluoroacetamide;
M.UN.X.6b) (E/Z)-N-[1-[(6-chloro-5-fluoro-3-pyridyl)methyl]-2-pyridylidene]-2,2,2-trifluoro-acetamide;
M.UN.X.6c) (E/Z)-2,2,2-trifluoro-N-[1-[(6-fluoro-3-pyridyl)methyl]-2-pyridylidene]acetamide;
M.UN.X.6d) (E/Z)-N-[1-[(6-bromo-3-pyridyl)methyl]-2-pyridylidene]-2,2,2-trifluoro-acetamide;
M.UN.X.6e) (E/Z)-N-[1-[1-(6-chloro-3-pyridyl)ethyl]-2-pyridylidene]-2,2,2-trifluoro-acetamide;
M.UN.X.6f) (E/Z)-N-[1-[(6-chloro-3-pyridyl)methyl]-2-pyridylidene]-2,2-difluoroacetamide;
M.UN.X.6g) (E/Z)-2-chloro-N-[1-[(6-chloro-3-pyridyl)methyl]-2-pyridylidene]-2,2-difluoroacetamide;
M.UN.X.6h) (E/Z)-N-[1-[(2-chloropyrimidin-5-yl)methyl]-2-pyridylidene]-2,2,2-trifluoroacetamide and
M.UN.X.6i) (E/Z)-N-[1-[(6-chloro-3-pyridyl)methyl]-2-pyridylidene]-2,2,3,3,3-pentafluoropropanamide); or the compounds
M.UN.X.7: 3-[3-chloro-5-(trifluoromethyl)phenyl]-4-oxo-1-(pyrimidin-5-ylmethyl)pyrido[1,2-a]pyrimidin-1-ium-2-olate; or
M.UN.X.8: 8-chloro-N-[2-chloro-5-methoxyphenyl)sulfonyl]-6-trifluoromethyl)imidazo[1,2-a]pyridine-2-carboxamide; or
M.UN.X.9: 4-[5-(3,5-dichlorophenyl)-5-(trifluoromethyl)-4H-isoxazol-3-yl]-2-methyl-N-(1-oxothietan-3-yl)benzamide; or
M.UN.X.10: 5-[3-[2,6-dichloro-4-(3,3-dichloroallyloxy)phenoxy]propoxy]-1H-pyrazole; or
M.UN.X.11: 4-[5-(3,5-dichlorophenyl)-5-(trifluoromethyl)-4H-isoxazol-3-yl]-2-methyl-N-[2-oxo-2-(2,2,2-trifluoroethylamino)ethyl]benzamide; or M.UN.X.12: 4-[5-[3-chloro-5-(trifluoromethyl)phenyl]-5-(trifluoromethyl)-4H-isoxazol-3-yl]-N-[2-oxo-2-(2,2,2-trifluoroethylamino)ethyl]naphthalene-1-carboxamide.

The commercially available compounds of the group M listed above may be found in The Pesticide Manual, 15th Edition, C. D. S. Tomlin, British Crop Protection Council (2011) among other publications.

The quinoline derivative flometoquin is shown in WO2006/013896. The aminofuranone compounds flupyradifurone is known from WO 2007/115644. The sulfoximine compound sulfoxaflor is known from WO2007/149134. The acaricide pyflubumide is known from WO2007/020986. The isoxazoline compounds have been described: M.UN.X.1 in WO2005/085216, M.UN.X.9 in WO2013/050317, M.UN.X.11 in WO2005/085216 and M.UN.X. in WO2009/002809 and in WO2011/149749. The pyripyropene derivative M.UN.X.2 has been described in WO 2006/129714. The spiroketal-substituted cyclic ketoenol derivative M.UN.X.3 is known from WO2006/089633 and the biphenyl-substituted spirocyclic ketoenol derivative M.UN.X.4 from WO2008/067911. Finally triazoylphenylsulfide like M.UN.X.5 have been described in WO2006/043635 and biological control agents on basis of *Bacillus firmus* in WO2009/124707. The neonicotinoids 4A.1 is known from WO20120/069266 and WO2011/06946, the M.4.A.2 from WO2013/003977, the M4.A.3. from WO2010/069266.

The Metaflumizone analogue M.22C is described in CN 10171577. The phthalamides M.28.1 and M.28.2 are both known from WO 2007/101540. The anthranilamide M.28.3 has been described in WO2005/077934. The hydrazide compound M.28.4 has been described in WO 2007/043677. The anthranilamides M.28.5a) to M.28.5h) can be prepared as described in WO 2007/006670, WO2013/024009 and WO2013/024010, the anthranilamide M.28.5i) is described in WO2011/085575, the M.28.5j) in WO2008/134969, the M.28.5k) in US2011/046186 and the M.28.5l) in WO2012/034403. The diamide compounds M.28.6 and M.28.7 can be found in CN102613183.

The compounds M.UN.X.6a) to M.UN.X.6i) listed in M.UN.X.6 have been described in WO2012/029672. The mesoionic antagonist compound M.UN.X.7 was described in WO2012/092115, the nematicide M.UN.X.8 in WO2013/055584 and the Pyridalyl-type analogue M.UN.X.10 in WO2010/060379.

Preferred additional pesticidally active ingredients are those selected from the IRAC group 1, the Acetylcholinesterase (AChE) inhibitors, herein from the group 1A (Carbamtes) Thiodicarb, Methomyl and Carbaryl, and from the group 1B (Organophosphates), especially Acephate, Chlorpyriphos and Dimethoate, from the group 2B, the fiproles, here especially ethiprole and fipronil, from the group 3, the pyrethroids, here especially lambda-cyhalothrin, alpha-cypermethrin or deltametrin, and from the group 4A, the neonicotinoids, here especially acetamiprid, clothianidin, dinotefuran, imidacloprid, nitenpyram, thiacloprid or thiomethoxam.

Especially combinations of compounds of the invention with fiproles, neonictinoids or pyrethroids may possibly exhibit synergistic control of stinkbugs (according to the Colby formula), in particular *Euschistus*, e.g. *Euschistus heros*.

The following list F of active substances, in conjunction with which the compounds according to the invention can be used, is intended to illustrate the possible combinations but does not limit them:

F.I) Respiration Inhibitors

F.I-1) Inhibitors of complex III at Qo site:
strobilurins: azoxystrobin, coumethoxystrobin, coumoxystrobin, dimoxystrobin, enestroburin, fluoxastrobin, kresoxim-methyl, metominostrobin, orysastrobin, picoxystrobin, pyraclostrobin, pyrametostrobin, pyraoxystrobin, pyribencarb, triclopyricarb/chlorodincarb, trifloxystrobin, 2-[2-(2,5-dimethyl-phenoxymethyl)-phenyl]-3-methoxy-acrylic acid methyl ester and 2 (2-(3-(2,6-dichlorophenyl)-1-methylallylideneaminooxymethyl)-phenyl)-2-methoxy-imino-N methyl-acetamide; oxazolidinediones and imidazolinones: famoxadone, fenamidone;

F.I-2) Inhibitors of complex II (e.g. carboxamides):
carboxanilides: benodanil, benzovindiflupyr, bixafen, boscalid, carboxin, fenfuram, fenhexamid, fluopyram, flutolanil, furametpyr, isopyrazam, isotianil, mepronil, oxycarboxin, penflufen, penthiopyrad, sedaxane, tecloftalam, thifluzamide, tiadinil, 2-amino-4 methyl-thiazole-5-carboxanilide, N-(3',4',5' trifluorobiphenyl-2 yl)-3-difluoromethyl-1-methyl-1H-pyrazole-4 carboxamide (fluxapyroxad), N-(4'-trifluoromethylthiobiphenyl-2-yl)-3 difluoromethyl-1-methyl-1H pyrazole-4-carboxamide, N-(2-(1,3,3-trimethyl-butyl)phenyl)-1,3-dimethyl-5 fluoro-1H-pyrazole-4 carboxamide, 3-(difluoromethyl)-1-methyl-N-(1,1,3-trimethylindan-4-yl)pyrazole-4-carboxamide, 3-(trifluoromethyl)-1-methyl-N-(1,1,3-trimethylindan-4-yl) pyrazole-4-carboxamide, 1,3-dimethyl-N-(1,1,3-trimethyl-indan-4-yl)pyrazole-4-carboxamide, 3-(trifluoromethyl)-1,5-dimethyl-N-(1,1,3-trimethylindan-4-yl)pyrazole-4-carboxamide, 3-(difluoromethyl)-1,5-dimethyl-N-(1,1,3-trimethylindan-4-yl)pyrazole-4-carboxamide, 1,3,5-trimethyl-N-(1,1,3-trimethylindan-4-yl)pyrazole-4-carboxamide, 3-(difluoromethyl)-1-methyl-N-(1,1,3-trimethylindan-4-yl)pyrazole-4-carboxamide, 3-(trifluoromethyl)-1-methyl-N-(1,1,3-trimethylindan-4-yl) pyrazole-4-carboxamide, 1,3-dimethyl-N-(1,1,3-trimethyl-indan-4-yl)pyrazole-4-carboxamide, 3-(trifluoromethyl)-1,5-dimethyl-N-(1,1,3-trimethylindan-4-yl)pyrazole-4-carboxamide, 3-(difluoromethyl)-1,5-dimethyl-N-(1,1,3-trimethylindan-4-yl)pyrazole-4-carboxamide, 1,3,5-trimethyl-N-(1,1,3-trimethylindan-4-yl)pyrazole-4-carboxamide;

F.I-3) Inhibitors of complex III at Qi site: cyazofamid, amisulbrom, [(3S,6S,7R,8R)-8-benzyl-3-[(3-acetoxy-4-methoxy-pyridine-2-carbonyl)amino]-6-methyl-4,9-dioxo-1,5-dioxonan-7-yl] 2-methylpropanoate, [(3S,6S,7R,8R)-8-benzyl-3-[[3-(acetoxymethoxy)-4-methoxy-pyridine-2-carbonyl]amino]-6-methyl-4,9-dioxo-1,5-dioxonan-7-yl] 2-methylpropanoate, [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl] 2-methylpropanoate, [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl] 2-methylpropanoate, 3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate;

F.I-4) Other respiration inhibitors (complex I, uncouplers) diflumetorim; (5,8-difluoroquinazolin-4-yl)-{2-[2-fluoro-4-(4-trifluoromethylpyridin-2-yloxy)-phenyl]-ethyl}-amine; tecnazen; ametoctradin; silthiofam; nitrophenyl derivates: binapacryl, dinobuton, dinocap, fluazinam, ferimzone, nitrthal-isopropyl,
and including organometal compounds: fentin salts, such as fentin-acetate, fentin chloride or fentin hydroxide;

F.II) Sterol biosynthesis inhibitors (SBI fungicides)

F.II-1) C14 demethylase inhibitors (DMI fungicides, e.g. triazoles, imidazoles) triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole, 1-[rel-(2S;3R)-3-(2-chlorophenyl)-2-(2,4-difluorophenyl)-oxiranylmethyl]-5-thiocyanato-1H[1,2,4]triazole, 2-[rel-(2S;3R)-3-(2-chlorophenyl)-2-(2,4-difluorophenyl)-oxiranylmethyl]-2H-[1,2,4]triazole-3-thiol;

imidazoles: imazalil, pefurazoate, oxpoconazole, prochloraz, triflumizole; pyrimidines, pyridines and piperazines: fenarimol, nuarimol, pyrifenox, triforine, 1-[rel-(2S;3R)-3-(2-chlorophenyl)-2-(2,4-difluorophenyl)-oxiranylmethyl]-5-thiocyanato-1H[1,2,4]triazole, 2-[rel-(2S;3R)-3-(2-chlorophenyl)-2-(2,4-difluorophenyl)-oxiranylmethyl]-2H-[1,2,4]triazole-3-thiol;

F.II-2) Delta14-reductase inhitors (Amines, e.g. morpholines, piperidines) morpholines: aldimorph, dodemorph, dodemorph-acetate, fenpropimorph, tridemorph; piperidines: fenpropidin, piperalin; spiroketalamines: spiroxamine;

F.II-3) Inhibitors of 3-keto reductase: hydroxyanilides: fenhexamid;

F.III) Nucleic acid synthesis inhibitors

F.III-1) RNA, DNA synthesis phenylamides or acyl amino acid fungicides: benalaxyl, benalaxyl-M, kiralaxyl, metalaxyl, metalaxyl-M (mefenoxam), ofurace, oxadixyl;

isoxazoles and iosothiazolones: hymexazole, octhilinone;

F.III-2) DNA topisomerase inhibitors: oxolinic acid;

F.III-3) Nucleotide metabolism (e.g. adenosin-deaminase), hydroxy (2-amino)pyrimidines: bupirimate;

F.IV) Inhibitors of cell division and or cytoskeleton

F.IV-1) Tubulin inhibitors: benzimidazoles and thiophanates: benomyl, carbendazim, fuberidazole, thiabendazole, thiophanate-methyl;

triazolopyrimidines: 5-chloro-7 (4-methylpiperidin-1-yl)-6-(2,4,6-trifluorophenyl)[1,2,4]triazolo[1,5 a]pyrimidine;

F.IV-2) Other cell division inhibitors benzamides and phenyl acetamides: diethofencarb, ethaboxam, pencycuron, fluopicolide, zoxamide;

F.IV-3) Actin inhibitors: benzophenones: metrafenone, pyriofenone;

F.V) Inhibitors of amino acid and protein synthesis

F.V-1) Methionine synthesis inhibitors (anilino-pyrimidines) anilino-pyrimidines: cyprodinil, mepanipyrim, nitrapyrin, pyrimethanil;

F.V-2) Protein synthesis inhibitors (anilino-pyrimidines) antibiotics: blasticidin-S, kasugamycin, kasugamycin hydrochloride-hydrate, mildiomycin, streptomycin, oxytetracyclin, polyoxine, validamycin A;

F.VI) Signal transduction inhibitors

F.VI-1) MAP/Histidine kinase inhibitors (e.g. anilino-pyrimidines) dicarboximides: fluoroimid, iprodione, procymidone, vinclozolin;

phenylpyrroles: fenpiclonil, fludioxonil;

F.VI-2) G protein inhibitors: quinolines: quinoxyfen;

F.VII) Lipid and membrane synthesis inhibitors

F.VII-1) Phospholipid biosynthesis inhibitors organophosphorus compounds: edifenphos, iprobenfos, pyrazophos; dithiolanes: isoprothiolane;

F.VII-2) Lipid peroxidation: aromatic hydrocarbons: dicloran, quintozene, tecnazene, tolclofos-methyl, biphenyl, chloroneb, etridiazole;

F.VII-3) Carboxyl acid amides (CAA fungicides)

cinnamic or mandelic acid amides: dimethomorph, flumorph, mandiproamid, pyrimorph; valinamide carbamates: benthiavalicarb, iprovalicarb, pyribencarb, valifenalate and N-(1-(1-(4-cyano-phenyl)ethanesulfonyl)-but-2-yl) carbamic acid-(4-fluorophenyl) ester;

F.VII-4) Compounds affecting cell membrane permeability and fatty acids: 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone, carbamates: propamocarb, propamocarb-hydrochlorid, F.VII-5) fatty acid amide hydrolase inhibitors: 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone;

F.VIII) Inhibitors with Multi Site Action

F.VIII-1) Inorganic active substances: Bordeaux mixture, copper acetate, copper hydroxide, copper oxychloride, basic copper sulfate, sulfur;

F.VIII-2) Thio- and dithiocarbamates: ferbam, mancozeb, maneb, metam, methasulphocarb, metiram, propineb, thiram, zineb, ziram;

F.VIII-3) Organochlorine compounds (e.g. phthalimides, sulfamides, chloronitriles): anilazine, chlorothalonil, captafol, captan, folpet, dichlofluanid, dichlorophen, flusulfamide, hexachlorobenzene, pentachlorphenole and its salts, phthalide, tolylfluanid, N-(4-chloro-2-nitro-phenyl)-N-ethyl-4-methyl-benzenesulfonamide;

F.VIII-4) Guanidines and other: guanidine, dodine, dodine free base, guazatine, guazatine-acetate, iminoctadine, iminoctadine-triacetate, iminoctadine-tris(albesilate), 2,6-dimethyl-1H,5H-[1,4]dithiino[2,3-c:5,6-c']dipyrrole-1,3,5,7 (2H,6H)-tetraone;

F.VIII-5) Ahtraquinones: dithianon;

F.IX) Cell wall synthesis inhibitors

F.IX-1) Inhibitors of glucan synthesis: validamycin, polyoxin B;

F.IX-2) Melanin synthesis inhibitors: pyroquilon, tricyclazole, carpropamide, dicyclomet, fenoxanil;

F.X) Plant defence inducers

F.X-1) Salicylic acid pathway: acibenzolar-S-methyl;

F.X-2) Others: probenazole, isotianil, tiadinil, prohexadione-calcium; phosphonates: fosetyl, fosetyl-aluminum, phosphorous acid and its salts;

F.XI) Unknown mode of action:bronopol, chinomethionat, cyflufenamid, cymoxanil, dazomet, debacarb, diclomezine, difenzoquat, difenzoquat-methylsulfate, diphenylamin, fenpyrazamine, flumetover, flusulfamide, flutianil, methasulfocarb, nitrapyrin, nitrothal-isopropyl, oxathiapiprolin, oxincopper, proquinazid, tebufloquin, tecloftalam, triazoxide, 2-butoxy-6-iodo-3-propylchromen-4-one, N-(cyclopropylmethoxyimino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N methyl formamidine, N' (4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2 methyl-4-(3-trimethylsilanyl-propoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)amide, 2-{1-[2-(5-methyl-3-trifluoromethyl-pyrazole-1-yl)-acetyl]-piperidin-4-yl}-thiazole-4-carboxylic acid methyl-(R)-1,2,3,4-tetrahydronaphthalen-1-yl-amide, methoxy-acetic acid 6-tert-butyl-8-fluoro-2,3-dimethyl-quinolin-4-yl ester and N-Methyl-2-{1-[(5-methyl-3-trifluoromethyl-1H-pyrazol-1-yl)-acetyl]- piperidin-4-yl}-N-[(1R)-1,2,3,4-tetrahydronaphthalen-1-yl]-4-thiazolecarboxamide, 3-[5-(4-chloro-phenyl)-2,3-dimethylisoxazolidin-3 yl]-pyridine, pyrisoxazole, 5-amino-2-isopropyl-3-oxo-4-ortho-tolyl-2,3-dihydro-pyrazole-1 carbothioic acid S-allyl ester, N-(6-methoxy-pyridin-3-yl) cyclopropanecarboxylic acid amide, 5-chloro-1 (4,6-dimethoxy-pyrimidin-2-yl)-2-methyl-1H-benzoimidazole, 2-(4-chloro-phenyl)-N-[4-(3,4-dimethoxy-phenyl)-isoxazol-5-yl]-2-prop-2-ynyloxy-acetamide, F.XII) Growth regulators: abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N 6-benzyladenine, paclobutrazol, prohexadione (prohexadione-calcium), prohydrojasmon, thidiazuron, triapenthenol, tributyl phosphorotrithioate, 2,3,5 tri iodobenzoic acid, trinexapac-ethyl and uniconazole;

F.XIII) Biological control agents

*Ampelomyces quisquakis* (e.g. AQ 10® from Intrachem Bio GmbH & Co. KG, Germany), *Aspergillus flavus* (e.g. AFLAGUARD® from Syngenta, CH), *Aureobasidium pullulans* (e.g. BOTECTOR® from bio-ferm GmbH, Germany), *Bacillus pumilus* (e.g. NRRL Accession No. B-30087 in SONATA® and BALLAD® Plus from AgraQuest Inc., USA), *Bacillus subtilis* (e.g. isolate NRRL-Nr. B-21661 in RHAPSODY®, SERENADE® MAX and SERENADE® ASO from AgraQuest Inc., USA), *Bacillus subtilis* var. *amylaquefaciens* FZB24 (e.g. TAEGRO® from Novozyme Biologicals, Inc., USA), *Candida oleophila* I-82 (e.g. ASPIRE® from Ecogen Inc., USA), *Candida saitoana* (e.g. BIOCURE® (in mixture with lysozyme) and BIOCOAT® from Micro Flo Company, USA (BASF SE) and Arysta), Chitosan (e.g. ARMOUR-ZEN from BotriZen Ltd., NZ), *Clonostachys rosea* f. *catenulata*, also named *Gliocladium catenulatum* (e.g. isolate J1446: PRESTOP® from Verdera, Finland), *Coniothyrium minitans* (e.g. CONTANS® from Prophyta, Germany), *Cryphonectria parasitica* (e.g. *Endothia parasitica* from CNICM, France), *Cryptococcus albidus* (e.g. YIELD PLUS® from Anchor Bio-Technologies, South Africa), *Fusarium oxysporum* (e.g. BIOFOX® from S.I.A.P.A., Italy, FUSACLEAN® from Natural Plant Protection, France), *Metschnikowia fructicola* (e.g. SHEMER® from Agrogreen, Israel), *Microdochium dimerum* (e.g. ANTIBOT® from Agrauxine, France), *Phlebiopsis gigantea* (e.g. ROTSOP® from Verdera, Finland), *Pseudozyma flocculosa* (e.g. SPORODEX® from Plant Products Co. Ltd., Canada), *Pythium oligandrum* DV74 (e.g. POLYVERSUM® from Remeslo SSRO, Biopreparaty, Czech Rep.), *Reynoutria sachlinensis* (e.g. REGALIA® from Marrone BioInnovations, USA), *Talaromyces flavus* V117b (e.g. PROTUS® from Prophyta, Germany), *Trichoderma asperellum* SKT-1 (e.g. ECO-HOPE® from Kumiai Chemical Industry Co., Ltd., Japan), *T. atroviride* LC52 (e.g. SENTINEL® from Agrimm Technologies Ltd, NZ), *T. harzianum* T-22 (e.g. PLANTSHIELD® der Firma BioWorks Inc., USA), *T. harzianum* TH 35 (e.g. ROOT PRO® from Mycontrol Ltd., Israel), *T. harzianum* T-39 (e.g. TRICHODEX® and TRICHODERMA 2000® from Mycontrol Ltd., Israel and Makhteshim Ltd., Israel), *T. harzianum* and *T. viride* (e.g. TRICHOPEL from Agrimm Technologies Ltd, NZ), *T. harzianum* ICC012 and *T. viride* ICC080 (e.g. REMEDIER® WP from Isagro Ricerca, Italy), *T. polysporum* and *T. harzianum* (e.g. BINAB® from BINAB Bio-Innovation AB, Sweden), *T. stromaticum* (e.g. TRICOVAB® from C.E.P.L.A.C., Brazil), *T. virens* GL-21 (e.g. SOILGARD® from Certis LLC, USA), *T. viride* (e.g. TRIECO® from Ecosense Labs. (India) Pvt. Ltd., Indien, BIOCURE® F from T. Stanes & Co. Ltd., Indien), *T. viride* TV1 (e.g. *T. viride* TV1 from Agribiotec srl, Italy), *Uloocladium oudemansii* HRU3 (e.g. BOTRY-ZEN® from Botry-Zen Ltd, NZ).

The commercially available compounds II of the group F listed above may be found in The Pesticide Manual, 15th Edition, C. D. S. Tomlin, British Crop Protection Council (2011) among other publications. Their preparation and their activity against harmful fungi is known (cf.: http://www.alanwood.net/pesticides/); these substances are commercially available. The compounds described by IUPAC nomenclature, their preparation and their fungicidal activity are also known (cf. Can. J. Plant Sci. 48(6), 587-94, 1968; EPA 141 317; EP-A 152 031; EP-A 226 917; EPA 243 970; EPA 256 503; EPA 428 941; EP-A 532 022; EP-A 1 028 125; EP-A 1 035 122; EPA 1 201 648; EPA 1 122 244, JP 2002316902; DE 19650197; DE 10021412; DE 102005009458; U.S. Pat. Nos. 3,296,272; 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 11/028657).

The compounds of the invention may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same The invertebrate pest (also referred to as "animal pest"), i.e. the insects, arachnids and nematodes, the plant, soil or water in which the plant is growing or may grow can be contacted with the compounds of the present invention or composition(s) comprising them by any application method known in the art. As such, "contacting" includes both direct contact (applying the compounds/compositions directly on the invertebrate pest or plant—typically to the foliage, stem or roots of the plant) and indirect contact (applying the compounds/compositions to the locus of the invertebrate pest or plant). The compounds of the present invention or the pesticidal compositions comprising them may be used to protect growing plants and crops from attack or infestation by animal pests, especially insects, acaridae or arachnids by contacting the plant/crop with a pesticidally effective amount of compounds of the present invention. The term "crop" refers both to growing and harvested crops.

The compounds of the present invention and the compositions comprising them are particularly important in the control of a multitude of insects on various cultivated plants, such as cereal, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, Brassica species, melons, beans, peas, garlic, onions, carrots, tuberous plants such as potatoes, sugar cane, tobacco, grapes, petunias, geranium/pelargoniums, pansies and impatiens.

The compounds of the present invention are employed as such or in form of compositions by treating the insects or the plants, plant propagation materials, such as seeds, soil, surfaces, materials or rooms to be protected from insecticidal attack with an insecticidally effective amount of the active compounds. The application can be carried out both before and after the infection of the plants, plant propagation materials, such as seeds, soil, surfaces, materials or rooms by the insects.

Moreover, invertebrate pests may be controlled by contacting the target pest, its food supply, habitat, breeding ground or its locus with a pesticidally effective amount of compounds of the present invention. As such, the application may be carried out before or after the infection of the locus, growing crops, or harvested crops by the pest.

The compounds of the present invention can also be applied preventively to places at which occurrence of the pests is expected.

The compounds of the present invention may be also used to protect growing plants from attack or infestation by pests by contacting the plant with a pesticidally effective amount of compounds of the present invention. As such, "contacting" includes both direct contact (applying the compounds/compositions directly on the pest and/or plant—typically to the foliage, stem or roots of the plant) and indirect contact (applying the compounds/compositions to the locus of the pest and/or plant).

"Locus" means a habitat, breeding ground, plant, seed, soil, area, material or environment in which a pest or parasite is growing or may grow.

In general, "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

In the case of soil treatment or of application to the pests dwelling place or nest, the quantity of active ingredient ranges from 0.0001 to 500 g per 100 m$^2$, preferably from 0.001 to 20 g per 100 m$^2$.

Customary application rates in the protection of materials are, for example, from 0.01 g to 1000 g of active compound per m$^2$ treated material, desirably from 0.1 g to 50 g per m$^2$.

Insecticidal compositions for use in the impregnation of materials typically contain from 0.001 to 95 weight %, preferably from 0.1 to 45 weight %, and more preferably from 1 to 25 weight % of at least one repellent and/or insecticide.

For use in treating crop plants, the rate of application of the active ingredients of this invention may be in the range of 0.1 g to 4000 g per hectare, desirably from 5 g to 500 g per hectare, more desirably from 5 g to 200 g per hectare.

The compounds of the present invention are effective through both contact (via soil, glass, wall, bed net, carpet, plant parts or animal parts), and ingestion (bait, or plant part).

The compounds of the present invention may also be applied against non-crop insect pests, such as ants, termites, wasps, flies, mosquitos, crickets, or cockroaches. For use against said non-crop pests, compounds of the present invention are preferably used in a bait composition.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spray devices, droplet sources, or evaporation sources. Gels can be based on aqueous or oily matrices and can be formulated to particular necessities in terms of stickyness, moisture retention or aging characteristics. The bait employed in the composition is a product, which is sufficiently attractive to incite insects such as ants, termites, wasps, flies, mosquitos, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art.

For use in bait compositions, the typical content of active ingredient is from 0.001 weight % to 15 weight %, desirably from 0.001 weight % to 5% weight % of active ingredient.

Formulations of compounds of the present invention as aerosols (e.g in spray cans), oil sprays or pump sprays are highly suitable for the non-professional user for controlling pests such as flies, fleas, ticks, mosquitos or cockroaches. Aerosol recipes are preferably composed of the active compound, solvents such as lower alcohols (e.g. methanol, ethanol, propanol, butanol), ketones (e.g. acetone, methyl ethyl ketone), paraffin hydrocarbons (e.g. kerosenes) having boiling ranges of approximately 50 to 250° C., dimethylformamide, N-methylpyrrolidone, dimethyl sulfoxide, aromatic hydrocarbons such as toluene, xylene, water, furthermore auxiliaries such as emulsifiers such as sorbitol monooleate, oleyl ethoxylate having 3-7 mol of ethylene oxide, fatty alcohol ethoxylate, perfume oils such as ethereal oils, esters of medium fatty acids with lower alcohols, aromatic carbonyl compounds, if appropriate stabilizers such as sodium benzoate, amphoteric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used.

For use in spray compositions, the content of active ingredient is from 0.001 to 80 weights %, preferably from 0.01 to 50 weight % and most preferably from 0.01 to 15 weight %.

The compounds of the present invention and its respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of the present invention and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a mixture including the insecticide, optionally a repellent and at least one binder. Suitable repellents for example are N,N-Diethyl-meta-toluamide (DEET), N,N-diethylphenylacetamide (DEPA), 1-(3-cyclohexan-1-yl-carbonyl)-2-methylpiperine, (2-hydroxymethylcyclohexyl) acetic acid lactone, 2-ethyl-1,3-hexandiol, indalone, Methylneodecanamide (MNDA), a pyrethroid not used for insect control such as {(+/−)-3-allyl-2-methyl-4-oxocyclopent-2-(+)-enyl-(+)-trans-chrysantemate (Esbiothrin), a repellent derived from or identical with plant extracts like limonene, eugenol, (+)-Eucamalol (1), (−)-1-epi-eucamalol or crude plant extracts from plants like *Eucalyptus maculata, Vitex rotundifolia, Cymbopogan martinii, Cymbopogan citratus* (lemon grass), *Cymbopogan nartdus* (citronella). Suitable binders are selected for example from polymers and copolymers of vinyl esters of aliphatic acids (such as such as vinyl acetate and vinyl versatate), acrylic and methacrylic esters of alcohols, such as butyl acrylate, 2-ethylhexylacrylate, and methyl acrylate, mono- and di-ethylenically unsaturated hydrocarbons, such as styrene, and aliphatic diens, such as butadiene.

The impregnation of curtains and bednets is done in general by dipping the textile material into emulsions or dispersions of the insecticide or spraying them onto the nets. The compounds of the present invention and their compositions can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). The compounds of the present invention are applied not only to the surrounding soil surface or into the under-floor soil in order to protect wooden materials but it can also be applied to lumbered articles such as surfaces of the under-floor concrete, alcove posts, beams, plywoods, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant controller of the present invention is applied to the crops or the surrounding soil, or is directly applied to the nest of ants or the like.

The compounds of the present invention are also suitable for the treatment of plant propagation material, especially seeds, in order to protect them from insect pest, in particular from soil-living insect pests and the resulting plant's roots and shoots against soil pests and foliar insects.

The compounds of the present invention are particularly useful for the protection of the seed from soil pests and the resulting plant's roots and shoots against soil pests and foliar insects. The protection of the resulting plant's roots and shoots is preferred. More preferred is the protection of resulting plant's shoots from piercing and sucking insects, wherein the protection from aphids is most preferred.

The present invention therefore comprises a method for the protection of seeds from insects, in particular from soil insects and of the seedlings' roots and shoots from insects, in particular from soil and foliar insects, said method comprising contacting the seeds before sowing and/or after pregermination with a compound of the present invention, including a salt thereof. Particularly preferred is a method, wherein the plant's roots and shoots are protected, more preferably a method, wherein the plants shoots are protected form piercing and sucking insects, most preferably a method, wherein the plants shoots are protected from aphids.

The term seed embraces seeds and plant propagules of all kinds including but not limited to true seeds, seed pieces, suckers, corms, bulbs, fruit, tubers, grains, cuttings, cut shoots and the like and means in a preferred embodiment true seeds.

The term seed treatment comprises all suitable seed treatment techniques known in the art, such as seed dressing, seed coating, seed dusting, seed soaking and seed pelleting.

The present invention also comprises seeds coated with or containing the active compound.

The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

Suitable seed is seed of cereals, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

In addition, the active compound may also be used for the treatment seeds from plants, which tolerate the action of herbicides or fungicides or insecticides owing to breeding, including genetic engineering methods.

For example, the active compound can be employed in treatment of seeds from plants, which are resistant to herbicides from the group consisting of the sulfonylureas, imidazolinones, glufosinate-ammonium or glyphosate-isopropylammonium and analogous active substances (see for example, EP-A 242 236, EP-A 242 246) (WO 92/00377) (EP-A 257 993, U.S. Pat. No. 5,013,659) or in transgenic crop plants, for example cotton, with the capability of producing *Bacillus thuringiensis* toxins (Bt toxins) which make the plants resistant to certain pests (EP-A 142 924, EP-A 193 259), Furthermore, the active compound can be used also for the treatment of seeds from plants, which have modified characteristics in comparison with existing plants consist, which can be generated for example by traditional breeding methods and/or the generation of mutants, or by recombinant procedures). For example, a number of cases have been described of recombinant modifications of crop plants for the purpose of modifying the starch synthesized in the plants (e.g. WO 92/11376, WO 92/14827, WO 91/19806) or of transgenic crop plants having a modified fatty acid composition (WO 91/13972).

The seed treatment application of the active compound is carried out by spraying or by dusting the seeds before sowing of the plants and before emergence of the plants.

Compositions which are especially useful for seed treatment are e.g.:
A Soluble concentrates (SL, LS)
D Emulsions (EW, EO, ES)
E Suspensions (SC, OD, FS)
F Water-dispersible granules and water-soluble granules (WG, SG)
G Water-dispersible powders and water-soluble powders (WP, SP, WS)
H Gel-Formulations (GF)
I Dustable powders (DP, DS)

Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter.

In a preferred embodiment a FS formulation is used for seed treatment. Typically, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

Especially preferred FS formulations of compounds of the present invention for seed treatment usually comprise from 0.1 to 80% by weight (1 to 800 g/l) of the active ingredient, from 0.1 to 20% by weight (1 to 200 g/l) of at least one surfactant, e.g. 0.05 to 5% by weight of a wetter and from 0.5 to 15% by weight of a dispersing agent, up to 20% by weight, e.g. from 5 to 20% of an anti-freeze agent, from 0 to 15% by weight, e.g. 1 to 15% by weight of a pigment and/or a dye, from 0 to 40% by weight, e.g. 1 to 40% by weight of a binder (sticker/adhesion agent), optionally up to 5% by weight, e.g. from 0.1 to 5% by weight of a thickener, optionally from 0.1 to 2% of an anti-foam agent, and optionally a preservative such as a biocide, antioxidant or the like, e.g. in an amount from 0.01 to 1% by weight and a filler/vehicle up to 100% by weight. Seed Treatment formulations may additionally also comprise binders and optionally colorants.

Binders can be added to improve the adhesion of the active materials on the seeds after treatment. Suitable binders are homo- and copolymers from alkylene oxides like ethylene oxide or propylene oxide, polyvinylacetate, polyvinylalcohols, polyvinylpyrrolidones, and copolymers thereof, ethylene-vinyl acetate copolymers, acrylic homo- and copolymers, polyethyleneamines, polyethyleneamides and polyethyleneimines, polysaccharides like celluloses, tylose and starch, polyolefin homo- and copolymers like olefin/maleic anhydride copolymers, polyurethanes, polyesters, polystyrene homo and copolymers.

Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of a gelling agent is carrageen (Satiagel®)

In the treatment of seed, the application rates of the compounds of the present invention are generally from 0.01 g to 10 kg per 100 kg of seed, preferably from 0.05 g to 5 kg per 100 kg of seed, more preferably from 0.1 g to 1000 g per 100 kg of seed and in particular from 0.1 g to 200 g per 100 kg of seed.

The invention therefore also relates to seed comprising a compound of the present invention, including an agriculturally useful salt of it, as defined herein. The amount of the compound of the present invention, including an agriculturally useful salt thereof will in general vary from 0.01 g to 10 kg per 100 kg of seed, preferably from 0.05 g to 5 kg per 100 kg of seed, in particular from 0.1 g to 1000 g per 100 kg of seed. For specific crops such as lettuce the rate can be higher.

Methods which can be employed for treating the seed are, in principle, all suitable seed treatment and especially seed dressing techniques known in the art, such as seed coating (e.g. seed pelleting), seed dusting and seed imbibition (e.g. seed soaking). Here, "seed treatment" refers to all methods that bring seeds and the compounds of the present invention into contact with each other, and "seed dressing" to methods of seed treatment which provide the seeds with an amount of the compounds of the present invention, i.e. which generate a seed comprising a compound of the present invention. In principle, the treatment can be applied to the seed at any time from the harvest of the seed to the sowing of the seed. The seed can be treated immediately before, or during, the planting of the seed, for example using the "planter's box" method. However, the treatment may also be carried out several weeks or months, for example up to 12 months, before planting the seed, for example in the form of a seed dressing treatment, without a substantially reduced efficacy being observed.

Expediently, the treatment is applied to unsown seed. As used herein, the term "unsown seed" is meant to include seed at any period from the harvest of the seed to the sowing of the seed in the ground for the purpose of germination and growth of the plant.

Specifically, a procedure is followed in the treatment in which the seed is mixed, in a suitable device, for example a mixing device for solid or solid/liquid mixing partners, with the desired amount of seed treatment formulations, either as such or after previous dilution with water, until the composition is distributed uniformly on the seed. If appropriate, this is followed by a drying step.

The compounds of the present invention, including their stereoisomers, veterinarily acceptable salts or N-oxides, are in particular also suitable for being used for combating parasites in and on animals.

An object of the present invention is therefore also to provide new methods to control parasites in and on animals. Another object of the invention is to provide safer pesticides for animals. Another object of the invention is further to provide pesticides for animals that may be used in lower doses than existing pesticides. And another object of the invention is to provide pesticides for animals, which provide a long residual control of the parasites.

The invention also relates to compositions comprising a parasiticidally effective amount of compounds of the present invention, including their stereoisomers, veterinarily acceptable salts or N-oxides, and an acceptable carrier, for combating parasites in and on animals.

The present invention also provides a method for treating, controlling, preventing and protecting animals against infestation and infection by parasites, which comprises orally, topically or parenterally administering or applying to the animals a parasiticidally effective amount of a compound of the present invention, including its stereoisomers, veterinarily acceptable salts or N-oxides, or a composition comprising it.

The invention also provides the use of a compound of the present invention, including its stereoisomers, veterinarily acceptable salts or N-oxides, for treating or protecting an animal from infestation or infection by invertebrate pests.

The invention also provides a process for the preparation of a composition for treating, controlling, preventing or protecting animals against infestation or infection by parasites which comprises a parasiticidally effective amount of a compound of the present invention, including its stereoisomers, veterinarily acceptable salts or N-oxides, or a composition comprising it.

Activity of compounds against agricultural pests does not suggest their suitability for control of endo- and ectoparasites in and on animals which requires, for example, low, non-emetic dosages in the case of oral application, metabolic compatibility with the animal, low toxicity, and a safe handling.

Surprisingly it has now been found that compounds of formula (I) and their stereoisomers, veterinarily acceptable salts, tautomers and N-oxides, are suitable for combating endo- and ectoparasites in and on animals.

The compounds of the present invention, especially compounds of formula (I) and their stereoisomers, veterinarily acceptable salts, tautomers and N-oxides, and compositions comprising them are preferably used for controlling and preventing infestations of and infections in animals including warm-blooded animals (including humans) and fish. They are for example suitable for controlling and preventing infestations and infections in mammals such as cattle, sheep, swine, camels, deer, horses, pigs, poultry, rabbits, goats, dogs and cats, water buffalo, donkeys, fallow deer and reindeer, and also in furbearing animals such as mink, chinchilla and raccoon, birds such as hens, geese, turkeys and ducks and fish such as fresh- and salt-water fish such as trout, carp and eels. Compounds of the present invention, including their stereoisomers, veterinarily acceptable salts or N-oxides, and compositions comprising them are preferably used for controlling and preventing infestations and infections in domestic animals, such as dogs or cats.

Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds of the present invention, including their stereoisomers, veterinarily acceptable salts or N-oxides, and compositions comprising them are suitable for systemic and/or non-systemic control of ecto- and/or endoparasites. They are active against all or some stages of development.

The compounds of the present invention are especially useful for combating parasites of the following orders and species, respectively:

fleas (Siphonaptera), e.g. *Ctenocephalides felis, Ctenocephalides canis, Xenopsylla cheopis, Pulex irritans, Tunga penetrans*, and *Nosopsyllus fasciatus*, cockroaches (Blattaria—Blattodea), e.g. *Blattella germanica, Blattella asahinae, Periplaneta americana, Periplaneta japonica, Periplaneta brunnea, Periplaneta fuliginosa, Periplaneta australasiae*, and *Blatta orientalis*, flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Chrysomya bezziana, Chrysomya hominivorax, Chrysomya macellaria, Chrysops discalis, Chrysops silacea, Chrysops atlanticus, Cochliomyia hominivorax, Cordylobia anthropophaga, Culicoides furens, Culex pipiens, Culex nigripalpus, Culex quinquefasciatus, Culex tarsalis, Culiseta inornata, Culiseta melanura, Dermatobia hominis, Fannia canicularis, Gasterophilus intestinalis, Glossina morsitans, Glossina palpalis, Glossina fuscipes, Glossina tachinoides, Haematobia irritans, Haplodiplosis equestris, Hippelates* spp., *Hypoderma lineata, Leptoconops torrens, Lucilia caprina, Lucilia cuprina, Lucilia sericata, Lycoria pectoralis, Mansonia* spp., *Musca domestica, Muscina stabulans, Oestrus ovis, Phlebotomus argentipes, Psorophora columbiae, Psorophora discolor, Prosimulium mixtum, Sarcophaga haemorrhoidalis, Sarcophaga* sp., *Simulium vittatum, Stomoxys calcitrans, Tabanus bovinus, Tabanus atratus, Tabanus lineola*, and *Tabanus similis*, lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus*.

ticks and parasitic mites (Parasitiformes): ticks (Ixodida), e.g. *Ixodes scapularis, Ixodes holocyclus, Ixodes pacificus, Rhiphicephalus sanguineus, Dermacentor andersoni, Dermacentor variabilis, Amblyomma americanum, Ambryomma maculatum, Ornithodorus hermsi, Ornithodorus turicata* and parasitic mites (Mesostigmata), e.g. *Ornithonyssus bacoti* and *Dermanyssus gallinae,*

Actinedida (Prostigmata) and Acaridida (Astigmata) e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., and *Laminosioptes* spp., Bugs (Heteropterida): *Cimex lectularius, Cimex hemipterus, Reduvius senilis, Triatoma* spp., *Rhodnius* ssp., *Panstrongylus* ssp. and *Arilus critatus,*

Anoplurida, e.g. *Haematopinus* spp., *Linognathus* spp., *Pediculus* spp., *Phtirus* spp., and *Solenopotes* spp, Mallophagida (suborders Amblycerina and Ischnocerina), e.g. *Trimenopon* spp., *Menopon* spp., *Trinoton* spp., *Bovicola* spp., *Werneckiella* spp., *Lepikentron* spp., *Trichodectes* spp., and *Felicola* spp, Roundworms Nematoda:

Wipeworms and Trichinosis (Trichosyringida), e.g. Trichinellidae (*Trichinella* spp.), (Trichuridae) *Trichuris* spp., *Capillaria* spp, Rhabditida, e.g. *Rhabditis* spp, *Strongyloides* spp., *Helicephalobus* spp, Strongylida, e.g. *Strongylus* spp., *Ancylostoma* spp., *Necator americanus, Bunostomum* spp. (Hookworm), *Trichostrongylus* spp., *Haemonchus contortus., Ostertagia* spp., *Cooperia* spp., *Nematodirus* spp., *Dictyocaulus* spp., *Cyathostoma* spp., *Oesophagostomum* spp., *Stephanurus dentatus, Ollulanus* spp., *Chabertia* spp., *Stephanurus dentatus, Syngamus trachea, Ancylostoma* spp., *Uncinaria* spp., *Globocephalus* spp., *Necator* spp., *Metastrongylus* spp., *Muellerius capil-* laris, *Protostrongylus* spp., *Angiostrongylus* spp., *Parelaphostrongylus* spp. *Aleurostrongylus abstrusus*, and *Dioctophyma renale*,
Intestinal roundworms (Ascaridida), e.g. *Ascaris lumbricoides, Ascaris suum, Ascaridia galli, Parascaris equorum, Enterobius vermicularis* (Threadworm), *Toxocara canis, Toxascaris leonine, Skrjabinema* spp., and *Oxyuris equi*,
Camallanida, e.g. *Dracunculus medinensis* (guinea worm)
Spirurida, e.g. *Thelazia* spp. *Wuchereria* spp., *Brugia* spp., *Onchocerca* spp., *Dirofilari* spp.a, *Dipetalonema* spp., *Setaria* spp., *Elaeophora* spp., *Spirocerca lupi*, and *Habronema* spp.,
Thorny headed worms (Acanthocephala), e.g. *Acanthocephalus* spp.,
*Macracanthorhynchus hirudinaceus* and *Oncicola* spp.,
Planarians (Plathelminthes):
Flukes (Trematoda), e.g. *Faciola* spp., *Fascioloides magna, Paragonimus* spp., *Dicrocoelium* spp., *Fasciolopsis buski, Clonorchis sinensis, Schistosoma* spp., *Trichobilharzia* spp., *Alaria alata, Paragonimus* spp., and *Nanocyetes* spp.,
Cercomeromorpha, in particular Cestoda (Tapeworms), e.g. *Diphyllobothrium* spp., *Tenia* spp., *Echinococcus* spp., *Dipylidium caninum, Multiceps* spp., *Hymenolepis* spp., *Mesocestoides* spp., *Vampirolepis* spp., *Moniezia* spp., *Anoplocephala* spp., *Sirometra* spp., *Anoplocephala* spp., and *Hymenolepis* spp.

The present invention relates to the therapeutic and the non-therapeutic use of compounds of the present invention and compositions comprising them for controlling and/or combating parasites in and/or on animals. The compounds of the present invention and compositions comprising them may be used to protect the animals from attack or infestation by parasites by contacting them with a parasiticidally effective amount of compounds of the present invention and compositions containing them.

The compounds of the present invention and compositions comprising them can be effective through both contact (via soil, glass, wall, bed net, carpet, blankets or animal parts) and ingestion (e.g. baits). As such, "contacting" includes both direct contact (applying the pesticidal mixtures/compositions containing the compounds of the present invention directly on the parasite, which may include an indirect contact at its locus-P, and optionally also administrating the pesticidal mixtures/composition directly on the animal to be protected) and indirect contact (applying the compounds/compositions to the locus of the parasite). The contact of the parasite through application to its locus is an example of a non-therapeutic use of compounds of the present invention. "Locus-P" as used above means the habitat, food supply, breeding ground, area, material or environment in which a parasite is growing or may grow outside of the animal.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions of the present invention. A parasiticidally effective amount of the compositions will also vary according to the prevailing conditions such as desired parasiticidal effect and duration, target species, mode of application, and the like.

The compounds of the present invention can also be applied preventively to places at which occurrence of the pests or parasites are expected.

Administration can be carried out both prophylactically and therapeutically.

Administration of the active compounds is carried out directly or in the form of suitable preparations, orally, topically/dermally or parenterally.

The isothiazoline compounds of the present invention are less persistent, bioaccumulative and/or toxic than the compounds of the prior art, and especially the isoxazoline insecticides of the prior art, which show a high persistency in the soil and thus accumulate there.

EXAMPLES

The present invention is now illustrated in further details by the following examples, without imposing any limitation thereto.

I. Preparation Examples

Compounds can be characterized e.g. by coupled High Performance Liquid Chromatography/mass spectrometry (HPLC/MS), by $^1$H-NMR and/or by their melting points.

Analytical HPLC Column:

Method A: Analytical UPLC column: Phenomenex Kinetex 1.7 μm XB-C18 100A; 50×2.1 mm from Phenomenex, Germany. Elution: acetonitrile+0.1% trifluoroacetic acid (TFA)/water+0.1% trifluoroacetic acid (TFA) in a ratio from 5:95 to 100:0 in 1.5 min at 60° C. Flow: 0.8 mL/min to 1 mL/min in 1.5 min. MS-method: ESI positive.

$^1$H-NMR: The signals are characterized by chemical shift (ppm, δ [delta]) vs. tetramethylsilane, respectively CDCl$_3$ for $^{13}$C-NMR, by their multiplicity and by their integral (relative number of hydrogen atoms given). The following abbreviations are used to characterize the multiplicity of the signals: m=multiplett, q=quartett, t=triplett, d=doublet and s=singulett.

Abbreviations used are: h for hour(s), min for minute(s), r.t./room temperature for 20-25° C., THF for tetrahydrofuran, t-BuOH for tert-butanol, MTBE for methyl-tert-butylether, OAc for acetate, BuLi for n-butyl lithium, DMF for dimethyl formamide.

C.1 Compound Examples 1

Compound examples 1-1 to 1-16 correspond to compounds of formula C.1:

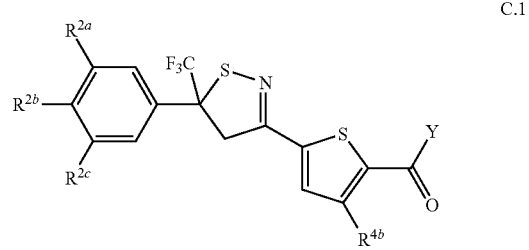

C.1 wherein $R^{2a}$, $R^{2b}$, $R^{2c}$, $R^{4b}$ and Y of each synthesized compound is defined in one row of table C.1 below.

The compounds were synthesized in analogy to Synthesis Example S.1 or S.2.

TABLE C.1

| Ex. | $R^{2a}, R^{2b}, R^{2c}$ | $R^{4b}$ | Y | HPLC-MS: Method, $R_t$ (min) & $[M + H]^+$ or $^1$H-NMR |
|---|---|---|---|---|
| 1-1 | Cl, Cl, Cl | $CH_3$ | $OC(CH_3)_3$ | $^1$H NMR (400 MHz, $CDCl_3$): δ 7.4 (m, 2H), 7.1 (s, 1H), 4.1 (d, 1H), 3.8 (d, 1H), 2.5 (s, 3H), 1.6 (s, 9H). |
| 1-2 | Cl, Cl, Cl | $CH_3$ | OH | $^1$H NMR (400 MHz, $d_6$-DMSO): δ 7.8 (s, 2H), 7.5 (s, 1H), 4.5 (d, 1H), 4.3 (d, 1H), 2.5 (s, 3H). |
| 1-3 | Cl, Cl, Cl | $CH_3$ | $NHCH_2C(=O)-NHCH_2CF_3$ | A  1.416  613.7 |
| 1-4 | Cl, Cl, Cl | $CH_3$ | $NHCH_2$-(2-pyridyl) | A  1.233  565.7 |
| 1-5 | Cl, Cl, Cl | $CH_3$ | $NHCH_2$-(2-thiazolyl) | A  1.423  571.8 |
| 1-6 | Cl, Cl, Cl | $CH_3$ | $NHCH_2$-(2-pyrimidinyl) | A  1.397  566.7 |
| 1-7 | Cl, Cl, Cl | $CH_3$ | $NHCH_2CF_3$ | A  1.531  557 |
| 1-8 | Cl, Cl, Cl | $CH_3$ | NH-(1,1-dioxo-thiethan-3-yl) | $^1$H NMR (400 MHz, $d_6$-DMSO): δ 8.9 (m, 1H), 7.8 (s, 2H), 7.5 (s, 1H), 4.6-4.5 (m, 4H), 4.4-4.2 (m, 3H), 2.5 (s, 3H). |
| 1-9 | Cl, F, Cl | $CF_3$ | OH | $^1$H NMR (400 MHz, $CDCl_3$): δ 7.4 (s, 1H), 7.3 (m, 2H), 4.2 (d, 1H), 3.85 (d, 1H). |
| 1-10 | Cl, F, Cl | $CF_3$ | $NHCH_2$-(2-pyridyl) | A  1.264  602.2 |
| 1-11 | Cl, F, Cl | $CF_3$ | $NHCH_2C(=O)-NHCH_2CF_3$ | A  1.433  650.2 |
| 1-12 | Cl, F, Cl | $CF_3$ | $NHCH_2$-(2-pyrimidinyl) | A  1.439  603.2 |
| 1-13 | Cl, F, Cl | $CF_3$ | NH-(1,1-dioxo-thiethan-3-yl) | A  1.370  614.7 |
| 1-14 | Cl, F, Cl | $CF_3$ | NH-(3-thiethanyl) | A  1.486  582.7 |
| 1-15 | Cl, F, Cl | $CF_3$ | $NHCH_2$(cyclopropyl) | A  1.501  564.8 |
| 1-16 | Cl, F, Cl | $CF_3$ | $OCH_3$ | $^1$H NMR (400 MHz, $CDCl_3$): δ 7.55 (s, 1H), 7.4-7.35 (m, 2H), 4.2 (d, 1H), 3.95 (s, 3H), 3.85 (d, 1H). |

Synthesis Example S.1

3-Methyl-5-[5-(3,4,5-trichlorophenyl)-5-(trifluoromethyl)-4H-isothiazol-3-yl]-N-(2,2,2-trifluoroethyl)thiophene-2-carboxamide (Compound example 1-7; compound of formula IA, wherein $R^{2a}$, $R^{2b}$ and $R^{2c}$ are Cl, $R^{4a}$ is H, $R^{4b}$ is $CH_3$, and A is $A^2$=—C(=O)$NHCH_2CF_3$)

Step 1: tert-Butyl 5-bromo-3-methyl-thiophene-2-carboxylate

To a solution of 5-bromo-3-methyl-thiophene-2-carboxylic acid (168 g, CAS 38239-45-1) and (Boc)$_2$O (250 g) in t-BuOH/THF (500 mL/500 mL) was added N,N-dimethyl-4-aminopyridine ("DMAP", 10 g) and the mixture was stirred overnight at 80° C. Then, the reaction was concentrated and water (500 mL) was added. The aqueous layer was extracted with MTBE (2×500 mL). The combined organic layers were dried (Na$_2$SO$_4$), filtered and concentrated to give a residue which was purified by flash chromatography on silica gel to afford the title product (35 g, 17%).

$^1$H NMR (400 MHz, CDCl$_3$): δ 6.8 (s, 1H), 2.5 (s, 3H), 1.5 (s, 9H).

Step 2: tert-Butyl 5-formyl-3-methyl-thiophene-2-carboxylate

To a solution of the product of step 1 (28 g) in THF (300 mL) at −78° C. was added nBuLi (2.5 M in hexanes, 50 mL) dropwise, and the reaction was stirred for 10 min at −78° C. 1-Formylpiperidine (18 g, CAS 2591-86-8) was added dropwise to the reaction, and the mixture was stirred for another 30 min at −78° C. The reaction was quenched with water and the aqueous layer was extracted with MTBE. The organic layers were dried (Na$_2$SO$_4$), filtered and concentrated to give a residue which was purified by flash chromatography on silica gel (ethyl acetate/petroleum ether) to afford the title product (17 g, 74%).

Step 3: tert-Butyl 5-acetyl-3-methyl-thiophene-2-carboxylate

A solution of the product of step 2 (17 g) in THF (200 mL) at 0° C. under N$_2$ was treated with methyl magnesium bromide (27.5 mL, 2.9 M solution in diethylether) over 15 min. The reaction was stirred at 0° C. for another 30 min. Then, a saturated aqueous NH$_4$Cl solution was added and the aqueous layer was extracted with MTBE. The organic layer was dried (Na$_2$SO$_4$), filtered and concentrated to afford the "crude alcohol" (20 g) which was used in the next step without any further purification.

The "crude alcohol" (20 g) in CH$_2$Cl$_2$ was treated with pyridinium chlorochromate ("PCC", 35.5 g) and stirred at r.t. overnight. The reaction was filtered and the filtrate was concentrated to afford a residue which was purified by flash chromatography on silica gel (ethyl acetate/petroleum ether) to afford the title product (7 g, 40%).

Step 4: tert-Butyl 3-methyl-5-[4,4,4-trifluoro-3-(3,4,5-trichlorophenyl)but-2-enoyl]thiophene-2-carboxylate A solution of the product of step 3 (7 g) in a mixture of DMF (30 mL) and THF (60 mL) was treated with 2,2,2-trifluoro-1-(3,4,5-trichlorophenyl)ethanone (8.8 g, CAS 158401-00-4). The reaction was stirred overnight at 70° C. using a Dean-Stark apparatus to remove water. Then, the mixture was concentrated to give a residue which was purified by flash chromatography on silica gel (ethyl acetate/petroleum ether) to afford the title product (5.8 g, 47%).

$^1$H NMR (400 MHz, CDCl$_3$): δ 7.45 (s, 1H), 7.4-7.2 (m, 3H), 2.5 (s, 3H), 1.6 (s, 9H).

Step 5: tert-Butyl 3-methyl-5-[4,4,4-trifluoro-3-sulfanyl-3-(3,4,5-trichlorophenyl)butanoyl]thiophene-2-carboxylate The product of step 4 (5.8 g, mixture of E/Z-isomers) in CH$_2$Cl$_2$ (100 mL) was treated with triethylamine (II.7 g). At 0° C., gaseous hydrogen sulfide ($H_2S$) was bubbled through the solution until the solution was saturated. The mixture was stirred for another 1 h at 0° C., and then diluted with $CH_2Cl_2$ (200 mL). The organic layer was washed with 10% aqueous hydrochloric acid solution (3×), dried ($Na_2SO_4$), filtered, and concentrated to afford the crude product (5.9 g, quant.), which was used in the next step without any further purification.

$^1$H NMR (400 MHz, $CDCl_3$): δ 7.7 (s, 2H), 7.5 (s, 1H), 4.1 (d, 1H), 3.8 (d, 1H), 3.3 (s, 1H (SH)), 2.5 (s, 3H), 1.6 (s, 9H).

Step 6: tert-Butyl 3-methyl-5-[5-(3,4,5-trichlorophenyl)-5-(trifluoromethyl)-4H-isothiazol-3-yl]thiophene-2-carboxylate At −15° C., the product of step 5 (5.9 g) in $CH_2Cl_2$ (100 mL) was treated with triethylamine (4.5 g) and with a solution of hydroxylamine-O-sulfonic acid ("HOSA", 1.5 g) in water (5 mL). The reaction was warmed to 0° C. and stirred at 0° C. for 1 h, and then diluted with $CH_2Cl_2$ (300 mL). The organic layer was washed with saturated aqueous $NH_4Cl$ solution (3×), dried ($Na_2SO_4$), and filtered. To the obtained solution, acid washed molecular sieves (AW 300, 150 g) were added and the mixture was stirred vigorously for 3 h at r.t. Then, the molecular sieves were filtered off over Celite, and the filtrate concentrated to afford the product (4.7 g, 80%), which was used in the next step without any further purification.

$^1$H NMR (400 MHz, $CDCl_3$): δ 7.4 (m, 2H), 7.1 (s, 1H), 4.1 (d, 1H), 3.8 (d, 1H), 2.5 (s, 3H), 1.6 (s, 9H).

Step 7: 3-Methyl-5-[5-(3,4,5-trichlorophenyl)-5-(trifluoromethyl)-4H-isothiazol-3-yl]thiophene-2-carboxylic acid At 0° C., the product of step 6 (7.7 g) in $CH_2Cl_2$ (100 mL) was treated with trifluoroacetic acid ("TFA", 50 mL), and the mixture stirred overnight at r.t. The reaction was concentrated, and co-evaporated with $CH_2Cl_2$ (5×) to afford the title product as a pale yellow solid (3.4 g, quant.) that was used in the next step without any further purification.

$^1$H NMR (400 MHz, $d_6$-DMSO): δ 7.8 (s, 2H), 7.5 (s, 1H), 4.5 (d, 1H), 4.3 (d, 1H), 2.5 (s, 3H).

Step 8: 3-Methyl-5-[5-(3,4,5-trichlorophenyl)-5-(trifluoromethyl)-4H-isothiazol-3-yl]-N-(2,2,2-trifluoroethyl)thiophene-2-carboxamide To a solution of the product of step 1 (0.3 g), 2,2,2-trifluoroethylamine (0.08 g) and bromotripyrrolidinophosphonium hexafluorophosphate ("PyBroP", 0.35 g) in $CH_2Cl_2$ (40 mL) at r.t. was added N,N-diisopropylethylamine (0.26 g). The reaction was stirred at r.t. overnight, then concentrated to afford a residue that was purified by flash chromatography on silica gel (ethyl acetate/cyclohexane) to afford the title product (0.21 g, 60%).

HPLC-MS (method A): 1.531 min, M=557.0.

Synthesis Example S.2

5-[5-(3,5-Dichloro-4-fluoro-phenyl)-5-(trifluoromethyl)-4H-isothiazol-3-yl]-N-(pyrimidin-2-ylmethyl)-3-(trifluoromethyl)thiophene-2-carboxamide (Compound example 1-12; compound of formula IA, wherein $R^{2a}$, and $R^{2c}$ are Cl, $R^{2b}$ is F, $R^{4a}$ is H, $R^{4b}$ is $CF_3$, and A is $A^2$=—C(=O)NH-(pyrimidin-2-yl)

For the synthesis of methyl 5-formyl-3-(trifluoromethyl)thiophene-2-carboxylate (CAS 189756-77-2), see US 2012/238569 (p. 34, paragraph [314]) or Helvetica Chimica Acta, 1997, Vol. 80, 531-537.

Step 1: Methyl 5-(1-hydroxyethyl)-3-(trifluoromethyl)-thiophene-2-carboxylate

To a solution of methyl 5-formyl-3-(trifluoromethyl)-thiophene-2-carboxylate (8.5 g) in THF (370 mL) at 0° C. was added a solution of methylmagnesium bromide (11.9 mL, 3 M in diethylether) and the mixture was stirred at 0° C. for 1 h. Then, the reaction was quenched by the addition of saturated aqueous $NH_4Cl$ solution (200 mL). The aqueous layer was extracted with ethyl acetate (2×100 mL). The combined organic layers were dried ($Na_2SO_4$), filtered and concentrated to give a residue which was purified by flash chromatography on silica gel (petroleum ether/ethyl acetate) to afford the title product (6 g, 66%).

$^1$H NMR (400 MHz, $CDCl_3$): δ 7.19 (s, 1H), 5.15 (q, 1H), 3.92 (s, 3H), 1.63 (d, 3H).

Step 2: Methyl 5-acetyl-3-(trifluoromethyl)-thiophene-2-carboxylate

To a solution of the product of step 1 (6 g) in $CH_2Cl_2$ (250 mL) at 0° C. was added Dess-Martin periodane (15 g, CAS 87413-09-0), and the reaction was stirred at 0° C. overnight. Then, a mixture of aqueous solutions of $Na_2SO_3$ and $NaHCO_3$ was added dropwise at 0° C. The aqueous layer was extracted with $CH_2Cl_2$. The organic layers were combined, dried ($Na_2SO_4$), filtered and concentrated to give a residue which was purified by flash chromatography on silica gel (ethyl acetate/petroleum ether) to afford the title product (3.5 g, 59%).

$^1$H NMR (400 MHz, $CDCl_3$): δ 7.82 (s, 1H), 3.97 (s, 3H), 2.62 (s, 3H).

Step 3: Methyl 5-[3-(3,5-dichloro-4-fluoro-phenyl)-4,4,4-trifluoro-but-2-enoyl]-3-(trifluoromethyl)-thiophene-2-carboxylate A solution of the product of step 2 (3.3 g) in a 1,2-dichloroethane ("DCE", 100 mL) was treated with 1-(3,5-dichloro-4-fluoro-phenyl)-2,2,2-trifluoro-ethanone (5.2 g, CAS 1190865-44-1), $K_2CO_3$ (1.8 g), triethylamine (0.9 mL). The reaction was stirred overnight at 100° C. Then, the mixture was diluted with water and extracted with ethyl acetate. The organic layer was dried ($Na_2SO_4$), filtered and concentrated to give a residue which was purified by flash chromatography on silica gel (ethyl acetate/petroleum ether) to afford the title product (2.4 g, 38%).

$^1$H NMR (400 MHz, $CDCl_3$): δ 8.19 (s, 1H), 7.78-7.72 (m, 1H), 7.47 (m, 2H), 3.95 (s, 3H).

Step 4: Methyl 5-[3-(3,5-dichloro-4-fluoro-phenyl)-4,4,4-trifluoro-3-sulfanyl-butanoyl]-3-(trifluoromethyl)-thiophene-2-carboxylate The product of step 3 (2.31 g, mixture of E/Z-isomers) in $CH_2Cl_2$ (30 mL) was treated with N,N-diisopropylethylamine (3.6 g). At 0° C., gaseous hydrogen sulfide ($H_2S$) was bubbled through the solution until the solution was saturated. The mixture was stirred for another 1 h at 0° C. Then, the pH was adjusted to pH 4-5 with aqueous 10% HCl solution) and the mixture diluted with $CH_2Cl_2$ (200 mL). The organic layer was washed with 10% aqueous HCl solution (1×) and water (2×), dried (Na$_2$SO$_4$), filtered, and concentrated to afford the crude product (2.4 g, 97%), which was used in the next step without any further purification.

$^1$H NMR (400 MHz, CDCl$_3$): δ 7.9 (s, 1H), 7.6 (m, 2H), 4.2 (d, 1H), 4.0-3.8 (m, 4H), 3.2 (s, 1H (SH)).

Step 5: Methyl 5-[5-(3,5-dichloro-4-fluoro-phenyl)-5-(trifluoromethyl)-4H-isothiazol-3-yl]-3-(trifluoromethyl)-thiophene-2-carboxylate (compound example 1-16)

At −10° C., the product of step 4 (2.4 g) in CH$_2$Cl$_2$ (30 mL) was treated with N,N-diisopropylethylamine (2.3 g) and with a solution of hydroxylamine-O-sulfonic acid ("HOSA", 0.62 g) in water (2 mL). The reaction was warmed to 0° C. and stirred at 0° C. for 2 h, and then diluted with CH$_2$Cl$_2$ (300 mL). The organic layer was washed with saturated aqueous NH$_4$Cl solution (3×). Then, Na$_2$SO$_4$ and para-toluenesulfonic acid (50 mg) were added, and the mixture was stirred at r.t. for 1 h. Then, the reaction was filtered and the organic layer was washed with 5% aqueous K$_2$CO$_3$ solution (2×), dried (Na$_2$SO$_4$), filtered, and concentrated to afford the crude product (2.24 g, 94%), which was used in the next step without any further purification.

$^1$H NMR (400 MHz, CDCl$_3$): δ 7.55 (s, 1H), 7.4-7.35 (m, 2H), 4.2 (d, 1H), 3.95 (s, 3H), 3.85 (d, 1H).

Step 6: 5-[5-(3,5-Dichloro-4-fluoro-phenyl)-5-(trifluoromethyl)-4H-isothiazol-3-yl]-3-(trifluoromethyl)-thiophene-2-carboxylic acid (compound example 1-9)

At 0° C., the product of step 5 (2.2 g) in THF (60 mL) was treated with a solution of LiOH (0.6 g) in water (20 mL), and the mixture stirred overnight at r.t. Then, 10% aqueous HCl was added to adjust the pH of the reaction to pH 3-4. The aqueous layer was extracted with ethyl acetate (3×). The organic layers were combined, washed with brine (1×), dried (Na$_2$SO$_4$), filtered, and concentrated. The obtained residue was purified by trituration (petroleum ether/ethyl acetate 20:1) to afford the product (3.9 g, 93%).

$^1$H NMR (400 MHz, CDCl$_3$): δ 7.4 (s, 1H), 7.3 (m, 2H), 4.2 (d, 1H), 3.85 (d, 1H).

Step 7: 5-[5-(3,5-Dichloro-4-fluoro-phenyl)-5-(trifluoromethyl)-4H-isothiazol-3-yl]-N-(pyrimidin-2-ylmethyl)-3-(trifluoromethyl)-thiophene-2-carboxamide To a solution of the product of step 6 (0.3 g), pyrimidin-2-ylmethanamine hydrochloride (0.1 g) and bromotripyrrolidinophosphonium hexafluorophosphate ("PyBroP", 0.33 g) in CH$_2$Cl$_2$ (40 mL) at r.t. was added N,N-diisopropylethylamine (0.24 g). The reaction was stirred at r.t. overnight. Then, water was added and the layers separated. The organic layer was dried (Na$_2$SO$_4$), filtered and concentrated to give a residue which was purified by flash chromatography on silica gel to afford the title product (0.14 g, 40%).

$^1$H NMR (400 MHz, CDCl$_3$): δ 8.8 (m, 2H), 7.7 (br. s, 1H), 7.4 (s, 1H), 7.35 (m, 2H), 4.9 (m, 2H), 4.15 (d, 1H), 3.85 (d, 1H).

II. Evaluation of Pesticidal Activity

The activity of the compounds of formula I of the present invention can be demonstrated and evaluated by the following biological test.

B.1 Diamond Back Moth (*Plutella xylostella*)

The active compound was dissolved at the desired concentration in a mixture of 1:1 (vol:vol) distilled water: aceteone. Surfactant (Kinetic HV) was added at a rate of 0.01% (vol/vol). The test solution was prepared at the day of use.

Leaves of cabbage were dipped in test solution and air-dried. Treated leaves were placed in petri dishes lined with moist filter paper and inoculated with ten 3$^{rd}$ instar larvae. Mortality was recorded 72 hours after treatment. Feeding damages were also recorded using a scale of 0-100%.

In this test, the compounds 1-3, 1-4, 1-5, 1-7, and 1-8 at 500 ppm, respectively, showed a mortality of at least 75% in comparison with untreated controls.

B.2 Green Peach Aphid (*Myzus persicae*)

For evaluating control of green peach aphid (*Myzus persicae*) through systemic means the test unit consisted of 96-well-microtiter plates containing liquid artificial diet under an artificial membrane.

The compounds were formulated using a solution containing 75% v/v water and 25% v/v DMSO. Different concentrations of formulated compounds were pipetted into the aphid diet, using a custom built pipetter, at two replications.

After application, 5-8 adult aphids were placed on the artificial membrane inside the microtiter plate wells. The aphids were then allowed to suck on the treated aphid diet and incubated at about 23±1° C. and about 50±5% relative humidity for 3 days. Aphid mortality and fecundity was then visually assessed.

In this test, the compounds 1-3, 1-4, 1-10, 1-11, 1-12, 1-13, 1-14 and 1-15 at 2500 ppm, respectively, showed a mortality of at least 75% in comparison with untreated controls.

B.3 Mediterranean Fruitfly (*Ceratitis capitata*)

For evaluating control of Mediterranean fruitfly (*Ceratitis capitata*) the test unit consisted of microtiter plates containing an insect diet and 50-80 *C. capitata* eggs.

The compounds were formulated using a solution containing 75% v/v water and 25% v/v DMSO. Different concentrations of formulated compounds were sprayed onto the insect diet at 5 μl, using a custom built micro atomizer, at two replications.

After application, microtiter plates were incubated at about 28±1° C. and about 80±5% relative humidity for 5 days. Egg and larval mortality was then visually assessed.

In this test, the compounds 1-3, 1-7, 1-8, 1-10, 1-11, 1-12, 1-13, 1-14 and 1-15 at 2500 ppm, respectively, showed a mortality of at least 75% in comparison with untreated controls.

B.4 Orchid Thrips (*Dichromothrips corbetti*)

*Dichromothrips corbetti* adults used for bioassay were obtained from a colony maintained continuously under laboratory conditions. For testing purposes, the test compound is diluted in a 1:1 mixture of acetone:water (vol:vol), plus Kinetic HV at a rate of 0.01% v/v.

Thrips potency of each compound was evaluated by using a floral-immersion technique. All petals of individual, intact orchid flowers were dipped into treatment solution and allowed to dry in Petri dishes. Treated petals were placed into individual resealable plastic along with about 20 adult thrips. All test arenas were held under continuous light and a temperature of about 28° C. for duration of the assay. After 3 days, the numbers of live thrips were counted on each petal. The percent mortality was recorded 72 hours after treatment.

In this test, the compounds 1-3, and 1-8 at 500 ppm, respectively, showed a mortality of at least 75% in comparison with untreated controls.

B.5 Southern Armyworm (*Spodoptera eridania*)

The active compounds were formulated by a Tecan liquid handler in 100% cyclohexanone as a 10,000 ppm solution supplied in tubes. The 10,000 ppm solution was serially diluted in 100% cyclohexanone to make interim solutions. These served as stock solutions for which final dilutions were made by the Tecan in 50% acetone:50% water (v/v) into 5 or 10 ml glass vials. A nonionic surfactant (Kinetic®) was included in the solution at a volume of 0.01% (v/v). The vials were then inserted into an automated electrostatic sprayer equipped with an atomizing nozzle for application to plants/insects.

Lima bean plants (variety Sieva) were grown 2 plants to a pot and selected for treatment at the 1$^{st}$ true leaf stage. Test solutions were sprayed onto the foliage by an automated electrostatic plant sprayer equipped with an atomizing spray nozzle. The plants were dried in the sprayer fume hood and then removed from the sprayer. Each pot was placed into perforated plastic bags with a zip closure. About 10 to 11 armyworm larvae were placed into the bag and the bags zipped closed. Test plants were maintained in a growth room at about 25° C. and about 20-40% relative humidity for 4 days, avoiding direct exposure to fluorescent light (24 hour photoperiod) to prevent trapping of heat inside the bags. Mortality and reduced feeding were assessed 4 days after treatment, compared to untreated control plants.

In this test, the compound 1-1 at 300 ppm showed a mortality of at least 75% in comparison with untreated controls.

B.6 Vetch Aphid (*Megoura viciae*)

For evaluating control of vetch aphid (*Megoura viciae*) through contact or systemic means the test unit consisted of 24-well-microtiter plates containing broad bean leaf disks.

The compounds were formulated using a solution containing 75% v/v water and 25% v/v DMSO. Different concentrations of formulated compounds were sprayed onto the leaf disks at 2.5 μl, using a custom built micro atomizer, at two replications. After application, the leaf disks were air-dried and 5-8 adult aphids placed on the leaf disks inside the microtiter plate wells. The aphids were then allowed to suck on the treated leaf disks and incubated at about 23±1° C. and about 50±5% relative humidity for 5 days. Aphid mortality and fecundity was then visually assessed.

In this test, the compounds 1-5, 1-7, 1-10, 1-11, 1-12, 1-13, 1-14 and 1-15 at 2500 ppm, respectively, showed a mortality of at least 75% in comparison with untreated controls.

B.7 Tobacco Budworm (*Heliothis virescens*)

For evaluating control of tobacco budworm (*Heliothis virescens*) the test unit consisted of 96-well-microtiter plates containing an insect diet and 15-25 *H. virescens* eggs. The compounds were formulated using a solution containing 75% v/v water and 25% v/v DMSO. Different concentrations of formulated compounds were sprayed onto the insect diet at 10 μl, using a custom built micro atomizer, at two replications.

After application, microtiter plates were incubated at about 28±1° C. and about 80±5% relative humidity for 5 days. Egg and larval mortality was then visually assessed.

In this test, the compounds 1-3, 1-4, 1-5, 1-7, 1-8, 1-9, 1-10, 1-11, 1-12, 1-13, 1-14 and 1-15 at 2500 ppm, respectively, showed a mortality of at least 75% in comparison with untreated controls.

B.8 Boll Weevil (*Anthonomus grandis*)

For evaluating control of boll weevil (*Anthonomus grandis*) the test unit consisted of 96-well-microtiter plates containing an insect diet and 5-10 *A. grandis* eggs.

The compounds were formulated using a solution containing 75% v/v water and 25% v/v DMSO. Different concentrations of formulated compounds were sprayed onto the insect diet at 5 μl, using a custom built micro atomizer, at two replications.

After application, microtiter plates were incubated at about 25±1° C. and about 75±5% relative humidity for 5 days. Egg and larval mortality was then visually assessed.

In this test, the compounds 1-3, 1-4, 1-5, 1-6, 1-7, 1-8, 1-9, 1-10, 1-11, 1-12, 1-13, 1-14 and 1-15 at 2500 ppm, respectively, showed a mortality of at least 75% in comparison with untreated controls.

We claim:

1. A compound of formula I

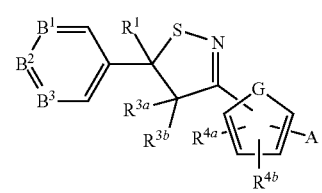

wherein

A is a group $A^1$, $A^2$, $A^3$ or $A^4$;

wherein $A^1$ is selected from the group consisting of —C(=NR$^6$)R$^8$, —S(O)$_n$R$^9$, —N(R$^5$)R$^6$ and —CN;

$A^2$ is a group of following formula:

wherein

\# denotes the bond to the thiophene ring of formula (I);

W is selected from O and S;

Y is selected from hydrogen, —N(R$^5$)R$^6$ and —OR$^9$;

$A^3$ is a group of following formula:

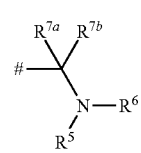

wherein

\# denotes the bond to the thiophene ring of formula (I);

$A^4$ is a 3-, 4-, 5-, 6- or 7-membered saturated, partially unsaturated or maximally unsaturated heteromonocyclic ring containing 1, 2, 3 or 4 heteroatoms or heteroatom groups selected from N, O, S, NO, SO and SO$_2$, as ring members, or is a 8-, 9- or 10-membered saturated, partially unsaturated or maximally unsaturated heterobicyclic ring containing 1, 2, 3 or 4 heteroatoms or heteroatom groups selected from N, O, S, NO, SO and $SO_2$, as ring members, where the heteromonocyclic or heterobicyclic ring is optionally substituted with one or more substituents $R^{11}$;

G is S;

$B^1$, $B^2$ and $B^3$ are each independently selected from the group consisting of N and $CR^2$, with the proviso that at most two of $B^1$, $B^2$ and $B^3$ are N;

$R^1$ is selected from the group consisting of $C_1$-$C_4$-alkyl, $C_1$-$C_4$-haloalkyl, $C_1$-$C_4$-alkoxy-$C_1$-$C_4$-alkyl, $C_1$-$C_4$-haloalkoxy-$C_1$-$C_4$-alkyl-, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl and —C(=O)$OR^{15}$;

each $R^2$ is independently selected from the group consisting of hydrogen, halogen, cyano, azido, nitro, —SCN, —$SF_5$, $C_1$-$C_6$-alkyl, $C_3$-$C_8$-cycloalkyl, $C_2$-$C_6$-alkenyl, $C_2$-$C_6$-alkynyl, wherein the four last mentioned aliphatic and cycloaliphatic radicals may be partially or fully halogenated and/or may be substituted by one or more radicals $R^8$;

—Si($R^{12}$)$_3$, —$OR^9$, —S(O)$_n R^9$, —$NR^{10a}R^{10b}$;

phenyl which may be substituted by 1, 2, 3, 4 or 5 radicals $R^{11}$, and a 3-, 4-, 5-, 6- 7-, 8-, 9- or 10-membered saturated, partially unsaturated or maximally unsaturated heteromonocyclic or heterobicyclic ring containing 1, 2, 3 or 4 heteroatoms or heteroatom groups selected from N, O, S, NO, SO and $SO_2$, as ring members, where the heteromono- or heterobicyclic ring may be substituted by one or more radicals $R^{11}$;

$R^{3a}$ and $R^{3b}$ are each independently selected from the group consisting of hydrogen, halogen, hydroxyl, —$CO_2 R^{3d}$, $C_1$-$C_3$-alkyl, $C_1$-$C_3$-haloalkyl, $C_2$-$C_3$-alkenyl, $C_2$-$C_3$-alkynyl, $C_1$-$C_3$-alkoxy, $C_1$-$C_3$-haloalkoxy, $C_1$-$C_3$-alkylthio, $C_1$-$C_3$-haloalkylthio, $C_1$-$C_3$-alkylsulfonyl and $C_1$-$C_3$-haloalkylsulfonyl; or $R^{3a}$ and $R^{3b}$ together form a group =O, =C($R^{3c}$)$_2$, =NOH or =$NOCH_3$;

each $R^{3c}$ is independently selected from the group consisting of hydrogen, halogen, $CH_3$ and $CF_3$;

$R^{3d}$ is selected from the group consisting of hydrogen, $C_1$-$C_6$-alkyl and $C_1$-$C_3$-alkyloxy-$C_1$-$C_3$-alkyl-;

$R^{4a}$ and $R^{4b}$ are independently selected from the group consisting of hydrogen, halogen, cyano, azido, nitro, —SCN, —$SF_5$, $C_1$-$C_6$-alkyl which may be partially or fully halogenated and/or may be substituted by one or more radicals $R^8$, $C_3$-$C_8$-cycloalkyl which may be partially or fully halogenated and/or may be substituted by one or more radicals $R^8$, $C_2$-$C_6$-alkenyl which may be partially or fully halogenated and/or may be substituted by one or more radicals $R^8$, $C_2$-$C_6$-alkynyl which may be partially or fully halogenated and/or may be substituted by one or more radicals $R^8$;

—Si($R^{12}$)$_3$, —$OR^9$, —S(O)$_n R^9$, —$NR^{10a}R^{10b}$; phenyl which may be substituted by 1, 2, 3, 4 or 5 radicals $R^{11}$, and a 3-, 4-, 5-, 6- 7-, 8-, 9- or 10-membered saturated, partially unsaturated or maximally unsaturated heteromonocyclic or heterobicyclic ring containing 1, 2, 3 or 4 heteroatoms or heteroatom groups selected from N, O, S, NO, SO and $SO_2$, as ring members, where the heteromonocyclic or heterobicyclic ring may be substituted by one or more radicals $R^{11}$;

each $R^5$ is independently selected from the group consisting of hydrogen, cyano, $C_1$-$C_{10}$-alkyl, $C_3$-$C_8$-cycloalkyl, $C_2$-$C_{10}$-alkenyl, $C_2$-$C_{10}$-alkynyl, wherein the four last-mentioned aliphatic and cycloaliphatic radicals may be partially or fully halogenated and/or may be substituted with one or more substituents $R^8$; and —S(O)$_n R^9$, each $R^6$ is independently selected from the group consisting of hydrogen, cyano, $C_1$-$C_{10}$-alkyl, $C_3$-$C_8$-cycloalkyl, $C_2$-$C_{10}$-alkenyl, $C_2$-$C_{10}$-alkynyl, wherein the four last-mentioned aliphatic and cycloaliphatic radicals may be partially or fully halogenated and/or may be substituted by one or more substituents $R^8$, —$OR^9$, —$NR^{10a}R^{10b}$, —S(O)$_n R^9$, —C(=O)$NR^{10a}N(R^{10a})R^{10b}$, —Si($R^{12}$)$_3$, —C(=O)$R^8$, —CH=$NOR^9$, phenyl which may be substituted with 1, 2, 3, 4, or 5 substituents $R^{11}$ and a 3-, 4-, 5-, 6-, 7-, 8-, 9- or 10-membered saturated, partially unsaturated or maximally unsaturated heteromonocyclic or heterobicyclic ring containing 1, 2, 3 or 4 heteroatoms or heteroatom groups independently selected from N, O, S, NO, SO and $SO_2$, as ring members, where the heteromonocyclic or heterobicyclic ring may be substituted with one or more substituents $R^{11}$;

or $R^5$ and $R^6$, together with the nitrogen atom to which they are bound, form a 3-, 4-, 5-, 6-, 7- or 8-membered saturated, partially unsaturated or maximally unsaturated heterocyclic ring, where the ring may further contain 1, 2, 3 or 4 heteroatoms or heteroatom-containing groups selected from O, S, N, SO, $SO_2$, C=O and C=S as ring members, wherein the heterocyclic ring may be substituted with 1, 2, 3, 4 or 5 substituents independently selected from the group consisting of halogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, wherein the aliphatic or cycloaliphatic moieties in the twelve last-mentioned radicals may be substituted by one or more radicals $R^8$, and phenyl which may be substituted with 1, 2, 3 or 5 substituents $R^{11}$;

or $R^5$ and $R^6$ together form a group =C($R^8$)$_2$, =S(O)$_m(R^9)_2$, =$NR^{10a}$ or =$NOR^9$;

$R^{7a}$ and $R^{7b}$ are each independently selected from the group consisting of hydrogen, halogen, cyano, $C_1$-$C_6$-alkyl, $C_3$-$C_8$-cycloalkyl, $C_2$-$C_6$-alkenyl and $C_2$-$C_6$-alkynyl, wherein the four last-mentioned aliphatic and cycloaliphatic radicals may be partially or fully halogenated and/or may be substituted by one or more radicals $R^8$;

each $R^8$ is independently selected from the group consisting of cyano, azido, nitro, —SCN, —$SF_5$, $C_3$-$C_8$-cycloalkyl, $C_3$-$C_8$-halocycloalkyl, $C_3$-$C_8$-cycloalkenyl, $C_3$-$C_8$-halocycloalkenyl, where the cycloaliphatic moieties in the four last-mentioned radicals may be substituted by one or more radicals $R^{13}$;

—Si($R^{12}$)$_3$, —$OR^9$, —$OSO_2 R^9$, —S(O)$_n R^9$, —N($R^{10a}$)$R^{10b}$, —C(=O)N($R^{10a}$)$R^{10b}$, —C(=S)N($R^{10a}$)$R^{10b}$, —C(=O)$OR^9$, —CH=$NOR^9$, phenyl, optionally substituted with 1, 2, 3, 4 or 5 substituents $R^{16}$, and a 3-, 4-, 5-, 6- or 7-membered saturated, partially unsaturated or maximally unsaturated heterocyclic ring comprising 1, 2 or 3 heteroatoms or heteroatom groups selected from N, O, S, NO, SO and $SO_2$, as ring members, where the heterocyclic ring is optionally substituted with one or more substituents $R^{16}$, or two $R^8$ present on the same carbon atom of an alkyl, alkenyl, alkynyl or cycloalkyl group together form a group =O, =C($R^{13}$)$_2$; =S; =S(O)$_m$($R^{15}$)$_2$, =S(O)$_m R^{15}$N($R^{14a}$)$R^{14b}$, =N$R^{10a}$, =NO$R^9$; or =NN($R^{10a}$)$R^{10b}$;

or two radicals $R^8$, together with the carbon atoms of an alkyl, alkenyl, alkynyl or cycloalkyl group which they are bonded to, form a 3-, 4-, 5-, 6-, 7- or 8-membered saturated or partially unsaturated carbocyclic or heterocyclic ring, where the heterocyclic ring comprises 1, 2, 3 or 4 heteroatoms or heteroatom groups independently selected from N, O, S, NO, SO and SO$_2$, as ring members, and where the carbocyclic or heterocyclic ring is optionally substituted with one or more substituents $R^{16}$; and $R^8$ as a substituent on a cycloalkyl ring is additionally selected from the group consisting of $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl and $C_2$-$C_6$-haloalkynyl, where the aliphatic moieties in these six radicals may be substituted by one or more radicals $R^{13}$; and $R^8$ in the groups —C(=N$R^6$)$R^8$, —C(=O)$R^8$ and =C($R^8$)$_2$ is additionally selected from the group consisting of hydrogen, halogen, $C_1$-$C_6$-alkyl, $C_1$-$C_6$-haloalkyl, $C_2$-$C_6$-alkenyl, 8 $C_2$-$C_6$-haloalkenyl, $C_2$-$C_6$-alkynyl and $C_2$-$C_6$-haloalkynyl, where the aliphatic moieties in the six last-mentioned radicals may be substituted by one or more radicals $R^{13}$;

each $R^9$ is independently selected from the group consisting of hydrogen, cyano, $C_1$-$C_6$-alkyl, $C_1$-$C_6$-haloalkyl, $C_3$-$C_8$-cycloalkyl, $C_3$-$C_8$-cycloalkyl-$C_1$-$C_4$-alkyl-, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, where the aliphatic and cycloaliphatic moieties in the nine last-mentioned radicals may be substituted by one or more radicals $R^{13}$, —$C_1$-$C_6$-alkyl-C(=O)O$R^{15}$, —$C_1$-$C_6$-alkyl-C(=O)N($R^{14a}$)$R^{14b}$, —$C_1$-$C_6$-alkyl-C(=S)N($R^{14a}$)$R^{14b}$, —$C_1$-$C_6$-alkyl-C(=N$R^{14}$)N($R^{14a}$)$R^{14b}$-Si($R^{12}$)$_3$, —S(O)$_n R^{15}$, —S(O)$_n$N($R^{14a}$)$R^{14b}$, —N($R^{10a}$)$R^{10b}$, —N=C($R^{13}$)$_2$, —C(=O)$R^{13}$, —C(=O)N($R^{14a}$)$R^{14b}$, —C(=S)N($R^{14a}$)$R^{14b}$, —C(=O)O$R^{15}$, phenyl, optionally substituted with one or more substituents $R^{16}$; and a 3-, 4-, 5-, 6- or 7-membered saturated, partially unsaturated or maximally unsaturated heterocyclic ring comprising 1, 2 or 3 heteroatoms or heteroatom groups selected from N, O, S, NO, SO and SO$_2$, as ring members, where the heterocyclic ring is optionally substituted with one or more substituents $R^{16}$; and $R^9$ in the groups —S(O)$_n R^9$ and —OSO$_2 R^9$ is additionally selected from the group consisting of $C_1$-$C_6$-alkoxy and $C_1$-$C_6$-haloalkoxy;

$R^{10a}$ and $R^{10b}$ are selected independently from one another from the group consisting of hydrogen, $C_1$-$C_6$-alkyl, $C_1$-$C_6$-haloalkyl, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, where the aliphatic and cycloaliphatic moieties in the eight last-mentioned radicals may be substituted by one or more radicals $R^{13}$;

—$C_1$-$C_6$-alkyl-C(=O)O$R^{15}$, —$C_1$-$C_6$-alkyl-C(=O)N($R^{14a}$)$R^{14b}$, —$C_1$-$C_6$-alkyl-C(=S)N($R^{14a}$)$R^{14b}$, —$C_1$-$C_6$-alkyl-C(=N$R^{14}$)N($R^{14a}$)$R^{14b}$, $C_1$-$C_6$-alkoxy, $C_1$-$C_6$-haloalkoxy, $C_1$-$C_6$-alkylthio, $C_1$-$C_6$-haloalkylthio, —S(O)$_n R^{15}$, —S(O)$_n$N($R^{14a}$)$R^{14b}$, —C(=O)$R^{13}$, —C(=O)O$R^{15}$, —C(=O)N($R^{14a}$)$R^{14b}$, —C(=S)$R^{13}$, —C(=S)S$R^{15}$, —C(=S)N($R^{14a}$)$R^{14b}$, —C(=N$R^{14}$)$R^{13}$;

phenyl, optionally substituted with 1, 2, 3, 4 or 5 substituents $R^{16}$; and a 3-, 4-, 5-, 6- or 7-membered saturated, partially unsaturated or maximally unsaturated heterocyclic ring comprising 1, 2, 3 or 4 heteroatoms or heteroatom groups selected from N, O, S, NO, SO and SO$_2$, as ring members, where the heterocyclic ring is optionally substituted with one or more substituents $R^{16}$;

or $R^{10a}$ and $R^{10b}$ form together with the nitrogen atom they are bonded to a 3-, 4-, 5-, 6-, 7- or 8-membered saturated, partially unsaturated or maximally unsaturated heterocyclic ring, wherein the heterocyclic ring may additionally contain one or two heteroatoms or heteroatom groups selected from N, O, S, NO, SO and SO$_2$, as ring members, where the heterocyclic ring optionally carries one or more substituents selected from halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, phenyl, optionally substituted with 1, 2, 3, 4 or 5 substituents $R^{16}$, and a 3-, 4-, 5-, 6,- or 7-membered saturated, partially unsaturated or maximally unsaturated heterocyclic ring comprising 1, 2 or 3 heteroatoms or heteroatom groups selected from N, O, S, NO, SO and SO$_2$, as ring members, where the heterocyclic ring optionally carries one or more substituents $R^{16}$;

or $R^{10a}$ and $R^{10b}$ together form a group =C($R^{13}$)$_2$, =S(O)$_m$($R^{15}$)$_2$, =S(O)$_m R^{15}$N($R^{14a}$)$R^{14b}$, =N$R^{14}$ or =NO$R^{15}$;

$R^{11}$ is independently selected from the group consisting of halogen, cyano, azido, nitro, —SCN, —SF$_5$, $C_1$-$C_{10}$-alkyl, $C_3$-$C_8$-cycloalkyl, $C_2$-$C_{10}$-alkenyl, $C_2$-$C_{10}$-alkynyl, wherein the four last-mentioned aliphatic and cycloaliphatic radicals may be partially or fully halogenated and/or may be substituted with one or more radicals $R^8$;

—O$R^9$, —N$R^{10a}R^{10b}$, —S(O)$_n R^9$, —Si($R^{12}$)$_3$;

phenyl, optionally substituted with 1, 2, 3, 4, or 5 substituents selected independently from $R^{16}$; and a 3-, 4-, 5-, 6- or 7-membered saturated, partially unsaturated or maximally unsaturated aromatic heterocyclic ring comprising 1, 2, 3 or 4 heteroatoms or heteroatom groups selected from N, O, S, NO, SO and SO$_2$, as ring members, where the heterocyclic ring is optionally substituted with one or more substituents selected independently from $R^{16}$;

or two $R^{11}$ present on the same ring carbon atom of an unsaturated or partially unsaturated heterocyclic ring may together form a group =O, =C($R^{13}$)$_2$; =S; =S(O)$_m$($R^{15}$)$_2$; =S(O)$_m R^{15}$N($R^{14a}$)$R^{14b}$, =N$R^{14}$, =NO$R^{15}$, or =NN($R^{14a}$)$R^{14b}$;

or two $R^{11}$ bound on adjacent ring atoms form together with the ring atoms to which they are bound a saturated 3-, 4-, 5-, 6-, 7-, 8- or 9-membered ring, wherein the ring may contain 1 or 2 heteroatoms or heteroatom groups selected from O, S, N, N$R^{14}$, NO, SO and SO$_2$ and/or 1 or 2 groups selected from C=O, C=S and C=NR$^{14}$ as ring members, and wherein the ring may be substituted by one or more radicals selected from the group consisting of halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, phenyl which may be substituted by 1, 2, 3, 4 or 5 radicals $R^{16}$, and a 3-, 4-, 5-, 6- or 7-membered saturated, partially unsaturated or maximally unsaturated heterocyclic ring containing 1, 2 or 3 heteroatoms or heteroatom groups selected from N, O, S, NO, SO and SO$_2$, as ring members, where the heterocyclic ring may be substituted by one or more radicals $R^{16}$;

each $R^{12}$ is independently selected from the group consisting of hydrogen, halogen, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy-$C_1$-$C_6$-alkyl, $C_1$-$C_6$-haloalkoxy-$C_1$-$C_6$-alkyl, and phenyl, optionally substituted with 1, 2, 3, 4, or 5 substituents $R^{16}$;

each $R^{13}$ is independently selected from the group consisting of cyano, nitro, —OH, —SH, —SCN, —SF$_5$, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —NR$^{14a}$R$^{14b}$, trimethylsilyl, triethylsilyl, tert-butyldimethylsilyl, —C(=O)N(R$^{14a}$)R$^{14b}$, $C_3$-$C_8$-cycloalkyl which may be unsubstituted, partially or fully halogenated and/or may carry 1 or 2 radicals selected from cyano, $C_1$-$C_4$-alkyl, $C_3$-$C_4$-cycloalkyl, $C_1$-$C_4$-alkoxy, $C_1$-$C_4$-haloalkoxy and oxo; phenyl, benzyl, phenoxy, where the phenyl moiety in the three last-mentioned radicals may be unsubstituted or carry 1, 2, 3, 4 or 5 substituents $R^{16}$; and a 3-, 4-, 5-, 6- or 7-membered saturated, partially unsaturated or maximally unsaturated heterocyclic ring containing 1, 2 or 3 heteroatoms or heteroatom groups selected from N, O, S, NO, SO and SO$_2$, as ring members, where the heterocyclic ring may be substituted by 1, 2 or 3 substituents $R^{16}$; or two $R^{13}$ present on the same carbon atom of an alkyl, alkenyl, alkynyl or cycloalkyl group may together be =O, =CH($C_1$-$C_4$-alkyl), =C($C_1$-$C_4$-alkyl)$C_1$-$C_4$-alkyl, =NR$^{17}$ or =NOR$^{17}$;
and $R^{13}$ as a substituent on a cycloalkyl ring is additionally selected from the group consisting of $C_1$-$C_6$-alkyl, $C_2$-$C_6$-alkenyl and $C_2$-$C_6$-alkynyl, wherein the three last-mentioned aliphatic radicals may be unsubstituted, partially or fully halogenated and/or may carry 1 or 2 substituents selected from CN, $C_3$-$C_4$-cycloalkyl, $C_1$-$C_4$-alkoxy, $C_1$-$C_4$-haloalkoxy and oxo;
and $R^{13}$ in the groups =C($R^{13}$)$_2$, —N=C($R^{13}$)$_2$, —C(=O)R$^{13}$, —C(=S)R$^{13}$ and —C(=NR$^{14}$)R$^{13}$ is additionally selected from the group consisting of hydrogen, halogen, $C_1$-$C_6$-alkyl, $C_2$-$C_6$-alkenyl and $C_2$-$C_6$-alkynyl, wherein the three last-mentioned aliphatic radicals may be unsubstituted, partially or fully halogenated and/or may carry 1 or 2 radicals selected from CN, $C_3$-$C_4$-cycloalkyl, $C_1$-$C_4$-alkoxy, $C_1$-$C_4$-haloalkoxy and oxo;

each $R^{14}$ is independently selected from the group consisting of hydrogen, cyano, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —C(=O)NR$^{8a}$R$^{18b}$, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last-mentioned aliphatic radicals may be unsubstituted, partially or fully halogenated and/or may carry 1 or 2 radicals selected from CN, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_3$-$C_6$-cycloalkyl which may be substituted by 1 or 2 substituents selected from halogen and cyano;

$C_3$-$C_8$-cycloalkyl which may be unsubstituted, partially or fully halogenated and/or may carry 1 or 2 radicals selected from cyano, $C_1$-$C_4$-alkyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_3$-$C_4$-cycloalkyl, $C_3$-$C_4$-cycloalkyl-$C_1$-$C_4$-alkyl-, where the cycloalkyl moiety in the two last-mentioned radicals may be substituted by 1 or 2 substituents selected from halogen and cyano;

phenyl, benzyl, pyridyl, phenoxy, wherein the cyclic moieties in the four last-mentioned radicals may be unsubstituted and/or carry 1, 2, 3 or 4 substituents selected from halogen, cyano, nitro, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, and ($C_1$-$C_6$-alkoxy)carbonyl; and a 3-, 4-, 5- or 6-membered saturated, partially unsaturated or maximally unsaturated heterocyclic ring comprising 1, 2 or 3 heteroatoms or heteroatom groups selected from N, O, S, NO, SO and SO$_2$, as ring members, where the heterocyclic ring is optionally substituted with one or more substituents $R^{16}$;

$R^{14a}$ and $R^{14b}$, independently of each other, have one of the meanings given for $R^{14}$; or $R^{14a}$ and $R^{14b}$, together with the nitrogen atom to which they are bound, form a 3-, 4-, 5-, 6- or 7-membered saturated, partially unsaturated or maximally unsaturated heterocyclic ring, wherein the heterocyclic ring may additionally contain 1 or 2 heteroatoms or heteroatom groups selected from N, O, S, NO, SO and SO$_2$, as ring members, where the heterocyclic ring optionally carries one or more substituents selected from halogen, $C_1$-$C_4$-alkyl, $C_1$-$C_4$-haloalkyl, $C_1$-$C_4$-alkoxy and $C_1$-$C_4$-haloalkoxy;
or $R^{14a}$ and $R^{14}$ or $R^{14b}$ and $R^{14}$, together with the nitrogen atoms to which they are bound in the group —C(=NR$^{14}$)N(R$^{14a}$)R$^{14b}$, form a 3-, 4-, 5-, 6- or 7-membered partially unsaturated or maximally unsaturated heterocyclic ring, wherein the heterocyclic ring may additionally contain 1 or 2 heteroatoms or heteroatom groups selected from N, O, S, NO, SO and SO$_2$, as ring members, where the heterocyclic ring optionally carries one or more substituents selected from halogen, $C_1$-$C_4$-haloalkyl, $C_1$-$C_4$-alkoxy and $C_1$-$C_4$-haloalkoxy;

each $R^{15}$ is independently selected from the group consisting of hydrogen, cyano, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last-mentioned aliphatic radicals may be unsubstituted, partially or fully halogenated and/or may carry 1 or 2 radicals selected from $C_3$-$C_4$-cycloalkyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl and oxo;

$C_3$-$C_8$-cycloalkyl which may be unsubstituted, partially or fully halogenated and/or may carry 1 or 2 radicals selected from $C_1$-$C_4$-alkyl, $C_3$-$C_4$-cycloalkyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl and oxo;

phenyl, benzyl, pyridyl and phenoxy, wherein the four last-mentioned radicals may be unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$-haloalkoxy and ($C_1$-$C_6$-alkoxy)carbonyl;

each $R^{16}$ is independently selected from the group consisting of halogen, nitro, cyano, —OH, —SH, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, aminocarbonyl, $C_1$-$C_4$-alkylaminocarbonyl, di-($C_1$-$C_4$-alkyl)-aminocarbonyl, trimethylsilyl, triethylsilyl, tert-butyldimethylsilyl;

$C_1$-$C_6$-alkyl, $C_2$-$C_6$-alkenyl, $C_2$-$C_6$-alkynyl, wherein the three last-mentioned aliphatic radicals may be unsubstituted, partially or fully halogenated and/or may carry 1 or 2 radicals selected from cyano, $C_3$-$C_4$-cycloalkyl, $C_1$-$C_4$-alkoxy, $C_1$-$C_4$-haloalkoxy and oxo;

$C_3$-$C_8$-cycloalkyl which may be unsubstituted, partially or fully halogenated and/or may carry 1 or 2 radicals selected from cyano, $C_1$-$C_4$-alkyl, $C_3$-$C_4$-cycloalkyl, $C_1$-$C_4$-alkoxy, $C_1$-$C_4$-haloalkoxy and oxo;

phenyl, benzyl, pyridyl and phenoxy, wherein the four last mentioned radicals may be unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$-haloalkoxy and ($C_1$-$C_6$-alkoxy)carbonyl;

or two $R^{16}$ present together on the same atom of an unsaturated or partially unsaturated ring may be =O, =S, =N($C_1$-$C_6$-alkyl), =NO($C_1$-$C_6$-alkyl), =CH($C_1$-$C_4$-alkyl) or =C($C_1$-$C_4$-alkyl)$C_1$-$C_4$-alkyl;

or two $R^{16}$ on two adjacent carbon atoms form together with the carbon atoms they are bonded to a 4-, 5-, 6-, 7- or 8-membered saturated, partially unsaturated or maximally unsaturated ring, wherein the ring may contain 1 or 2 heteroatoms or heteroatom groups selected from N, O, S, NO, SO and $SO_2$, as ring members, and wherein the ring optionally carries one or more substituents selected from halogen, $C_1$-$C_4$-alkyl, $C_1$-$C_4$-haloalkyl, $C_1$-$C_4$-alkoxy and $C_1$-$C_4$-haloalkoxy;

$R^{17}$, $R^{18a}$ and $R^{18b}$, independently of each other and independently of each occurrence, are selected from the group consisting of hydrogen, $C_1$-$C_6$-alkyl, $C_2$-$C_6$-alkenyl, $C_2$-$C_6$-alkynyl, wherein the three last-mentioned aliphatic radicals may be unsubstituted, partially or fully halogenated and/or may carry 1 or 2 radicals selected from CN, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_3$-$C_4$-cycloalkyl which may be substituted by 1 or 2 substituents selected from halogen and cyano; oxo;

$C_3$-$C_8$-cycloalkyl which may be unsubstituted, partially or fully halogenated and/or may carry 1 or 2 radicals selected from cyano, $C_1$-$C_4$-alkyl and $C_1$-$C_4$-haloalkyl;

phenyl and benzyl;

each n is independently 0, 1 or 2; and each m is independently 0 or 1;

or an N-oxide, a stereoisomer or an agriculturally or veterinarily acceptable salt thereof.

2. The compound as claimed in claim 1, wherein compound of formula (I) is selected from the group consisting of formulae II.1, II.2 and II.3

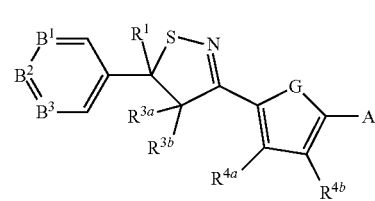

II.1

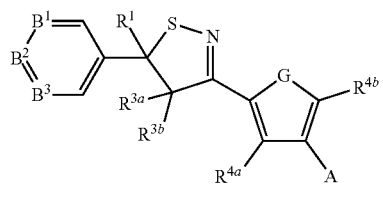

II.2

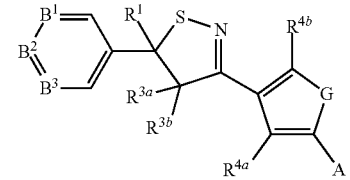

II.3 wherein

G, A, $R^{4a}$ and $R^{4b}$ are as defined in claim 1.

3. The compound as claimed in claim 2, wherein the compound of formula (I) is the compound of formula 11.1.

4. The compound of claim 1, where A is $A^2$ and in $A^2$ W is O.

5. The compound of claim 4, wherein Y is —N($R^5$)$R^6$.

6. The compound of claim 5, where $R^5$ selected from hydrogen, $C_1$-$C_6$-alkyl, $C_2$-$C_3$-alkynyl and $CH_2$—CN; and $R^6$ is selected from hydrogen, unsubstituted $C_1$-$C_6$-alkyl, $C_1$-$C_6$-haloalkyl, $C_1$-$C_4$-alkyl which carries one radical $R^8$; $C_2$-$C_6$-alkenyl, $C_2$-$C_6$-haloalkenyl, $C_2$-$C_6$-alkynyl, $C_3$-$C_6$-cycloalkyl which may be substituted by 1 or 2 substituents selected from F, CN and pyridyl;

N($R^{10a}$)$R^{10b}$, wherein $R^{10a}$ is selected from hydrogen and $C_1$-$C_6$-alkyl; and $R^{10b}$ is selected from hydrogen, —C(=O)N($R^{14a}$)$R^{14b}$, phenyl, optionally substituted with 1, 2, 3, 4 or 5 substituents $R^{16}$, and a heterocyclic ring selected from rings of formulae E-1 to E-54

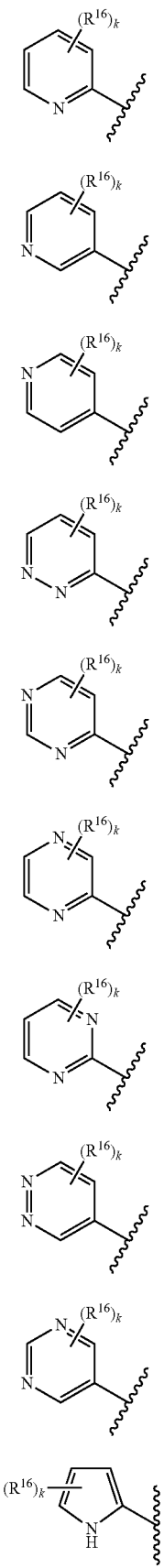
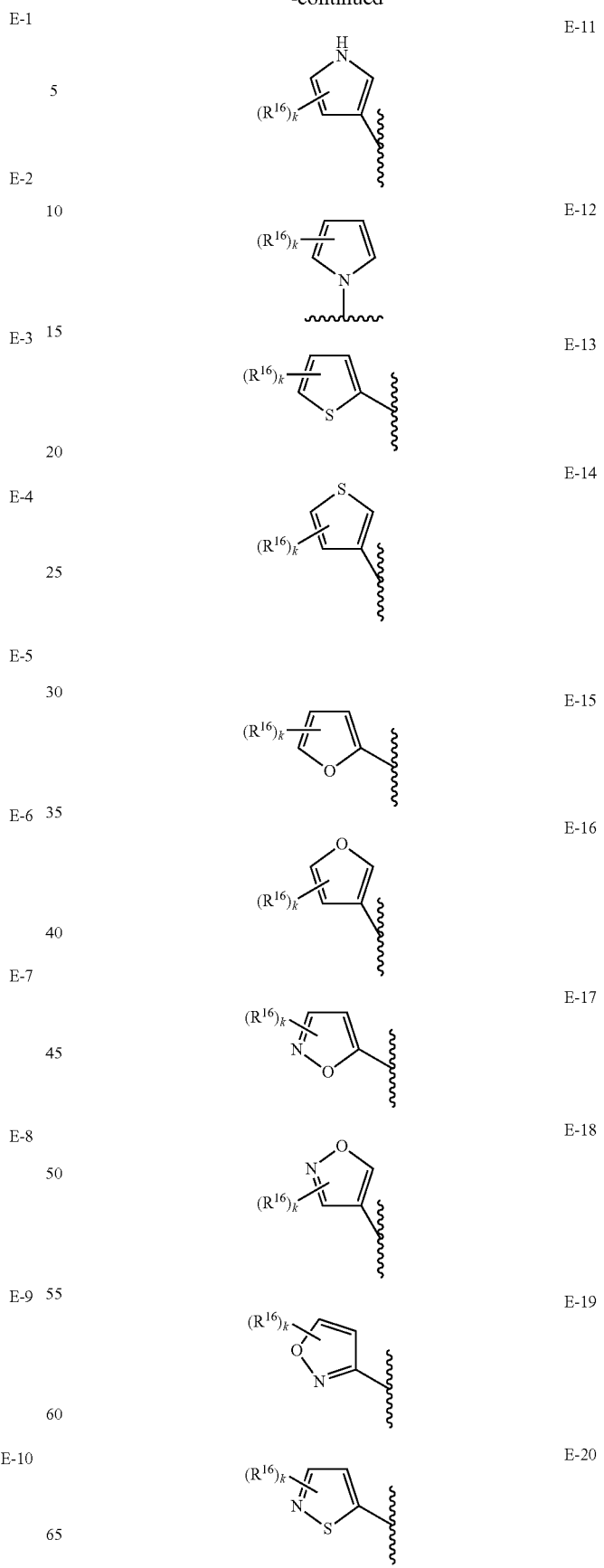

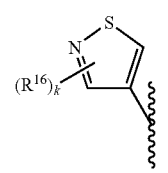 E-21
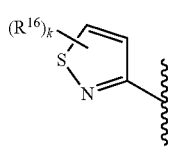 E-22
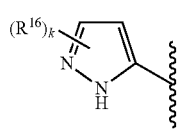 E-23
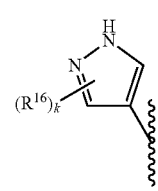 E-24
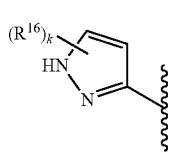 E-25
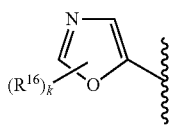 E-26
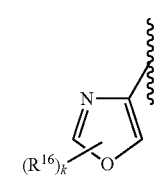 E-27
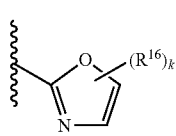 E-28
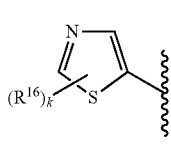 E-29
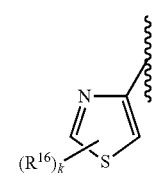 E-30
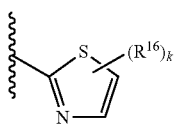 E-31
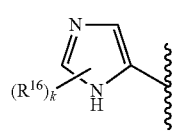 E-32
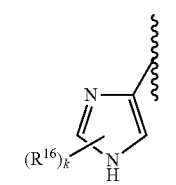 E-33
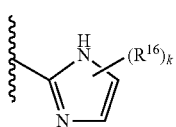 E-34
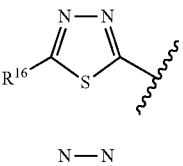 E-35
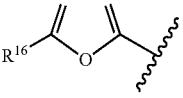 E-36
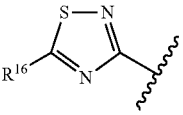 E-37
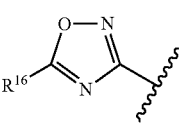 E-38
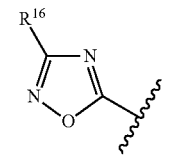 E-39
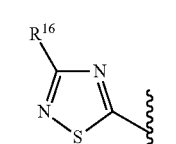 E-40
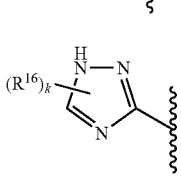 E-41

E-42 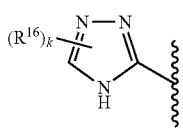

E-43 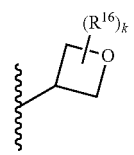

E-44 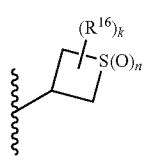

E-45 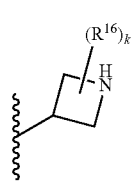

E-46 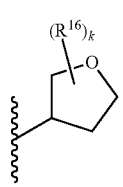

E-47 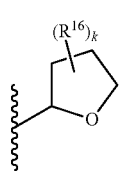

E-48 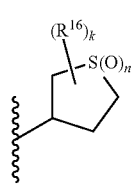

E-49 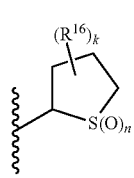

E-50 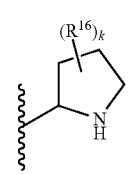

E-51 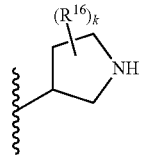

E-52 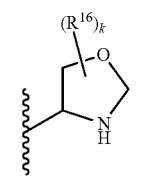

E-53 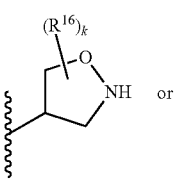 or

E-54 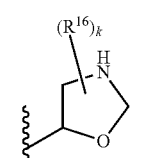

wherein
k is 0, 1, 2 or 3,
n is 0, 1 or 2; and
wherein
$R^9$ is selected from hydrogen, $C_1$-$C_6$-alkyl and $C_1$-$C_6$-haloalkyl;
phenyl which may be substituted with 1, 2, 3, 4, or 5 substituents $R^{11}$, and a 3-, 4-, 5- or 6-membered saturated, partially unsaturated or maximally unsaturated heteromonocyclic ring containing 1, 2 or 3 heteroatoms or heteroatom groups independently selected from N, O, S, NO, SO and $SO_2$, as ring members, where the heteromonocyclic ring may be substituted with one or more substituents $R^{11}$;
wherein
each $R^{11}$ is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_2$-$C_4$-haloalkynyl; or
two $R^{11}$ present on the same carbon atom of a saturated heterocyclic ring may form together =O or =S;
each $R^8$ is independently selected from OH, CN, $C_3$-$C_8$-cycloalkyl which optionally carries a CN substituent, $C_3$-$C_8$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfonyl, $C_1$-$C_6$-haloalkylsulfonyl, —C(=O)N($R^{10aa}$)($R^{10bb}$), phenyl, optionally substituted with 1, 2, 3, 4 or 5 substituents $R^{16}$, and a 3-, 4-, 5- or 6-membered saturated, partially unsaturated or maximally unsaturated heteromonocyclic ring containing 1, 2 or 3 heteroatoms or heteroatom groups independently selected from N, O, S, NO, SO and SO$_2$, as ring members, where the heteromonocyclic ring may be substituted with one or more substituents R$^{16}$;

wherein each R$^{10aa}$ and R$^{10bb}$ are selected independently from one another from the group consisting of hydrogen, C$_1$-C$_6$-alkyl, C$_1$-C$_6$-haloalkyl, C$_3$-C$_8$-cycloalkyl, C$_3$-C$_8$-halocycloalkyl, C$_2$-C$_6$-alkenyl, C$_2$-C$_6$-haloalkenyl, C$_2$-C$_6$-alkynyl, C$_2$-C$_6$-haloalkynyl, where the aliphatic and cycloaliphatic moieties in the eight last-mentioned radicals may be substituted by one or more radicals R$^{13}$;

—C$_1$-C$_6$-alkyl-C(=O)OR$^{15}$, —C$_1$-C$_6$-alkyl-C(=O)N(R$^{14a}$)R$^{14b}$, —C$_1$-C$_6$-alkyl-C(=S)N(R$^{14a}$)R$^{14b}$, —C$_1$-C$_6$-alkyl-C(=NR$^{14}$)N(R$^{14a}$)R$^{14b}$, C$_1$-C$_6$-alkoxy, C$_1$-C$_6$-haloalkoxy, C$_1$-C$_6$-alkylthio, C$_1$-C$_6$-haloalkylthio, —S(O)$_n$R$^{15}$, —S(O)$_n$N(R$^{14a}$)R$^{14b}$, —C(=O)R$^{13}$, —C(=O)OR$^{15}$, —C(=O)N(R$^{14a}$)R$^{14b}$, —C(=S)R$^{13}$, —C(=S)SR$^{15}$, —C(=S)N(R$^{14a}$)R$^{14b}$, —C(=NR$^{14}$)R$^{13}$;

phenyl, optionally substituted with 1, 2, 3, 4 or 5 substituents R$^{16}$; and a 3-, 4-, 5-, 6- or 7-membered saturated, partially unsaturated or maximally unsaturated heterocyclic ring comprising 1, 2, 3 or 4 heteroatoms or heteroatom groups selected from N, O, S, NO, SO and SO$_2$, as ring members, where the heterocyclic ring is optionally substituted with one or more substituents R$^{16}$;

or

R$^{10aa}$ and R$^{10bb}$ form together with the nitrogen atom they are bonded to a 3-, 4-, 5-, 6-, 7- or 8-membered saturated, partially unsaturated or maximally unsaturated heterocyclic ring, wherein the heterocyclic ring may additionally contain one or two heteroatoms or heteroatom groups selected from N, O, S, NO, SO and SO$_2$, as ring members, where the heterocyclic ring optionally carries one or more substituents selected from halogen, C$_1$-C$_6$-alkyl, C$_1$-C$_6$-haloalkyl, C$_1$-C$_6$-alkoxy, C$_1$-C$_6$-haloalkoxy, C$_1$-C$_6$-alkylthio, C$_1$-C$_6$-haloalkylthio, C$_3$-C$_8$-cycloalkyl, C$_3$-C$_8$-halocycloalkyl, C$_2$-C$_6$-alkenyl, C$_2$-C$_6$-haloalkenyl, C$_2$-C$_6$-alkynyl, C$_2$-C$_6$-haloalkynyl, phenyl, optionally substituted with 1, 2, 3, 4 or 5 substituents R$^{16}$, and a 3-, 4-, 5-, 6,- or 7-membered saturated, partially unsaturated or maximally unsaturated heterocyclic ring comprising 1, 2 or 3 heteroatoms or heteroatom groups selected from N, O, S, NO, SO and SO$_2$, as ring members, where the heterocyclic ring optionally carries one or more substituents R$^{16}$;

or R$^{10aa}$ and R$^{10bb}$ together form a group =C(R$^{13}$)$_2$, =S(O)$_m$(R$^{15}$)$_2$, =S(O)$_m$R$^{15}$N(R$^{14a}$)R$^{14b}$, =NR$^{14}$ or =NOR$^{15}$;

each R$^{16}$ as a substituent on phenyl or the heterocyclic rings is independently selected from the group consisting of halogen, cyano, nitro, C$_1$-C$_4$-alkyl, C$_1$-C$_4$-haloalkyl, C$_1$-C$_4$-alkoxy, C$_1$-C$_4$-haloalkoxy, C$_1$-C$_4$-alkylthio, C$_1$-C$_4$-haloalkylthio, C$_3$-C$_6$-cycloalkyl, C$_3$-C$_6$-halocycloalkyl, C$_2$-C$_4$-alkenyl, C$_2$-C$_4$-haloalkenyl, C$_2$-C$_4$-alkynyl and C$_2$-C$_4$-haloalkynyl; or two R$^{16}$ present on the same carbon atom of a saturated heterocyclic ring may form together =O or =S.

7. The compound of claim 6, where

R$^5$ is hydrogen;

R$^6$ is selected from hydrogen, unsubstituted C$_1$-C$_6$-alkyl, C$_1$-C$_6$-haloalkyl, C$_1$-C$_4$-alkyl which carries one radical R$^8$; C$_2$-C$_6$-alkenyl, C$_2$-C$_6$-haloalkenyl, C$_2$-C$_6$-alkynyl, C$_3$-C$_6$-cycloalkyl which may be substituted by 1 or 2 substituents selected from F and CN;

—N(R$^{10a}$)R$^{10b}$, wherein R$^{10a}$ is hydrogen and R$^{10b}$ is —C(=O)N(R$^{14a}$)R$^{14b}$, wherein R$^{14a}$ is selected from the group consisting of hydrogen and C$_1$-C$_6$-alkyl; and R$^{14b}$ is selected from the group consisting of hydrogen, C$_1$-C$_6$-alkyl, C$_1$-C$_6$-haloalkyl, C$_2$-C$_4$-alkynyl, C$_3$-C$_6$-cycloalkyl, C$_3$-C$_6$-halocycloalkyl, CH$_2$—CN, C$_1$-C$_4$-alkoxy and C$_1$-C$_4$-haloalkoxy;

—CH=NOR$^9$, wherein R$^9$ is selected from hydrogen, C$_1$-C$_6$-alkyl and C$_1$-C$_6$-haloalkyl;

phenyl which may be substituted with 1, 2, 3, 4, or 5 substituents R$^{11}$, and a heteromonocyclic ring selected from rings of formulae F-1 to F-54;

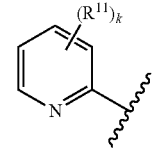

F-1

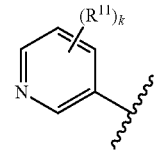

F-2

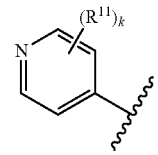

F-3

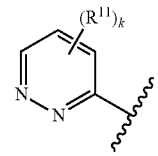

F-4

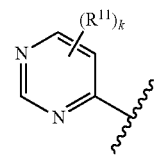

F-5

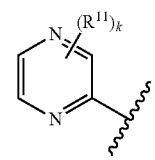

F-6

-continued
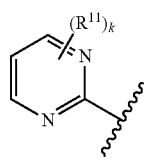 F-7
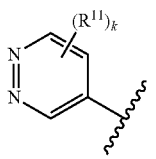 F-8
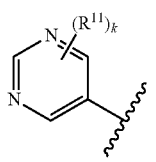 F-9
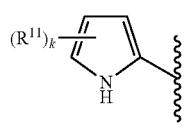 F-10
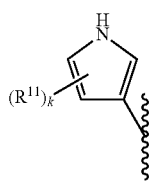 F-11
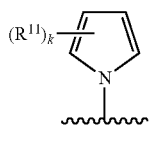 F-12
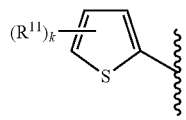 F-13
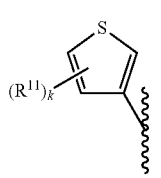 F-14
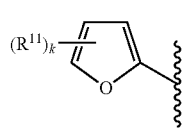 F-15
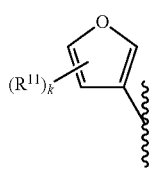 F-16
-continued
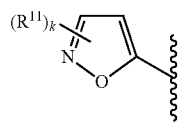 F-17
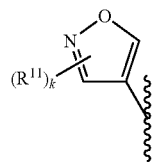 F-18
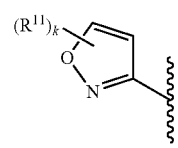 F-19
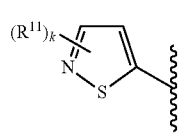 F-20
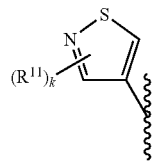 F-21
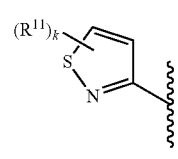 F-22
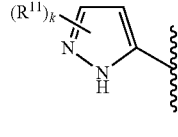 F-23
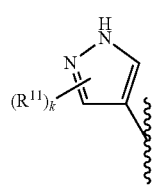 F-24
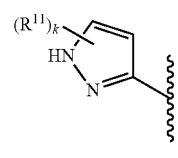 F-25
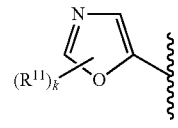 F-26

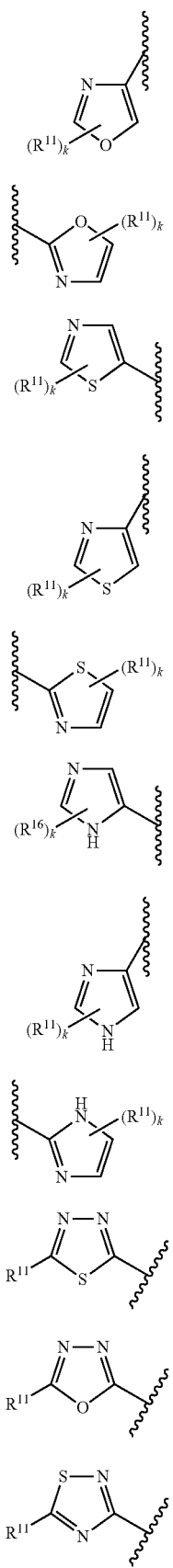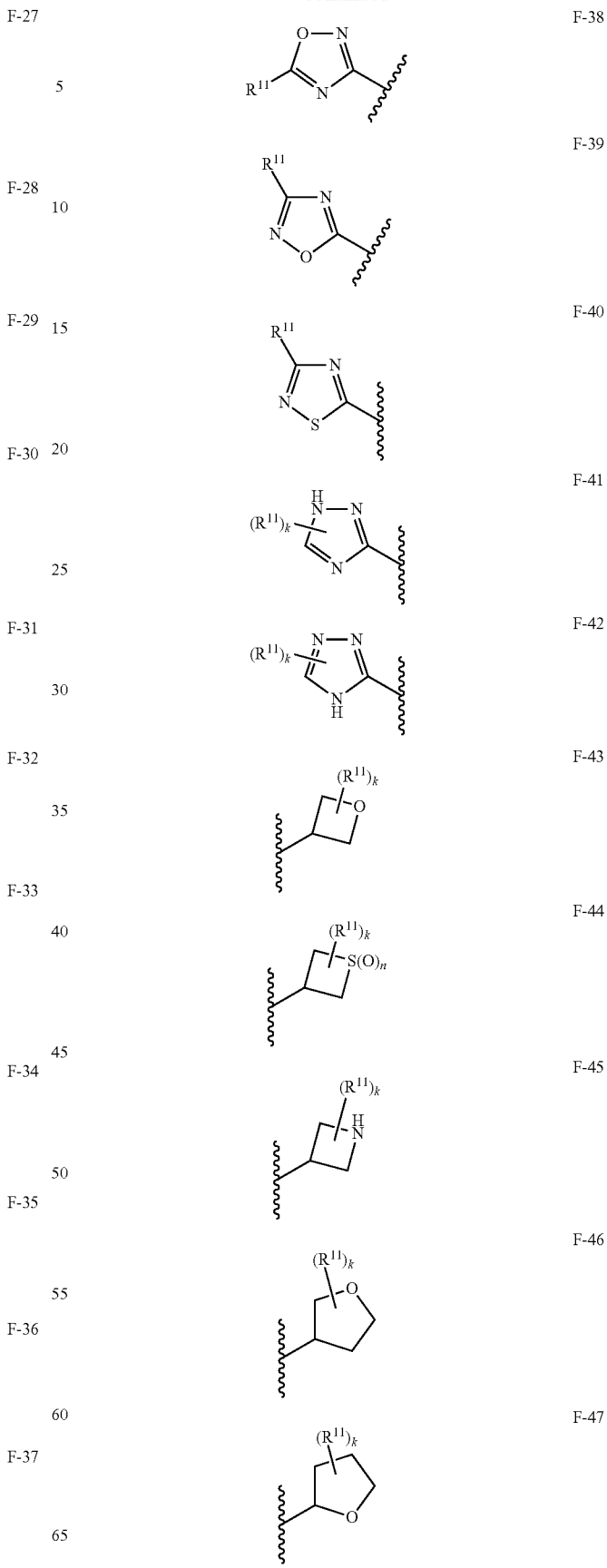

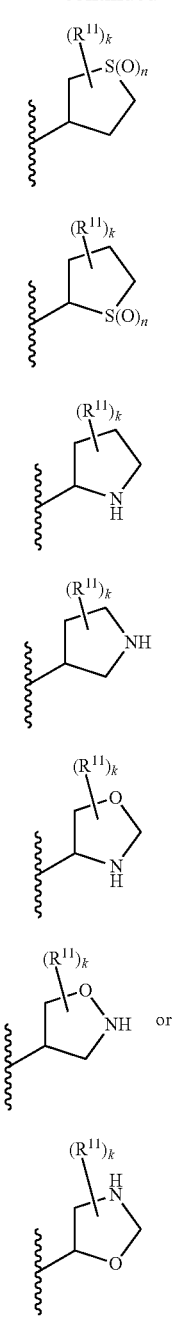

wherein
k is 0, 1, 2 or 3,
n is 0, 1 or 2, and
$R^8$ is selected from CN, $C_3$-$C_8$-cycloalkyl which optionally carries a CN substituent, $C_3$-$C_8$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfonyl, $C_1$-$C_6$-haloalkylsulfonyl, —C(=O)N($R^{10aa}$)$R^{10bb}$, phenyl, optionally substituted with 1, 2, 3, 4 or 5 substituents $R^{16}$, and a heterocyclic ring selected from rings of formulae E-1 to E-54; wherein
$R^{10aa}$ is selected from the group consisting of hydrogen and $C_1$-$C_6$-alkyl;
$R^{10bb}$ is selected from the group consisting of hydrogen, $C_1$-$C_6$-alkyl, $C_2$-$C_4$-alkynyl, $CH_2$—CN, $C_1$-$C_6$-haloalkyl, $C_3$-$C_6$-cycloalkyl, $C_3$-$C_6$-halocycloalkyl, $C_1$-$C_4$-alkoxy and $C_1$-$C_4$-haloalkoxy, and
each $R^{11}$ is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_2$-$C_4$-haloalkynyl;
each $R^{16}$ as a substituent on phenyl or the heterocyclic rings is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_2$-$C_4$-haloalkynyl; or
two $R^{11}$ present on the same carbon atom of a saturated heterocyclic ring may form together =O or =S; or
two $R^{16}$ present on the same carbon atom of a saturated heterocyclic ring may form together =O or =S.

8. The compound of claim 7, where
$R^5$ is hydrogen;
$R^6$ is selected from unsubstituted $C_1$-$C_6$-alkyl, $C_1$-$C_6$-haloalkyl, $C_1$-$C_4$-alkyl which carries one radical $R^8$; and a heteromonocyclic ring selected from rings of formulae F-1 to F-54,
wherein
$R^8$ is selected from CN, $C_3$-$C_8$-cycloalkyl which optionally carries a CN substituent, $C_3$-$C_8$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfonyl, $C_1$-$C_6$-haloalkylsulfonyl, —C(=O)N($R^{10aa}$)$R^{10bb}$, phenyl, optionally substituted with 1, 2, 3, 4 or 5 substituents $R^{16}$, and a heterocyclic ring selected from rings of formulae E-1 to E-54, wherein
$R^{10aa}$ is selected from the group consisting of hydrogen and $C_1$-$C_6$-alkyl;
$R^{10bb}$ is selected from the group consisting of hydrogen, $C_1$-$C_6$-alkyl, and $C_1$-$C_6$-haloalkyl.

9. The compound of claim 1 where $B^1$, $B^2$ and $B^3$ are independently selected from $CR^2$.

10. The compound of claim 9, where $B^1$ is $CR^2$, where $R^2$ is selected from the group consisting of halogen, cyano, azido, nitro, —SCN, —$SF_5$, $C_1$-$C_6$-alkyl, $C_3$-$C_8$-cycloalkyl, $C_2$-$C_6$-alkenyl, $C_2$-$C_6$-alkynyl, wherein the four last mentioned aliphatic and cycloaliphatic radicals may be partially or fully halogenated and/or may be substituted by one or more radicals $R^8$; —Si($R^{12}$)$_3$, —$OR^9$, —S(O)$_n$$R^9$, —$NR^{10a}R^{10b}$;
phenyl which may be substituted by 1, 2, 3, 4 or 5 radicals $R^{11}$; and a 3-, 4-, 5-, 6- 7-, 8-, 9- or 10-membered saturated, partially unsaturated or maximally unsaturated heteromonocyclic or heterobicyclic ring containing 1, 2, 3 or 4 heteroatoms or heteroatom groups selected from N, O, S, NO, SO and $SO_2$, as ring members, where the heteromono- or heterobicyclic ring may be substituted by one or more radicals $R^{11}$; and
$B^2$ and $B^3$ are $CR^{2a}$, where $R^{2a}$ is selected from hydrogen, halogen, cyano, azido, nitro, —SCN, —$SF_5$, $C_1$-$C_6$-alkyl, $C_3$-$C_8$-cycloalkyl, $C_2$-$C_6$-alkenyl, $C_2$-$C_6$-alkynyl, wherein the four last mentioned aliphatic and cycloaliphatic radicals may be partially or fully halogenated and/or may be substituted by one or more radicals $R^8$; —$OR^9$, —S(O)$_n$$R^9$ and —$NR^{10a}R^{10b}$.

11. The compound of claim 10, where $B^2$ and $B^3$ are $CR^{2a}$ and wherein $R^{2a}$ is selected from hydrogen, halogen and $C_1$-$C_2$-haloalkyl.

12. The compound of claim 1, where $R^1$ is selected from $C_1$-$C_4$-haloalkyl and —C(=O)OR$^{15}$, wherein $R^{15}$ is $C_1$-$C_4$-alkyl.

13. The compound of claim 1 where $R^{3a}$ and $R^{3b}$ are selected, independently of each other, from hydrogen and halogen.

14. The compounds of claim 1, where $R^{4a}$ and $R^{4b}$, independently of each other, are selected from hydrogen, halogen, cyano, $C_1$-$C_4$-alkyl, $C_1$-$C_4$-haloalkyl, $C_3$-$C_5$-cycloalkyl, $C_3$-$C_5$-halocycloalkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkoxy, $C_1$-$C_4$-haloalkoxy, $C_1$-$C_4$-alkylthio and $C_1$-$C_4$-haloalkylthio.

15. The compound of claim 11 wherein $R^{2a}$ is selected from the group consisting of hydrogen, F, Cl, Br and $CF_3$.

16. The compound of claim 12 wherein $R^1$ is $CF_3$.

17. The compound of claim 13 wherein $R^{3a}$ and $R^{3b}$ are independently selected from H and F.

18. The compound of claim 17 wherein $R^{3a}$ and $R^{3b}$ are each H.

19. The compound of claim 14 wherein $R^{4a}$ is H.

20. The compound of claim 14 wherein $R^{4b}$ is selected from the group consisting of hydrogen, F, Cl, Br, $CH_3$ and $CF_3$.

21. The compound of claim 8 wherein the heteromonocyclic ring is selected from the group consisting of F-43 to F-49.

22. The compound of claim 21 wherein the heteromonocyclic ring is F-44.

23. The compound of claim 8 wherein the heterocyclic ring is selected from the group consisting of E1-E34.

24. The compound of claim 23 wherein the heterocyclic ring is selected from the group consisting of E1, E2, E3, E7, E26, E27, E28, E29, E30, and E31.

25. An agricultural composition comprising the compound of formula I, as defined in claim 1, a stereoisomer thereof and/or at least one agriculturally acceptable salt thereof, and at least one inert liquid and/or solid agriculturally acceptable carrier.

26. A veterinary composition comprising the compound of formula I, as defined in claim 1, a stereoisomer thereof and/or at least one veterinarily acceptable salt thereof, and at least one inert liquid and/or solid veterinarily acceptable carrier.

27. A method for controlling invertebrate pests which method comprises treating the pests, their food supply, their habitat or their breeding ground or a plant, plant propagation material, soil, area, material or environment in which the pests are growing or may grow, or materials, plants, plant propagation material, soils, surfaces or spaces to be protected from invertebrate pest attack or infestation with a pesticidally effective amount of the compound of formula I as defined in claim 1, a stereoisomer thereof and/or at least one agriculturally acceptable salt thereof.

28. The method as claimed in claim 27, wherein the method comprises treating the plants to be protected from invertebrate pest attack or infestation.

29. The method as claimed in claim 28, which method comprises treating plant propagation material in which the pests are growing or may grow.

30. Plant propagation material, comprising at least one compound of the formula I as defined in claim 1, a stereoisomer thereof and/or at least one agriculturally acceptable salt thereof.

31. A method for treating or protecting an animal from infestation or infection by invertebrate pests which comprises bringing the animal in contact with a pesticidally effective amount of the compound of formula I as defined in claim 1, a stereoisomer thereof and/or at least one veterinarily acceptable salt thereof.

* * * * *